(12) United States Patent
Corum et al.

(10) Patent No.: US 10,447,342 B1
(45) Date of Patent: Oct. 15, 2019

(54) ARRANGEMENTS FOR COUPLING THE PRIMARY COIL TO THE SECONDARY COIL

(71) Applicant: CPG Technologies, LLC, Italy, TX (US)

(72) Inventors: James F. Corum, Morgantown, WV (US); Kenneth L. Corum, Plymouth, NH (US); Christopher R. Lamon, Southlake, TX (US); James M. Salvitti, Jr., Fort Worth, TX (US); Robert S. Galloway, Jr., Keller, TX (US); James T. Darnell, Ponder, TX (US); Fredrick A. Genz, Saint Charles, IL (US); Wes Pogorzelski, Ontario (CA); Michael P. Taylor, Midlothian, TX (US); Philip V. Pesavento, Waxahachie, TX (US); Timothy J. Lougheed, Jr., Midlothian, TX (US); Jerry A. Lomax, Katy, TX (US)

(73) Assignee: CPG Technologies, LLC, Italy, TX (US)

( * ) Notice: Subject to any disclaimer, the term of this patent is extended or adjusted under 35 U.S.C. 154(b) by 0 days.

(21) Appl. No.: 15/912,719

(22) Filed: Mar. 6, 2018

Related U.S. Application Data

(60) Provisional application No. 62/468,272, filed on Mar. 7, 2017.

(51) Int. Cl.
*H02J 50/10* (2016.01)
*H04B 3/52* (2006.01)
*H02J 7/02* (2016.01)

(52) U.S. Cl.
CPC ................ *H04B 3/52* (2013.01); *H02J 7/025* (2013.01); *H02J 50/10* (2016.02)

(58) Field of Classification Search
CPC .......... H04B 3/52; H04B 5/0037; H04B 7/00; H02J 17/00; H02J 50/20; H01P 3/00; H01P 5/00; H01Q 9/30; H01Q 1/04
See application file for complete search history.

(56) References Cited

U.S. PATENT DOCUMENTS

| 645,576 A | 3/1900 | Tesla |
|---|---|---|
| 649,621 A | 5/1900 | Tesla |

(Continued)

FOREIGN PATENT DOCUMENTS

| EP | 0639301 | 2/1995 |
|---|---|---|
| EP | 1898532 | 3/2008 |

(Continued)

OTHER PUBLICATIONS

Singh et al., "Excitation of surface electromagnetic waves on water", Nov. 1978, Applied Optics, vol. 17 No. 21, pp. 3459-3465 (Year: 1978).*

(Continued)

*Primary Examiner* — Dean O Takaoka
*Assistant Examiner* — Alan Wong
(74) *Attorney, Agent, or Firm* — Thomas | Horstemeyer, LLP

(57) ABSTRACT

Disclosed is a guided surface waveguide probe with a charge terminal that is elevated over a lossy conducting medium. A primary coil can be coupled to an excitation source within a substructure. A secondary coil can provide a voltage to the charge terminal with a phase delay ($\Phi$) that matches a wave tilt angle ($\Psi$) associated with a complex Brewster angle of incidence ($\theta_{i,B}$) associated with the lossy conducting medium. The primary coil can be configured to inductively couple to the secondary coil.

20 Claims, 41 Drawing Sheets

(56) References Cited

U.S. PATENT DOCUMENTS

| | | | |
|---|---|---|---|
| 685,012 A | 10/1901 | Tesla | |
| 685,953 A | 11/1901 | Tesla | |
| 685,954 A | 11/1901 | Tesla | |
| 685,955 A | 11/1901 | Tesla | |
| 685,956 A | 11/1901 | Tesla | |
| 723,188 A | 3/1903 | Tesla | |
| 725,605 A | 4/1903 | Tesla | |
| 787,412 A | 4/1905 | Tesla | |
| 851,336 A | 4/1907 | Von Arco | |
| 1,119,732 A * | 12/1914 | Tesla | H01Q 1/38 200/48 R |
| 1,452,849 A | 4/1923 | Round | |
| 1,652,516 A | 12/1927 | Conrad | |
| 1,691,338 A | 11/1928 | Conrad | |
| 1,947,256 A | 2/1934 | Friis | |
| 2,685,068 A | 7/1954 | Goubau | |
| 2,921,277 A | 1/1960 | Goubau | |
| 3,123,767 A | 3/1964 | Ghose | |
| 3,219,954 A | 11/1965 | Rutelli | |
| 3,445,844 A | 5/1969 | Grossi et al. | |
| 3,582,838 A | 6/1971 | Devries | |
| 3,670,247 A | 6/1972 | Gutton et al. | |
| 3,742,509 A | 6/1973 | De Bettencourt et al. | |
| 3,742,511 A | 6/1973 | Smith et al. | |
| 4,751,515 A | 6/1988 | Corum | |
| 4,808,950 A | 2/1989 | Apostolos et al. | |
| 5,045,825 A | 9/1991 | McJunkin | |
| 5,074,489 A | 12/1991 | Gamzon | |
| 5,155,495 A | 10/1992 | Hately et al. | |
| 5,293,308 A | 3/1994 | Boys et al. | |
| 5,301,096 A | 3/1994 | Klontz et al. | |
| 5,714,917 A | 2/1998 | Ella | |
| 5,835,067 A | 11/1998 | Goodman | |
| 5,920,261 A | 7/1999 | Hughes | |
| 6,025,813 A | 2/2000 | Hately et al. | |
| 6,075,498 A | 6/2000 | Talwar | |
| 6,104,107 A | 8/2000 | Avramenko et al. | |
| 6,107,791 A | 8/2000 | Lee | |
| 6,486,846 B1 | 11/2002 | Hart | |
| 6,515,878 B1 | 2/2003 | Meins et al. | |
| 6,650,556 B2 | 11/2003 | Dinh | |
| 6,864,849 B2 | 3/2005 | Hart | |
| 6,956,535 B2 | 10/2005 | Hart | |
| 7,113,138 B2 | 9/2006 | Hately | |
| 7,307,589 B1 | 12/2007 | Gregoire | |
| 7,561,096 B2 | 7/2009 | Hellsten | |
| 7,741,734 B2 | 6/2010 | Joannopoulos et al. | |
| 7,775,112 B2 | 8/2010 | Amemiya | |
| 7,782,264 B1 | 8/2010 | Vincent | |
| 7,825,543 B2 | 11/2010 | Karalis et al. | |
| 7,890,053 B2 | 2/2011 | Washiro | |
| 7,894,770 B2 | 2/2011 | Washiro | |
| 8,063,717 B2 | 11/2011 | Bradley et al. | |
| 8,076,801 B2 | 12/2011 | Karalis et al. | |
| 8,084,889 B2 | 12/2011 | Joannopoulos et al. | |
| 8,097,983 B2 | 1/2012 | Karalis et al. | |
| 8,299,936 B2 | 10/2012 | Papadopoulos | |
| 8,338,991 B2 | 12/2012 | Von Novak et al. | |
| 8,350,769 B1 | 1/2013 | Crawley | |
| 8,378,524 B2 | 2/2013 | Mita | |
| 8,384,247 B2 | 2/2013 | Yerazunis et al. | |
| 8,395,282 B2 | 3/2013 | Joannopoulos et al. | |
| 8,536,738 B2 | 9/2013 | Bella | |
| 8,587,490 B2 | 11/2013 | Niver et al. | |
| 8,890,472 B2 | 11/2014 | Mashinsky | |
| 8,897,697 B1 | 11/2014 | Bennett et al. | |
| 8,941,448 B2 | 1/2015 | Yu et al. | |
| 9,030,363 B2 * | 5/2015 | Kenington | H01Q 25/00 343/757 |
| 9,042,812 B1 | 5/2015 | Bennett et al. | |
| 9,154,966 B2 | 10/2015 | Bennett et al. | |
| 9,156,364 B2 | 10/2015 | Miller et al. | |
| 9,178,504 B2 | 11/2015 | Komori | |
| 9,960,470 B2 * | 5/2018 | Corum | H01P 3/00 |
| 2004/0227667 A1 | 11/2004 | Sievenpiper | |
| 2004/0263409 A1 | 12/2004 | Hart | |
| 2005/0111533 A1 | 5/2005 | Berkman | |
| 2005/0128154 A1 | 6/2005 | Hately | |
| 2006/0281423 A1 | 12/2006 | Caimi | |
| 2007/0035356 A1 | 2/2007 | Ranta | |
| 2007/0132489 A1 | 6/2007 | Corum | |
| 2008/0122449 A1 | 5/2008 | Besser et al. | |
| 2008/0273201 A1 | 11/2008 | Brooks et al. | |
| 2010/0194206 A1 | 8/2010 | Burdo | |
| 2010/0259111 A1 | 10/2010 | Ruocco et al. | |
| 2010/0260076 A1 | 10/2010 | Corman | |
| 2010/0264748 A1 | 10/2010 | Tucker | |
| 2011/0049997 A1 | 3/2011 | Urano | |
| 2011/0062916 A1 | 3/2011 | Farahani | |
| 2011/0080050 A1 | 4/2011 | Thundat et al. | |
| 2011/0133564 A1 | 6/2011 | Ted | |
| 2011/0133565 A1 | 6/2011 | Teo et al. | |
| 2011/0156494 A1 * | 6/2011 | Mashinsky | H02J 17/00 307/104 |
| 2011/0169336 A1 | 7/2011 | Yerazunis | |
| 2012/0119575 A1 | 5/2012 | Kurs | |
| 2012/0169568 A1 | 7/2012 | Oh et al. | |
| 2012/0248889 A1 | 10/2012 | Fukushi | |
| 2012/0249449 A1 | 10/2012 | Tseng | |
| 2013/0029595 A1 | 1/2013 | Widmer et al. | |
| 2013/0049674 A1 | 2/2013 | Davis | |
| 2013/0064311 A1 * | 3/2013 | Turner | H01P 3/00 375/259 |
| 2013/0099584 A1 | 4/2013 | Von Novak | |
| 2014/0015344 A1 | 1/2014 | Mohamadi | |
| 2014/0062813 A1 | 3/2014 | Alrabadi | |
| 2014/0104132 A1 | 4/2014 | Bakalski et al. | |
| 2014/0252865 A1 | 9/2014 | Corum et al. | |
| 2014/0252886 A1 | 9/2014 | Corum et al. | |
| 2014/0308901 A1 | 10/2014 | Turner et al. | |
| 2014/0319922 A1 | 10/2014 | Shinohara | |
| 2015/0042172 A1 | 2/2015 | Howard | |
| 2015/0109181 A1 | 4/2015 | Hyde | |
| 2015/0145339 A1 | 5/2015 | Chiyo et al. | |
| 2015/0207334 A1 | 7/2015 | Mitcheson et al. | |
| 2015/0207335 A1 | 7/2015 | Madawala | |
| 2015/0280444 A1 | 10/2015 | Smith et al. | |
| 2017/0005529 A1 | 1/2017 | Burling | |
| 2017/0018852 A1 | 1/2017 | Adriazola et al. | |

FOREIGN PATENT DOCUMENTS

| | | |
|---|---|---|
| EP | 1965223 | 9/2008 |
| EP | 2221743 | 8/2010 |
| EP | 2568528 | 3/2013 |
| GB | 20981 | 11/1896 |
| GB | 24421 | 3/1898 |
| GB | 11293 | 11/1901 |
| GB | 13563 | 11/1901 |
| GB | 14579 | 4/1902 |
| GB | 8200 | 4/1906 |
| GB | 142352 | 8/1912 |
| GB | 1471860 | 4/1977 |
| GB | 2215524 | 9/1989 |
| GB | 2330695 B | 6/2002 |
| GB | 2387969 B | 11/2005 |
| JP | H06225481 | 8/1994 |
| JP | 2007244015 | 9/2007 |
| RU | 2143775 | 12/1999 |
| RU | 2161850 | 1/2001 |
| RU | 2183376 | 6/2002 |
| RU | 2255406 | 6/2005 |
| RU | 2273939 | 4/2006 |
| RU | 2310964 | 11/2007 |
| RU | 2340064 | 11/2008 |
| RU | 2341860 | 12/2008 |
| RU | 2342761 | 12/2008 |
| RU | 2366057 | 8/2009 |
| RU | 2366058 | 8/2009 |
| RU | 2409883 | 1/2011 |
| RU | 2423772 | 7/2011 |
| RU | 2459340 | 8/2012 |
| RU | 2473160 | 1/2013 |
| RU | 2474031 | 1/2013 |

(56) References Cited

FOREIGN PATENT DOCUMENTS

| | | |
|---|---|---|
| RU | 2488207 | 7/2013 |
| RU | 2488208 | 7/2013 |
| RU | 2533060 | 11/2014 |
| RU | 2544380 | 3/2015 |
| RU | 2548571 | 4/2015 |
| RU | 2554723 | 6/2015 |
| WO | 9313495 | 7/1993 |
| WO | WO9323907 | 11/1993 |
| WO | 9529516 A1 | 11/1995 |
| WO | 0191238 A1 | 11/2001 |
| WO | 2007146164 | 12/2007 |
| WO | 2010020813 | 2/2010 |
| WO | 2010111541 | 9/2010 |
| WO | 2010129369 | 11/2010 |
| WO | 2011097046 | 8/2011 |
| WO | 2013093922 | 6/2013 |

OTHER PUBLICATIONS

Peterson, G., The Application of Electromagnetic Surface Waves to Wireless Energy Transfer, 2015 IEEE Wireless Sower Transfer Conference (WPTC), May 1, 2015, pp. 1-4, Shoreham, Long Island, New York, USA.

Kukushkin, A. V., On the Existence and Physical Meaning of the Zenneck Wave, UFN, 2009, vol. 179, No. 7, 801-803.

Kistovich, Yu. V., On the Possibility of Observing Surface Zenneck Waves in the Radiation of a Source with a Small Vertical Aperture, Journal of Technical Physics, 1989, vol. 59(4), 16-21.

Datsko, V.N. and A.A. Kopylov, On Surface Electromagnetic Waves, UFN, 2008, vol. 178, No. 1, 109-110.

Baybakov et al., Experimental Discovery of Zenneck's Surface Electromagnetic Waves, UFN, 1989, vol. 157, 722-724.

Hesse et al., A Single Probe Spatial Averaging Technique for Guided Waves and Its Application to Surface Wave Rail Inspection, IEEE Transactions on Ultrasonics, Ferroelectrics, and Frequency Control, vol. 54, No. 11, Nov. 2007, 2344-2356.

Andriyas, T., Surface Wave Propagation in a Dielectric Waveguide Loaded with an Anistropic, Conductive, and Spatially Dispersive Substrate, Utah State University, May 2009, p. 12.

U.S. Appl. No. 14/483,089, filed Sep. 10, 2014, Non-Final Office Action dated Apr. 6, 2017.

U.S. Appl. No. 14/728,507, filed Jun. 2, 2015, Final Office Action dated Jul. 28, 2017.

Beaty, W., Tesla's Big Mistake?, Sep. 1999, http://amasci.com/tesla/tmistk.html.

4nonymous, Tesla Wireless Technology, Mar. 8, 2007, http://montalk.net/notes/tesla-wireless-technology.

Examination Report issued in Australian Application No. 2014226221 dated Sep. 20, 2017.

U.S. Appl. No. 14/848,653, filed Sep. 9, 2015, Final Office Action dated Sep. 25, 2017.

Wolff, Christian, "Over the Horizon Oceanography Radar WERA," Oct. 13, 2011, https://web.archive.org/web/20111013010047/http://www.radartutorial.eu/19.kartei/karte712.en.html.

Kume, Hideyoshi, "Dengyo Converts Microwave Into Electricity with High Efficiency," Nikkei Electronics, May 17, 2011, http://techon.nikkeibp.co.jp/english/NEWS_EN/20110517/191846/.

Examination Report issued in New Zealand Application No. 712566 dated Jun. 10, 2016.

Examination Report issued in New Zealand for Application No. 720048 dated Jun. 28, 2016.

Singh A. K. et al., Excitation of surface electromagnetic waves on water, App Optics, Nov. 1, 1978, pp. 3459-3465, vol. 17, No. 21.

Olivier Balosso et al., Brief overview about Surface Wave theory and applications, 2012 15th International Symposium on Antenna Technology and Applied Electromagnetics (Antem), Jun. 25, 2012, pp. 1-7, IEEE.

International Search Report and Written Opinion for PCT/US2015/035598 dated Jul. 21, 2014.

Menelle M et al., Full digital high frequency surface wave radar: French trials in the Biscay bay, 2008 International conference on Radar, Sep. 2, 2008, pp. 224-229, IEEE, Piscataway, NJ, USA.

J. O. Hinz et al., A MIMO FMCW radar approach to HFSWR, Advances in Radio Science: ARS, Jul. 29, 2011, pp. 159-163, retrieved from the Internet: http://www.adv-radio-sci.net/9/159/2011/ars-9-159-2011.pdf (retrieved on Dec. 4, 2015), Katlenburg-Lindau, Germany.

Guohua Wang et al., High Resolution MIMO-HFSWR Radar Using Sparse Frequency Waveforms, Wireless Sensor Network, Oct. 1, 2009, pp. 152-162, vol. 1, No. 3.

International Search Report and Written Opinion for PCT/US2015/049505 dated Dec. 14, 2015.

International Search Report and Written Opinion for PCT/US2015/049394 dated Dec. 14, 2015.

International Search Report and Written Opinion for PCT/US2015/049064 date Dec. 11, 2015.

International Search Report and Written Opinion for PCT/US2015/049509 dated Dec. 18, 2015.

H. M. Barlow et al., Surface Waves, Proceedings of the IRE, Nov. 1, 1953, pp. 329-341, vol. 100, No. 68, US.

International Search Report and Written Opinion for PCT/US2015/049171 date Dec. 16, 2015.

International Search Report and Written Opinion for PCT/US2015/049435 dated Dec. 22, 2015.

International Search Report and Written Opinion for PCT/US2015/049424 date Dec. 18, 2015.

International Search Report and Written Opinion for PCT/US2015/049151 dated Dec. 17, 2015.

International Search Report and Written Opinion for PCT/US2015/049161 dated Dec. 17, 2015.

International Search Report and Written Opinion for PCT/US2015/049518 dated Dec. 18, 2015.

International Search Report and Written Opinion for PCT/US2015/049154 dated Dec. 15, 2015.

Hambling, David, "Skimming the Surface: The Return of Tesla's Surface Waves", Published by Popular Mechanics on the Internet at http://www.popularmechanics.com/technology/infrastructure/a8778/ skimming-the-surface-the-return-of-teslas-surface-waves-15322250/, Apr. 8, 2013, Popular Mechanics.

Garfield, R. H., "The Attenuation of Wireless Waves Over Land," Journal of the I.E.E. (British), Jan. 1928, pp. 204-214, vol. 66.

Michalski, K. A. et al., "The Sommerfeld half-space problem revisited: from radio frequencies and Zenneck waves to risible light and Fano modes," Journal of Electromagnetic Waves and Applications, Jan. 2016, pp. 1-42, vol. 30, No. 1, Taylor & Francis.

Noether, F., "Spreading of Electric Waves Along the Earth," published in the book translation Theory of Functions As Applied to Engineering Problems, Technology Press, 1942, pp. 167-184, Part 2, Section E, MIT [Originally published by Springer, Berlin, in 1931 under the title Funktionentheorie und Ihre Anwendung in der Technik, Part II, R. Rothe, F. Ollendorf, and K. Pohlhausen, editors.].

Patent Application PCT/US2016/047344 filed on Aug. 17, 2016, International Search Report dated Feb. 8, 2017.

Patent Application PCT/US2016/047676 filed on Aug. 19, 2016, International Search Report dated Jan. 31, 2017.

Patent Application PCT/US2016/047672 filed on Aug. 19, 2016, International Search Report dated Nov. 3, 2016.

Patent Application PCT/US2016/046488 filed on Aug. 11, 2016, International Search Report dated Dec. 19, 2016.

Patent Application PCT/US2016/047674 filed on Aug. 19, 2016, International Search Report dated Dec. 20, 2016.

Patent Application PCT/US2016/047167 filed on Aug. 16, 2016, International Search Report dated Oct. 27, 2016.

Patent Application PCT/US2016/047375 filed on Aug. 17, 2016, International Search Report dated Dec. 2, 2016.

Patent Application PCT/US2016/047599 filed on Aug. 18, 2016, International Search Report dated Nov. 23, 2016.

Patent Application PCT/US2016/047673 filed on Aug. 19, 2016, International Search Report dated Nov. 29, 2016.

Patent Application PCT/US2016/047446 filed on Aug. 18, 2016, International Search Report dated Nov. 3, 2016.

(56) References Cited

OTHER PUBLICATIONS

Patent Application PCT/US2016/047353 filed on Aug. 17, 2016, International Search Report dated Nov. 16, 2016.
Patent Application PCT/US2016/047170 filed on Aug. 16, 2016, International Search Report dated Nov. 11, 2016.
Patent Application PCT/US2016/047611 filed on Aug. 18, 2016, International Search Report dated Nov. 11, 2016.
Patent Application PCT/US2016/047455 filed on Aug. 18, 2016, International Search Report and Written Opinion dated Nov. 7, 2016.
Patent Application PCT/US2016/047452 filed on Aug. 18, 2016, International Search Report and Written Opinion dated Nov. 17, 2016.
Leonhard, W., Electrical Engineering Between Energy and Information, Power Electronics and Motion Control Conference, 2000. Proceedings. PI EMC 2000. The Third International Aug. 15-18, 2000, IEEE, vol. 1, Aug. 15, 2000, pp. 197-202, Piscataway, NJ, USA.
Patent Application PCT/US2016/047451 filed on Aug. 18, 2016, International Search Report and Written Opinion dated Nov. 17, 2016.
Patent Application PCT/US16/47986 filed on Aug. 22, 2016, International Search Report and Written Opinion dated Nov. 17, 2016.
Patent Application PCT/US2016/047954 filed on Aug. 22, 2016, International Search Report and Written Opinion dated Nov. 24, 2016.
Zoran, B. et al, Some Notes on Transmission Line Representations of Tesla's Transmitters, 16th International Conference on Software, Telecommunications and Computer Networks, Softcom 2008, IEEE. Sep. 25, 2008, pp. 60-69, Piscataway. NJ, USA.
Patent Application PCT/US2016/047957 filed on Aug. 22, 2016, International Search Report and Written Opinion dated Nov. 17, 2016.
Patent Application PCT/US2016/048314 filed on Aug. 24, 2016, International Search Report and Written Opinion dated Nov. 17, 2016.
Patent Application PCT/US2016/047675 filed on Aug. 19, 2016, International Search Report and Written Opinion dated Nov. 25, 2016.
Patent Application PCT/US2016/047955 filed on Aug. 22, 2016, International Search Report and Written Opinion dated Nov. 17, 2016.
Patent Application PCT/US2016/047457 filed on Aug. 18, 2016, International Search and Written Opinion dated Nov. 18, 2016.
Patent Application PCT/US2016/047368 filed on Aug. 17, 2016, International Search Report and Written Opinion dated Nov. 4, 2016.
Patent Application PCT/US2016/047338 filed on Aug. 17, 2016, International Search Report and Written Opinion dated Nov. 17, 2016.
Patent Application PCT/US2016/047598 filed on Aug. 18, 2016, International Search Report and Written Opinion dated Nov. 3, 2016.
Patent Application PCT/US2015/049236 filed on Sep. 9, 2015, International Search Report and Written Opinion dated Jan. 4, 2016.
Patent Application PCT/US2015/049511 filed on Sep. 10, 2015, International Search Report and Written Opinion dated Jan. 5, 2016.
Patent Application PCT/US2015/049523 filed on Sep. 10, 2015, International Search Report and Written Opinion dated Jan. 7, 2016.
Patent Application PCT/US2015/049497 filed on Sep. 10, 2015, International Search Report and Written Opinion dated Dec. 23, 2015.
Patent Application PCT/US2015/049520 filed on Sep. 10, 2015, International Search Report and Written Opinion dated Jan. 15, 2016.
Rich, G. J., The Launching of a Plane Surface Wave, Proceedings of the IEEE—Part B: Radio and Electronic Engineering, Mar. 1, 1955, pp. 237-246, vol. 102, No. 2, US.

Ranfagni, A. et al, Observation of Zenneck-type Waves in Microwave Propagation Experiments, Journal of Applied Physics, Jul. 2006, pp. 024910-1-024910-5, vol. 100, No. 2, US.
Mahmoud, S. F. et al, Reflection of Surface Waves on a Dielectric Image Line with Application to 'Guided RADAR', Microwave Symposium, 1972 IEEE GMTT International, May 22, 1972, pp. 139-141, Piscataway, NJ, US.
Examination Report issued in New Zealand Application No. 720048 dated May 12, 2017.
Examination Report issued in New Zealand Application No. 720048 dated Jan. 25, 2017.
Patent Application PCT/US2016/047350 filed on Aug. 17, 2016, International Search Report dated Mar. 9, 2017.
Patent Application PCT/US2015/049171 filed on Sep. 9, 2015, International Search Report and Written Opinion dated Dec. 16, 2015.
International Search Report and Written Opinion for PCT/US2016/047677 dated Oct. 18, 2016.
International Search Report and Written Opinion for PCT/US2016/047956 dated Oct. 21, 2016.
Wu, Ke et al., Wireless Power Transmission, Technology, and Applications, Proceedings of the IEEE, Jun. 2013, pp. 1271-1275, vol. 101, No. 6.
Massa, Andrea et al., Array Designs for Long-Distance Wireless Power Transmission: State-of-the-Art and Innovative Solutions, Proceedings of the IEEE, Jun. 2013, pp. 1464-1481, vol. 101, No. 6.
Norton, K. A., The Propagation of Radio Waves Over the Surface of the Earth and in the Upper Atmosphere: Part I Ground-Wave Propagation from Short Antennas, Proc. IRE, Oct. 1936, pp. 1367-1387, vol. 24, No. 10.
Shinohara, Naoki, Beam Control Technologies with a High-Efficiency Phased Array for Microwave Power Transmission in Japan, Proceedings of the IEEE, Jun. 2013, pp. 1448-1463, vol. 101, No. 6.
Miyakoshi, Junji, Cellular and Molecular Responses to Radio-Frequency Electromagnetic Fields, Proceedings of the IEEE, Jun. 2013, pp. 1494-1502, vol. 101, No. 6.
Kim, Jiseong et al., Coil Design and Shielding Methods for a Magnetic Resonant Wireless Power Transfer System, Proceedings of the IEEE, Jun. 2013, pp. 1332-1342, vol. 101, No. 6.
Shoki, Hiroki, Issues and Initiatives for Practical Deployment of Wireless Power Transfer Technologies in Japan, Proceedings of the IEEE, Jun. 2013, pp. 1312-1320, vol. 101, No. 6.
Covic, Grant A. et al., Inductive Power Transfer, Proceedings of the IEEE, Jun. 2013, pp. 1276-1289, vol. 101, No. 6.
Strassner, Bernd et al., Microwave Power Transmission: Historical Milestones and System Components, Proceedings of the IEEE, Jun. 2013, pp. 1379-1396, vol. 101, No. 6.
Christ, Andreas et al., Assessing Human Exposure to Electromagnetic Fields from Wireless Power Transmission Systems, Proceedings of the IEEE, Jun. 2013, pp. 1482-1493, vol. 101, No. 6.
Jaffe, Paul et al., Energy Conversion and Transmission Modules for Space Solar Power, Proceedings of the IEEE, Jun. 2013, pp. 1424-1437, vol. 101, No. 6.
Tesla, Nikola, The Transmission of Electrical Energy Without Wires, Electrical World & Engineer, Mar. 5, 1904, pp. 429-431.
Hui, S. Y., Planar Wireless Charging Technology for Portable Electronic Products and Qi, Proceedings of the IEEE, Jun. 2013, pp. 1290-1301, vol. 101, No. 6.
Sasaki, Susumu et al., Microwave Power Transmission Technologies for Solar Power Satellites, Proceedings of the IEEE, Jun. 2013, pp. 1438-1447, vol. 101, No. 6.
Wang, Bingnan et al., Wireless Power Transfer: Metamaterials and Array of Coupled Resonators, Proceedings of the IEEE, Jun. 2013, pp. 1359-1368, vol. 101, No. 6.
Sample, Alanson P. et al., Enabling Seamless Wireless Power Delivery in Dynamic Environments, Proceedings of the IEEE, Jun. 2013, pp. 1343-1358, vol. 101, No. 6.
Visser, Hubregt J. et al., RF Energy Harvesting and Transport for Wireless Sensor Network Applications: Principles and Requirements, Proceedings of the IEEE, Jun. 2013, pp. 1410-1423, vol. 101, No. 6.

(56) References Cited

OTHER PUBLICATIONS

Popovic, Zoya et al., Low-Power Far-Field Wireless Powering for Wireless Sensors, Proceedings of the IEEE, Jun. 2013, pp. 1397-1409, vol. 101, No. 6.

Mayordomo, Iker et al., An Overview of Technical Challenges and Advances of Inductive Wireless Power Transmission, Proceedings of the IEEE, Jun. 2013, pp. 1302-1311, vol. 101, No. 6.

Garnica, Jaime et al., Wireless Power Transmission: From Far Field to Near Field, Proceedings of the IEEE, Jun. 2013, pp. 1321-1331, vol. 101, No. 6.

Ho, John S. et al., Midfield Wireless Powering for Implantable Systems, Proceedings of the IEEE, Jun. 2013, pp. 1369-1378, vol. 101, No. 6.

O'Neill, John J., Prodigal Genius: The Life of Nikola Tesla, 2008, pp. 121-217, Adventures Unlimited Press, Kempton, Illinois.

Cheney, Margaret, Tesla: Man Out of Time, 1981, pp. 171-191, Touchstone, New York, NY.

Burrows, C. R., The Surface Wave in Radio Transmission, Bell Laboratories Record, Jun. 1937, pp. 321-324, vol. 15.

Valone, Thomas, Harnessing the Wheelwork of Nature, Tesla's Science of Energy, 2002, pp. 147-269, Adventures Unlimited Press, Kempton, Illinois.

Tesla, Nikola, My Inventions, The Autobiography of Nikola Tesla, 2013, pp. 61-72, Lexington, KY.

Tesla, Nikola, From Colorado Springs to Long Island, Research Notes: Colorado Springs 1899-1900 New York 1900-1901, 2008, Nikola Tesla Museum.

McMichael, I., A Note on the Brewster Angle in Lossy Dielectric Media, Night Vision and Electronic Sensors Directorate, Oct. 2010, pp. 1-11, US Army RDECOM CERDEC NVESD, Fort Belvior, Virginia.

Karalis, A., et al., Efficient Wireless Non-radiative Mid-range Energy Transfer, Annals of Physics, 2008, pp. 34-48, No. 323, Elsevier, Inc. (also made available online on Apr. 27, 2007).

Wadsworth, D., Approximate Integration Methods Applied to Wave Propagation (Thesis), Department of Geology and Geophysics, Massachusetts Institute of Technology, Thesis Submitted in Feb. 1958, pp. 1-128, Massachusetts Institute of Technology, Cambridge, Massachusetts, United States.

Pover, B., Report on the Performance of the Silsden 8 Metre Crossed Field Antenna, Published on the Internet at ok1mjo.com/all/ostatni/t-dab_dvb-t.../CFA_antena_silsden-report.pdf, Oct. 2009, pp. 1-28.

Corum, J. et al., The Application of Transmission Line Resonators to High Voltage RF Power Processing: History, Analysis and Experiment, IEEE 19th Southeastern Symposium on System Theory, Mar. 1987, pp. 45-50, Held at Clemson University, Clemson, South Carolina, United States.

Search Report and Written Opinion, PCT/US2014/019477, International Publication No. Wo 2014/137817, entitled Excitation and Use of Guided Surface Waves on Lossy Media, International Publication Date: Sep. 12, 2014, International Filing Date: Feb. 28, 2014.

Wait, J. R., Excitation of Surface Waves on Conducting, Stratified, Dielectric-clad and Corrugated Surfaces, Research of the National Bureau of Standards, Dec. 1957, pp. 365-377, vol. 59, No. 6.

Marincic, A. S., Nikola Tesla and the Wireless Transmission of Energy, IEEE Transactions on Power Apparatus and Systems, Oct. 1982, pp. 58-59, vol. PAS-101, No. 10, IEEE, University of Belgrade, Belgrade, Yugoslavia.

Valentinuzzi, M.E, Nikola Tesla: Why Was He So Much Resisted and Forgotten?, IEEE Engineering in Medicine and Biology Magazine, Jul./Aug. 1998, pp. 74-75, vol. 17, No. 4, IEEE, Inst. de Bioingenieria, Univ. Nacional de Tucuman, Mexico.

Leyh, G.E. et al., Efficient Wireless Transmission of Power Using Resonators with Coupled Electric Fields, Power Symposium, 2008. NAPS '08. 40th North American, pp. 1-4, IEEE, Nevada Lightning Lab., NV, USA.

Marincic, A. et al., Tesla's Contribution to Radiowave Propagation, Telecommunications in Modern Satellite, Cable and Broadcasting Service, Sep. 2001, pp. 327-331, vol. 1, IEEE, Belgrade, Serbia.

Garnica, J. et al., Wireless Power Transmission: From Far Field to Near Field, Proceedings of the IEEE, Apr. 4, 2013, pp. 1321-1331, vol. 101, No. 6, IEEE, Gainesville, FL, USA.

Poljak, D. et al., Full Wave Model versus Transmission Line Representation of Tesla's Wave Propagation: 155th Anniversary of Birth of Nikola Tesla, 2011 19th International Conference on Software, Telecommunications and computer Networks (SoftCOM), Sep. 15-17, 2011, pp. 1-5, IEEE, Split, Croatia.

Li, Joshua Le-Wei et al., Keynote Speakers: Wireless Power Transfer: From Long-Distance Transmission to Short-Range Charging, 2013 IEEE International RF and Microwave Conference (RFM), 9-11 Dec. 2013, IEEE, Penang, Malaysia.

Keller, J. B. et al., Surface Waves Excitation and Propagation, Journal of Applied Physics, Jun. 1960, pp. 1039-1046, vol. 31, No. 6., AIP Publishing.

Chu, L. J., Physical Limitations on Omni-Directional Antennas, Journal of Applied Physics, Dec. 1948, pp. 1163-1175, vol. 19, AIP Publishing.

Mise, W. H., Note on Dipole Radiation Theory, Journal of Applied Physics, Oct. 1933, pp. 354-358, vol. 4, AIP Publishing.

Van Der Pol, B., Theory of the Reflection of the Light from a Point Source by a Finitely Conducting Flat Mirror, with an Application to Radiotelegraphy, Physica, Aug. 1935, pp. 843-853, vol. 2.

Friedman, B., Excitation of Surface Waves, the Institution of Electrical Engineers, Jan. 1958, pp. 252-258, Monograph No. 277 R.

Kabbary, F. M., Extremely Small High Power Mw Broadcasting Antennas, IEE International Broadcasting Convention, Sep. 12-16, 1997, Conference Publication No. 447, Amsterdam.

Jordan, E. C. et al., Electromagnetic Waves and Radiating Systems, Second Edition, 1968, pp. 558-560, 730-734, Prentice-Hall, Inc., Englewood Cliffs, New Jersey.

Smythe, W. R., Static and Dynamic Electricity, 1950, pp. 542-547, McGraw-Hill Book Company, Inc., New York.

Zenneck, J., Wireless Telegraphy, Mar. 1918, McGraw-Hill Book Company, Inc., New York, NY, USA. (submitted in 2 parts).

Hendry, J. Surface Waves: what Are They? Why Are They Interesting?, Roke Manor Research Limited, 2009, pp. 1-10, Romsey, England.

Turner, J., Isolation of the Zenneck Surface Wave: Update, Roke Manor Research Limited, Romsey, England.

Schelkunoff, S. A., Modified Sommerfeld's Integral and Its Applications, Proceedings of the Institute of Radio Engineers, Oct. 1936, pp. 1388-1398, vol. 24, No. 10, IEEE, New York, NY, USA.

Wells, C.B., CFA Experiments, Electronics World + Wireless World, Mar. 1990, pp. 253-255, vol. 96.

Wells, C.B., The Cross-Field Antenna in Practice, Electronics World + Wireless World, Nov. 1989, pp. 1109-1111, vol. 95.

Wait, J.R., Theory of Ground Wave Propagation, Electromagnetic Probing in Geophysics, 1971, pp. 163-207, Golem Press.

Sarkar et al., History of Wireless, Jan. 17, 2006, Wiley-IEEE Press, Hoboken, NJ, USA. (submitted in 4 parts).

Stark III, J.C., Wireless Power Transmission Utilizing a Phased Array of Tesla Coils (Master's Thesis), May 13, 2004, pp. 1-247, MIT, Cambridge, MA, USA. (submitted in 2 parts).

Hardesty et al., Electrical Storms in Tesla's Colorado Springs Notes (& the Transmission of Energy w/o Wires), Testa Science Center Conference, Nov. 5, 2011, Long Island, NY, USA. (Power Point Presentation).

Forum et al., A Technical Analysis of the Extra Coil as a Slow Wave Helical Resonator, Proceedings of the 2nd International Tesla Symposium, 1986, pp. 2-1 to 2-24, International Tesla Society, Colorado Springs, CO, USA.

Corum et al., Dr. Mahlon Loomis: Terra Alta's Neglected Discoverer of RF Communication, Proceedings of the 1992 International Tesla Symposium, pp. 19-34, International Tesla Society, Colorado Springs, CO, USA.

(56) References Cited

OTHER PUBLICATIONS

Corum et al., Summary Notes on Tesla Coils, Tesla Conference 2011, Published as Appendix 8 in Electrical Storms in Tesla's Colorado Springs Notes and the Transmission of Energy Without Wires, Nov. 5, 2011, pp. 1-14, Tesla Science Center at Wardenclyffe, Shoreham, NY, USA.
Hardesty et al., Franklin—Loomis—Tesla: The Origin and Development of Wireless Technology, Tesla Science Foundation Conference, Jul. 9-11, 2010, Philadelphia, PA, USA. (Power Point Presentation).
Hardesty et al., Franklin—Loomis13 Tesla: The Origin of Modern Wireless Phenomena, Tesla Science Foundation Conference, Jul. 9-11, 2010, pp. 1-99, Philadelphia, PA, USA.
Corum et al., Goodness, Q and Power Factor in Electrical Science and Machinery, Infinite Energy Magazine, Jan./Feb. 2010, pp. 1-17, vol. 15, No. 89, New Energy Foundation, Concord, NH, USA.
Marriott, R. H, How Radio Grew Up, Radio Broadcast, Dec. 1925, pp. 159-162, vol. VIII, No. 2, Doubleday, Page & Co., Garden City, NY, USA.
Goubau, G., Über die Zennecksche Bodenwelle (On the Zenneck Surface Wave), Zeitschrift fur Angewandte Physik, 1951, pp. 103-107, vol. 3, No. 3/4, as translated by James F. Comm.
Pinzone, B.F., Pinzone Antiskywave Design, Radio World, May 15, 1988, pp. 45-46.
Corum et al., Experimental Replication of Loomis' RF Experiments, AAPT Summer Meeting, Jul. 24, 2006, Syracuse, NY, USA. (Power Point Presentation).
Corum et al., Tesla Coil Research, U.S. Army Armament Research, Development and Engineering Center, Contract No. DAAA21-90-C-0084, Jun. 1992.
Lebo, J.R., The Man Before Marconi: A Biography of Dr. Mahlon Loomis, QST, Aug. 1948, pp. 42-44.
Winters, S.R., The Story of Mahlon Loomis: Pioneer of Radio, Radio News, Nov. 1922, pp. 836-837, 966-980.
Kogan, S.H., Distribution of Waves Along an Infinite Helix, Reports of the Academy of Sciences of the USSR, 1949, pp. 1-5, vol. 66, No. 5, as translated by P.J. Pesavento and E. Corum.
Niessen, K.F., Zur Entscheidung zwischen den beiden Sommerfeldschen Formeln für die Fortpflanzung von drahtlosen Wellen, Ann. der Physik, 1937, pp. 585-596, vol. 29 (Includes English Translation and German Original).
Niessen, K.F., Über die enffernten Raumwellen eines vertikalen Dipolsenders oberhalb einer ebenen Erde von beliebiger Dielektrizitätskonstante und beliebiger Leitfähigkeit, Ann. der Physik, Dec. 24, 1933, pp. 893-912, Series 5, vol. 18 (Includes English Translation and German Original).
Niessen, K.F., Bemerkung zu einer Arbeit von Murray und einer Arbeit von van der Pol und Niessen über die Ausbreitung elektromagnetischer Wellen, Ann. der Physik, Apr. 3, 1933, pp. 810-820, Series 5, vol. 16 (Includes English Translation and German Original).
Hack, F., Die Ausbreitung ebener elektromagnetischer Wellen längs eines geschichteten Leiters, besonders in den Fällen der drahtlosen Telegraphie, Annalen der Physik, 1908, pp. 43-63, vol. 27 (Includes English Translation and German Original).
True, H., Über die Erdströme in der Nähe einer Sendeantenne für drahtlose Telegraphie, Jahrbuch der drahtlosen Telegraphie und Telephonie, Feb. 1911, pp. 125-175, vol. 5, No. 2 (Includes English Translation and German Original).
Van Der Pol et al., Über die Ausbreitung elektromagnetischer Wellen über eine ebene Erde, Ann. der Physik, Aug. 22, 1930, pp. 273-294, Ser. 5, vol. 6 (Includes English Translation and German Original).
Van Der Pol, B., Über die Ausbreitung elektromagnetischer Wellen, Jahrbuch der drahtlosen Telegraphie und Telephonie, Apr. 1931, pp. 152-156, vol. 37 (Includes English Translation and German Original).
Zenneck, J., "Über die Fortpflanzung ebener elektromagnetischer Wellen längs einer ebenen Leiterfläche und ihre Beziehung zur drahtlosen Telegraphie," (On the propagation of plane electromagnetic waves along a flat conducting surface and their relation to wireless telegraphy), Annalen der Physik, Sep. 20, 1907, pp. 846-866, Serial 4, vol. 23 (Includes English Translation and German Original).
Sommerfeld, A., Über die Ausbreitung der Wellen in der drahtlosen Telegraphie, Annalen der Physik, 1909, pp. 665-737, vol. 28, No. 4 (Includes English Translation and German Original).
Weyl, H., Ausbreitung elektromagnetischer Wellen über einem ebenen Leiter (Propagation of Electromagnetic Waves Over a Plane Conductor), Annalen der Physik, Nov. 1919, pp. 97-109, vol. 60 (Includes English Translation and German Original).
Sommerfeld, A., Ausbreitung der Wellen in der drahtlosen Telegraphie. Einfluss der Bodenbeschaffenheit auf gerichtete und ungerichtete Wellenzüge, Jahrbuch der drahtlosen Telegraphie und Telephonie, Dec. 1910, pp. 157-176 (Includes English Translation and German Original).
Van Der Pol et al., Über die Raumwellen von einem vertikalen Dipolsender auf ebener Erde, Ann. der Physik, Jul. 21, 1931, pp. 485-510, Ser. 5, vol. 10 (Includes English Translation and German Original).
Sommerfeld, A., Über die Fortpflanzung elektrodynamischer Wellen längs eines Drahtes, Annalen der Physik, 1899, pp. 233-290, vol. 67 (Includes English Translation and German Original).
Sommerfeld, A., Über die Ausbreitung der Wellen in der drahtlosen Telegraphie, Annalen der Physik, Dec. 1926, pp. 1135-1153, vol. 81 (Includes English Translation and German Original).
Weyl, H., Erwiderung auf Herrn Sommerfelds Bemerkungen über die Ausbreitung der Wellen in der drahtlosen Telegraphie, Annalen der Physik, 1920, pp. 110-112, vol. 62 (Includes English Translation and German Original).
Sommerfeld, A., Über die Ausbreitung der Wellen in der drahtlosen Telegraphie, Annalen der Physik, 1920, pp. 95-96, vol. 367, No. 9 (Includes English Translation and German Original).
Fujimoto et al., Small Antennas, Research Studies Press, 1987, p. 4.
Corum et al., Class Notes: Tesla Coils and the Failure of Lumped-Element Circuit Theory, published on the World Wide Web at http://www.teslatechnologyresearch.com/corum/, 1999.
Corum et al., RF Coils, Helical Resonators and Voltage Magnification by Coherent Spatial Modes, Microwave Review, Sep. 2001, pp. 36-45.
Burrows, Charles R., The Surface Wave in Radio Propagation, Proceedings of the Radio Club of America, Aug. 1937, pp. 15-18, vol. 14, No. 2.
Burrows, Charles R., The History of Radio Wave Propagation Up to the End of World War I, Proceedings of the IRE, May 1962, pp. 682-684, vol. 50, Issue 5.
Wolff, Edward A., Antenna Analysis, 1966, p. 33, John Wiley & Sons, Inc.
Vogler, L.E., A Note on the Attenuation Function for Propagation Over a Flat Layered Ground, IEEE Transactions on Antennas and Propagation, Mar. 1964, pp. 240-242, vol. AP-12, No. 2.
Banos, A., Dipole Radiation in the Presence of a Conducting Half-Space, 1966, pp. 148-158, Pergamon Press.
Barlow et al., Radio Surface Waves, 1962, pp. 1-5, 10-12, 29-33, Oxford University Press.
Brainerd et al., Ultra High Frequency Techniques, 1942, pp. 477-480, D. Van Nostrand Company, Inc., New York.
Bronwell et al., Theory and Application of Microwaves, 1947, pp. 384-387, 390, McGraw-Hill.
Clemmow, P.C., The Plane Wave Spectrum Representation of Electromagnetic Fields, 1966, pp. 30-31, Pergamon Press.
Collin, R.E., Field Theory of Guided Waves, 1960, pp. 453-454, McGraw-Hill.
Collin et al., Electromagnetic Fields, Antenna Theory—Part 1, 1969, p. 18, vol. 7, McGraw-Hill.
Collin, R.E., Antennas and Radiowave Propagation, 1985, pp. 377-385, McGraw-Hill.
Everitt et al., Communication Engineering, 3rd edition, 1956, p. 407, McGraw-Hill.
Felsen et al., Radiation and Scattering of Waves, 1973, pp. 506-513, 554-559, Prentice-Hall.
Friedman, B., Principles and Techniques of Applied Mathematics, 1956, pp. 213-214, 283-286, 290, 298-300, Wiley.
Hansen, R.C., Electrically Small, Superdirective, and Superconducting Antennas, 2006, pp. 62-64, Wiley Interscience.
Hansen et al., Small Antenna Handbook, 2011, pp. 147-150, Wiley, New Jersey.

(56) References Cited

OTHER PUBLICATIONS

Harrington, R.F., Time-Harmonic Electromagnetic Fields, 1961, pp. 460-463, McGraw-Hill.
Ishimaru, A., Electromagnetic Wave Propagation, Radiation and Scattering, 1991, pp. 456-461, Prentice-Hall, New Jersey.
Mise, W.H., The Grounded Condenser Antenna Radiation Formula, Proc. IRE, Sep. 1931, pp. 1684-1689, vol. 19, No. 9.
Kraus, J.D., Antennas, 1950, pp. 33-34, 452-453, 461-463, McGraw-Hill.
Wise, W.H., Asymptotic Dipole Radiation Formulas, Bell System Technical Journal, Oct. 1929, pp. 662-671, vol. 8.
Ramo et al., Fields and Waves in Communication Electronics, 3rd Edition, 1994, pp. 435-437, Wiley.
Ryder, J.D., Networks, Lines and Fields, 1949, pp. 422-425, Prentice Hall, New York.
Reich et al., Microwave Theory and Techniques, 1953, pp. 291-293, Van Nostrand.
Sarbacher et al., Hyper and Ultrahigh Frequency Engineering, 1943, pp. 201-202, Wiley & Sons, Inc.
Schelkunoff, S.A., Electromagnetic Waves, 1943, pp. 49, 428-437, Van Nostrand Company, New York.
Tesla, N., The Problem of Increasing Human Energy with Special References to the Harnessing of the Sun's Energy, The Century Illustrated Monthly Magazine, Jun. 1900, pp. 1-35.
Van Der Pol, B., On Discontinuous Electromagnetic Waves and the Occurrence of a Surface Wave, IEEE Transactions on Antennas and Propagation, Jul. 1956, pp. 288-293, vol. AP-4.
Eckert, Robert P., Modern Methods for Calculating Ground-Wave Field Strength Over a Smooth Spherical Earth, Report to the Federal Communications Division, Feb. 1986.
Wait et al., Radiation from a Vertical Dipole over a Stratified Ground (Part II), IRE Transactions on Antennas and Propagation, Oct. 1954, pp. 144-146, vol. AP-3, No. 4.
Tesla, N., From Colorado Springs to Long Island, Nikola Tesla Museum, 2008, pp. 485, 487, Nikola Tesla Museum.
Cross et al., an Advanced VHF/UHF Short Range, Groundwave Propagation Model for Paths with Near-Earth Antennas, MegaWave Corporation, Nov. 1, 2006, Boylston, MA.
Tyras, G., Radiation and Propagation of Electromagnetic Waves, 1969, pp. 33-36, Academic Press.
Wait, J.R., Wave Propagation Theory, 1981, pp. 67-75, 117-127, Pergamon Press.
Wait, J.R., Electromagnetic Wave Theory, 1985, pp. 254-259, Harper and Row, Publishers, New York.
Wait, J.R., Electromagnetic Waves in Stratified Media, 1996, pp. 8-10, IEEE Press, Reprint from 1962 edition, Pergamon Press.
Hissel, A., General Characteristics of Traveling-Wave Antennas, Antenna Theory—Part 2, Chapter 19, Appendix B, 1969, pp. 238-241, McGraw-Hill Book Company, New York.
Sarkar et al., Electromagnetic Macro Modeling of Propagation in Mobile Wireless Communication: Theory and Experiment, IEEE Antennas and Propagation Magazine, Dec. 2012, pp. 17-43, vol. 54, No. 6.
Wait, J.R., Characteristics of Antennas over Lossy Earth, Antenna Theory—Part 2, Chapter 23, 1969, pp. 386-391, McGraw-Hill Book Company, New York.
Wait, J.R., Theory of Ground Wave Propagation, Electromagnetic Probing in Geophysics, Chapter 5, 1971, pp. 163-172, 204-207, Golem Press, Boulder, Colorado.
Smith, M.S., Conventional Explanation for Crossed-Field Antenna, Electronics Letters, Feb. 13, 1992, pp. 360-361, vol. 28, No. 4.
Tesla, N., The Transmission of Electrical Energy Without Wires as a Means of Furthering Peace, Electrical World and Engineer, Jan. 7, 1905, pp. 21-24.
Wait et al., Excitation of the HF Surface Wave by Vertical and Horizontal Antennas, Radio Science, Sep.-Oct. 1979, pp. 767-780, vol. 14, No. 5.
Wait, J.R., A Note on Surface Waves and Ground Waves, IEEE Transactions on Antennas and Propagation, Nov. 1965, pp. 996-997, vol. AP-13.

Nikola Tesla, Nikola Tesla on His Work With Alternating Currents and Their Application to Wireless Telegraphy, Telephony, and Transmission of Power, 2002, pp. 1-240, Twenty First Century Books, Breckenridge, Colorado.
Tesla, N., Colorado Springs Notes: 1899-1900, 1978, pp. 1-437, Nolit, Beograd, Yugoslavia.
U.S. Appl. No. 14/849,643, filed Sep. 10, 2015, Non-Final Office Action dated Nov. 17, 2017.
U.S. Appl. No. 13/789,525, filed Mar. 7, 2013, Restriction Requirement dated Oct. 7, 2015.
U.S. Appl. No. 13/789,525, filed Mar. 7, 2013, Response to Restriction Requirement dated Oct. 7, 2015.
U.S. Appl. No. 13/789,525, filed Mar. 7, 2013, Non-Final Office Action dated Feb. 11, 2016.
U.S. Appl. No. 13/789,525, filed Mar. 7, 2013, Response to Non-Final Office Action dated Feb. 11, 2016.
U.S. Appl. No. 13/789,525, filed March 7, 2013, Final Office Action dated Sep. 16, 2016.
International Search Report and Written Opinion for PCT/USZ015/053242 dated Jan. 25, 2016.
Examination Report issued in New Zealand Application No. 712566 dated Nov. 30, 2015.
Office Action Issued in Chilean Application No. 2506-2015 dated Sep. 29, 2016. (Partial English Translation included).
"Wireless Transmission Theory, the Tesla Effect," Tesla Radio, 23 Dec. 2011, pp. 1-6.
Peterson, Gary, "Comparing the Hertz-Wave and Tesla Wireless Systems," Feedline, Oct. 27, 2012, pp. 1-7, 9, 21st Century Books, Breckenridge, CO.
International Search Report and Written Opinion for PCT/US2015/035598 dated Sep. 11, 2015.
Examination Report issued in Australian Application No. 2014226221 on Sep. 22, 2016.
U.S. Appl. No. 13/789,538, filed Mar. 7, 2013, Restriction Requirement dated Oct. 7, 2015.
U.S. Appl. No. 13/789,538, filed Mar. 7, 2013, Response to Restriction Requirement dated Oct. 7, 2015.
U.S. Appl. No. 13/789,538, filed Mar. 7, 2013, Non-Final Office Action dated Feb. 8, 2016.
U.S. Appl. No. 13/789,538, filed Mar. 7, 2013, Response to Non-Final Office Action dated Feb. 8, 2016.
U.S. Appl. No. 13/789,538, filed Mar. 7, 2013, Notice of Allowance dated Oct. 7, 2016.
Hill, et. al. "On the excitation of the Zenneck surface wave over the ground at 1OHz," May 1980, Ann ales des Telecommunications, vol. 35, Issue 5, pp. 179-182.
U.S. Appl. No. 13/789,525, filed Mar. 7, 2013, Response to Final Office Action dated Sep. 16, 2016.
Peterson, Gary, "Rediscovering the zenneck surface wave," Feb. 8, 2008, Feedline No. 4, 1-5.
U.S. Appl. No. 14/728,492, filed Jun. 2, 2015, Non-Final Office Action dated Dec. 16, 2016.
U.S. Appl. No. 14/728,507, filed Jun. 2, 2015, Non-Final Office Action dated Jan. 3, 2017.
ling et al., The Propagation and Excitation of Surface Waves in an Absorbing Layer, Progress in Electromagnetics Research, 1998, pp. 49-91, vol. 19.
Wise, W. Howard, Note on the Accuracy of Rolfs Graphs of Sommerfeld's Attenuation Formula, Proceedings of the Institute of Radio Engineers, Nov. 1930, pp. 1971-1972, vol. 18, No. 11.
Barlow et al., Surface Waves, The Proceedings of the Institution of Electrical Engineers, Nov. 1953, pp. 329-347, vol. 100, part iii.
Barlow et al., An Investigation of the Characteristics of Cylindrical Surface Waves, The Proceedings of the Institution of Electrical Engineers, Nov. 1953, pp. 321-328, vol. 100, Part III, No. 68.
Brown et al., The Launching of Radial Cylindrical Surface Waves by a Circumferential Slot, The Proceedings of the Institution of Electrical Engineers, Mar. 1959, pp. 123-128, vol. 106, Part B.
Burrows, Charles R., Radio Propagation Over Plane Earth-Field Strength Curves, Bell System Technical Journal, Jan. 1937, pp. 45-75, vol. 16, No. 1.

(56) References Cited

OTHER PUBLICATIONS

Burrows, Charles R., Addendum to: Radio Propagation Over Plane Earth-Field Strength Curves, Bell System Technical Journal, Oct. 1937, pp. 574-577, vol. 16, No. 4.

Burrows, Charles R., Existence of a Surface Wave in Radio Propagation, Nature, Aug. 15, 1936, p. 284, vol. 138, Nature Publishing Group.

Burrows, Charles R., the Surface Wave in Radio Propagation Over Plane Earth, Proceedings of the Institute of Radio Engineers, Feb. 1937, pp. 219-229, vol. 25, No. 2.

Collin, R.E., Hertzian Dipole Radiating Over a Lossy Earth or Sea: Some Early and Late 20th-Century controversies, IEEE Antennas and Propagation Magazine, Apr. 2004, pp. 64-79, vol. 46, No. 2.

Jones, E.M.T., An Annular Corrugated-Surface Antenna, Proceedings of the I.R.E., Jun. 1952, pp. 721-725, vol. 40.

Fernando et al., An Investigation of the Properties of Radial Cylindrical Surface Waves Launched Over Flat Reactive Surfaces, the Proceedings of the Institution of Electrical Engineers, May 1956, pp. 307-318, vol. 103, Part B.

Belrose, John S., A Radioscientist's Reaction to Marconi's First Transatlantic Wireless Experiment—Revisited, Conference Digest, Jul. 2001, pp. 22-25, vol. 1, IEEE Antennas & Propagation Society International Symposium, Boston, MA, US.

Marconi, Guglielmo, Wireless Telegraphic Communication, Nobel Lecture, Dec. 11, 1909, pp. 196-222.

Norton, K.A., Propagation of Radio Waves Over a Plane Earth, Nature, Jun. 8, 1935, pp. 954-955, Nature Publishing Group.

Kukushkin, A.V., On the Existence and Physical Meaning of the Zenneck Wave, Physics—Uspekhi, 2009, pp. 755-756, vol. 52, No. 7, Uspekhi Fizicheskikh Nauk, Russian Academy of Sciences.

Michaels, Charles J., A Load-Tracking L Network, QST, Apr. 1992, p. 74, American Radio Relay League, Inc.

Feldman, C.B., The Optical Behavior of the Ground for Short Radio Waves, Proceedings of the IRE, Jun. 1933, pp. 764-801, vol. 21, No. 6.

Rolf, Bruno, Graphs to Prof. Sommerfeld's Attenuation Formula for Radio Waves, Proceedings of the Institute of Radio Engineers, Mar. 1930, pp. 391-402, vol. 18, No. 3.

Wait, James R., The Ancient and Modern History of EM Ground-Wave Propagation, IEEE Antennas and Propagation Magazine, Oct. 1998, pp. 7-24, vol. 40, No. 5.

Zucker, Francis J., Surface-Wave Antennas, Antenna Engineering Handbook, 2007, pp. 10.1-10.32, Chp. 10, McGraw-Hill.

Smith, Carl E., Short Low Loss AM Antenna, IEEE Transactions on Broadcasting, Jun. 1989, pp. 237-240, vol. 35, No. 2, IEEE.

Belrose, John S., An Electrically Small Umbrella Antenna for 160 Meters, ARRL Antenna Compendium, 2002, pp. 3-8, vol. 7.

Belrose, John S., Characteristics of the Crossed Field Antenna Obtained by Numerical and Experimental Modelling, IEEE Antennas and Propagation Society International Symposium, 2005, pp. 21-24, vol. 1B.

Belrose, John S., Radiation Characteristics of an Electrically Small MF Broadcast Antenna—by Simulation, 11th International Conference on Antennas and Propagation, Apr. 17-20, 2001, pp. 90-94, IEEE Conference Publication No. 480.

Cobos et al., A Modified Goubau-Type Antenna with Two Octaves of Impedance Bandwidth, Antennas and Propagation Society International Symposium, Jun. 2004, pp. 3051-3054, vol. 3, IEEE.

Goubau, Georg, Surface Waves and Their Application to Transmission Lines, Journal of Applied Physics, Nov. 1950, pp. 1119-1128, vol. 21.

Ravipati et al., The Goubau Multi Element Monopole Antenna—Revisited, Antennas and Propagation Society International Symposium, Jun. 2007, pp. 233-236, IEEE.

Pinzone et al., A New Low Profile Anti-Skywave Antenna for AM Broadcasting, NAB Engineering Conference Proceedings, 1988, 7-15.

Underhill, Mike, All sorts of small antennas—they are better than you think—heuristics shows why!, Lecture Presentation to the Adelaide Hills Amateur Radio Society, Feb. 2008, pp. 1-144.

Belrose, John S., The Crossed Field Antenna—Analyzed by Simulation and Experiment, ICAP-TINA Millennium Conference on Antennas and Propagation, Apr. 9-12, 2000, pp. 1-4, Davos, Switzerland.

Belrose, John S., The Truth and Untruth About Electrically Small Antennas, Amateur Radio Technical Session, QCWA 2004 International Convention, Oct. 15, 2004, pp. 1-8, Ottawa, ON, Canada.

Hately et al., An Operational MF Broadcast Antenna Using Poynting Vector Synthesis, IEEE ICAP Seventh International Conference 1991, Apr. 1991, pp. 645-648, Conference Publication 333, Part 2.

Kabbary et al., Phasing and Matching Units for the CFA, URSI Seventeenth National Radio Science Conference, Feb. 22-24, 2000, pp. B22.1-B22.8, Minufiya University, Egypt.

Underhill, M.J., The Estimation and Measurement of the Efficiency and Effectiveness of Small Antennas in an Environment, HF Radio 2003—Ninth International IEE Conference on HF Radio Systems and Techniques, Jun. 23-26, 2003, pp. 1-6, University of Bath, UK.

Trainotti et al., On the Crossed Field Antenna Performance, IEEE Transactions on Broadcasting, Sep. 2006, pp. 299-317, vol. 52, No. 3.

Trainotti, Valentin, Short Medium Frequency AM Antennas, IEEE Transactions on Broadcasting, Sep. 2001, pp. 263-284, vol. 47, No. 3.

Underhill, Mike, Tuneable Coupled (Multi-) Mode Small Antennas—CFA, CFL, EH etc?, Lecture Presentation at the Radio Society of Great Britain Convention, Oct. 2010, pp. 1-167.

Letter to James Corum from John Musselman regarding the Antenna Installation at Kodiak, Alaska, Jun. 2011.

Smith, Carl E., Antenna Coupling Unit Network Fig. 2.4, Installed at Radio Station KVOK, exact date unknown, installed some time around or before 1980, Kodiak, Alaska.

Rice, S.O., Series for the Wave Functions of a Radiating Dipole at the Earth's Surface, BSTJ, Jan. 1937, pp. 101-109, vol. 16, No. 1.

Mcdonald, Kirk T., "Crossed-Field" and "EH" Antennas Including Radiation from the Feed Lines and Reflection from the Earth's Surface, Published at http://www.physics.princeton.edu/~mcdonald/examples/crossedfield.pdf, Jul. 2006; updated Mar. 2010, pp. 1-11.

Mcdonald, Kirk T., "Crossed-Field" and "EH" Antennas Including Radiation from the Feed Lines and Reflection from the Earth's Surface, Published at http://www.physics.princeton.edu/~mcdonald/examples/crossedfield.pdf, Jul. 2006; updated Jun. 2008, pp. 1-18.

Belrose, John S., On the EH Antenna, antenneX Online, Apr. 2003, pp. 1-4, Issue No. 72.

Stewart, Brian G., Planning Application submitted by Isle of Man International Broadcasting plc to construct a grossed Field Antenna at Cranstal, near Bride, Isle of Man, Department of Engineering Glasgow Caledonian University, Aug. 2000, pp. 1-19.

Hendry et al., Surface Waves for Communication Systems, 3rd SEAS DTC Technical Conference, 2008, A18, Edinburgh, Scotland.

Watson, W.H., The Physical Principles of Wave Guide Transmission and Antenna Systems, 1947, p. 25, Oxford at the Clarendon Press.

Pover et al., The Silsden Crossed Field Antenna, Extracts from the report on the performance of an elevated 8 Metre CFA constructed and tested at Silsden in West Yorkshire on Sep. 23-26, 2009.

Holland, Ralph, Egyptian Daytime Wave Pockets—Speculative Causes, antenneX Online, Apr. 2002, pp. 1-38, Issue No. 60.

Corum et al., Multiple Resonances in RF Coils and the Failure of Lumped Inductance Models, Sixth International Symposium Nikola Tesla, Oct. 18-20, 2006, Belgrade, SASA, Serbia.

Jahnke et al., Tables of Functions with Formulae and Curves, 1945, p. 145, 4th Edition, Dover Publications, New York.

Milligan, T., Modem Antenna Design, 1985, pp. 8-9, 1st Edition, McGraw-Hill, New York.

Reinartz, J. L., 1XAM's transmitter, QST, Jan. 1924, pp. 26-27.

Sommerfeld, A., Problems of Radio, Partial Differential Equations in Physics—Lectures on Theoretical Physics, 1949, pp. 246-257, vol. VI, Academic Press, New York.

Stratton, J. A, Electromagnetic Theory, 1941, p. 516, McGraw-Hill, New York.

Stutzman et al., Antenna Theory and Design, 1981, p. 82, 92-93, Wiley & Sons, New York.

Wait, J. R., Complex Image Theory—Revisited, IEEE Antennas and Propagation Magazine, Aug. 1991, pp. 27-29, vol. 33, No. 4.

(56) References Cited

OTHER PUBLICATIONS

Counterpoises, QST, Sep. 1920, pp. 24-25.
Ashe, G. B., A Counterpoise Investigation, QST, Dec. 1924, pp. 34-35.
Bannister, P. R., Summary of Image Theory Expressions for the Quasi-Static Fields of Antennas at or Above the Earth's Surface, Jul. 1979, pp. 1001-1008, vol. 67, No. 7, Proceedings of the IEEE.
Banos et al., Sommerfeld Surface Wave, Summary of Normal Mode Theory Symposium, IRE Transactions on Antennas and Propagation, Jan. 1956, p. 92, vol. AP-4, No. 1.
Barlow, H. M., Launching a Surface Wave over the Earth, Electronics Letters, Jul. 1967, pp. 304-305, vol. 3, No. 7.
Nestman, H. P., Antenna—Counterpoise Fundamentals, QST, May 1926, p. 46.
Beverage, H.H., Improving the CW Ground System, OST, Nov. 1921, pp. 25-26.
Bucher, E E., The Alexanderson System for Radio Communication, General Electric Review, Oct. 1920, pp. 813-839 (See Fig. 11, p. 820.) vol. 23, No. 10.
Paknys, R., Evaluation of Hankel Functions with Complex Argument and Complex Order, IEEE Transactions on Antennas and Propagation, May 1992, pp. 569-578, vol. 40, No. 5.
Burrows, C. R., Radio Propagation Over Spherical Earth, Proc. IRE, May 1935, pp. 470-480, vol. 23, No. 5; Reprinted in Bell System Tech. Jour., Jul. 1935, pp. 477-488, Vol. 14, No. 3.
Wise, W. H., The Physical Reality of Zenneck's Surface Wave, Bell System Technical Journal, No. 1, Jan. 1937, pp. 35-44, vol. 16, No. 1.
Burrows, C. R., Addendum to the Effect of the Earth's Curvature on Ground Wave Propagation, IEEE Transactions on Antennas and Propagation, Nov. 1964, pp. 789-791, vol. 12, No. 6.
Burrows, C. R., Radio Gain, IEEE Transactions on Antennas and Propagation, May 1967, pp. 404-410, vol. AP-15, No. 3.
Chu et al., Electromagnetic Waves in Hollow Metal Tubes of Rectangular Cross Section, Proceedings of the IRE, Dec. 1938, pp. 1520-1555, vol. 26, No. 12.
Ufimtsev et al., Transformation of Surface Waves in Homogeneous Absorbing Layers, IEEE Transactions on Antennas and Propagation, Feb. 2000, pp. 214-222, vol. 48, No. 2.
Corum et al., Toroidal Helix Antenna, IEEE Antennas and Propagation Society International Symposium, Jun. 14-19, 1987, pp. 832-835, vol. 25.
Pinzone et al., A Novel Structure for Improved Directivity, 1988 Antennas and Propagation Society International Symposium Digest, Jun. 1988, pp. 824-827, vol. 2, IEEE, Syracuse, NY.
Corum et al., Experimental Validation of the Improved Directivity Element—Elevation Plane Control, 1989 Antennas and Propagation Society International Symposium Digest, Jun. 1989, pp. 702-705, vol. 2, IEEE, San Jose, CA.
Corum et al., A Concentric Array for Low and Medium Frequencies, 1990 Antennas and Propagation Society International Symposium Digest, May 1990, pp. 832-835, vol. 2, IEEE, Dallas, Texas.
Deminco, N., Propagation Prediction Techniques and Antenna Modeling (150 to 1750 kHz) for Intelligent Transportation Systems (ITS) Broadcast Applications, IEEE Antennas and Propagation Magazine, Aug. 2000, pp. 9-34, vol. 42, No. 4.
Eckert, R. P., History of Ground Wave Propagation Prediction Curves for AM Standard Broadcast, IEEE Transactions on Broadcasting, Mar. 1986, pp. 1-4, vol. BC-32, No. 1.
Epstein, P., Radio-Wave Propagation and Electromagnetic Surface Waves, Proc. National Academy of Sciences, Jun. 1947, pp. 195-199, vol. 33, No. 6.
Epstein, P., On the Possibility of Electromagnetic Surface Waves, Proc. National Academy of Sciences, Dec. 1954, pp. 1158-1165, vol. 40, No. 12.
Norton, K A., The Physical Reality of Space and Surface Waves in the Radiation Field of Radio Antennas, Proceedings of the IRE, Sep. 1937, pp. 1192-1202, vol. 25, No. 9.
Goubau, G., Single Conductor Surface Wave Transmission Lines, Proc. IRE, Jun. 1951, pp. 619-624, vol. 39, No. 6.
Norton, K.A., The Propagation of Radio Waves over the Surface of the Earth and in the Upper Atmosphere: Part II The Propagation from Vertical, Horizontal, and Loop Antennas Over a Plane Earth of Finite Conductivity, Proceedings of the IRE, Sep. 1937, pp. 1203-1236, vol. 25, No. 9.
Hately et al., CFA: Working Assumption, Electronics World + Wireless World, Dec. 1990, pp. 1094-1099, vol. 96.
Hill et al., Excitation of the Zenneck Surface Wave by a Vertical Aperture, Radio Science, Nov.-Dec. 1978, pp. 969-977, vol. 13, No. 6.
Kabbary et al., Maxwell's Equations and the Crossed-Field Antenna, Electronics World + Wireless World, Mar. 1989, pp. 216-218, vol. 95.
Trainotti et al., Short Low and Medium Frequency Antenna Performance, IEEE Antennas and Propagation Magazine, Oct. 2005, pp. 66-90, vol. 47, No. 5.
Kabbary et al., Four Egyptian MW Broadcast Crossed-Field Antennas, Proceedings of the National Association of Broadcasters 1999 Engineering Conference, Apr. 1999, pp. 235-241, Las Vegas, Nevada.
Kahan et al., On the Existence of a Surface Wave in Dipole Radiation over a Plane Earth, Proc. IRE, Jul. 1950, pp. 807-812, vol. 38, No. 7.
Karbowiak, A. E, Theory of Composite Guides: Stratified Guides for Surface Waves, Proc. IEE (British), 1954, pp. 238-242, vol. 101, No. 72.
Tesla, N., The True Wireless, Electrical Experimenter, May 1919, pp. 1-13.
King et al., Groundwave Attenuation Function for Propagation Over a Highly Inductive Earth, Radio Science, Jul. 1967, pp. 687-693, vol. 2, No. 7.
Li, R. The Accuracy of Norton's Empirical Approximations for Ground Wave Attenuation, IEEE Trans. Antennas and Propagation, Jul. 1983, pp. 624-628, vol. AP-31, No. 4.
Lindell et al., Exact Image Theory for the Sommerfeld Half-Space Problem, Part I: Vertical Magnetic Dipole, IEEE Transactions on Antennas and Propagation, Feb. 1984, pp. 126-133, vol. AP-32, No. 2.
Lindell et al., Exact Image Theory for the Sommerfeld Half-Space Problem, Part II: Vertical Electric Dipole, IEEE Transactions on Antennas and Propagation, Aug. 1984, pp. 841-847, vol. AP-32, No. 8.
Lindell et al., Exact Image Theory for the Sommerfeld Half-Space Problem, Part III: General Formulation, IEEE Transactions on Antennas and Propagation, Oct. 1984, pp. 1027-1032, vol. AP-32, No. 10.
Lodge et al., Syntonic Wireless Telegraphy; with Specimens of Large-scale Measurements, Proceedings of the Royal Society—London, Series A, May 26, 1909, pp. 227-256, vol. 82, No. 554.
Marincic, A. S., Nikola Tesla and the Wireless Transmission of Energy, IEEE Transactions on Power Apparatus and Systems, Oct. 1982, pp. 4064-4068, vol. PAS-101, No. 10.
Mason, H. F., The Nodal Point Explained, QST, Sep. 1923, pp. 11-14.
Norton, K. A., The Calculation of Ground-Wave Field Intensity Over a Finitely Conducting Spherical Earth, Proceedings of the IRE, Dec. 1941, pp. 623-639, vol. 29, No. 12.

\* cited by examiner

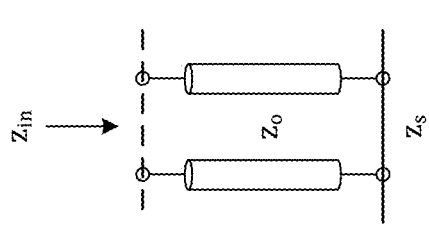
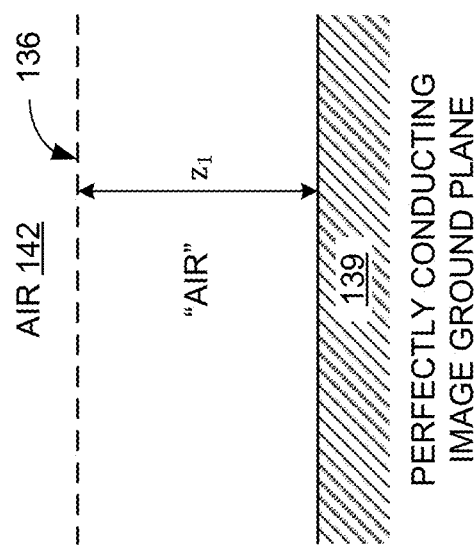
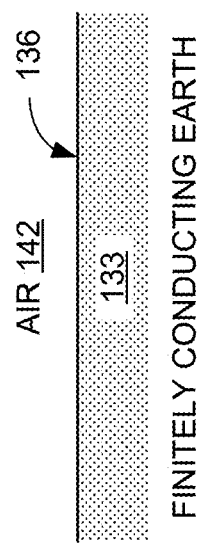
FIG. 8A
FIG. 8B
FIG. 8C

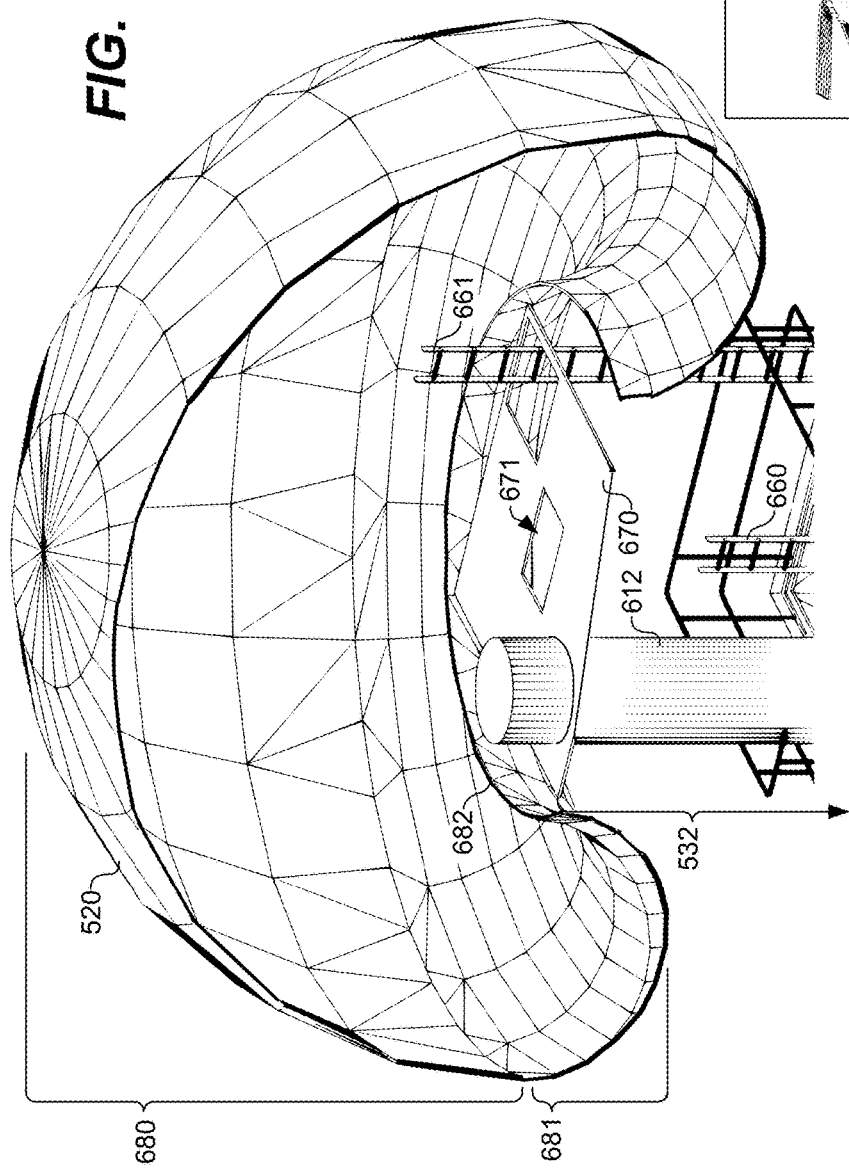

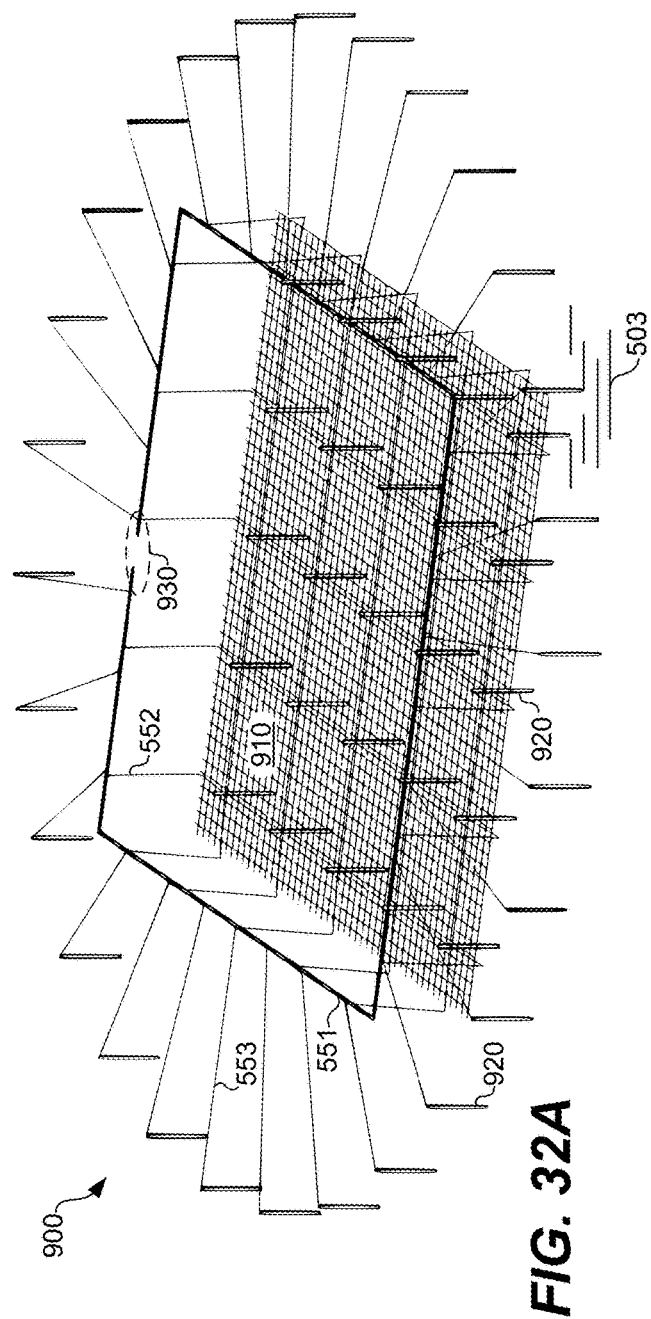
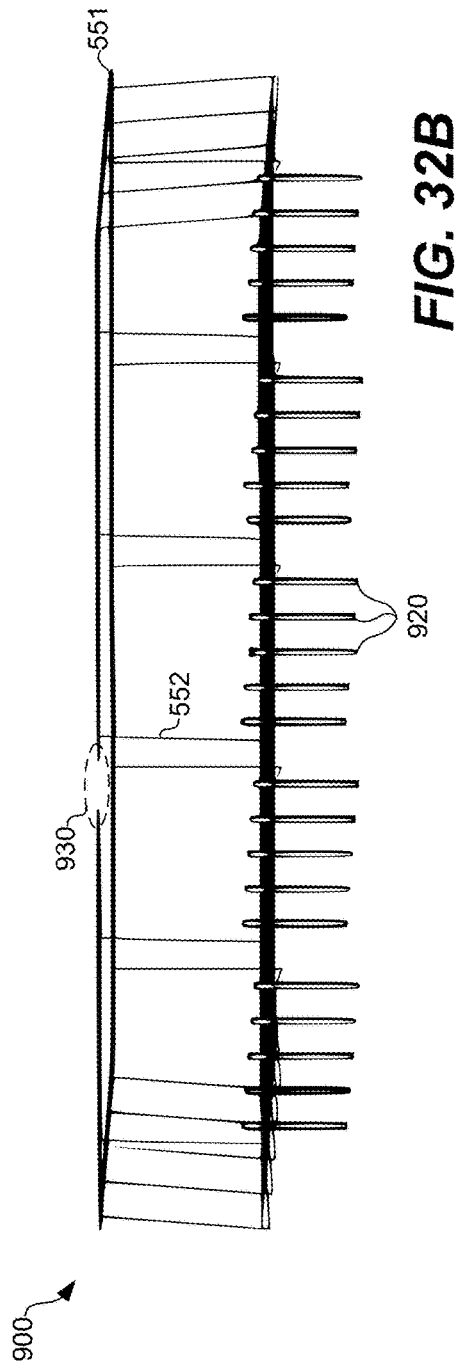

ARRANGEMENTS FOR COUPLING THE PRIMARY COIL TO THE SECONDARY COIL

CROSS REFERENCE TO RELATED APPLICATIONS

This application claims the benefit of U.S. Provisional Application No. 62/468,272, filed Mar. 7, 2017, the entire contents of which are hereby incorporated by reference. This application is related to co-pending U.S. Non-provisional Patent Application entitled "Excitation and Use of Guided Surface Wave Modes on Lossy Media," which was filed on Mar. 7, 2013 and assigned application Ser. No. 13/789,538, and was published on Sep. 11, 2014 as Publication Number US2014/0252886 A1, and which is incorporated herein by reference in its entirety. This application is also related to co-pending U.S. Non-provisional Patent Application entitled "Excitation and Use of Guided Surface Wave Modes on Lossy Media," which was filed on Mar. 7, 2013 and assigned application Ser. No. 13/789,525, was published on Sep. 11, 2014 as Publication Number US2014/0252865 A1, and which is incorporated herein by reference in its entirety. This application is further related to co-pending U.S. Non-provisional Patent Application entitled "Excitation and Use of Guided Surface Wave Modes on Lossy Media," which was filed on Sep. 10, 2014 and assigned application Ser. No. 14/483,089, and which is incorporated herein by reference in its entirety. This application is further related to co-pending U.S. Non-provisional Patent Application entitled "Excitation and Use of Guided Surface Waves," which was filed on Jun. 2, 2015 and assigned application Ser. No. 14/728,492, and which is incorporated herein by reference in its entirety. This application is further related to co-pending U.S. Non-provisional Patent Application entitled "Excitation and Use of Guided Surface Waves," which was filed on Jun. 2, 2015 and assigned application Ser. No. 14/728,507, and which is incorporated herein by reference in its entirety.

BACKGROUND

For over a century, signals transmitted by radio waves involved radiation fields launched using conventional antenna structures. In contrast to radio science, electrical power distribution systems in the last century involved the transmission of energy guided along electrical conductors. This understanding of the distinction between radio frequency (RF) and power transmission has existed since the early 1900's.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

FIGS. 8A through 8C are graphical representations illustrating examples of equivalent image plane models of the guided surface waveguide probe of FIGS. 3 and 7A-7C according to various embodiments of the present disclosure.

FIG. 28 is a cross-sectional view of the charge terminal of the probe shown in FIG. 20 according to various embodiments of the present disclosure.

FIGS. 32A and 32B illustrate a grounding system of the probe shown in FIG. 20 according to various embodiments of the present disclosure.

DETAILED DESCRIPTION

Figure 1:
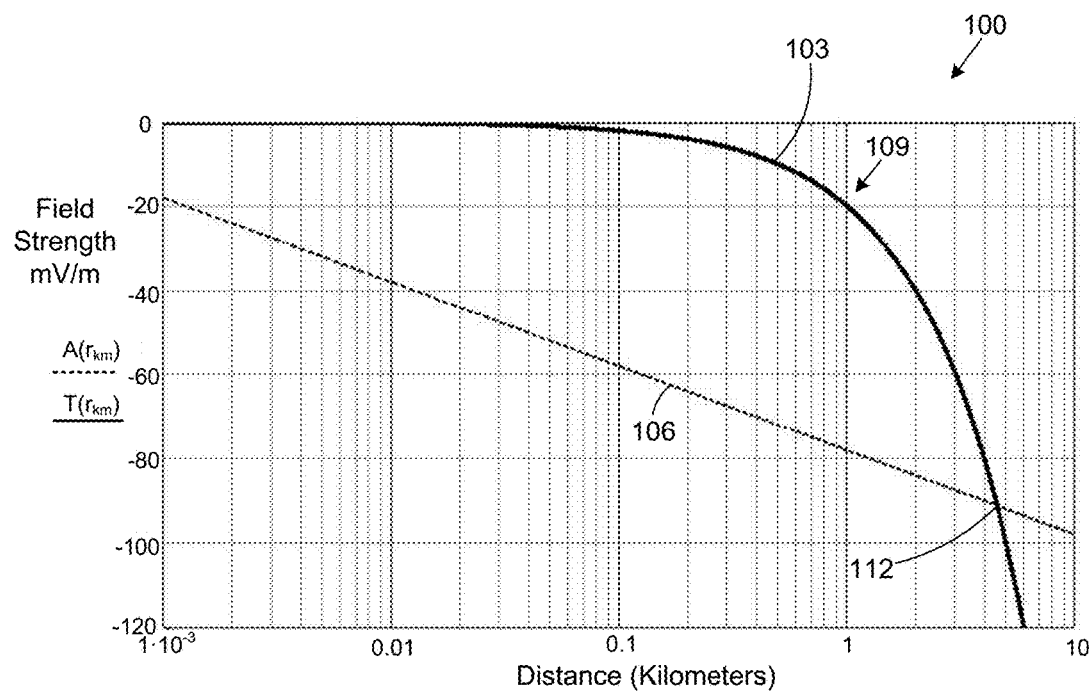
FIG. 1 is a chart that depicts field strength as a function of distance for a guided electromagnetic field and a radiated electromagnetic field.

To begin, some terminology shall be established to provide clarity in the discussion of concepts to follow. First, as contemplated herein, a formal distinction is drawn between radiated electromagnetic fields and guided electromagnetic fields.

As contemplated herein, a radiated electromagnetic field comprises electromagnetic energy that is emitted from a source structure in the form of waves that are not bound to a waveguide. For example, a radiated electromagnetic field is generally a field that leaves an electric structure such as an antenna and propagates through the atmosphere or other medium and is not bound to any waveguide structure. Once radiated electromagnetic waves leave an electric structure such as an antenna, they continue to propagate in the medium of propagation (such as air) independent of their source until they dissipate regardless of whether the source continues to operate. Once electromagnetic waves are radiated, they are not recoverable unless intercepted, and, if not intercepted, the energy inherent in the radiated electromagnetic waves is lost forever. Electrical structures such as antennas are designed to radiate electromagnetic fields by maximizing the ratio of the radiation resistance to the structure loss resistance. Radiated energy spreads out in space and is lost regardless of whether a receiver is present. The energy density of the radiated fields is a function of distance due to geometric spreading. Accordingly, the term "radiate" in all its forms as used herein refers to this form of electromagnetic propagation.

A guided electromagnetic field is a propagating electromagnetic wave whose energy is concentrated within or near boundaries between media having different electromagnetic properties. In this sense, a guided electromagnetic field is one that is bound to a waveguide and may be characterized as being conveyed by the current flowing in the waveguide. If there is no load to receive and/or dissipate the energy conveyed in a guided electromagnetic wave, then no energy is lost except for that which is dissipated in the conductivity of the guiding medium. Stated another way, if there is no load for a guided electromagnetic wave, then no energy is consumed. Thus, a generator or other source generating a guided electromagnetic field does not deliver real power unless a resistive load is present. To this end, such a generator or other source essentially runs idle until a load is presented. This is akin to running a generator to generate a 60 Hertz electromagnetic wave that is transmitted over power lines where there is no electrical load. It should be noted that a guided electromagnetic field or wave is the equivalent to what is termed a "transmission line mode." This contrasts with radiated electromagnetic waves in which real power is supplied at all times in order to generate radiated waves. Unlike radiated electromagnetic waves, guided electromagnetic energy does not continue to propagate along a finite length waveguide after the energy source is turned off. Accordingly, the term "guide" in all its forms as used herein refers to this transmission mode of electromagnetic propagation.

Referring now to FIG. 1, shown is a graph 100 of field strength in decibels (dB) above an arbitrary reference in volts per meter as a function of distance in kilometers on a log-dB plot to further illustrate the distinction between radiated and guided electromagnetic fields. The graph 100 of FIG. 1 depicts a guided field strength curve 103 that shows the field strength of a guided electromagnetic field as a function of distance. This guided field strength curve 103 is essentially the same as a transmission line mode. Also, the graph 100 of FIG. 1 depicts a radiated field strength curve 106 that shows the field strength of a radiated electromagnetic field as a function of distance.

Of interest are the shapes of the curves 103 and 106 for guided wave and for radiation propagation, respectively. The radiated field strength curve 106 falls off geometrically (1/d, where d is distance), which is depicted as a straight line on the log-log scale. The guided field strength curve 103, on the other hand, has a characteristic exponential decay of $e^{-\alpha d}/\sqrt{d}$ and exhibits a distinctive knee 109 on the log-log scale. The guided field strength curve 103 and the radiated field strength curve 106 intersect at point 112, which occurs at a crossing distance. At distances less than the crossing distance at intersection point 112, the field strength of a guided electromagnetic field is significantly greater at most locations than the field strength of a radiated electromagnetic field. At distances greater than the crossing distance, the opposite is true. Thus, the guided and radiated field strength curves 103 and 106 further illustrate the fundamental propagation difference between guided and radiated electromagnetic fields. For an informal discussion of the difference between guided and radiated electromagnetic fields, reference is made to Milligan, T., *Modern Antenna Design*, McGraw-Hill, 1$^{st}$ Edition, 1985, pp. 8-9, which is incorporated herein by reference in its entirety.

The distinction between radiated and guided electromagnetic waves, made above, is readily expressed formally and placed on a rigorous basis. That two such diverse solutions could emerge from one and the same linear partial differential equation, the wave equation, analytically follows from the boundary conditions imposed on the problem. The Green function for the wave equation, itself, contains the distinction between the nature of radiation and guided waves.

In empty space, the wave equation is a differential operator whose eigenfunctions possess a continuous spectrum of eigenvalues on the complex wave-number plane. This transverse electro-magnetic (TEM) field is called the radiation field, and those propagating fields are called "Hertzian waves." However, in the presence of a conducting boundary, the wave equation plus boundary conditions mathematically lead to a spectral representation of wave-numbers composed of a continuous spectrum plus a sum of discrete spectra. To this end, reference is made to Sommerfeld, A., "Uber die Ausbreitung der Wellen in der Drahtlosen Telegraphie," Annalen der Physik, Vol. 28, 1909, pp. 665-736. Also see Sommerfeld, A., "Problems of Radio," published as Chapter 6 in *Partial Differential Equations in Physics—Lectures on Theoretical Physics: Volume VI*, Academic Press, 1949, pp. 236-289, 295-296; Collin, R. E., "Hertzian Dipole Radiating Over a Lossy Earth or Sea: Some Early and Late 20$^{th}$ Century Controversies," *IEEE Antennas and Propagation Magazine*, Vol. 46, No. 2, April 2004, pp. 64-79; and Reich, H. J., Ordnung, P. F, Krauss, H. L., and Skalnik, J. G., *Microwave Theory and Techniques*, Van Nostrand, 1953, pp. 291-293, each of these references being incorporated herein by reference in its entirety.

The terms "ground wave" and "surface wave" identify two distinctly different physical propagation phenomena. A surface wave arises analytically from a distinct pole yielding a discrete component in the plane wave spectrum. See, e.g., "The Excitation of Plane Surface Waves" by Cullen, A. L., (*Proceedings of the IEE* (British), Vol. 101, Part IV, August 1954, pp. 225-235). In this context, a surface wave is considered to be a guided surface wave. The surface wave (in the Zenneck-Sommerfeld guided wave sense) is, physically and mathematically, not the same as the ground wave (in the Weyl-Norton-FCC sense) that is now so familiar from radio broadcasting. These two propagation mechanisms arise from the excitation of different types of eigenvalue spectra (continuum or discrete) on the complex plane. The field strength of the guided surface wave decays exponentially with distance as illustrated by guided field strength curve 103 of FIG. 1 (much like propagation in a lossy waveguide) and resembles propagation in a radial transmission line, as opposed to the classical Hertzian radiation of the ground wave, which propagates spherically, possesses a continuum of eigenvalues, falls off geometrically as illustrated by radiated field strength curve 106 of FIG. 1, and results from branch-cut integrals. As experimentally demonstrated by C. R. Burrows in "The Surface Wave in Radio Propagation over Plane Earth" (*Proceedings of the IRE*, Vol. 25, No. 2, February, 1937, pp. 219-229) and "The Surface Wave in Radio Transmission" (*Bell Laboratories Record*, Vol. 15, June 1937, pp. 321-324), vertical antennas radiate ground waves but do not launch guided surface waves.

To summarize the above, first, the continuous part of the wave-number eigenvalue spectrum, corresponding to branch-cut integrals, produces the radiation field, and second, the discrete spectra, and corresponding residue sum arising from the poles enclosed by the contour of integration, result in non-TEM traveling surface waves that are exponentially damped in the direction transverse to the propagation. Such surface waves are guided transmission line modes. For further explanation, reference is made to Friedman, B., *Principles and Techniques of Applied Mathematics*, Wiley, 1956, pp. pp. 214, 283-286, 290, 298-300.

In free space, antennas excite the continuum eigenvalues of the wave equation, which is a radiation field, where the outwardly propagating RF energy with $E_z$ and $H_\phi$ in-phase is lost forever. On the other hand, waveguide probes excite discrete eigenvalues, which results in transmission line propagation. See Collin, R. E., *Field Theory of Guided Waves*, McGraw-Hill, 1960, pp. 453, 474-477. While such theoretical analyses have held out the hypothetical possibility of launching open surface guided waves over planar or spherical surfaces of lossy, homogeneous media, for more than a century no known structures in the engineering arts have existed for accomplishing this with any practical efficiency. Unfortunately, since it emerged in the early 1900's, the theoretical analysis set forth above has essentially remained a theory and there have been no known structures for practically accomplishing the launching of open surface guided waves over planar or spherical surfaces of lossy, homogeneous media.

According to the various embodiments of the present disclosure, various guided surface waveguide probes are described that are configured to excite electric fields that couple into a guided surface waveguide mode along the surface of a lossy conducting medium. Such guided electromagnetic fields are substantially mode-matched in magnitude and phase to a guided surface wave mode on the surface of the lossy conducting medium. Such a guided surface wave mode can also be termed a Zenneck waveguide mode. By virtue of the fact that the resultant fields excited by the guided surface waveguide probes described herein are substantially mode-matched to a guided surface waveguide mode on the surface of the lossy conducting medium, a guided electromagnetic field in the form of a guided surface wave is launched along the surface of the lossy conducting medium. According to one embodiment, the lossy conducting medium comprises a terrestrial medium such as the Earth.

Figure 2:
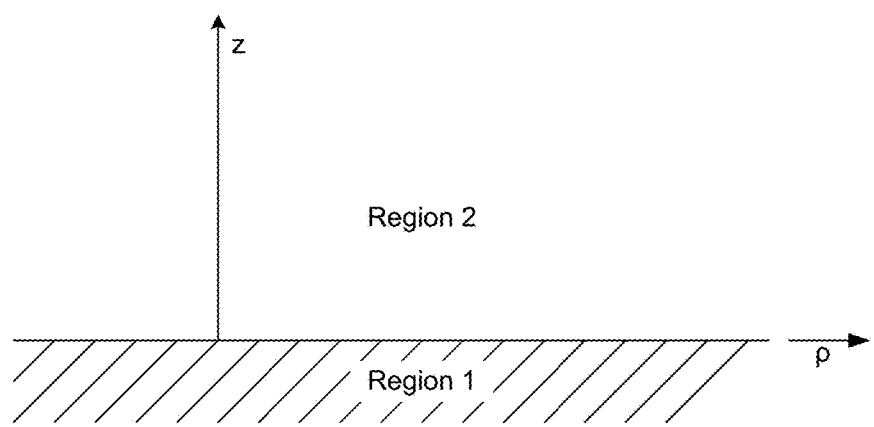
FIG. 2 is a drawing that illustrates a propagation interface with two regions employed for transmission of a guided surface wave according to various embodiments of the present disclosure.

Referring to FIG. 2, shown is a propagation interface that provides for an examination of the boundary value solutions to Maxwell's equations derived in 1907 by Jonathan Zenneck as set forth in his paper Zenneck, J., "On the Propagation of Plane Electromagnetic Waves Along a Flat Conducting Surface and their Relation to Wireless Telegraphy," Annalen der Physik, Serial 4, Vol. 23, Sep. 20, 1907, pp. 846-866. FIG. 2 depicts cylindrical coordinates for radially propagating waves along the interface between a lossy conducting medium specified as Region 1 and an insulator specified as Region 2. Region 1 can comprise, for example, any lossy conducting medium. In one example, such a lossy conducting medium can comprise a terrestrial medium such as the Earth or other medium. Region 2 is a second medium that shares a boundary interface with Region 1 and has different constitutive parameters relative to Region 1. Region 2 can comprise, for example, any insulator such as the atmosphere or other medium. The reflection coefficient for such a boundary interface goes to zero only for incidence at a complex Brewster angle. See Stratton, J. A., *Electromagnetic Theory*, McGraw-Hill, 1941, p. 516.

According to various embodiments, the present disclosure sets forth various guided surface waveguide probes that generate electromagnetic fields that are substantially mode-matched to a guided surface waveguide mode on the surface of the lossy conducting medium comprising Region 1. According to various embodiments, such electromagnetic fields substantially synthesize a wave front incident at a complex Brewster angle of the lossy conducting medium that can result in zero reflection.

To explain further, in Region 2, where an $e^{j\omega t}$ field variation is assumed and where $\rho \neq 0$ and $z \geq 0$ (with z being the vertical coordinate normal to the surface of Region 1, and $\rho$ being the radial dimension in cylindrical coordinates), Zenneck's closed-form exact solution of Maxwell's equations satisfying the boundary conditions along the interface are expressed by the following electric field and magnetic field components:

$$H_{2\phi} = A e^{-u_2 z} H_1^{(2)}(-j\gamma\rho), \qquad (1)$$

$$E_{2\rho} = A\left(\frac{u_2}{j\omega\varepsilon_o}\right) e^{-u_2 z} H_1^{(2)}(-j\gamma\rho), \text{ and} \qquad (2)$$

$$E_{2z} = A\left(\frac{-\gamma}{\omega\varepsilon_o}\right) e^{-u_2 z} H_0^{(2)}(-j\gamma\rho). \qquad (3)$$

In Region 1, where the $e^{j\omega t}$ field variation is assumed and where $\rho \neq 0$ and $z \leq 0$, Zenneck's closed-form exact solution of Maxwell's equations satisfying the boundary conditions along the interface is expressed by the following electric field and magnetic field components:

$$H_{1\phi} = A e^{u_1 z} H_1^{(2)}(-j\gamma\rho), \qquad (4)$$

$$E_{1\rho} = A\left(\frac{-u_1}{\sigma_1 + j\omega\varepsilon_1}\right) e^{u_1 z} H_1^{(2)}(-j\gamma\rho), \text{ and} \qquad (5)$$

$$E_{1z} = A\left(\frac{-j\gamma}{\sigma_1 + j\omega\varepsilon_1}\right) e^{u_1 z} H_0^{(2)}(-j\gamma\rho). \qquad (6)$$

In these expressions, z is the vertical coordinate normal to the surface of Region 1 and $\rho$ is the radial coordinate, $H_2^{(2)}(-j\gamma\rho)$ is a complex argument Hankel function of the second kind and order n, $u_1$ is the propagation constant in the positive vertical (z) direction in Region 1, $u_2$ is the propagation constant in the vertical (z) direction in Region 2, $\sigma_1$ is the conductivity of Region 1, $\omega$ is equal to $2\pi f$, where f is a frequency of excitation, $\varepsilon_0$ is the permittivity of free space, $\varepsilon_1$ is the permittivity of Region 1, A is a source constant imposed by the source, and $\gamma$ is a surface wave radial propagation constant.

The propagation constants in the ±z directions are determined by separating the wave equation above and below the interface between Regions 1 and 2, and imposing the boundary conditions. This exercise gives, in Region 2, $$u_2 = \frac{-jk_o}{\sqrt{1 + (\varepsilon_r - jx)}} \qquad (7)$$

and gives, in Region 1, $$u_1 = -u_2(\varepsilon_r - jx). \qquad (8)$$

The radial propagation constant $\gamma$ is given by $$\gamma = j\sqrt{k_o^2 + u_2^2} = j\frac{k_o n}{\sqrt{1+n^2}}, \qquad (9)$$

which is a complex expression where n is the complex index of refraction given by $$n = \sqrt{\varepsilon_r - jx}. \qquad (10)$$

In all of the above Equations, $$x = \frac{\sigma_1}{\omega\varepsilon_0}, \text{ and} \qquad (11)$$

$$k_o = \omega\sqrt{\mu_o\varepsilon_o} = \frac{\lambda_o}{2\pi}, \qquad (12)$$

where $\varepsilon_r$ comprises the relative permittivity of Region 1, $\sigma_1$ is the conductivity of Region 1, $\varepsilon_0$ is the permittivity of free space, and $\mu_o$ comprises the permeability of free space. Thus, the generated surface wave propagates parallel to the interface and exponentially decays vertical to it. This is known as evanescence.

Thus, Equations (1)-(3) can be considered to be a cylindrically-symmetric, radially-propagating waveguide mode. See Barlow, H. M., and Brown, J., *Radio Surface Waves*, Oxford University Press, 1962, pp. 10-12, 29-33. The present disclosure details structures that excite this "open boundary" waveguide mode. Specifically, according to various embodiments, a guided surface waveguide probe is provided with a charge terminal of appropriate size that is fed with voltage and/or current and is positioned relative to the boundary interface between Region 2 and Region 1. This may be better understood with reference to FIG. 3, which shows an example of a guided surface waveguide probe 200a that includes a charge terminal $T_1$ elevated above a lossy conducting medium 203 (e.g., the Earth) along a vertical axis z that is normal to a plane presented by the lossy conducting medium 203. The lossy conducting medium 203 makes up Region 1, and a second medium 206 makes up Region 2 and shares a boundary interface with the lossy conducting medium 203.

According to one embodiment, the lossy conducting medium 203 can comprise a terrestrial medium such as the planet Earth. To this end, such a terrestrial medium comprises all structures or formations included thereon whether natural or man-made. For example, such a terrestrial medium can comprise natural elements such as rock, soil, sand, fresh water, sea water, trees, vegetation, and all other natural elements that make up our planet. In addition, such a terrestrial medium can comprise man-made elements such as concrete, asphalt, building materials, and other man-made materials. In other embodiments, the lossy conducting medium 203 can comprise some medium other than the Earth, whether naturally occurring or man-made. In other embodiments, the lossy conducting medium 203 can comprise other media such as man-made surfaces and structures such as automobiles, aircraft, man-made materials (such as plywood, plastic sheeting, or other materials) or other media.

In the case where the lossy conducting medium 203 comprises a terrestrial medium or Earth, the second medium 206 can comprise the atmosphere above the ground. As such, the atmosphere can be termed an "atmospheric medium" that comprises air and other elements that make up the atmosphere of the Earth. In addition, it is possible that the second medium 206 can comprise other media relative to the lossy conducting medium 203.

The guided surface waveguide probe 200a includes a feed network 209 that couples an excitation source 212 to the charge terminal $T_1$ via, e.g., a vertical feed line conductor. The excitation source 212 may comprise, for example, an Alternating Current (AC) source or some other source. As contemplated herein, an excitation source can comprise an AC source or other type of source. According to various embodiments, a charge $Q_1$ is imposed on the charge terminal $T_1$ to synthesize an electric field based upon the voltage applied to terminal $T_1$ at any given instant. Depending on the angle of incidence ($\theta_1$) of the electric field (E), it is possible to substantially mode-match the electric field to a guided surface waveguide mode on the surface of the lossy conducting medium 203 comprising Region 1.

By considering the Zenneck closed-form solutions of Equations (1)-(6), the Leontovich impedance boundary condition between Region 1 and Region 2 can be stated as $$\hat{z} \times \vec{H}_2(\rho,\varphi,0) = \vec{J}_S, \tag{13}$$

where $\hat{z}$ is a unit normal in the positive vertical (+z) direction and $\vec{H}_2$ is the magnetic field strength in Region 2 expressed by Equation (1) above. Equation (13) implies that the electric and magnetic fields specified in Equations (1)-(3) may result in a radial surface current density along the boundary interface, where the radial surface current density can be specified by $$J_\rho(\rho') \sim AH_1^{(2)}(-j\gamma\rho') \tag{14}$$

where A is a constant. Further, it should be noted that close-in to the guided surface waveguide probe 200 (for $\rho \ll \lambda$), Equation (14) above has the behavior $$J_{close}(\rho') = \frac{-A(j2)}{\pi(-j\gamma\rho')} = -H_\phi = -\frac{I_o}{2\pi\rho'}. \tag{15}$$

Figure 3:
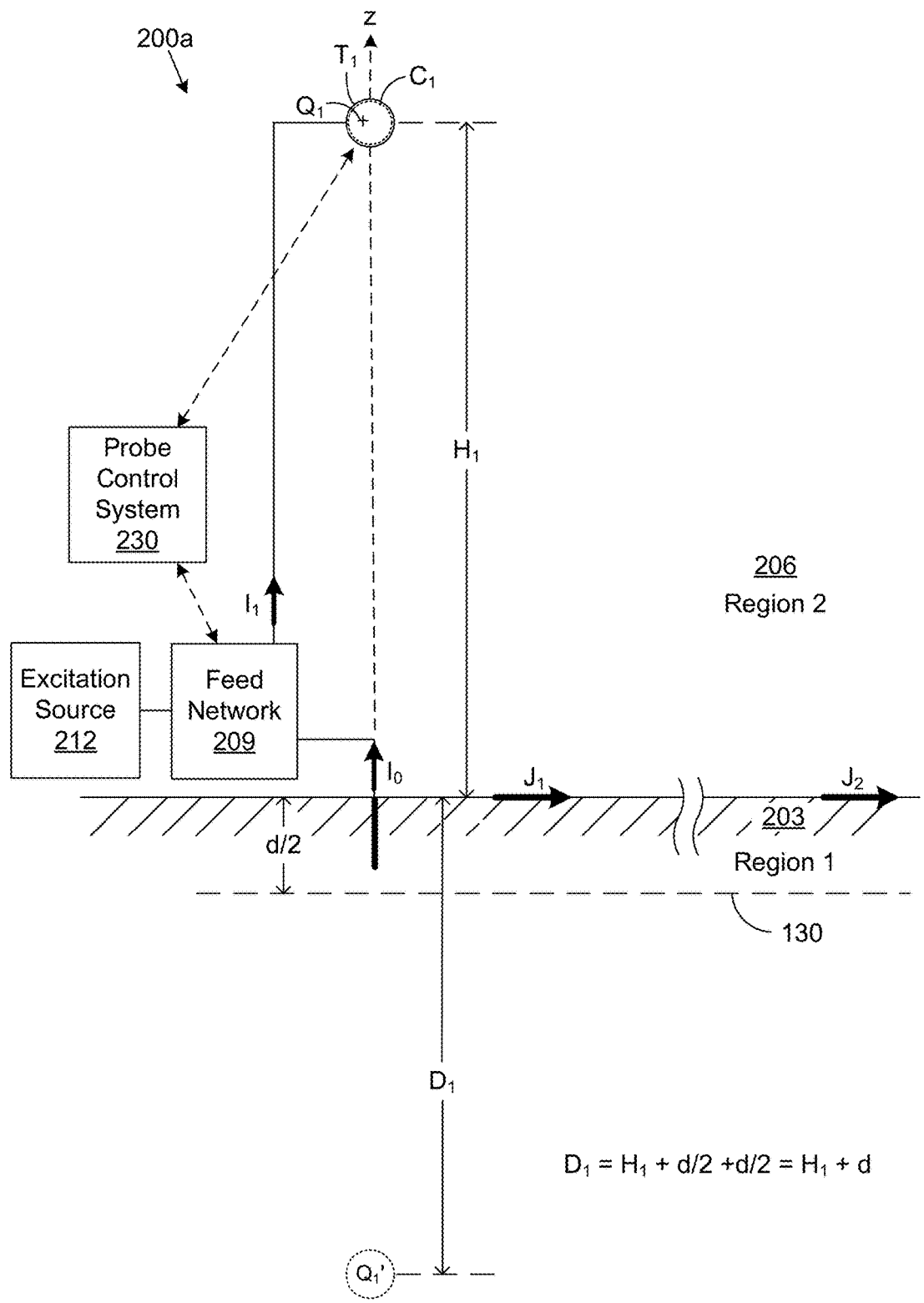
FIG. 3 is a drawing that illustrates a guided surface waveguide probe disposed with respect to a propagation interface of FIG. 2 according to various embodiments of the present disclosure.

The negative sign means that when source current ($I_o$) flows vertically upward as illustrated in FIG. 3, the "close-in" ground current flows radially inward. By field matching on $H_\phi$ "close-in," it can be determined that $$A = -\frac{I_o \gamma}{4} = -\frac{\omega q_1 \gamma}{4} \tag{16}$$

where $q_1 = C_1 V_1$, in Equations (1)-(6) and (14). Therefore, the radial surface current density of Equation (14) can be restated as $$J_\rho(\rho') = \frac{I_o \gamma}{4} H_1^{(2)}(-j\gamma\rho'). \tag{17}$$

The fields expressed by Equations (1)-(6) and (17) have the nature of a transmission line mode bound to a lossy interface, not radiation fields that are associated with ground-wave propagation. See Barlow, H. M. and Brown, J., *Radio Surface Waves*, Oxford University Press, 1962, pp. 1-5.

At this point, a review of the nature of the Hankel functions used in Equations (1)-(6) and (17) is provided for these solutions of the wave equation. One might observe that the Hankel functions of the first and second kind and order n are defined as complex combinations of the standard Bessel functions of the first and second kinds $$H_n^{(1)}(x) = J_n(x) + jN_n(x), \text{ and} \tag{18}$$

$$H_n^{(2)}(x) = J_n(x) - jN_n(x). \tag{19}$$

These functions represent cylindrical waves propagating radially inward ($H_n^{(1)}$) and outward ($H_n^{(2)}$), respectively. The definition is analogous to the relationship $e^{\pm jx} = \cos x \pm j \sin x$. See, for example, Harrington, R. F., *Time-Harmonic Fields*, McGraw-Hill, 1961, pp. 460-463.

That $H_n^{(2)}(k_\rho \rho)$ is an outgoing wave can be recognized from its large argument asymptotic behavior that is obtained directly from the series definitions of $J_n(x)$ and $N_n(x)$. Far-out from the guided surface waveguide probe:

$$H_n^{(2)}(x) \xrightarrow[x \to \infty]{} \sqrt{\frac{2j}{\pi x}} j^n e^{-jx} = \sqrt{\frac{2}{\pi x}} j^n e^{-j\left(x-\frac{\pi}{4}\right)}, \tag{20a}$$

which, when multiplied by $e^{j\omega t}$, is an outward propagating cylindrical wave of the form $e^{j(\omega t - k\rho)}$ with a $1/\sqrt{\rho}$ spatial variation. The first order (n=1) solution can be determined from Equation (20a) to be $$H_1^{(2)}(x) \xrightarrow[x \to \infty]{} j\sqrt{\frac{2j}{\pi x}} e^{-jx} = \sqrt{\frac{2}{\pi x}} e^{-j\left(x-\frac{\pi}{2}-\frac{\pi}{4}\right)}. \tag{20b}$$

Close-in to the guided surface waveguide probe (for $\rho \ll \lambda$), the Hankel function of first order and the second kind behaves as $$H_1^{(2)}(x) \xrightarrow[x \to 0]{} \frac{2j}{\pi x}. \tag{21}$$

Note that these asymptotic expressions are complex quantities. When x is a real quantity, Equations (20b) and (21) differ in phase by $\sqrt{j}$, which corresponds to an extra phase advance or "phase boost" of 45° or, equivalently, $\lambda/8$. The close-in and far-out asymptotes of the first order Hankel function of the second kind have a Hankel "crossover" or transition point where they are of equal magnitude at a distance of $\rho = R_x$.

Thus, beyond the Hankel crossover point the "far out" representation predominates over the "close-in" representation of the Hankel function. The distance to the Hankel crossover point (or Hankel crossover distance) can be found by equating Equations (20b) and (21) for $-j\gamma\rho$, and solving for $R_x$. With $x = \sigma/\omega\varepsilon_o$, it can be seen that the far-out and close-in Hankel function asymptotes are frequency dependent, with the Hankel crossover point moving out as the frequency is lowered. It should also be noted that the Hankel function asymptotes may also vary as the conductivity ($\sigma$) of the lossy conducting medium changes. For example, the conductivity of the soil can vary with changes in weather conditions.

Figure 4:
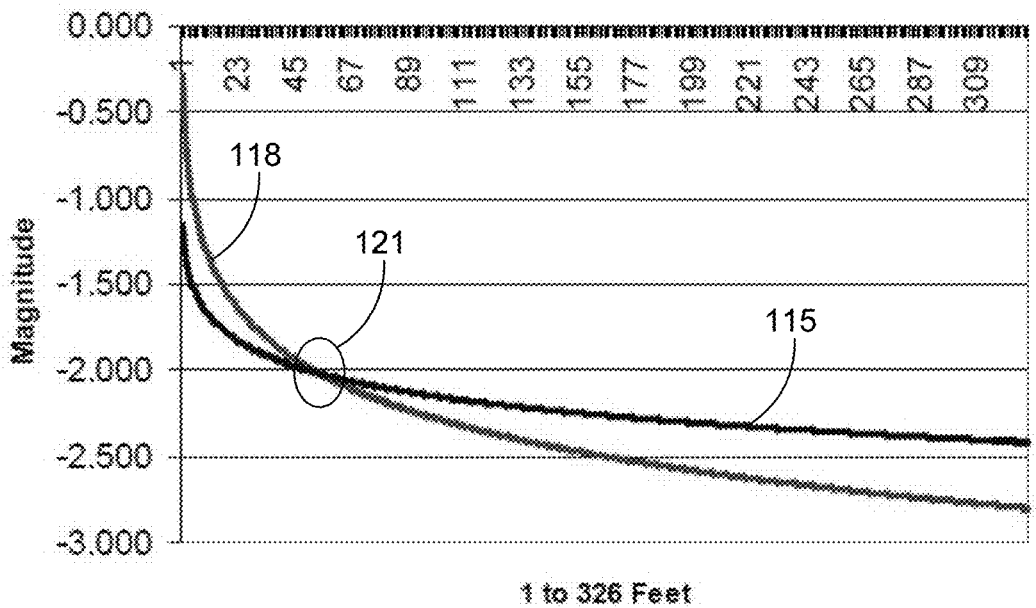
FIG. 4 is a plot of an example of the magnitudes of close-in and far-out asymptotes of first order Hankel functions according to various embodiments of the present disclosure.

Referring to FIG. 4, shown is an example of a plot of the magnitudes of the first order Hankel functions of Equations (20b) and (21) for a Region 1 conductivity of σ=0.010 mhos/m and relative permittivity $\varepsilon_r$=15, at an operating frequency of 1850 kHz. Curve 115 is the magnitude of the far-out asymptote of Equation (20b) and curve 118 is the magnitude of the close-in asymptote of Equation (21), with the Hankel crossover point 121 occurring at a distance of $R_x$=54 feet. While the magnitudes are equal, a phase offset exists between the two asymptotes at the Hankel crossover point 121. It can also be seen that the Hankel crossover distance is much less than a wavelength of the operation frequency.

Considering the electric field components given by Equations (2) and (3) of the Zenneck closed-form solution in Region 2, it can be seen that the ratio of $E_z$ and $E_\rho$ asymptotically passes to $$\frac{E_z}{E_\rho} = \left(\frac{-j\gamma}{u_2}\right)\frac{H_0^{(2)}(-j\gamma\rho)}{H_1^{(2)}(-j\gamma\rho)} \xrightarrow[\rho\to\infty]{} \sqrt{\varepsilon_r - j\frac{\sigma}{\omega\varepsilon_o}} = n = \tan\theta_i, \quad (22)$$

where n is the complex index of refraction of Equation (10) and $\theta_i$ is the angle of incidence of the electric field. In addition, the vertical component of the mode-matched electric field of Equation (3) asymptotically passes to $$E_{2z} \xrightarrow[\rho\to\infty]{} \left(\frac{q_{free}}{\varepsilon_0}\right)\sqrt{\frac{\gamma^3}{8\pi}}\, e^{-u_2 z}\, \frac{e^{-j(\gamma\rho-\pi/4)}}{\sqrt{\rho}}, \quad (23)$$

which is linearly proportional to free charge on the isolated component of the elevated charge terminal's capacitance at the terminal voltage, $q_{free}=C_{free}\times V_T$.

For example, the height $H_1$ of the elevated charge terminal $T_1$ in FIG. 3 affects the amount of free charge on the charge terminal $T_1$. When the charge terminal $T_1$ is near the ground plane of Region 1, most of the charge $Q_1$ on the terminal is "bound." As the charge terminal $T_1$ is elevated, the bound charge is lessened until the charge terminal $T_1$ reaches a height at which substantially all of the isolated charge is free.

The advantage of an increased capacitive elevation for the charge terminal $T_1$ is that the charge on the elevated charge terminal $T_1$ is further removed from the ground plane, resulting in an increased amount of free charge $q_{free}$ to couple energy into the guided surface waveguide mode. As the charge terminal $T_1$ is moved away from the ground plane, the charge distribution becomes more uniformly distributed about the surface of the terminal. The amount of free charge is related to the self-capacitance of the charge terminal $T_1$.

For example, the capacitance of a spherical terminal can be expressed as a function of physical height above the ground plane. The capacitance of a sphere at a physical height of h above a perfect ground is given by $$C_{elevated\,sphere}=4\pi\varepsilon_o\alpha(1+M+M^2+M^3+2M^4+3M^5+\ldots), \quad (24)$$

where the diameter of the sphere is $2\alpha$, and where M=$\alpha$/2h with h being the height of the spherical terminal. As can be seen, an increase in the terminal height h reduces the capacitance C of the charge terminal. It can be shown that for elevations of the charge terminal $T_1$ that are at a height of about four times the diameter (4D=8$\alpha$) or greater, the charge distribution is approximately uniform about the spherical terminal, which can improve the coupling into the guided surface waveguide mode.

In the case of a sufficiently isolated terminal, the self-capacitance of a conductive sphere can be approximated by C=$4\pi\varepsilon_o\alpha$, where a is the radius of the sphere in meters, and the self-capacitance of a disk can be approximated by C=$8\varepsilon_o\alpha$, where $\alpha$ is the radius of the disk in meters. The charge terminal $T_1$ can include any shape such as a sphere, a disk, a cylinder, a cone, a torus, a hood, one or more rings, or any other randomized shape or combination of shapes. An equivalent spherical diameter can be determined and used for positioning of the charge terminal $T_1$.

This may be further understood with reference to the example of FIG. 3, where the charge terminal $T_1$ is elevated at a physical height of $h_p$=$H_1$ above the lossy conducting medium 203. To reduce the effects of the "bound" charge, the charge terminal $T_1$ can be positioned at a physical height that is at least four times the spherical diameter (or equivalent spherical diameter) of the charge terminal $T_1$ to reduce the bounded charge effects.

Figure 5A:
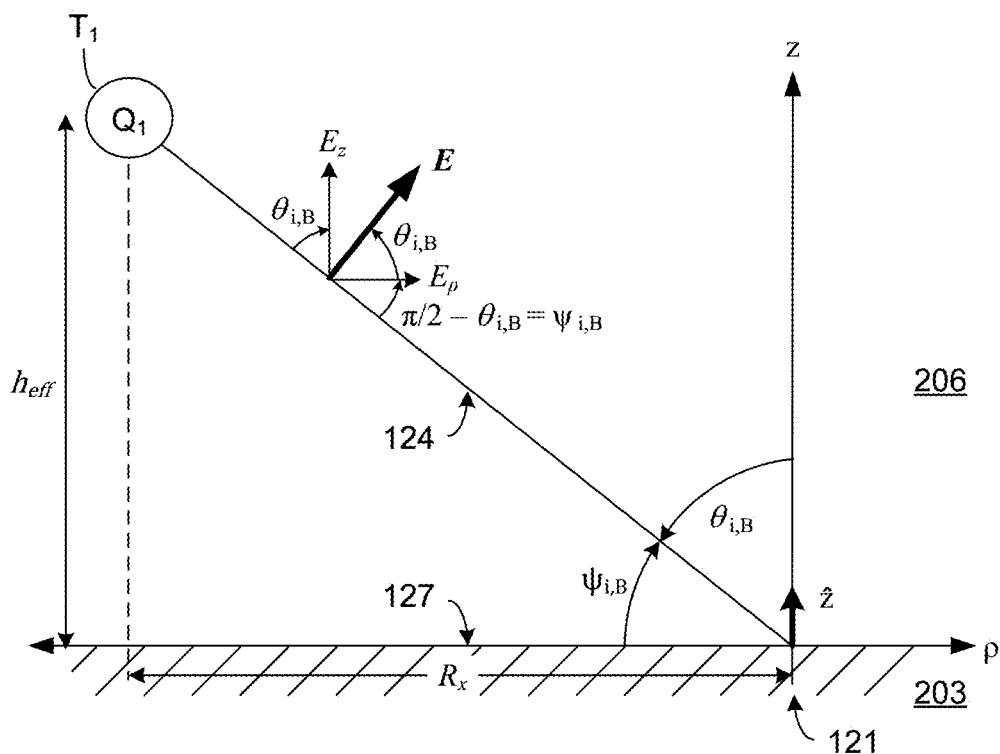
FIGS. 5A and 5B are drawings that illustrate a complex angle of incidence of an electric field synthesized by a guided surface waveguide probe according to various embodiments of the present disclosure.

Referring next to FIG. 5A, shown is a ray optics interpretation of the electric field produced by the elevated charge $Q_1$ on charge terminal $T_1$ of FIG. 3. As in optics, minimizing the reflection of the incident electric field can improve and/or maximize the energy coupled into the guided surface waveguide mode of the lossy conducting medium 203. For an electric field ($E_\parallel$) that is polarized parallel to the plane of incidence (not the boundary interface), the amount of reflection of the incident electric field may be determined using the Fresnel reflection coefficient, which can be expressed as $$\Gamma_\parallel(\theta_i) = \frac{E_{\parallel,R}}{E_{\parallel,i}} = \frac{\sqrt{(\varepsilon_r - jx) - \sin^2\theta_i} - (\varepsilon_r - jx)\cos\theta_i}{\sqrt{(\varepsilon_r - jx) - \sin^2\theta_i} + (\varepsilon_r - jx)\cos\theta_i}, \quad (25)$$

where $\theta_i$ is the conventional angle of incidence measured with respect to the surface normal.

In the example of FIG. 5A, the ray optic interpretation shows the incident field polarized parallel to the plane of incidence having an angle of incidence of $\theta_i$, which is measured with respect to the surface normal ($\hat{z}$). There will be no reflection of the incident electric field when $\Gamma_\parallel(\theta_i)$=0 and thus the incident electric field will be completely coupled into a guided surface waveguide mode along the surface of the lossy conducting medium 203. It can be seen that the numerator of Equation (25) goes to zero when the angle of incidence is $$\theta_i=\arctan(\varepsilon_r-jx)=\theta_{i,B}, \quad (26)$$

where x=$\sigma/\omega\varepsilon_o$. This complex angle of incidence ($\theta_{i,B}$) is referred to as the Brewster angle. Referring back to Equation (22), it can be seen that the same complex Brewster angle ($\theta_{i,B}$) relationship is present in both Equations (22) and (26).

As illustrated in FIG. 5A, the electric field vector E can be depicted as an incoming non-uniform plane wave, polarized parallel to the plane of incidence. The electric field vector E can be created from independent horizontal and vertical components as $$\vec{E}(\theta_i)=E_\rho\hat{\rho}+E_z\hat{z}. \quad (27)$$

Geometrically, the illustration in FIG. 5A suggests that the electric field vector E can be given by $$E_\rho(\rho,z)=E(\rho,z)\cos\theta_i, \text{ and} \quad (28a)$$

$$E_z(\rho, z) = E(\rho, z)\cos\left(\frac{\pi}{2} - \theta_i\right) = E(\rho, z)\sin\theta_i, \quad (28b)$$

which means that the field ratio is $$\frac{E_\rho}{E_z} = \frac{1}{\tan\theta_i} = \tan\psi_i. \qquad (29)$$

Figure 5B:
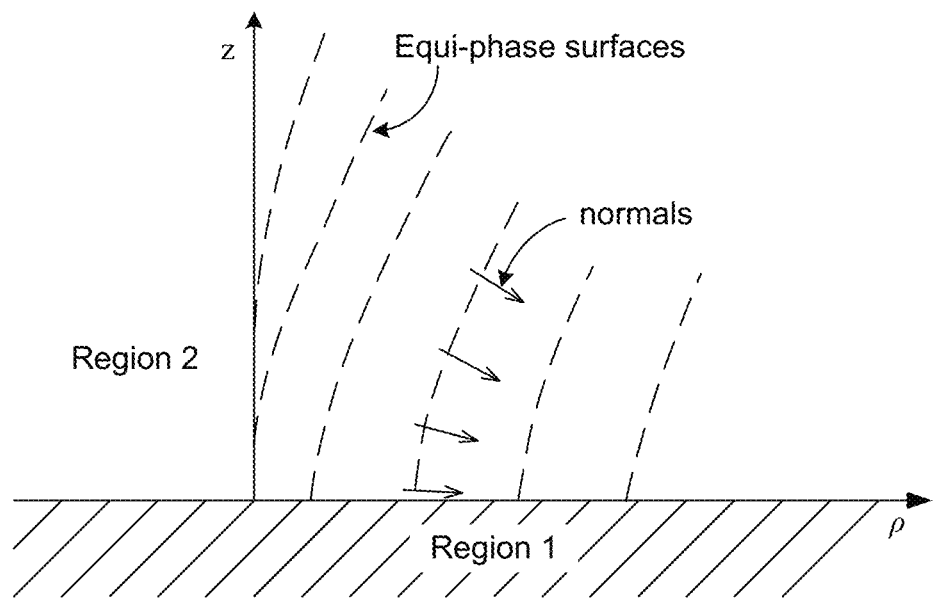

A generalized parameter W, called "wave tilt," is noted herein as the ratio of the horizontal electric field component to the vertical electric field component given by $$W = \frac{E_\rho}{E_z} = |W|e^{j\Psi}, \text{ or} \qquad (30a)$$

$$\frac{1}{W} = \frac{E_z}{E_\rho} = \tan\theta_i = \frac{1}{|W|}e^{j\Psi}, \qquad (30b)$$

which is complex and has both magnitude and phase. For an electromagnetic wave in Region 2 (FIG. 2), the wave tilt angle ($\Psi$) is equal to the angle between the normal of the wave-front at the boundary interface with Region 1 (FIG. 2) and the tangent to the boundary interface. This may be easier to see in FIG. 5B, which illustrates equi-phase surfaces of an electromagnetic wave and their normals for a radial cylindrical guided surface wave. At the boundary interface (z=0) with a perfect conductor, the wave-front normal is parallel to the tangent of the boundary interface, resulting in W=0. However, in the case of a lossy dielectric, a wave tilt W exists because the wave-front normal is not parallel with the tangent of the boundary interface at z=0.

Applying Equation (30b) to a guided surface wave gives $$\tan\theta_{i,B} = \frac{E_z}{E_\rho} = \frac{u_2}{\gamma} = \sqrt{\varepsilon_r - jx} = n = \frac{1}{W} = \frac{1}{|W|}e^{-j\Psi}. \qquad (31)$$

With the angle of incidence equal to the complex Brewster angle ($\theta_{i,B}$), the Fresnel reflection coefficient of Equation (25) vanishes, as shown by $$\Gamma_\|(\theta_{i,B}) = \left.\frac{\sqrt{(\varepsilon_r - jx) - \sin^2\theta_i} - (\varepsilon_r - jx)\cos\theta_i}{\sqrt{(\varepsilon_r - jx) - \sin^2\theta_i} + (\varepsilon_r - jx)\cos\theta_i}\right|_{\theta_i = \theta_{i,B}} = 0. \qquad (32)$$

By adjusting the complex field ratio of Equation (22), an incident field can be synthesized to be incident at a complex angle at which the reflection is reduced or eliminated. Establishing this ratio as $n=\sqrt{\varepsilon_r - jx}$ results in the synthesized electric field being incident at the complex Brewster angle, making the reflections vanish.

The concept of an electrical effective height can provide further insight into synthesizing an electric field with a complex angle of incidence with a guided surface waveguide probe 200. The electrical effective height ($h_{eff}$) has been defined as $$h_{eff} = \frac{1}{I_0}\int_0^{h_p} I(z)dz \qquad (33)$$

for a monopole with a physical height (or length) of $h_p$. Since the expression depends upon the magnitude and phase of the source distribution along the structure, the effective height (or length) is complex in general. The integration of the distributed current I(z) of the structure is performed over the physical height of the structure ($h_p$), and normalized to the ground current ($I_0$) flowing upward through the base (or input) of the structure. The distributed current along the structure can be expressed by $$I(z) = I_c \cos(\beta_0 z), \qquad (34)$$

where $\beta_0$ is the propagation factor for current propagating on the structure. In the example of FIG. 3, $I_c$ is the current that is distributed along the vertical structure of the guided surface waveguide probe 200a.

For example, consider a feed network 209 that includes a low loss coil (e.g., a helical coil) at the bottom of the structure and a vertical feed line conductor connected between the coil and the charge terminal $T_1$. The phase delay due to the coil (or helical delay line) is $\theta_c = \beta_p l_c$, with a physical length of $l_c$ and a propagation factor of $$\beta_p = \frac{2\pi}{\lambda_p} = \frac{2\pi}{V_f \lambda_0}, \qquad (35)$$

where $V_f$ is the velocity factor on the structure, $\lambda_0$ is the wavelength at the supplied frequency, and $\lambda_p$ is the propagation wavelength resulting from the velocity factor $V_f$. The phase delay is measured relative to the ground (stake or system) current $I_0$.

In addition, the spatial phase delay along the length $l_w$ of the vertical feed line conductor can be given by $\theta_y = \beta_w l_w$ where $\beta_w$ is the propagation phase constant for the vertical feed line conductor. In some implementations, the spatial phase delay may be approximated by $\theta_y = \beta_w h_p$, since the difference between the physical height $h_p$ of the guided surface waveguide probe 200a and the vertical feed line conductor length $l_w$ is much less than a wavelength at the supplied frequency ($\lambda_0$). As a result, the total phase delay through the coil and vertical feed line conductor is $\Phi = \theta_c + \theta_y$, and the current fed to the top of the coil from the bottom of the physical structure is $$I_c(\theta_c + \theta_y) = I_0 e^{j\Phi}, \qquad (36)$$

with the total phase delay $\Phi$ measured relative to the ground (stake or system) current $I_0$. Consequently, the electrical effective height of a guided surface waveguide probe 200 can be approximated by $$h_{eff} = \frac{1}{I_0}\int_0^{h_p} I_0 e^{j\Phi}\cos(\beta_0 z)dz \cong h_p e^{j\Phi}, \qquad (37)$$

for the case where the physical height $h_p \ll \lambda_0$. The complex effective height of a monopole, $h_{eff} = h_p$ at an angle (or phase delay) of $\Phi$, may be adjusted to cause the source fields to match a guided surface waveguide mode and cause a guided surface wave to be launched on the lossy conducting medium 203.

In the example of FIG. 5A, ray optics are used to illustrate the complex angle trigonometry of the incident electric field (E) having a complex Brewster angle of incidence ($\theta_{i,B}$) at the Hankel crossover distance ($R_x$) 121. Recall from Equation (26) that, for a lossy conducting medium, the Brewster angle is complex and specified by $$\tan\theta_{i,B} = \sqrt{\varepsilon_r - j\frac{\sigma}{\omega\varepsilon_0}} = n. \quad (38)$$

Electrically, the geometric parameters are related by the electrical effective height ($h_{eff}$) of the charge terminal $T_1$ by $$R_x \tan\psi_{i,B} = R_x \times W = h_{eff} = h_p e^{j\Phi}, \quad (39)$$

where $\psi_{i,B} = (\pi/2) - \theta_{i,B}$ is the Brewster angle measured from the surface of the lossy conducting medium. To couple into the guided surface waveguide mode, the wave tilt of the electric field at the Hankel crossover distance can be expressed as the ratio of the electrical effective height and the Hankel crossover distance $$\frac{h_{eff}}{R_x} = \tan\psi_{i,B} = W_{Rx}. \quad (40)$$

Since both the physical height ($h_p$) and the Hankel crossover distance ($R_x$) are real quantities, the angle ($\Psi$) of the desired guided surface wave tilt at the Hankel crossover distance ($R_x$) is equal to the phase ($\Phi$) of the complex effective height ($h_{eff}$). This implies that by varying the phase at the supply point of the coil, and thus the phase delay in Equation (37), the phase, $\Phi$, of the complex effective height can be manipulated to match the angle of the wave tilt, $\Psi$, of the guided surface waveguide mode at the Hankel crossover point 121: $\Phi = \Psi$.

In FIG. 5A, a right triangle is depicted having an adjacent side of length $R_x$ along the lossy conducting medium surface and a complex Brewster angle $\psi_{i,B}$ measured between a ray 124 extending between the Hankel crossover point 121 at $R_x$ and the center of the charge terminal $T_1$, and the lossy conducting medium surface 127 between the Hankel crossover point 121 and the charge terminal $T_1$. With the charge terminal $T_1$ positioned at physical height $h_p$ and excited with a charge having the appropriate phase delay $\Phi$, the resulting electric field is incident with the lossy conducting medium boundary interface at the Hankel crossover distance $R_x$, and at the Brewster angle. Under these conditions, the guided surface waveguide mode can be excited without reflection or substantially negligible reflection.

Figure 6:
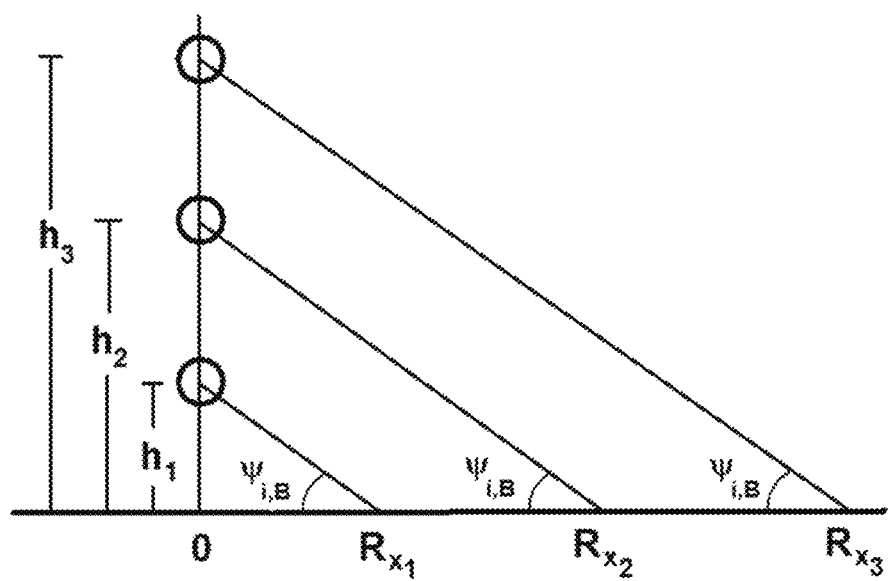
FIG. 6 is a graphical representation illustrating the effect of elevation of a charge terminal on the location where the electric field of FIG. 5A intersects with the lossy conducting medium at a Brewster angle according to various embodiments of the present disclosure.

If the physical height of the charge terminal $T_1$ is decreased without changing the phase delay $\Phi$ of the effective height ($h_{eff}$), the resulting electric field intersects the lossy conducting medium 203 at the Brewster angle at a reduced distance from the guided surface waveguide probe 200. FIG. 6 graphically illustrates the effect of decreasing the physical height of the charge terminal $T_1$ on the distance where the electric field is incident at the Brewster angle. As the height is decreased from h3 through $h_2$ to $h_1$, the point where the electric field intersects with the lossy conducting medium (e.g., the Earth) at the Brewster angle moves closer to the charge terminal position. However, as Equation (39) indicates, the height $H_1$ (FIG. 3) of the charge terminal $T_1$ should be at or higher than the physical height ($h_p$) in order to excite the far-out component of the Hankel function. With the charge terminal $T_1$ positioned at or above the effective height ($h_{eff}$), the lossy conducting medium 203 can be illuminated at the Brewster angle of incidence ($\psi_{i,B} = (\pi/2) - \theta_{i,B}$) at or beyond the Hankel crossover distance ($R_x$) 121 as illustrated in FIG. 5A. To reduce or minimize the bound charge on the charge terminal $T_1$, the height should be at least four times the spherical diameter (or equivalent spherical diameter) of the charge terminal $T_1$ as mentioned above.

A guided surface waveguide probe 200 can be configured to establish an electric field having a wave tilt that corresponds to a wave illuminating the surface of the lossy conducting medium 203 at a complex Brewster angle, thereby exciting radial surface currents by substantially mode-matching to a guided surface wave mode at (or beyond) the Hankel crossover point 121 at $R_x$.

Figure 7A:
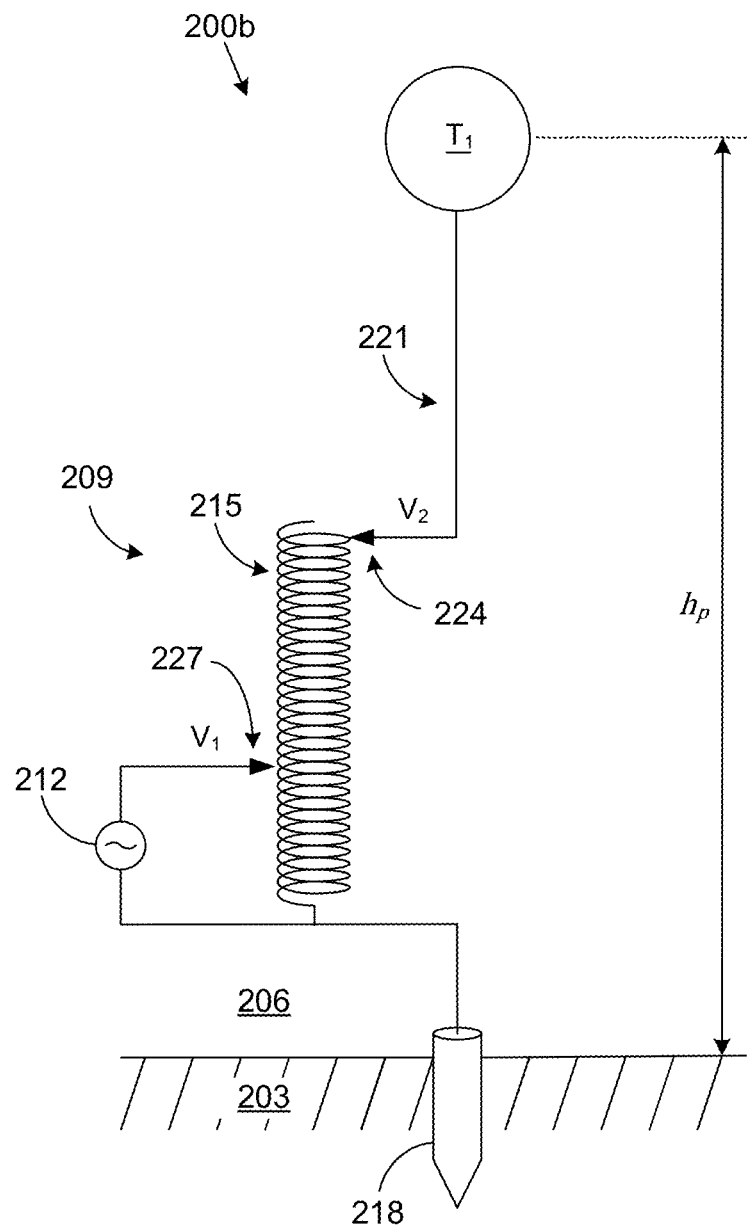
FIGS. 7A through 7C are graphical representations of examples of guided surface waveguide probes according to various embodiments of the present disclosure.

Referring to FIG. 7A, shown is a graphical representation of an example of a guided surface waveguide probe 200b that includes a charge terminal $T_1$. As shown in FIG. 7A, an excitation source 212 such as an AC source acts as the excitation source for the charge terminal $T_1$, which is coupled to the guided surface waveguide probe 200b through a feed network 209 (FIG. 3) comprising a coil 215 such as, e.g., a helical coil. In other implementations, the excitation source 212 can be inductively coupled to the coil 215 through a primary coil. In some embodiments, an impedance matching network may be included to improve and/or maximize coupling of the excitation source 212 to the coil 215.

As shown in FIG. 7A, the guided surface waveguide probe 200b can include the upper charge terminal $T_1$ (e.g., a sphere at height $h_p$) that is positioned along a vertical axis z that is substantially normal to the plane presented by the lossy conducting medium 203. A second medium 206 is located above the lossy conducting medium 203. The charge terminal $T_1$ has a self-capacitance $C_T$. During operation, charge $Q_1$ is imposed on the terminal $T_1$ depending on the voltage applied to the terminal $T_1$ at any given instant.

In the example of FIG. 7A, the coil 215 is coupled to a ground stake (or grounding system) 218 at a first end and to the charge terminal $T_1$ via a vertical feed line conductor 221. In some implementations, the coil connection to the charge terminal $T_1$ can be adjusted using a tap 224 of the coil 215 as shown in FIG. 7A. The coil 215 can be energized at an operating frequency by the excitation source 212 comprising, for example, an excitation source through a tap 227 at a lower portion of the coil 215. In other implementations, the excitation source 212 can be inductively coupled to the coil 215 through a primary coil. The charge terminal $T_1$ can be configured to adjust its load impedance seen by the vertical feed line conductor 221, which can be used to adjust the probe impedance.

Figure 7B:
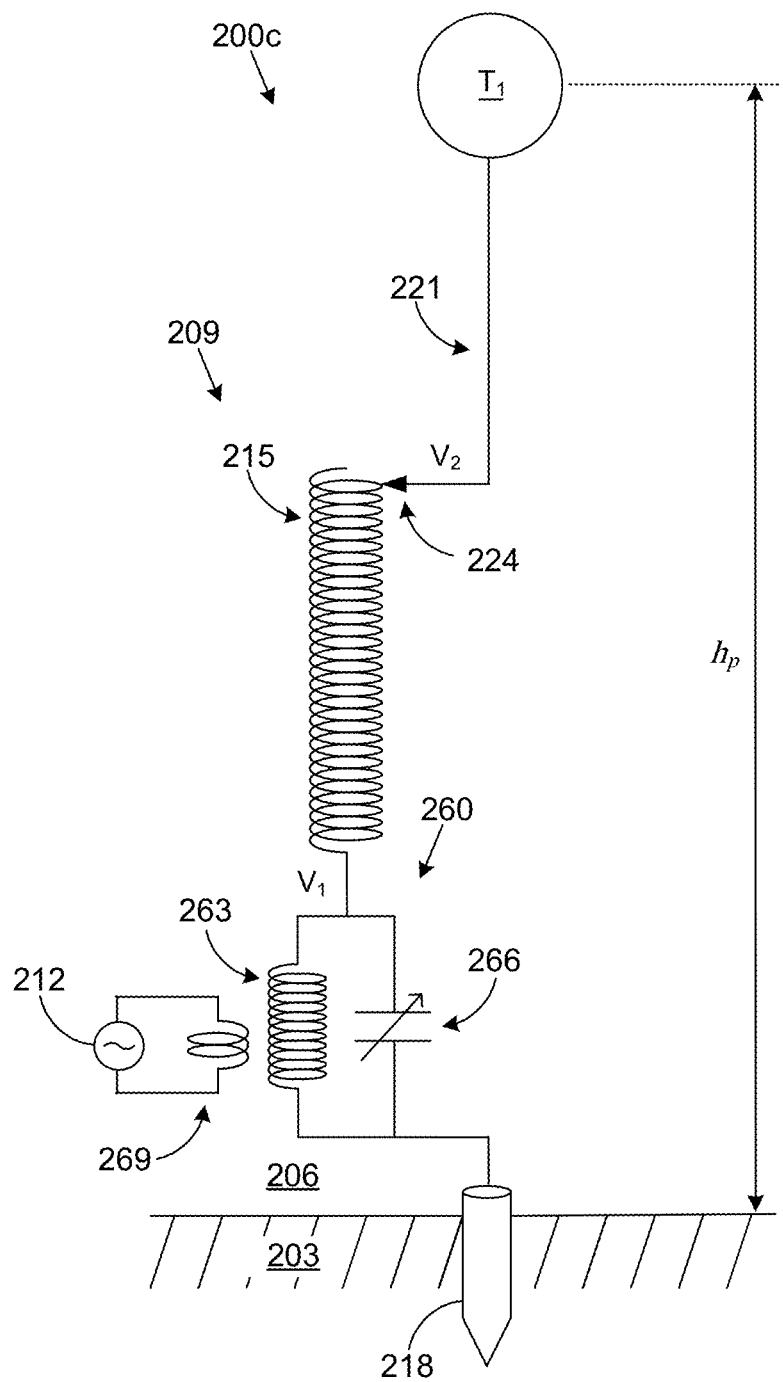

FIG. 7B shows a graphical representation of another example of a guided surface waveguide probe 200c that includes a charge terminal $T_1$. As in FIG. 7A, the guided surface waveguide probe 200c can include the upper charge terminal $T_1$ positioned over the lossy conducting medium 203 (e.g., at height $h_p$). In the example of FIG. 7B, the phasing coil 215 is coupled at a first end to a ground stake (or grounding system) 218 via a lumped element tank circuit 260 and to the charge terminal $T_1$ at a second end via a vertical feed line conductor 221. The phasing coil 215 can be energized at an operating frequency by the excitation source 212 through, e.g., a tap 227 at a lower portion of the coil 215, as shown in FIG. 7A. In other implementations, the excitation source 212 can be inductively coupled to the phasing coil 215 or an inductive coil 263 of a tank circuit 260 through a primary coil 269. The inductive coil 263 may also be called a "lumped element" coil as it behaves as a lumped element or inductor. In the example of FIG. 7B, the phasing coil 215 is energized by the excitation source 212 through inductive coupling with the inductive coil 263 of the lumped element tank circuit 260. The lumped element tank circuit 260 comprises the inductive coil 263 and a capacitor 266.

The inductive coil 263 and/or the capacitor 266 can be fixed or variable to allow for adjustment of the tank circuit resonance, and thus the probe impedance.

Figure 7C:
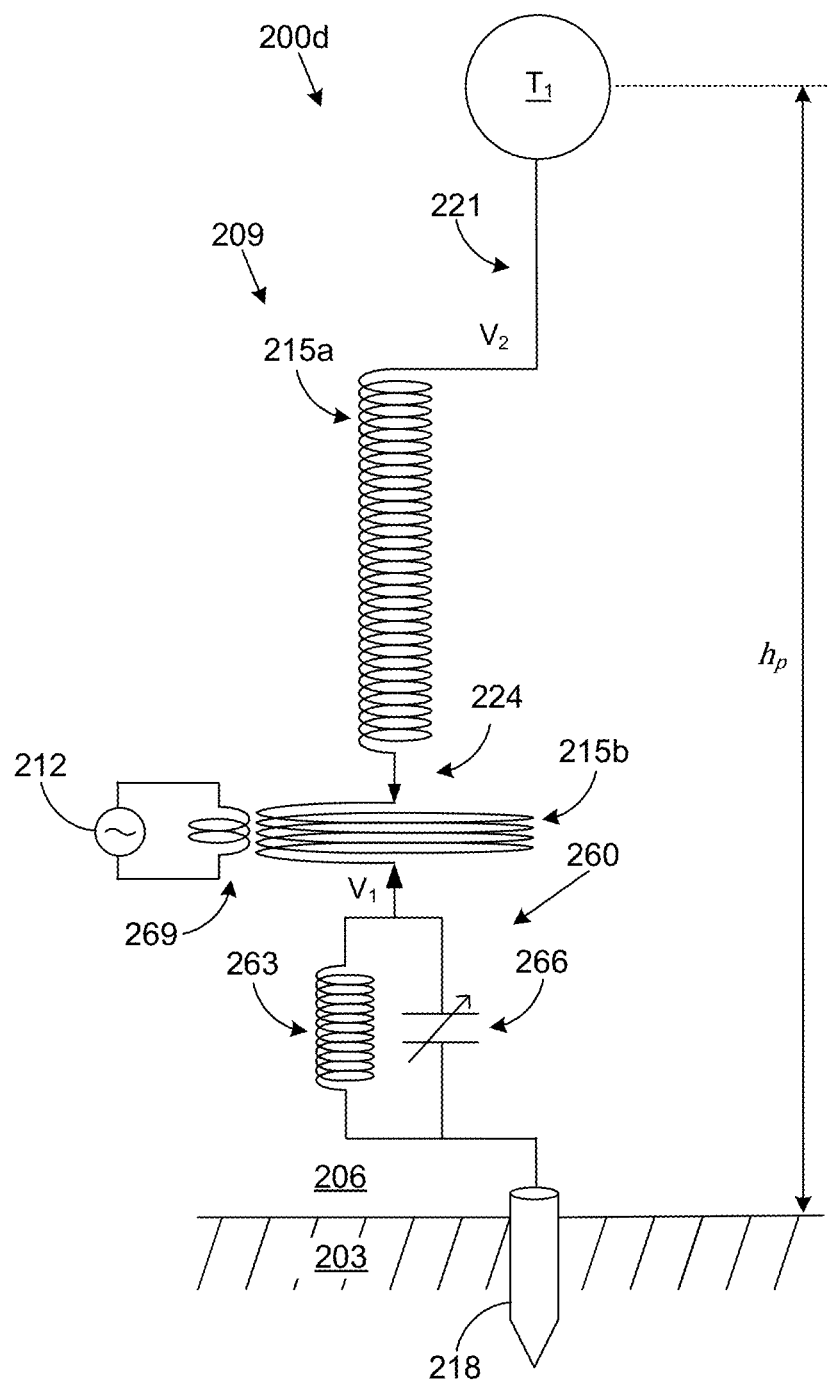

FIG. 7C shows a graphical representation of another example of a guided surface waveguide probe 200d that includes a charge terminal $T_1$. As in FIG. 7A, the guided surface waveguide probe 200d can include the upper charge terminal $T_1$ positioned over the lossy conducting medium 203 (e.g., at height $h_p$). The feed network 209 can comprise a plurality of phasing coils (e.g., helical coils) instead of a single phasing coil 215 as illustrated in FIGS. 7A and 7B. The plurality of phasing coils can include a combination of helical coils to provide the appropriate phase delay (e.g., $\theta_c=\theta_{ca}+\theta_{cb}$, where $\theta_{ca}$ and $\theta_{cb}$ correspond to the phase delays of coils 215a and 215b, respectively) to launch a guided surface wave. In the example of FIG. 7C, the feed network includes two phasing coils 215a and 215b connected in series with the lower coil 215b coupled to a ground stake (or grounding system) 218 via a lumped element tank circuit 260 and the upper coil 215a coupled to the charge terminal $T_1$ via a vertical feed line conductor 221. The phasing coils 215a and 215b can be energized at an operating frequency by the excitation source 212 through, e.g., inductive coupling via a primary coil 269 with, e.g., the upper phasing coil 215a, the lower phasing coil 215b, and/or an inductive coil 263 of the tank circuit 260. For example, as shown in FIG. 7C, the coil 215 can be energized by the excitation source 212 through inductive coupling from the primary coil 269 to the lower phasing coil 215b. Alternatively, as in the example shown in FIG. 7B, the coil 215 can be energized by the excitation source 212 through inductive coupling from the primary coil 269 to the inductive coil 263 of the lumped element tank circuit 260. The inductive coil 263 and/or the capacitor 266 of the lumped element tank circuit 260 can be fixed or variable to allow for adjustment of the tank circuit resonance, and thus the probe impedance.

At this point, it should be pointed out that there is a distinction between phase delays for traveling waves and phase shifts for standing waves. Phase delays for traveling waves, $\theta=\beta l$, are due to propagation time delays on distributed element wave guiding structures such as, e.g., the coil(s) 215 and vertical feed line conductor 221. A phase delay is not experienced as the traveling wave passes through the lumped element tank circuit 260. As a result, the total traveling wave phase delay through, e.g., the guided surface waveguide probes 200c and 200d is still $\Phi=\theta_c+\theta_y$.

However, the position dependent phase shifts of standing waves, which comprise forward and backward propagating waves, and load dependent phase shifts depend on both the line-length propagation delay and at transitions between line sections of different characteristic impedances. It should be noted that phase shifts do occur in lumped element circuits. Phase shifts also occur at the impedance discontinuities between transmission line segments and between line segments and loads. This comes from the complex reflection coefficient, $\Gamma=|\Gamma|e^{j\Phi}$, arising from the impedance discontinuities, and results in standing waves (wave interference patterns of forward and backward propagating waves) on the distributed element structures. As a result, the total standing wave phase shift of the guided surface waveguide probes 200c and 200d includes the phase shift produced by the lumped element tank circuit 260.

Accordingly, it should be noted that coils that produce both a phase delay for a traveling wave and a phase shift for standing waves can be referred to herein as "phasing coils." The coils 215 are examples of phasing coils. It should be further noted that coils in a tank circuit, such as the lumped element tank circuit 260 as described above, act as a lumped element and an inductor, where the tank circuit produces a phase shift for standing waves without a corresponding phase delay for traveling waves. Such coils acting as lumped elements or inductors can be referred to herein as "inductor coils" or "lumped element" coils. Inductive coil 263 is an example of such an inductor coil or lumped element coil. Such inductor coils or lumped element coils are assumed to have a uniform current distribution throughout the coil, and are electrically small relative to the wavelength of operation of the guided surface waveguide probe 200 such that they produce a negligible delay of a traveling wave.

The construction and adjustment of the guided surface waveguide probe 200 is based upon various operating conditions, such as the transmission frequency, conditions of the lossy conducting medium (e.g., soil conductivity σ and relative permittivity $\varepsilon_r$), and size of the charge terminal $T_1$. The index of refraction can be calculated from Equations (10) and (11) as $$n=\sqrt{\varepsilon_r-jx},\tag{41}$$

where $x=\sigma/\omega\varepsilon_o$ with $\omega=2\pi f$. The conductivity σ and relative permittivity $\varepsilon_r$ can be determined through test measurements of the lossy conducting medium 203. The complex Brewster angle $(\theta_{i,B})$ measured from the surface normal can also be determined from Equation (26) as $$\theta_{i,B}=\arctan(\sqrt{\varepsilon_r-jx}),\tag{42}$$

or measured from the surface as shown in FIG. 5A as $$\psi_{i,B}=\frac{\pi}{2}-\theta_{i,B}.\tag{43}$$

The wave tilt at the Hankel crossover distance $(W_{Rx})$ can also be found using Equation (40).

The Hankel crossover distance can also be found by equating the magnitudes of Equations (20b) and (21) for $-j\gamma\rho$, and solving for $R_x$ as illustrated by FIG. 4. The electrical effective height can then be determined from Equation (39) using the Hankel crossover distance and the complex Brewster angle as $$h_{eff}=h_p e^{j\Phi}=R_x \tan \psi_{i,B}.\tag{44}$$

As can be seen from Equation (44), the complex effective height $(h_{eff})$ includes a magnitude that is associated with the physical height $(h_p)$ of the charge terminal $T_1$ and a phase delay $(\Phi)$ that is to be associated with the angle $(\Psi)$ of the wave tilt at the Hankel crossover distance $(R_x)$. With these variables and the selected charge terminal $T_1$ configuration, it is possible to determine the configuration of a guided surface waveguide probe 200.

With the charge terminal $T_1$ positioned at or above the physical height $(h_p)$, the feed network 209 (FIG. 3) and/or the vertical feed line connecting the feed network to the charge terminal $T_1$ can be adjusted to match the phase delay $(\Phi)$ of the charge $Q_1$ on the charge terminal $T_1$ to the angle $(\Psi)$ of the wave tilt (W). The size of the charge terminal $T_1$ can be chosen to provide a sufficiently large surface for the charge $Q_1$ imposed on the terminals. In general, it is desirable to make the charge terminal $T_1$ as large as practical. The size of the charge terminal $T_1$ should be large enough to avoid ionization of the surrounding air, which can result in electrical discharge or sparking around the charge terminal.

The phase delay $\theta_c$ of a helically-wound coil can be determined from Maxwell's equations as has been discussed by Corum, K. L. and J. F. Corum, "RF Coils, Helical Resonators and Voltage Magnification by Coherent Spatial Modes," *Microwave Review*, Vol. 7, No. 2, September 2001, pp. 36-45, which is incorporated herein by reference in its entirety. For a helical coil with H/D>1, the ratio of the velocity of propagation (v) of a wave along the coil's longitudinal axis to the speed of light (c), or the "velocity factor," is given by $$V_f = \frac{v}{c} = \frac{1}{\sqrt{1 + 20\left(\frac{D}{s}\right)^{2.5}\left(\frac{D}{\lambda_o}\right)^{0.5}}}, \quad (45)$$

where H is the axial length of the solenoidal helix, D is the coil diameter, N is the number of turns of the coil, s=H/N is the turn-to-turn spacing (or helix pitch) of the coil, and $\lambda_o$ is the free-space wavelength. Based upon this relationship, the electrical length, or phase delay, of the helical coil is given by $$\theta_c = \beta_p H = \frac{2\pi}{\lambda_p} H = \frac{2\pi}{V_f \lambda_o} H. \quad (46)$$

The principle is the same if the helix is wound spirally or is short and fat, but $V_f$ and $\theta_c$ are easier to obtain by experimental measurement. The expression for the characteristic (wave) impedance of a helical transmission line has also been derived as $$Z_c = \frac{60}{V_f}\left[\ln\left(\frac{V_f \lambda_o}{D}\right) - 1.027\right]. \quad (47)$$

The spatial phase delay $\theta_y$ of the structure can be determined using the traveling wave phase delay of the vertical feed line conductor 221 (FIGS. 7A-7C). The capacitance of a cylindrical vertical conductor above a prefect ground plane can be expressed as $$C_A = \frac{2\pi\varepsilon_o h_w}{\ln\left(\frac{h}{a}\right) - 1} \text{ Farads}, \quad (48)$$

where $h_w$ is the vertical length (or height) of the conductor and a is the radius (in mks units). As with the helical coil, the traveling wave phase delay of the vertical feed line conductor can be given by $$\theta_y = \beta_w h_w = \frac{2\pi}{\lambda_w} h_w = \frac{2\pi}{V_w \lambda_o} h_w, \quad (49)$$

where $\beta_w$ is the propagation phase constant for the vertical feed line conductor, $h_w$ is the vertical length (or height) of the vertical feed line conductor, $V_w$ is the velocity factor on the wire, $\lambda_0$ is the wavelength at the supplied frequency, and $\lambda_w$ is the propagation wavelength resulting from the velocity factor $V_w$. For a uniform cylindrical conductor, the velocity factor is a constant with $V_w \approx 0.94$, or in a range from about 0.93 to about 0.98. If the mast is considered to be a uniform transmission line, its average characteristic impedance can be approximated by $$Z_w = \frac{60}{V_w}\left[\ln\left(\frac{h_w}{a}\right) - 1\right], \quad (50)$$

where $V_w \approx 0.94$ for a uniform cylindrical conductor and a is the radius of the conductor. An alternative expression that has been employed in amateur radio literature for the characteristic impedance of a single-wire feed line can be given by $$Z_w = 138 \log\left(\frac{1.123 V_w \lambda_o}{2\pi a}\right). \quad (51)$$

Equation (51) implies that $Z_w$ for a single-wire feeder varies with frequency. The phase delay can be determined based upon the capacitance and characteristic impedance.

With a charge terminal $T_1$ positioned over the lossy conducting medium 203 as shown in FIG. 3, the feed network 209 can be adjusted to excite the charge terminal $T_1$ with the phase delay ($\Phi$) of the complex effective height ($h_{eff}$) equal to the angle ($\Psi$) of the wave tilt at the Hankel crossover distance, or $\Phi=\Psi$. When this condition is met, the electric field produced by the charge oscillating $Q_1$ on the charge terminal $T_1$ is coupled into a guided surface waveguide mode traveling along the surface of a lossy conducting medium 203. For example, if the Brewster angle ($\theta_{i,B}$), the phase delay ($\theta_y$) associated with the vertical feed line conductor 221 (FIGS. 7A-7C), and the configuration of the coil(s) 215 (FIGS. 7A-7C) are known, then the position of the tap 224 (FIGS. 7A-7C) can be determined and adjusted to impose an oscillating charge $Q_1$ on the charge terminal $T_1$ with phase $\Phi=\Psi$. The position of the tap 224 may be adjusted to maximize coupling the traveling surface waves into the guided surface waveguide mode. Excess coil length beyond the position of the tap 224 can be removed to reduce the capacitive effects. The vertical wire height and/or the geometrical parameters of the helical coil may also be varied.

The coupling to the guided surface waveguide mode on the surface of the lossy conducting medium 203 can be improved and/or optimized by tuning the guided surface waveguide probe 200 for standing wave resonance with respect to a complex image plane associated with the charge $Q_1$ on the charge terminal $T_1$. By doing this, the performance of the guided surface waveguide probe 200 can be adjusted for increased and/or maximum voltage (and thus charge $Q_1$) on the charge terminal $T_1$. Referring back to FIG. 3, the effect of the lossy conducting medium 203 in Region 1 can be examined using image theory analysis.

Physically, an elevated charge $Q_1$ placed over a perfectly conducting plane attracts the free charge on the perfectly conducting plane, which then "piles up" in the region under the elevated charge $Q_1$. The resulting distribution of "bound" electricity on the perfectly conducting plane is similar to a bell-shaped curve. The superposition of the potential of the elevated charge $Q_1$, plus the potential of the induced "piled up" charge beneath it, forces a zero equipotential surface for the perfectly conducting plane. The boundary value problem solution that describes the fields in the region above the perfectly conducting plane may be obtained using the classical notion of image charges, where the field from the elevated charge is superimposed with the field from a corresponding "image" charge below the perfectly conducting plane.

This analysis may also be used with respect to a lossy conducting medium 203 by assuming the presence of an effective image charge $Q_1'$ beneath the guided surface waveguide probe 200. The effective image charge $Q_1'$ coincides with the charge $Q_1$ on the charge terminal $T_1$ about a conducting image ground plane 130, as illustrated in FIG. 3. However, the image charge $Q_1'$ is not merely located at some real depth and 180° out of phase with the primary source charge $Q_1$ on the charge terminal $T_1$, as they would be in the case of a perfect conductor. Rather, the lossy conducting medium 203 (e.g., a terrestrial medium) presents a phase shifted image. That is to say, the image charge $Q_1'$ is at a complex depth below the surface (or physical boundary) of the lossy conducting medium 203. For a discussion of complex image depth, reference is made to Wait, J. R., "Complex Image Theory—Revisited," *IEEE Antennas and Propagation Magazine*, Vol. 33, No. 4, August 1991, pp. 27-29, which is incorporated herein by reference in its entirety.

Instead of the image charge $Q_1'$ being at a depth that is equal to the physical height ($H_1$) of the charge $Q_1$, the conducting image ground plane 130 (representing a perfect conductor) is located at a complex depth of $z=-d/2$ and the image charge $Q_1'$ appears at a complex depth (i.e., the "depth" has both magnitude and phase), given by $-D_1=-(d/2+d/2+H_1)\neq H_1$. For vertically polarized sources over the Earth, $$d = \frac{2\sqrt{\gamma_e^2 + k_o^2}}{\gamma_e^2} \approx \frac{2}{\gamma_e} = d_r + jd_i = |d|\angle\zeta, \quad (52)$$

where $$\gamma_e^2 = j\omega\mu_1\sigma_1 - \omega^2\mu_1\varepsilon_1, \text{ and} \quad (53)$$

$$k_o = \omega\sqrt{\mu_o\varepsilon_o}, \quad (54)$$

as indicated in Equation (12). The complex spacing of the image charge, in turn, implies that the external field will experience extra phase shifts not encountered when the interface is either a dielectric or a perfect conductor. In the lossy conducting medium, the wave front normal is parallel to the tangent of the conducting image ground plane 130 at $z=-d/2$, and not at the boundary interface between Regions 1 and 2.

Consider the case illustrated in FIG. 8A where the lossy conducting medium 203 is a finitely conducting Earth 133 with a physical boundary 136. The finitely conducting Earth 133 may be replaced by a perfectly conducting image ground plane 139 as shown in FIG. 8B, which is located at a complex depth $z_1$ below the physical boundary 136. This equivalent representation exhibits the same impedance when looking down into the interface at the physical boundary 136. The equivalent representation of FIG. 8B can be modeled as an equivalent transmission line, as shown in FIG. 8C. The cross-section of the equivalent structure is represented as a (z-directed) end-loaded transmission line, with the impedance of the perfectly conducting image plane being a short circuit ($z_s=0$). The depth $z_1$ can be determined by equating the TEM wave impedance looking down at the Earth to an image ground plane impedance $z_{in}$ seen looking into the transmission line of FIG. 8C.

In the case of FIG. 8A, the propagation constant and wave intrinsic impedance in the upper region (air) 142 are $$\gamma_o = j\omega\sqrt{\mu_o\varepsilon_o} = 0 + j\beta_o, \text{ and} \quad (55)$$

$$z_o = \frac{j\omega\mu_o}{\gamma_o} = \sqrt{\frac{\mu_o}{\varepsilon_o}}. \quad (56)$$

In the lossy Earth 133, the propagation constant and wave intrinsic impedance are $$\gamma_e = j\omega\mu_1(\sigma_1 + j\omega\varepsilon_1), \text{ and} \quad (57)$$

$$Z_e = \frac{j\omega\mu_1}{\gamma_e}. \quad (58)$$

For normal incidence, the equivalent representation of FIG. 8B is equivalent to a TEM transmission line whose characteristic impedance is that of air ($z_o$), with propagation constant of $\gamma_o$, and whose length is $z_1$. As such, the image ground plane impedance $Z_{in}$ seen at the interface for the shorted transmission line of FIG. 8C is given by $$Z_{in} = Z_o \tanh(\gamma_o z_1). \quad (59)$$

Equating the image ground plane impedance $Z_{in}$ associated with the equivalent model of FIG. 8C to the normal incidence wave impedance of FIG. 8A and solving for $z_1$ gives the distance to a short circuit (the perfectly conducting image ground plane 139) as $$z_1 = \frac{1}{\gamma_o}\tanh^{-1}\left(\frac{Z_e}{Z_o}\right) = \frac{1}{\gamma_o}\tanh^{-1}\left(\frac{\gamma_o}{\gamma_e}\right) \approx \frac{1}{\gamma_e}, \quad (60)$$

where only the first term of the series expansion for the inverse hyperbolic tangent is considered for this approximation. Note that in the air region 142, the propagation constant is $\gamma_o = j\beta_o$, so $Z_{in} = jZ_o \tan\beta_o z_1$ (which is a purely imaginary quantity for a real $z_1$), but $z_e$ is a complex value if $\sigma \neq 0$. Therefore, $Z_{in} = Z_e$ only when $z_1$ is a complex distance.

Since the equivalent representation of FIG. 8B includes a perfectly conducting image ground plane 139, the image depth for a charge or current lying at the surface of the Earth (physical boundary 136) is equal to distance $z_1$ on the other side of the image ground plane 139, or $d=2\times z_1$ beneath the Earth's surface (which is located at $z=0$). Thus, the distance to the perfectly conducting image ground plane 139 can be approximated by $$d = 2z_1 \approx \frac{2}{\gamma_e}. \quad (61)$$

Additionally, the "image charge" will be "equal and opposite" to the real charge, so the potential of the perfectly conducting image ground plane 139 at depth $z_1=-d/2$ will be zero.

If a charge $Q_1$ is elevated a distance $H_1$ above the surface of the Earth as illustrated in FIG. 3, then the image charge $Q_1'$ resides at a complex distance of $D_1=d+H_1$ below the surface, or a complex distance of $d/2+H_1$ below the image ground plane 130. The guided surface waveguide probes 200 of FIGS. 7A-7C can be modeled as an equivalent single-wire transmission line image plane model that can be based upon the perfectly conducting image ground plane 139 of FIG. 8B.

Figure 9A:
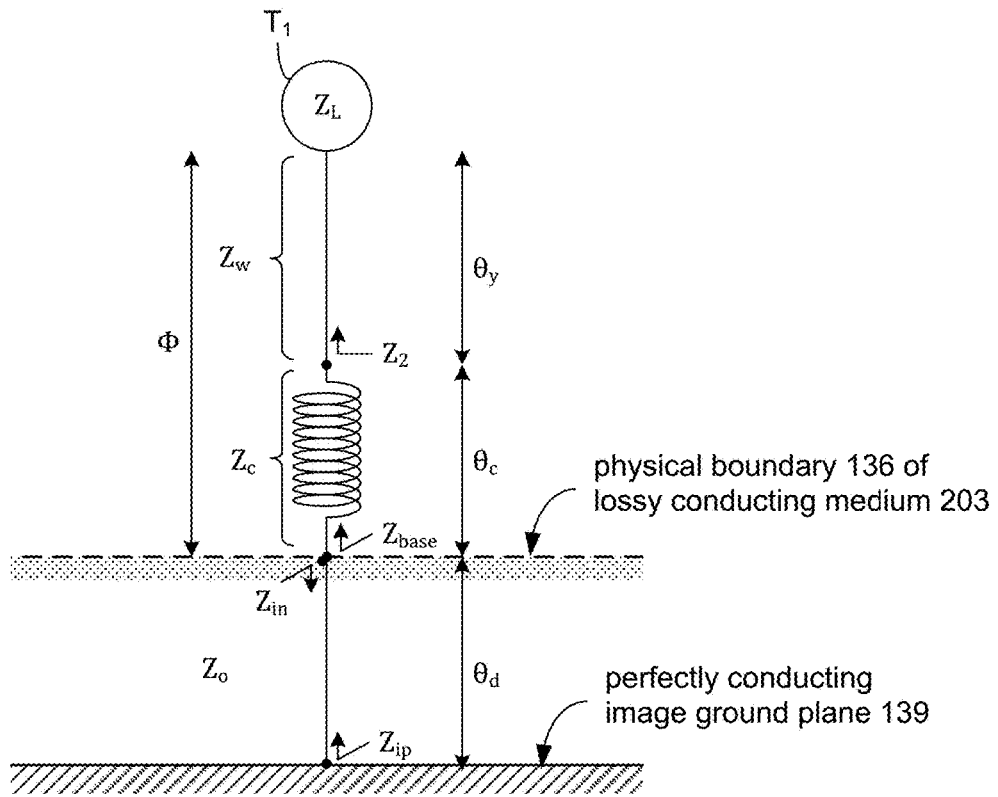
FIGS. 9A through 9C are graphical representations illustrating examples of single-wire transmission line and classic transmission line models of the equivalent image plane models of FIGS. 8B and 8C according to various embodiments of the present disclosure.
Figure 9B:
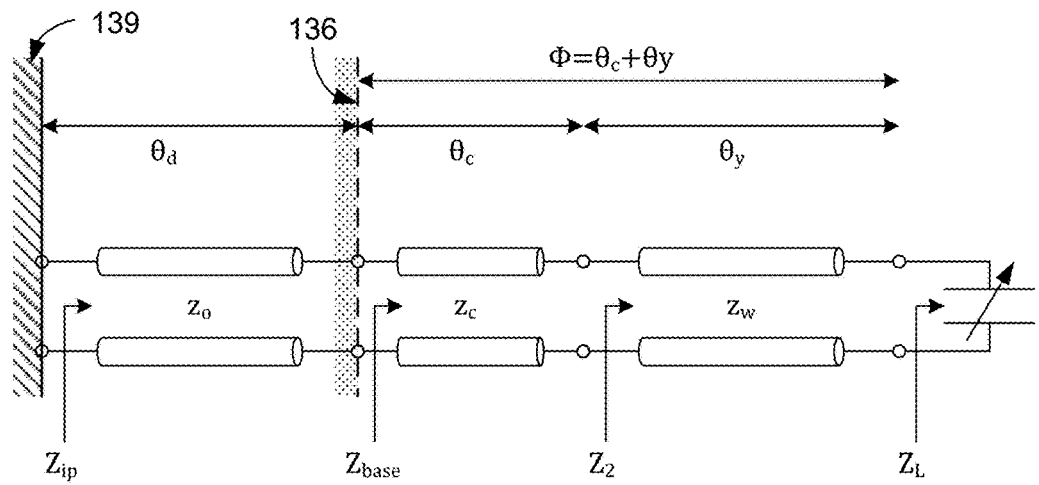

FIG. 9A shows an example of the equivalent single-wire transmission line image plane model, and FIG. 9B illustrates an example of the equivalent classic transmission line model, including the shorted transmission line of FIG. 8C.

Figure 9C:
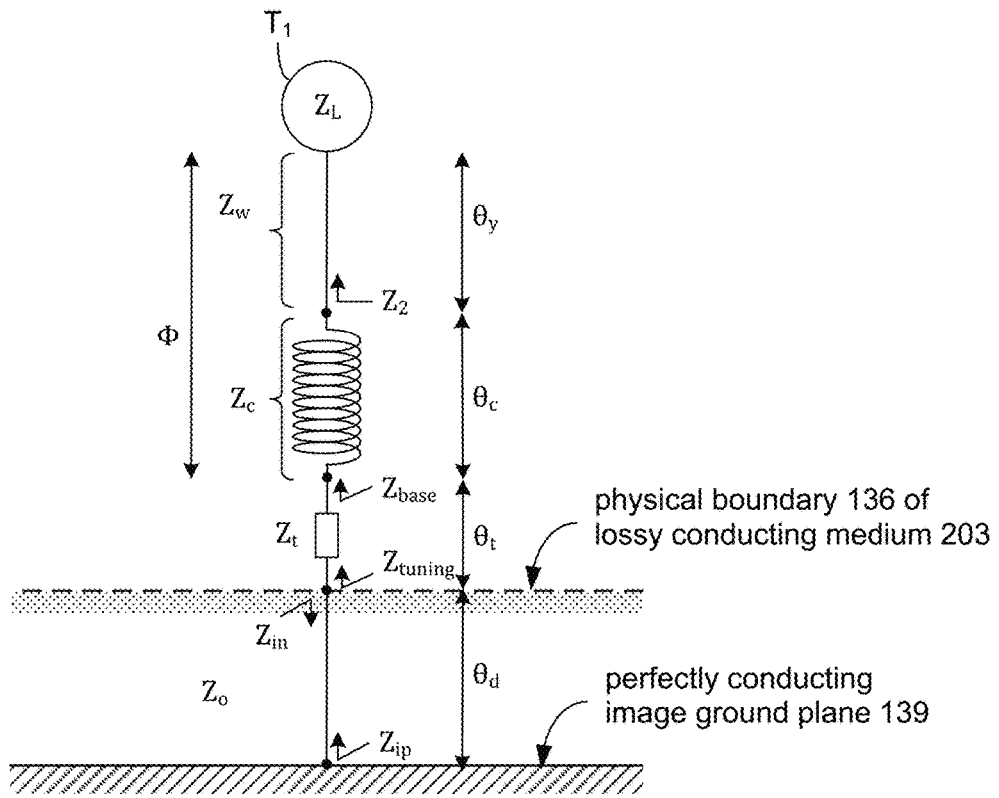

FIG. 9C illustrates an example of the equivalent classic transmission line model including the lumped element tank circuit 260.

In the equivalent image plane models of FIGS. 9A-9C, $\Phi=\theta_y+\theta_c$ is the traveling wave phase delay of the guided surface waveguide probe 200 referenced to Earth 133 (or the lossy conducting medium 203), $\theta_c=\beta_p H$ is the electrical length of the coil or coils 215 (FIGS. 7A-7C), of physical length H, expressed in degrees, $\theta_y=\beta_w h_w$ is the electrical length of the vertical feed line conductor 221 (FIGS. 7A-7C), of physical length $h_w$, expressed in degrees. In addition, $\theta_d=\beta_o d/2$ is the phase shift between the image ground plane 139 and the physical boundary 136 of the Earth 133 (or lossy conducting medium 203). In the example of FIGS. 9A-9C, $Z_w$ is the characteristic impedance of the elevated vertical feed line conductor 221 in ohms, $Z_c$ is the characteristic impedance of the coil(s) 215 in ohms, and $Z_0$ is the characteristic impedance of free space. In the example of FIG. 9C, $Z_t$ is the characteristic impedance of the lumped element tank circuit 260 in ohms and $\theta_t$ is the corresponding phase shift at the operating frequency.

At the base of the guided surface waveguide probe 200, the impedance seen "looking up" into the structure is $Z_\uparrow=Z_{base}$. With a load impedance of:

$$Z_L = \frac{1}{j\omega C_T}, \tag{62}$$

where $C_T$ is the self-capacitance of the charge terminal $T_1$, the impedance seen "looking up" into the vertical feed line conductor 221 (FIGS. 7A-7C) is given by:

$$Z_2 = Z_W \frac{Z_L + Z_w \tanh(j\beta_w h_w)}{Z_w + Z_L \tanh(j\beta_w h_w)} = Z_W \frac{Z_L + Z_w \tanh(j\theta_y)}{Z_w + Z_L \tanh(j\theta_y)}, \tag{63}$$

and the impedance seen "looking up" into the coil 215 (FIGS. 7A and 7B) is given by:

$$Z_{base} = Z_c \frac{Z_2 + Z_c \tanh(j\beta_p H)}{Z_c + Z_2 \tanh(j\beta_p H)} = Z_c \frac{Z_2 + Z_c \tanh(j\theta_c)}{Z_c + Z_2 \tanh(j\theta_c)}. \tag{64}$$

Where the feed network 209 includes a plurality of coils 215 (e.g., FIG. 7C), the impedance seen at the base of each coil 215 can be sequentially determined using Equation (64). For example, the impedance seen "looking up" into the upper coil 215a of FIG. 7C is given by:

$$Z_{coil} = Z_{ca} \frac{Z_2 + Z_{ca}\tanh(j\beta_p H)}{Z_{ca} + Z_2\tanh(j\beta_p H)} = Z_{ca} \frac{Z_2 + Z_{ca}\tanh(j\theta_{ca})}{Z_{ca} + Z_2\tanh(j\theta_{ca})}, \tag{64.1}$$

and the impedance seen "looking up" into the lower coil 215b of FIG. 7C can be given by:

$$Z_{base} = Z_{cb} \frac{Z_{coil} + Z_{cb}\tanh(j\beta_p H)}{Z_{cb} + Z_{coil}\tanh(j\beta_p H)} = Z_{cb} \frac{Z_{coil} + Z_{cb}\tanh(j\theta_{cb})}{Z_{ca} + Z_{coil}\tanh(j\theta_c b)}, \tag{64.2}$$

where $Z_{ca}$ and $Z_{cb}$ are the characteristic impedances of the upper and lower coils. This can be extended to account for additional coils 215 as needed. At the base of the guided surface waveguide probe 200, the impedance seen "looking down" into the lossy conducting medium 203 is $Z_\downarrow=Z_{in}$, which is given by:

$$Z_{in} = Z_o \frac{Z_s + Z_o\tanh[j\beta_o(d/2)]}{Z_o + Z_s\tanh[j\beta_o(d/2)]} = Z_o\tanh(j\theta_d), \tag{65}$$

where $Z_s=0$.

Neglecting losses, the equivalent image plane model can be tuned to resonance when $Z_\downarrow+Z_\uparrow=0$ at the physical boundary 136. Or, in the low loss case, $X_\downarrow+X_\uparrow=0$ at the physical boundary 136, where X is the corresponding reactive component. Thus, the impedance at the physical boundary 136 "looking up" into the guided surface waveguide probe 200 is the conjugate of the impedance at the physical boundary 136 "looking down" into the lossy conducting medium 203. By adjusting the probe impedance via the load impedance $Z_L$ of the charge terminal $T_1$ while maintaining the traveling wave phase delay $\Phi$ equal to the angle of the media's wave tilt IF, so that $\Phi=\Psi$, which improves and/or maximizes coupling of the probe's electric field to a guided surface waveguide mode along the surface of the lossy conducting medium 203 (e.g., Earth), the equivalent image plane models of FIGS. 9A and 9B can be tuned to resonance with respect to the image ground plane 139. In this way, the impedance of the equivalent complex image plane model is purely resistive, which maintains a superposed standing wave on the probe structure that maximizes the voltage and elevated charge on terminal $T_1$, and by equations (1)-(3) and (16) maximizes the propagating surface wave.

While the load impedance $Z_L$ of the charge terminal $T_1$ can be adjusted to tune the probe 200 for standing wave resonance with respect to the image ground plane 139, in some embodiments a lumped element tank circuit 260 located between the coil(s) 215 (FIGS. 7B and 7C) and the ground stake (or grounding system) 218 can be adjusted to tune the probe 200 for standing wave resonance with respect to the image ground plane 139 as illustrated in FIG. 9C. A phase delay is not experienced as the traveling wave passes through the lumped element tank circuit 260. As a result, the total traveling wave phase delay through, e.g., the guided surface waveguide probes 200c and 200d is still $\Phi=\theta_c+\theta_y$. However, it should be noted that phase shifts do occur in lumped element circuits. Phase shifts also occur at impedance discontinuities between transmission line segments and between line segments and loads. Thus, the tank circuit 260 may also be referred to as a "phase shift circuit."

Figure 9D:
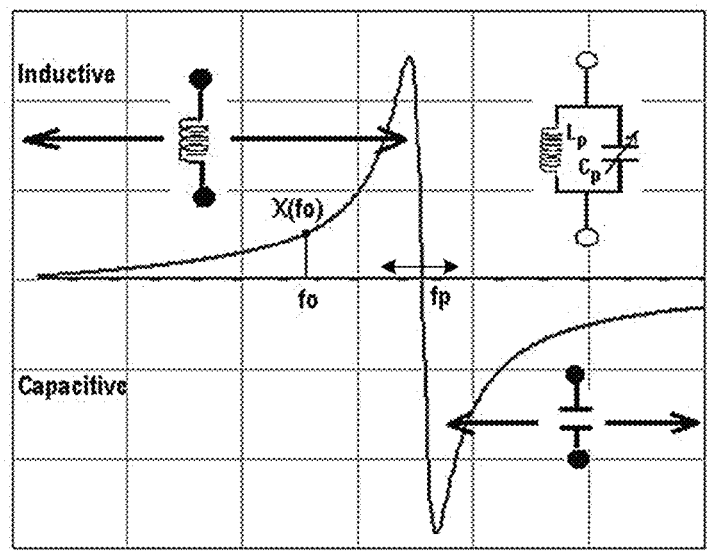
FIG. 9D is a plot illustrating an example of the reactance variation of a lumped element tank circuit with respect to operating frequency according to various embodiments of the present disclosure.

With the lumped element tank circuit 260 coupled to the base of the guided surface waveguide probe 200, the impedance seen "looking up" into the tank circuit 260 is $Z_\uparrow=Z_{tuning}$, which can be given by:

$$Z_{tuning}=Z_{base}-Z_t,$$

where $Z_t$ is the characteristic impedance of the tank circuit 260 and $Z_{base}$ is the impedance seen "looking up" into the coil(s) as given in, e.g., Equations (64) or (64.2). FIG. 9D illustrates the variation of the impedance of the lumped element tank circuit 260 with respect to operating frequency ($f_0$) based upon the resonant frequency ($f_p$) of the tank circuit 260. As shown in FIG. 9D, the impedance of the lumped element tank 260 can be inductive or capacitive depending on the tuned self-resonant frequency of the tank circuit. When operating the tank circuit 260 at a frequency below its self-resonant frequency ($f_p$), its terminal point impedance is inductive, and for operation above $f_p$ the terminal point impedance is capacitive. Adjusting either the inductance 263 or the capacitance 266 of the tank circuit 260 changes $f_p$ and shifts the impedance curve in FIG. 9D, which affects the terminal point impedance seen at a given operating frequency $f_0$.

Neglecting losses, the equivalent image plane model with the tank circuit 260 can be tuned to resonance when $Z_\downarrow + Z_\uparrow = 0$ at the physical boundary 136. Or, in the low loss case, $X_\downarrow + X_\uparrow = 0$ at the physical boundary 136, where X is the corresponding reactive component. Thus, the impedance at the physical boundary 136 "looking up" into the lumped element tank circuit 260 is the conjugate of the impedance at the physical boundary 136 "looking down" into the lossy conducting medium 203. By adjusting the lumped element tank circuit 260 while maintaining the traveling wave phase delay $\Phi$ equal to the angle of the media's wave tilt $\Psi$, so that $\Phi = \Psi$, the equivalent image plane models can be tuned to resonance with respect to the image ground plane 139. In this way, the impedance of the equivalent complex image plane model is purely resistive, which maintains a superposed standing wave on the probe structure that maximizes the voltage and elevated charge on terminal $T_1$, and improves and/or maximizes coupling of the probe's electric field to a guided surface waveguide mode along the surface of the lossy conducting medium 203 (e.g., earth).

It follows from the Hankel solutions, that the guided surface wave excited by the guided surface waveguide probe 200 is an outward propagating traveling wave. The source distribution along the feed network 209 between the charge terminal $T_1$ and the ground stake (or grounding system) 218 of the guided surface waveguide probe 200 (FIGS. 3 and 7A-7C) is actually composed of a superposition of a traveling wave plus a standing wave on the structure. With the charge terminal $T_1$ positioned at or above the physical height $h_p$, the phase delay of the traveling wave moving through the feed network 209 is matched to the angle of the wave tilt associated with the lossy conducting medium 203. This mode-matching allows the traveling wave to be launched along the lossy conducting medium 203. Once the phase delay has been established for the traveling wave, the load impedance $Z_L$ of the charge terminal $T_1$ and/or the lumped element tank circuit 260 can be adjusted to bring the probe structure into standing wave resonance with respect to the image ground plane (130 of FIG. 3 or 139 of FIG. 8), which is at a complex depth of $-d/2$. In that case, the impedance seen from the image ground plane has zero reactance and the charge on the charge terminal $T_1$ is maximized.

The distinction between the traveling wave phenomenon and standing wave phenomena is that (1) the phase delay of traveling waves ($\theta = \beta d$) on a section of transmission line of length d (sometimes called a "delay line") is due to propagation time delays; whereas (2) the position-dependent phase of standing waves (which are composed of forward and backward propagating waves) depends on both the line length propagation time delay and impedance transitions at interfaces between line sections of different characteristic impedances. In addition to the phase delay that arises due to the physical length of a section of transmission line operating in sinusoidal steady-state, there is an extra reflection coefficient phase at impedance discontinuities that is due to the ratio of $Z_{oa}/Z_{ob}$, where $Z_{oa}$ and $Z_{ob}$ are the characteristic impedances of two sections of a transmission line such as, e.g., a helical coil section of characteristic impedance $Z_{oa} = Z_c$ (FIG. 9B) and a straight section of vertical feed line conductor of characteristic impedance $Z_{ob} = Z_w$ (FIG. 9B).

As a result of this phenomenon, two relatively short transmission line sections of widely differing characteristic impedance may be used to provide a very large phase shift. For example, a probe structure composed of two sections of transmission line, one of low impedance and one of high impedance, together totaling a physical length of, say, $0.05\lambda$, may be fabricated to provide a phase shift of $90°$, which is equivalent to a $0.25\lambda$ resonance. This is due to the large jump in characteristic impedances. In this way, a physically short probe structure can be electrically longer than the two physical lengths combined. This is illustrated in FIGS. 9A and 9B, where the discontinuities in the impedance ratios provide large jumps in phase. The impedance discontinuity provides a substantial phase shift where the sections are joined together.

Figure 10:
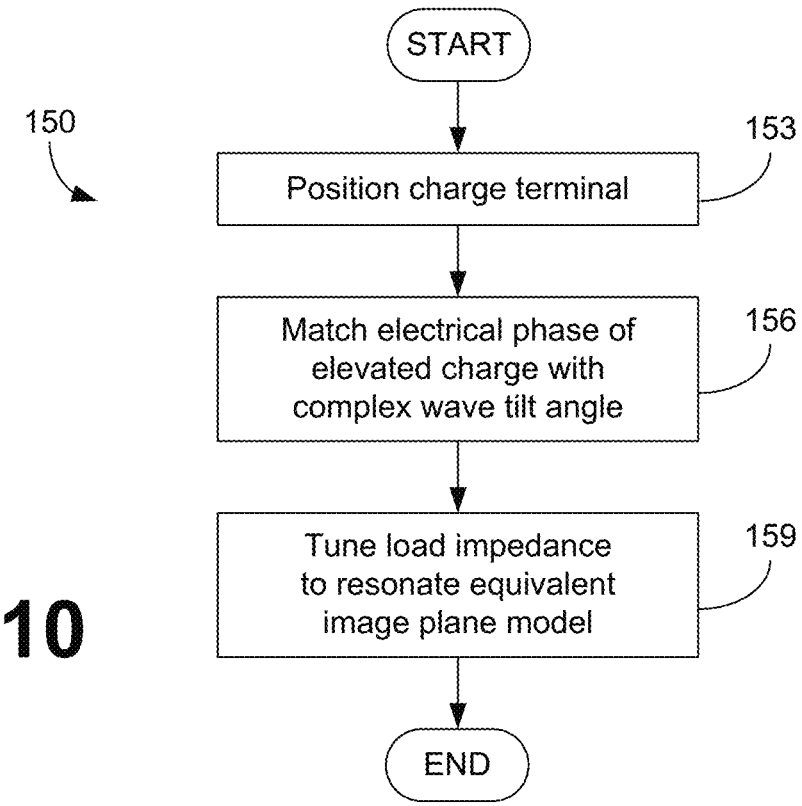
FIG. 10 is a flow chart illustrating an example of adjusting a guided surface waveguide probe of FIGS. 3 and 7A-7C to launch a guided surface wave along the surface of a lossy conducting medium according to various embodiments of the present disclosure.

Referring to FIG. 10, shown is a flow chart 150 illustrating an example of adjusting a guided surface waveguide probe 200 (FIGS. 3 and 7A-7C) to substantially mode-match to a guided surface waveguide mode on the surface of the lossy conducting medium, which launches a guided surface traveling wave along the surface of a lossy conducting medium 203 (FIGS. 3 and 7A-7C). Beginning with 153, the charge terminal $T_1$ of the guided surface waveguide probe 200 is positioned at a defined height above a lossy conducting medium 203. Utilizing the characteristics of the lossy conducting medium 203 and the operating frequency of the guided surface waveguide probe 200, the Hankel crossover distance can also be found by equating the magnitudes of Equations (20b) and (21) for $-j\gamma\rho$, and solving for $R_x$ as illustrated by FIG. 4. The complex index of refraction (n) can be determined using Equation (41), and the complex Brewster angle ($\theta_{i,B}$) can then be determined from Equation (42). The physical height ($h_p$) of the charge terminal $T_1$ can then be determined from Equation (44). The charge terminal $T_1$ should be at or higher than the physical height ($h_p$) in order to excite the far-out component of the Hankel function. This height relationship is initially considered when launching surface waves. To reduce or minimize the bound charge on the charge terminal $T_1$, the height should be at least four times the spherical diameter (or equivalent spherical diameter) of the charge terminal $T_1$.

At 156, the electrical phase delay $\Phi$ of the elevated charge $Q_1$ on the charge terminal $T_1$ is matched to the complex wave tilt angle $\Psi$. The phase delay ($\theta_c$) of the helical coil(s) and/or the phase delay ($\theta_y$) of the vertical feed line conductor can be adjusted to make $\Phi$ equal to the angle ($\Psi$) of the wave tilt (W). Based on Equation (31), the angle ($\Psi$) of the wave tilt can be determined from:

$$W = \frac{E_\rho}{E_z} = \frac{1}{\tan\theta_{i,B}} = \frac{1}{n} = |W|e^{j\Psi}. \qquad (66)$$

The electrical phase delay $\Phi$ can then be matched to the angle of the wave tilt. This angular (or phase) relationship is next considered when launching surface waves. For example, the electrical phase delay $\Phi = \theta_c + \theta_y$ can be adjusted by varying the geometrical parameters of the coil(s) 215 (FIGS. 7A-7C) and/or the length (or height) of the vertical feed line conductor 221 (FIGS. 7A-7C). By matching $\Phi = \Psi$, an electric field can be established at or beyond the Hankel crossover distance ($R_x$) with a complex Brewster angle at the boundary interface to excite the surface waveguide mode and launch a traveling wave along the lossy conducting medium 203.

Next at 159, the impedance of the charge terminal $T_1$ and/or the lumped element tank circuit 260 can be tuned to resonate the equivalent image plane model of the guided surface waveguide probe 200. The depth (d/2) of the conducting image ground plane 139 of FIGS. 9A and 9B (or 130 of FIG. 3) can be determined using Equations (52), (53) and (54) and the values of the lossy conducting medium 203 (e.g., the Earth), which can be measured. Using that depth, the phase shift ($\theta_d$) between the image ground plane 139 and the physical boundary 136 of the lossy conducting medium 203 can be determined using $\theta_d = \beta_o \, d/2$. The impedance ($Z_{in}$) as seen "looking down" into the lossy conducting medium 203 can then be determined using Equation (65). This resonance relationship can be considered to maximize the launched surface waves.

Based upon the adjusted parameters of the coil(s) 215 and the length of the vertical feed line conductor 221, the velocity factor, phase delay, and impedance of the coil(s) 215 and vertical feed line conductor 221 can be determined using Equations (45) through (51). In addition, the self-capacitance ($C_T$) of the charge terminal $T_1$ can be determined using, e.g., Equation (24). The propagation factor ($\beta_p$) of the coil(s) 215 can be determined using Equation (35) and the propagation phase constant ($\beta_w$) for the vertical feed line conductor 221 can be determined using Equation (49). Using the self-capacitance and the determined values of the coil(s) 215 and vertical feed line conductor 221, the impedance ($Z_{base}$) of the guided surface waveguide probe 200 as seen "looking up" into the coil(s) 215 can be determined using Equations (62), (63), (64), (64.1) and/or (64.2).

The equivalent image plane model of the guided surface waveguide probe 200 can be tuned to resonance by, e.g., adjusting the load impedance $Z_L$ such that the reactance component $X_{base}$ of $Z_{base}$ cancels out the reactance component $X_{in}$ of $Z_{in}$, or $X_{base} + X_{in} = 0$. Thus, the impedance at the physical boundary 136 "looking up" into the guided surface waveguide probe 200 is the conjugate of the impedance at the physical boundary 136 "looking down" into the lossy conducting medium 203. The load impedance $Z_L$ can be adjusted by varying the capacitance ($C_T$) of the charge terminal $T_1$ without changing the electrical phase delay $\Phi = \theta_c + \theta_y$ of the charge terminal $T_1$. An iterative approach may be taken to tune the load impedance $Z_L$ for resonance of the equivalent image plane model with respect to the conducting image ground plane 139 (or 130). In this way, the coupling of the electric field to a guided surface waveguide mode along the surface of the lossy conducting medium 203 (e.g., Earth) can be improved and/or maximized.

The equivalent image plane model of the guided surface waveguide probe 200 can also be tuned to resonance by, e.g., adjusting the lumped element tank circuit 260 such that the reactance component $X_{tuning}$ of $Z_{tuning}$, cancels out the reactance component $X_{in}$ of $Z_{in}$, or $X_{tuning} + X_{in} = 0$. Consider the parallel resonance curve in FIG. 9D, whose terminal point impedance at some operating frequency ($f_o$) is given by $$jX_T(f) = \frac{(j2\pi f L_p)(j2\pi f C_p)^{-1}}{(j2\pi f L_p) + (j2\pi f C_p)^{-1}} = j\frac{2\pi f L_p}{1 - (2\pi f L_p)^2 L_p C_p}.$$

As $C_p$ (or $L_p$) is varied, the self-resonant frequency ($f_p$) of the parallel tank circuit 260 changes and the terminal point reactance $X_T(L)$ at the frequency of operation varies from inductive (+) to capacitive (−) depending on whether $f_o < f_p$ or $f_p < f_o$. By adjusting $f_p$, a wide range of reactance at $f_o$ (e.g., a large inductance $L_{eq}(f_o) = X_T(f_o)/\omega$ or a small capacitance $C_{eq}(f_o) = -1/\omega X_T(f_o)$) can be seen at the terminals of the tank circuit 260.

To obtain the electrical phase delay ($\Phi$) for coupling into the guided surface waveguide mode, the coil(s) 215 and vertical feed line conductor 221 are usually less than a quarter wavelength. For this, an inductive reactance can be added by the lumped element tank circuit 260 so that the impedance at the physical boundary 136 "looking up" into the lumped element tank circuit 260 is the conjugate of the impedance at the physical boundary 136 "looking down" into the lossy conducting medium 203.

As seen in FIG. 9D, adjusting $f_p$ of the tank circuit 260 (FIG. 7C) above the operating frequency ($f_0$) can provide the needed impedance, without changing the electrical phase delay $\Phi = \theta_c + \theta_y$ of the charge terminal $T_1$, to tune for resonance of the equivalent image plane model with respect to the conducting image ground plane 139 (or 130). In some cases, a capacitive reactance may be needed and can be provided by adjusting $f_p$ of the tank circuit 260 below the operating frequency. In this way, the coupling of the electric field to a guided surface waveguide mode along the surface of the lossy conducting medium 203 (e.g., earth) can be improved and/or maximized.

This may be better understood by illustrating the situation with a numerical example. Consider a guided surface waveguide probe 200$b$ (FIG. 7A) comprising a top-loaded vertical stub of physical height $h_p$ with a charge terminal $T_1$ at the top, where the charge terminal $T_1$ is excited through a helical coil and vertical feed line conductor at an operational frequency ($f_0$) of 1.85 MHz. With a height ($H_1$) of 16 feet and the lossy conducting medium 203 (e.g., Earth) having a relative permittivity of $\varepsilon_r = 15$ and a conductivity of $\sigma_1 = 0.010$ mhos/m, several surface wave propagation parameters can be calculated for $f_o = 1.850$ MHz. Under these conditions, the Hankel crossover distance can be found to be $R_x = 54.5$ feet with a physical height of $h_p = 5.5$ feet, which is well below the actual height of the charge terminal $T_1$. While a charge terminal height of $H_1 = 5.5$ feet could have been used, the taller probe structure reduced the bound capacitance, permitting a greater percentage of free charge on the charge terminal $T_1$ providing greater field strength and excitation of the traveling wave.

The wave length can be determined as:

$$\lambda_o = \frac{c}{f_o} = 162.162 \text{ meters,} \tag{67}$$

where c is the speed of light. The complex index of refraction is:

$$n = \sqrt{\varepsilon_r - jx} = 7.529 - j6.546, \tag{68}$$

from Equation (41), where $x = \sigma_1/\omega\varepsilon_o$ with $\omega = 2\pi f_o$, and the complex Brewster angle is:

$$\theta_{i,B} = \arctan(\sqrt{\varepsilon_r - jx}) = 85.6 - j3.744°. \tag{69}$$

from Equation (42). Using Equation (66), the wave tilt values can be determined to be:

$$W = \frac{1}{\tan\theta_{i,B}} = \frac{1}{n} = |W|e^{j\Psi} = 0.101e^{j40.614°}. \tag{70}$$

Thus, the helical coil can be adjusted to match $\Phi = \Psi = 40.614°$

The velocity factor of the vertical feed line conductor (approximated as a uniform cylindrical conductor with a diameter of 0.27 inches) can be given as $V_w \approx 0.93$. Since $h_p \ll \lambda_o$, the propagation phase constant for the vertical feed line conductor can be approximated as:

$$\beta_w = \frac{2\pi}{\lambda_w} = \frac{2\pi}{V_w \lambda_0} = 0.042 \text{ m}^{-1}. \tag{71}$$

From Equation (49) the phase delay of the vertical feed line conductor is:

$$\theta_y = \beta_w h_w \approx \beta_w h_p = 11.640°. \tag{72}$$

Figure 11:
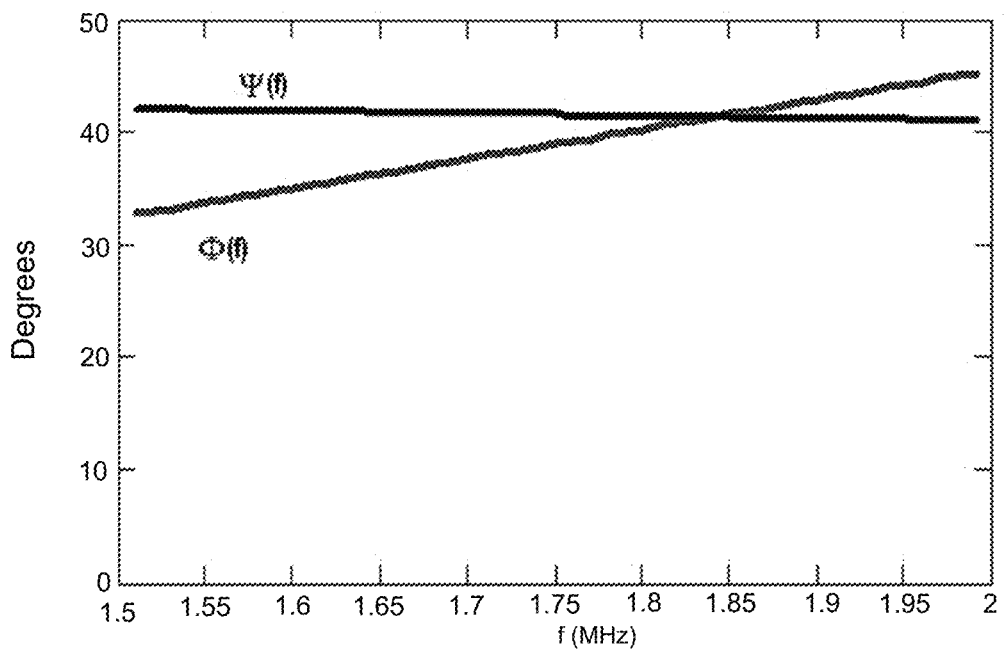
FIG. 11 is a plot illustrating an example of the relationship between a wave tilt angle and the phase delay of a guided surface waveguide probe of FIGS. 3 and 7A-C according to various embodiments of the present disclosure.

By adjusting the phase delay of the helical coil so that $\theta_c = 28.974° = 40.614° - 11.640°$, $\Phi$ will equal $\Psi$ to match the guided surface waveguide mode. To illustrate the relationship between $\Phi$ and $\Psi$, FIG. 11 shows a plot of both over a range of frequencies. As both $\Phi$ and $\Psi$ are frequency dependent, it can be seen that their respective curves cross over each other at approximately 1.85 MHz.

For a helical coil having a conductor diameter of 0.0881 inches, a coil diameter (D) of 30 inches and a turn-to-turn spacing (s) of 4 inches, the velocity factor for the coil can be determined using Equation (45) as:

$$V_f = \frac{1}{\sqrt{1 + 20\left(\frac{D}{s}\right)^{2.5}\left(\frac{D}{\lambda_o}\right)^{0.5}}} = 0.069, \tag{73}$$

and the propagation factor from Equation (35) is:

$$\beta_p = \frac{2\pi}{V_f \lambda_0} = 0.564 \text{ m}^{-1}. \tag{74}$$

With $\theta_c = 28.974°$, the axial length of the solenoidal helix (H) can be determined using Equation (46) such that:

$$H = \frac{\theta_c}{\beta_p} = 35.2732 \text{ inches}. \tag{75}$$

This height determines the location on the helical coil where the vertical feed line conductor is connected, resulting in a coil with 8.818 turns (N=H/s).

With the traveling wave phase delay of the coil and vertical feed line conductor adjusted to match the wave tilt angle ($1 = \theta_c + \theta_y = \Psi$), the load impedance ($Z_L$) of the charge terminal $T_1$ can be adjusted for standing wave resonance of the equivalent image plane model of the guided surface waveguide probe 200. From the measured permittivity, conductivity and permeability of the Earth, the radial propagation constant can be determined using Equation (57)

$$\gamma_e = \sqrt{j\omega\mu_1(\sigma_1 + j\omega\varepsilon_1)} = 0.25 + j0.292 \text{ m}^{-1}, \tag{76}$$

and the complex depth of the conducting image ground plane can be approximated from Equation (52) as:

$$d \approx \frac{2}{\gamma_e} = 3.364 + j\,3.963 \text{ meters}, \tag{77}$$

with a corresponding phase shift between the conducting image ground plane and the physical boundary of the Earth given by:

$$\theta_d = \beta_0(d/2) = 4.015 - j4.73°. \tag{78}$$

Using Equation (65), the impedance seen "looking down" into the lossy conducting medium 203 (i.e., Earth) can be determined as:

$$Z_{in} = Z_o \tan h(j\theta_d) = R_{in} + jX_{in} = 31.191 + j26.27 \text{ ohms}. \tag{79}$$

By matching the reactive component ($X_{in}$) seen "looking down" into the lossy conducting medium 203 with the reactive component ($X_{base}$) seen "looking up" into the guided surface waveguide probe 200, the coupling into the guided surface waveguide mode may be maximized. This can be accomplished by adjusting the capacitance of the charge terminal $T_1$ without changing the traveling wave phase delays of the coil and vertical feed line conductor. For example, by adjusting the charge terminal capacitance ($C_T$) to 61.8126 pF, the load impedance from Equation (62) is:

$$Z_L = \frac{1}{j\omega C_T} = -j\,1392 \text{ ohms}, \tag{80}$$

and the reactive components at the boundary are matched.

Using Equation (51), the impedance of the vertical feed line conductor (having a diameter (2a) of 0.27 inches) is given as $$Z_w = 138 \log\left(\frac{1.123\,V_w\lambda_0}{2\pi a}\right) = 537.534 \text{ ohms}, \tag{81}$$

and the impedance seen "looking up" into the vertical feed line conductor is given by Equation (63) as:

$$Z_2 = Z_W \frac{Z_L + Z_w \tanh(j\theta_y)}{Z_w + Z_L \tanh(j\theta_y)} = -j\,835.438 \text{ ohms}. \tag{82}$$

Using Equation (47), the characteristic impedance of the helical coil is given as $$Z_c = \frac{60}{V_f}\left[\ln\left(\frac{V_f \lambda_0}{D}\right) - 1.027\right] = 1446 \text{ ohms}, \tag{83}$$

and the impedance seen "looking up" into the coil at the base is given by Equation (64) as:

$$Z_{base} = Z_c \frac{Z_2 + Z_c \tanh(j\theta_c)}{Z_c + Z_2 \tanh(j\theta_c)} = -j\,26.271 \text{ ohms}. \tag{84}$$

When compared to the solution of Equation (79), it can be seen that the reactive components are opposite and approximately equal, and thus are conjugates of each other. Thus, the impedance ($Z_{ip}$) seen "looking up" into the equivalent image plane model of FIGS. 9A and 9B from the perfectly conducting image ground plane is only resistive or $Z_{ip} = R + j0$.

When the electric fields produced by a guided surface waveguide probe 200 (FIG. 3) are established by matching the traveling wave phase delay of the feed network to the wave tilt angle and the probe structure is resonated with respect to the perfectly conducting image ground plane at complex depth z=−d/2, the fields are substantially mode-matched to a guided surface waveguide mode on the surface of the lossy conducting medium, a guided surface traveling wave is launched along the surface of the lossy conducting medium. As illustrated in FIG. 1, the guided field strength curve 103 of the guided electromagnetic field has a characteristic exponential decay of $e^{-\alpha d}/\sqrt{d}$ and exhibits a distinctive knee 109 on the log-log scale.

If the reactive components of the impedance seen "looking up" into the coil and "looking down" into the lossy conducting medium are not opposite and approximately equal, then a lumped element tank circuit 260 (FIG. 7C) can be included between the coil 215 (FIG. 7A) and ground stake 218 (FIG. 7A) (or grounding system). The self-resonant frequency of the lumped element tank circuit can then be adjusted so that the reactive components "looking up" into the tank circuit of the guided surface waveguide probe and "looking down" into the into the lossy conducting medium are opposite and approximately equal. Under that condition, by adjusting the impedance ($Z_{ip}$) seen "looking up" into the equivalent image plane model of FIG. 9C from the perfectly conducting image ground plane is only resistive or $Z_{ip}$=R+j0.

In summary, both analytically and experimentally, the traveling wave component on the structure of the guided surface waveguide probe 200 has a phase delay (Φ) at its upper terminal that matches the angle (Ψ) of the wave tilt of the surface traveling wave (Φ=Ψ). Under this condition, the surface waveguide may be considered to be "mode-matched". Furthermore, the resonant standing wave component on the structure of the guided surface waveguide probe 200 has a $V_{MAX}$ at the charge terminal $T_1$ and a $V_{MIN}$ down at the image plane 139 (FIG. 8B) where $Z_{ip}$=$R_{ip}$+j0 at a complex depth of z=−d/2, not at the connection at the physical boundary 136 of the lossy conducting medium 203 (FIG. 8B). Lastly, the charge terminal $T_1$ is of sufficient height $H_1$ of FIG. 3 (h≥$R_x$ tan $\psi_{i,B}$) so that electromagnetic waves incident onto the lossy conducting medium 203 at the complex Brewster angle do so out at a distance (≥$R_x$) where the 1/√r term is predominant. Receive circuits can be utilized with one or more guided surface waveguide probes to facilitate wireless transmission and/or power delivery systems.

Referring back to FIG. 3, operation of a guided surface waveguide probe 200 may be controlled to adjust for variations in operational conditions associated with the guided surface waveguide probe 200. For example, an adaptive probe control system 230 can be used to control the feed network 209 and/or the charge terminal $T_1$ to control the operation of the guided surface waveguide probe 200. Operational conditions can include, but are not limited to, variations in the characteristics of the lossy conducting medium 203 (e.g., conductivity σ and relative permittivity $\varepsilon_r$), variations in field strength and/or variations in loading of the guided surface waveguide probe 200. As can be seen from Equations (31), (41) and (42), the index of refraction (n), the complex Brewster angle ($\theta_{i,B}$), and the wave tilt ($|W|e^{j\Psi}$) can be affected by changes in soil conductivity and permittivity resulting from, e.g., weather conditions.

Equipment such as, e.g., conductivity measurement probes, permittivity sensors, ground parameter meters, field meters, current monitors and/or load receivers can be used to monitor for changes in the operational conditions and provide information about current operational conditions to the adaptive probe control system 230. The probe control system 230 can then make one or more adjustments to the guided surface waveguide probe 200 to maintain specified operational conditions for the guided surface waveguide probe 200. For instance, as the moisture and temperature vary, the conductivity of the soil will also vary. Conductivity measurement probes and/or permittivity sensors may be located at multiple locations around the guided surface waveguide probe 200. Generally, it would be desirable to monitor the conductivity and/or permittivity at or about the Hankel crossover distance $R_x$ for the operational frequency. Conductivity measurement probes and/or permittivity sensors may be located at multiple locations (e.g., in each quadrant) around the guided surface waveguide probe 200.

The conductivity measurement probes and/or permittivity sensors can be configured to evaluate the conductivity and/or permittivity on a periodic basis and communicate the information to the probe control system 230. The information may be communicated to the probe control system 230 through a network such as, but not limited to, a LAN, WLAN, cellular network, or other appropriate wired or wireless communication network. Based upon the monitored conductivity and/or permittivity, the probe control system 230 may evaluate the variation in the index of refraction (n), the complex Brewster angle ($\theta_{i,B}$), and/or the wave tilt ($|W|e^{j\Psi}$) and adjust the guided surface waveguide probe 200 to maintain the phase delay Φ of the feed network 209 equal to the wave tilt angle (Ψ) and/or maintain resonance of the equivalent image plane model of the guided surface waveguide probe 200. This can be accomplished by adjusting, e.g., $\theta_y$, $\theta_c$ and/or $C_T$. For instance, the probe control system 230 can adjust the self-capacitance of the charge terminal $T_1$ and/or the phase delay ($\theta_y$, $\theta_c$) applied to the charge terminal $T_1$ to maintain the electrical launching efficiency of the guided surface wave at or near its maximum. For example, the self-capacitance of the charge terminal $T_1$ can be varied by changing the size of the terminal. The charge distribution can also be improved by increasing the size of the charge terminal $T_1$, which can reduce the chance of an electrical discharge from the charge terminal $T_1$. In other embodiments, the charge terminal $T_1$ can include a variable inductance that can be adjusted to change the load impedance $Z_L$. The phase applied to the charge terminal $T_1$ can be adjusted by varying the tap position on the coil(s) 215 (FIGS. 7A-7C), and/or by including a plurality of predefined taps along the coil(s) 215 and switching between the different predefined tap locations to maximize the launching efficiency.

Field or field strength (FS) meters may also be distributed about the guided surface waveguide probe 200 to measure field strength of fields associated with the guided surface wave. The field or FS meters can be configured to detect the field strength and/or changes in the field strength (e.g., electric field strength) and communicate that information to the probe control system 230. The information may be communicated to the probe control system 230 through a network such as, but not limited to, a LAN, WLAN, cellular network, or other appropriate communication network. As the load and/or environmental conditions change or vary during operation, the guided surface waveguide probe 200 may be adjusted to maintain specified field strength(s) at the FS meter locations to ensure appropriate power transmission to the receivers and the loads they supply.

For example, the phase delay (Φ=$\theta_y$+$\theta_c$) applied to the charge terminal $T_1$ can be adjusted to match the wave tilt angle (Ψ). By adjusting one or both phase delays, the guided surface waveguide probe 200 can be adjusted to ensure the wave tilt corresponds to the complex Brewster angle. This can be accomplished by adjusting a tap position on the coil(s) 215 (FIGS. 7A-7C) to change the phase delay supplied to the charge terminal $T_1$. The voltage level supplied to the charge terminal $T_1$ can also be increased or decreased to adjust the electric field strength. This may be accomplished by adjusting the output voltage of the excitation source 212 or by adjusting or reconfiguring the feed network 209. For instance, the position of the tap 227 (FIG. 7A) for the excitation source 212 can be adjusted to increase the voltage seen by the charge terminal $T_1$, where the excitation source 212 comprises, for example, an AC source as mentioned above. Maintaining field strength levels within predefined ranges can improve coupling by the receivers, reduce ground current losses, and avoid interference with transmissions from other guided surface waveguide probes 200.

The probe control system 230 can be implemented with hardware, firmware, software executed by hardware, or a combination thereof. For example, the probe control system 230 can include processing circuitry including a processor and a memory, both of which can be coupled to a local interface such as, for example, a data bus with an accompanying control/address bus as can be appreciated by those with ordinary skill in the art. A probe control application may be executed by the processor to adjust the operation of the guided surface waveguide probe 200 based upon monitored conditions. The probe control system 230 can also include one or more network interfaces for communicating with the various monitoring devices. Communications can be through a network such as, but not limited to, a LAN, WLAN, cellular network, or other appropriate communication network. The probe control system 230 may comprise, for example, a computer system such as a server, desktop computer, laptop, or other system with like capability.

Referring back to the example of FIG. 5A, the complex angle trigonometry is shown for the ray optic interpretation of the incident electric field (E) of the charge terminal $T_1$ with a complex Brewster angle ($\theta_{i,B}$) at the Hankel crossover distance ($R_x$). Recall that, for a lossy conducting medium, the Brewster angle is complex and specified by Equation (38). Electrically, the geometric parameters are related by the electrical effective height ($h_{eff}$) of the charge terminal $T_1$ by equation (39). Since both the physical height ($h_p$) and the Hankel crossover distance ($R_x$) are real quantities, the angle of the desired guided surface wave tilt at the Hankel crossover distance ($W_{Rx}$) is equal to the phase delay ($\Phi$) of the complex effective height ($h_{eff}$). With the charge terminal $T_1$ positioned at the physical height $h_p$ and excited with a charge having the appropriate phase $\Phi$, the resulting electric field is incident with the lossy conducting medium boundary interface at the Hankel crossover distance $R_x$, and at the Brewster angle. Under these conditions, the guided surface waveguide mode can be excited without reflection or substantially negligible reflection.

However, Equation (39) means that the physical height of the guided surface waveguide probe 200 can be relatively small. While this will excite the guided surface waveguide mode, this can result in an unduly large bound charge with little free charge. To compensate, the charge terminal $T_1$ can be raised to an appropriate elevation to increase the amount of free charge. As one example rule of thumb, the charge terminal $T_1$ can be positioned at an elevation of about 4-5 times (or more) the effective diameter of the charge terminal $T_1$. FIG. 6 illustrates the effect of raising the charge terminal $T_1$ above the physical height ($h_p$) shown in FIG. 5A. The increased elevation causes the distance at which the wave tilt is incident with the lossy conductive medium to move beyond the Hankel crossover point 121 (FIG. 5A). To improve coupling in the guided surface waveguide mode, and thus provide for a greater launching efficiency of the guided surface wave, a lower compensation terminal $T_2$ can be used to adjust the total effective height ($h_{TE}$) of the charge terminal $T_1$ such that the wave tilt at the Hankel crossover distance is at the Brewster angle.

Figure 12:
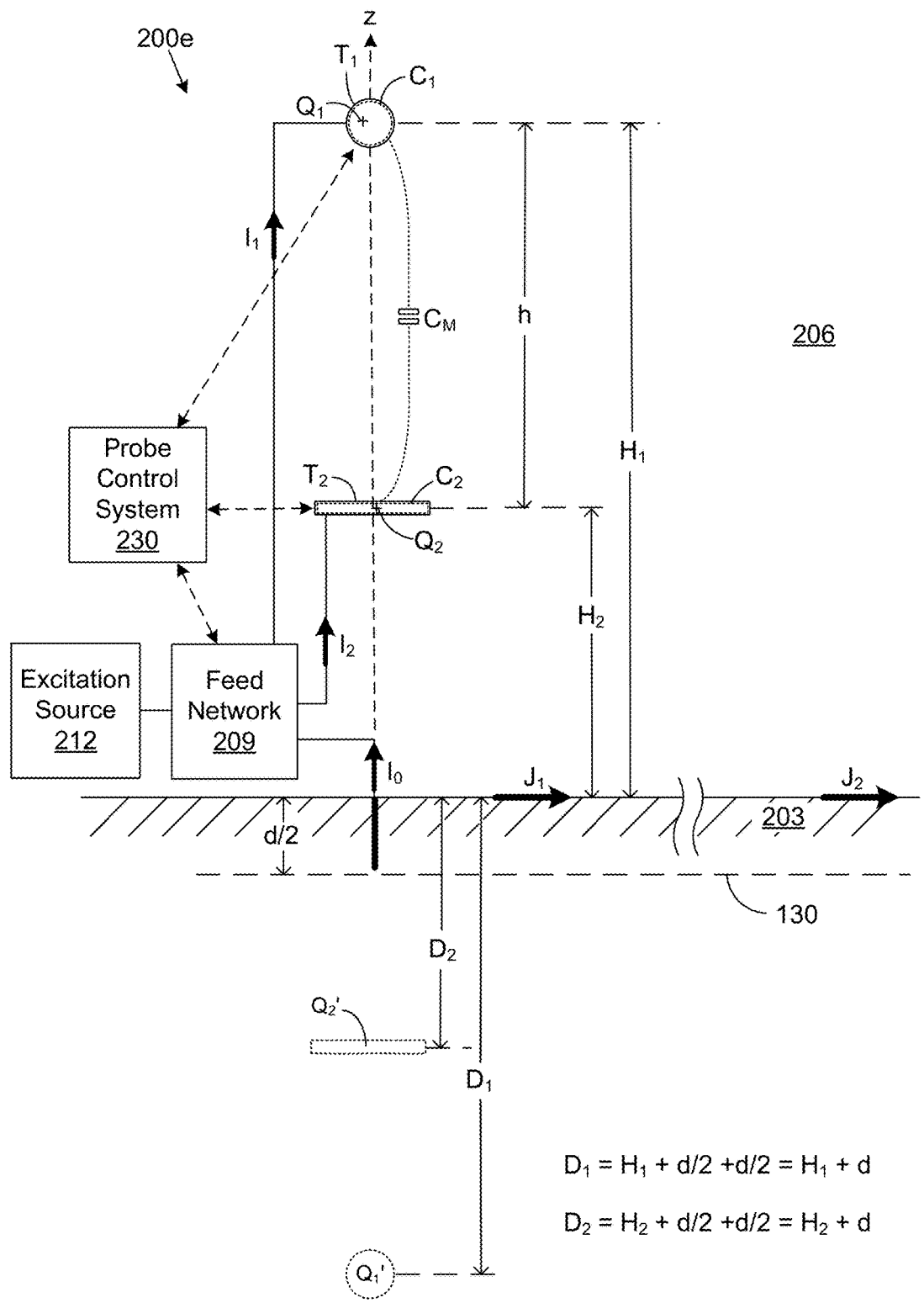
FIG. 12 is a drawing that illustrates an example of a guided surface waveguide probe according to various embodiments of the present disclosure.

Referring to FIG. 12, shown is an example of a guided surface waveguide probe 200e that includes an elevated charge terminal $T_1$ and a lower compensation terminal $T_2$ that are arranged along a vertical axis z that is normal to a plane presented by the lossy conducting medium 203. In this respect, the charge terminal $T_1$ is placed directly above the compensation terminal $T_2$ although it is possible that some other arrangement of two or more charge and/or compensation terminals TN can be used. The guided surface waveguide probe 200e is disposed above a lossy conducting medium 203 according to an embodiment of the present disclosure. The lossy conducting medium 203 makes up Region 1 with a second medium 206 that makes up Region 2 sharing a boundary interface with the lossy conducting medium 203.

The guided surface waveguide probe 200e includes a feed network 209 that couples an excitation source 212 to the charge terminal $T_1$ and the compensation terminal $T_2$. According to various embodiments, charges $Q_1$ and $Q_2$ can be imposed on the respective charge and compensation terminals $T_1$ and $T_2$, depending on the voltages applied to terminals $T_1$ and $T_2$ at any given instant. $I_1$ is the conduction current feeding the charge $Q_1$ on the charge terminal $T_1$ via the terminal lead, and $I_2$ is the conduction current feeding the charge $Q_2$ on the compensation terminal $T_2$ via the terminal lead.

According to the embodiment of FIG. 12, the charge terminal $T_1$ is positioned over the lossy conducting medium 203 at a physical height $H_1$, and the compensation terminal $T_2$ is positioned directly below $T_1$ along the vertical axis z at a physical height $H_2$, where $H_2$ is less than $H_1$. The height h of the transmission structure may be calculated as $h = H_1 - H_2$. The charge terminal $T_1$ has an isolated (or self) capacitance $C_1$, and the compensation terminal $T_2$ has an isolated (or self) capacitance $C_2$. A mutual capacitance $C_M$ can also exist between the terminals $T_1$ and $T_2$ depending on the distance therebetween. During operation, charges $Q_1$ and $Q_2$ are imposed on the charge terminal $T_1$ and the compensation terminal $T_2$, respectively, depending on the voltages applied to the charge terminal $T_1$ and the compensation terminal $T_2$ at any given instant.

Figure 13:
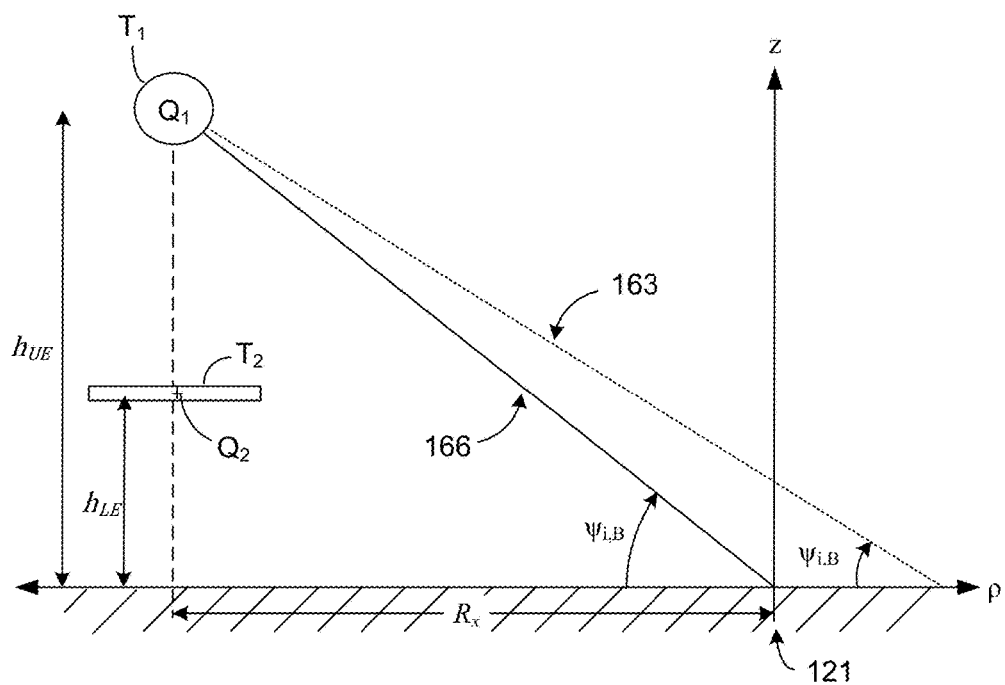
FIG. 13 is a graphical representation illustrating the incidence of a synthesized electric field at a complex Brewster angle to match the guided surface waveguide mode at the Hankel crossover distance according to various embodiments of the present disclosure.

Referring next to FIG. 13, shown is a ray optics interpretation of the effects produced by the elevated charge $Q_1$ on charge terminal $T_1$ and compensation terminal $T_2$ of FIG. 12. With the charge terminal $T_1$ elevated to a height where the ray intersects with the lossy conductive medium at the Brewster angle at a distance greater than the Hankel crossover point 121 as illustrated by line 163, the compensation terminal $T_2$ can be used to adjust $h_{TE}$ by compensating for the increased height. The effect of the compensation terminal $T_2$ is to reduce the electrical effective height of the guided surface waveguide probe (or effectively raise the lossy medium interface) such that the wave tilt at the Hankel crossover distance is at the Brewster angle as illustrated by line 166.

The total effective height can be written as the superposition of an upper effective height ($h_{UE}$) associated with the charge terminal $T_1$ and a lower effective height ($h_{LE}$) associated with the compensation terminal $T_2$ such that $$h_{TE} h_{UE} h_{LE} = h_p e^{j(\beta h_p + \Phi_U)} + h_d e^{j(\beta h_d + \Phi_L)} = R_x \times W, \quad (85)$$

where $\Phi_U$ is the phase delay applied to the upper charge terminal $T_1$, $\Phi_L$ is the phase delay applied to the lower compensation terminal $T_2$, $\beta=2\pi/\lambda_p$ is the propagation factor from Equation (35), $h_p$ is the physical height of the charge terminal $T_1$ and $h_d$ is the physical height of the compensation terminal $T_2$. If extra lead lengths are taken into consideration, they can be accounted for by adding the charge terminal lead length z to the physical height $h_p$ of the charge terminal $T_1$ and the compensation terminal lead length y to the physical height $h_d$ of the compensation terminal $T_2$ as shown in $$h_{TE}=(h_p+z)e^{j(\beta(h_p+z)+\Phi_U)}+(h_d+y)e^{j(\beta(h_d+y)+\Phi_L)}=R_x \times W. \quad (86)$$

The lower effective height can be used to adjust the total effective height ($h_{TE}$) to equal the complex effective height ($h_{eff}$) of FIG. 5A.

Equations (85) or (86) can be used to determine the physical height of the lower disk of the compensation terminal $T_2$ and the phase angles to feed the terminals in order to obtain the desired wave tilt at the Hankel crossover distance. For example, Equation (86) can be rewritten as the phase delay applied to the charge terminal $T_1$ as a function of the compensation terminal height ($h_d$) to give $$\Phi_U(h_d) = -\beta(h_p+z) - j\ln\left(\frac{R_x \times W - (h_d+y)e^{j(\beta h_d+\beta y+\Phi_L)}}{(h_p+z)}\right). \quad (87)$$

To determine the positioning of the compensation terminal $T_2$, the relationships discussed above can be utilized. First, the total effective height ($h_{TE}$) is the superposition of the complex effective height ($h_{UE}$) of the upper charge terminal $T_1$ and the complex effective height ($h_{LE}$) of the lower compensation terminal $T_2$ as expressed in Equation (86). Next, the tangent of the angle of incidence can be expressed geometrically as $$\tan\psi_E = \frac{h_{TE}}{R_x}, \quad (88)$$

which is equal to the definition of the wave tilt, W. Finally, given the desired Hankel crossover distance $R_x$, the $h_{TE}$ can be adjusted to make the wave tilt of the incident ray match the complex Brewster angle at the Hankel crossover point 121. This can be accomplished by adjusting $h_p$, $\Phi_U$, and/or $h_d$.

Figure 14:
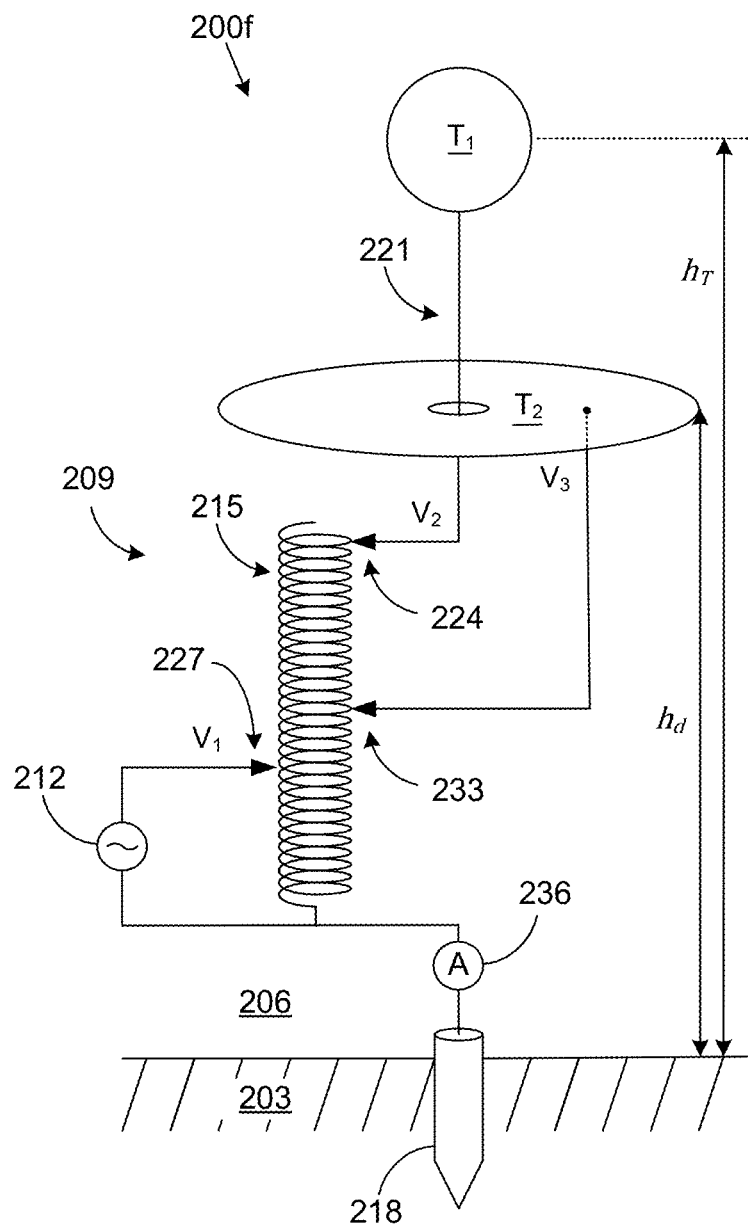
FIG. 14 is a graphical representation of an example of a guided surface waveguide probe of FIG. 12 according to various embodiments of the present disclosure.

These concepts may be better understood when discussed in the context of an example of a guided surface waveguide probe. Referring to FIG. 14, shown is a graphical representation of an example of a guided surface waveguide probe 200f including an upper charge terminal $T_1$ (e.g., a sphere at height $h_T$) and a lower compensation terminal $T_2$ (e.g., a disk at height $h_d$) that are positioned along a vertical axis z that is substantially normal to the plane presented by the lossy conducting medium 203. During operation, charges $Q_1$ and $Q_2$ are imposed on the charge and compensation terminals $T_1$ and $T_2$, respectively, depending on the voltages applied to the terminals $T_1$ and $T_2$ at any given instant.

An AC source can act as the excitation source 212 for the charge terminal which is coupled to the guided surface waveguide probe 200f through a feed network 209 comprising a phasing coil 215 such as, e.g., a helical coil. The excitation source 212 can be connected across a lower portion of the coil 215 through a tap 227, as shown in FIG. 14, or can be inductively coupled to the coil 215 by way of a primary coil. The coil 215 can be coupled to a ground stake (or grounding system) 218 at a first end and the charge terminal $T_1$ at a second end. In some implementations, the connection to the charge terminal $T_1$ can be adjusted using a tap 224 at the second end of the coil 215. The compensation terminal $T_2$ is positioned above and substantially parallel with the lossy conducting medium 203 (e.g., the ground or Earth), and energized through a tap 233 coupled to the coil 215. An ammeter 236 located between the coil 215 and ground stake (or grounding system) 218 can be used to provide an indication of the magnitude of the current flow ($I_0$) at the base of the guided surface waveguide probe. Alternatively, a current clamp may be used around the conductor coupled to the ground stake (or grounding system) 218 to obtain an indication of the magnitude of the current flow ($I_0$).

In the example of FIG. 14, the coil 215 is coupled to a ground stake (or grounding system) 218 at a first end and the charge terminal $T_1$ at a second end via a vertical feed line conductor 221. In some implementations, the connection to the charge terminal $T_1$ can be adjusted using a tap 224 at the second end of the coil 215 as shown in FIG. 14. The coil 215 can be energized at an operating frequency by the excitation source 212 through a tap 227 at a lower portion of the coil 215. In other implementations, the excitation source 212 can be inductively coupled to the coil 215 through a primary coil. The compensation terminal $T_2$ is energized through a tap 233 coupled to the coil 215. An ammeter 236 located between the coil 215 and ground stake (or grounding system) 218 can be used to provide an indication of the magnitude of the current flow at the base of the guided surface waveguide probe 200f. Alternatively, a current clamp may be used around the conductor coupled to the ground stake (or grounding system) 218 to obtain an indication of the magnitude of the current flow. The compensation terminal $T_2$ is positioned above and substantially parallel with the lossy conducting medium 203 (e.g., the ground).

In the example of FIG. 14, the connection to the charge terminal $T_1$ is located on the coil 215 above the connection point of tap 233 for the compensation terminal $T_2$. Such an adjustment allows an increased voltage (and thus a higher charge $Q_1$) to be applied to the upper charge terminal $T_1$. In other embodiments, the connection points for the charge terminal $T_1$ and the compensation terminal $T_2$ can be reversed. It is possible to adjust the total effective height ($h_{TE}$) of the guided surface waveguide probe 200f to excite an electric field having a guided surface wave tilt at the Hankel crossover distance $R_x$. The Hankel crossover distance can also be found by equating the magnitudes of equations (20b) and (21) for $-j\gamma\rho$, and solving for $R_x$ as illustrated by FIG. 4. The index of refraction (n), the complex Brewster angle ($\theta_{i,B}$ and $\psi_{i,B}$), the wave tilt ($|W|e^{j\Psi}$) and the complex effective height ($h_{eff}=h_p e^{j\Phi}$) can be determined as described with respect to Equations (41)-(44) above.

With the selected charge terminal $T_1$ configuration, a spherical diameter (or the effective spherical diameter) can be determined. For example, if the charge terminal $T_1$ is not configured as a sphere, then the terminal configuration may be modeled as a spherical capacitance having an effective spherical diameter. The size of the charge terminal $T_1$ can be chosen to provide a sufficiently large surface for the charge $Q_1$ imposed on the terminals. In general, it is desirable to make the charge terminal $T_1$ as large as practical. The size of the charge terminal $T_1$ should be large enough to avoid ionization of the surrounding air, which can result in electrical discharge or sparking around the charge terminal. To reduce the amount of bound charge on the charge terminal $T_1$, the desired elevation to provide free charge on the charge terminal $T_1$ for launching a guided surface wave should be at least 4-5 times the effective spherical diameter above the lossy conductive medium (e.g., the Earth). The compensation terminal $T_2$ can be used to adjust the total effective height ($h_{TE}$) of the guided surface waveguide probe 200f to excite an electric field having a guided surface wave tilt at $R_x$. The compensation terminal $T_2$ can be positioned below the charge terminal $T_1$ at $h_d = h_T - h_p$, where $h_T$ is the total physical height of the charge terminal $T_1$. With the position of the compensation terminal $T_2$ fixed and the phase delay $\Phi_U$ applied to the upper charge terminal $T_1$, the phase delay $\Phi_L$ applied to the lower compensation terminal $T_2$ can be determined using the relationships of Equation (86), such that:

$$\Phi_U(h_d) = -\beta(h_d + y) - j\ln\left(\frac{R_x \times W - (h_p + z)e^{j(\beta h_p + \beta z + \Phi_L)}}{(h_d + y)}\right). \quad (89)$$

Figure 15A:
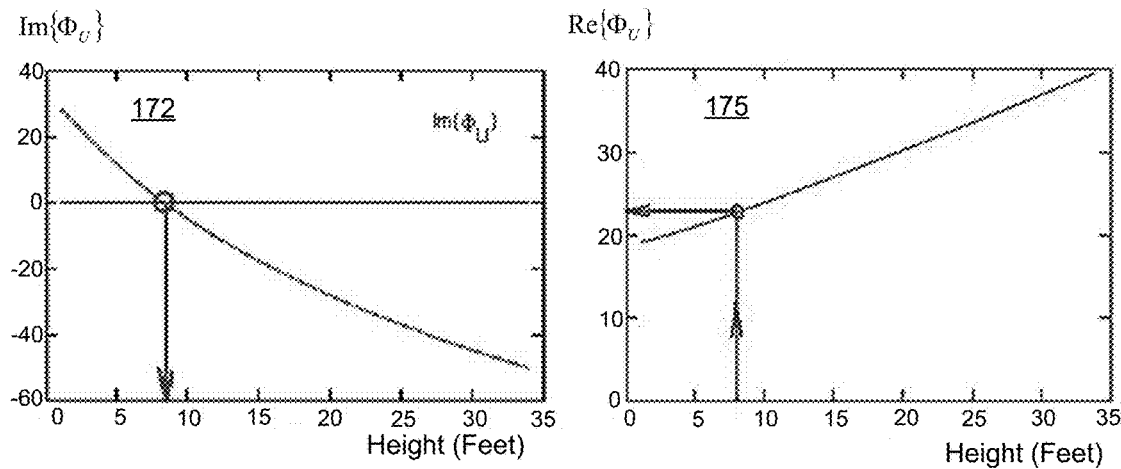
FIG. 15A includes plots of an example of the imaginary and real parts of a phase delay ($\Phi D_{U}$) of a charge terminal $T_1$ of a guided surface waveguide probe according to various embodiments of the present disclosure.

In alternative embodiments, the compensation terminal $T_2$ can be positioned at a height $h_d$ where $\text{Im}\{\Phi_L\}=0$. This is graphically illustrated in FIG. 15A, which shows plots 172 and 175 of the imaginary and real parts of $\Phi_U$, respectively. The compensation terminal $T_2$ is positioned at a height $h_d$ where $\text{Im}\{\Phi_U\}=0$, as graphically illustrated in plot 172. At this fixed height, the coil phase $\Phi_U$ can be determined from $\text{Re}\{\Phi_U\}$, as graphically illustrated in plot 175.

Figure 15B:
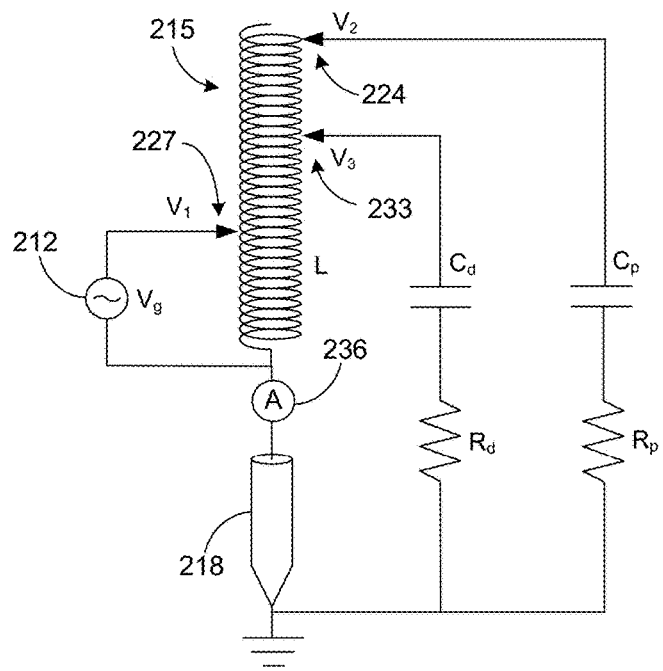
FIG. 15B is a schematic diagram of the guided surface waveguide probe of FIG. 14 according to various embodiments of the present disclosure.

With the excitation source 212 coupled to the coil 215 (e.g., at the 50Ω point to maximize coupling), the position of tap 233 may be adjusted for parallel resonance of the compensation terminal $T_2$ with at least a portion of the coil at the frequency of operation. FIG. 15B shows a schematic diagram of the general electrical hookup of FIG. 14 in which $V_1$ is the voltage applied to the lower portion of the coil 215 from the excitation source 212 through tap 227, $V_2$ is the voltage at tap 224 that is supplied to the upper charge terminal $T_1$, and V3 is the voltage applied to the lower compensation terminal $T_2$ through tap 233. The resistances $R_p$ and $R_d$ represent the ground return resistances of the charge terminal $T_1$ and compensation terminal $T_2$, respectively. The charge and compensation terminals $T_1$ and $T_2$ may be configured as spheres, cylinders, toroids, rings, hoods, or any other combination of capacitive structures. The size of the charge and compensation terminals $T_1$ and $T_2$ can be chosen to provide a sufficiently large surface for the charges $Q_1$ and $Q_2$ imposed on the terminals. In general, it is desirable to make the charge terminal $T_1$ as large as practical. The size of the charge terminal $T_1$ should be large enough to avoid ionization of the surrounding air, which can result in electrical discharge or sparking around the charge terminal. The self-capacitance $C_p$ and $C_d$ of the charge and compensation terminals $T_1$ and $T_2$ respectively, can be determined using, for example, Equation (24).

As can be seen in FIG. 15B, a resonant circuit is formed by at least a portion of the inductance of the coil 215, the self-capacitance $C_d$ of the compensation terminal $T_2$, and the ground return resistance $R_d$ associated with the compensation terminal $T_2$. The parallel resonance can be established by adjusting the voltage V3 applied to the compensation terminal $T_2$ (e.g., by adjusting a tap 233 position on the coil 215) or by adjusting the height and/or size of the compensation terminal $T_2$ to adjust $C_d$. The position of the coil tap 233 can be adjusted for parallel resonance, which will result in the ground current through the ground stake (or grounding system) 218 and through the ammeter 236 reaching a maximum point. After parallel resonance of the compensation terminal $T_2$ has been established, the position of the tap 227 for the excitation source 212 can be adjusted to the 50Ω point on the coil 215.

Voltage $V_2$ from the coil 215 can be applied to the charge terminal $T_1$, and the position of tap 224 can be adjusted such that the phase delay ($\Phi$) of the total effective height ($h_{TE}$) approximately equals the angle of the guided surface wave tilt ($W_{Rx}$) at the Hankel crossover distance ($R_x$). The position of the coil tap 224 can be adjusted until this operating point is reached, which results in the ground current through the ammeter 236 increasing to a maximum. At this point, the resultant fields excited by the guided surface waveguide probe 200f are substantially mode-matched to a guided surface waveguide mode on the surface of the lossy conducting medium 203, resulting in the launching of a guided surface wave along the surface of the lossy conducting medium 203. This can be verified by measuring field strength along a radial extending from the guided surface waveguide probe 200.

Resonance of the circuit including the compensation terminal $T_2$ may change with the attachment of the charge terminal $T_1$ and/or with adjustment of the voltage applied to the charge terminal $T_1$ through tap 224. While adjusting the compensation terminal circuit for resonance aids the subsequent adjustment of the charge terminal connection, it is not necessary to establish the guided surface wave tilt ($W_{Rx}$) at the Hankel crossover distance ($R_x$). The system may be further adjusted to improve coupling by iteratively adjusting the position of the tap 227 for the excitation source 212 to be at the 50Ω point on the coil 215 and adjusting the position of tap 233 to maximize the ground current through the ammeter 236. Resonance of the circuit including the compensation terminal $T_2$ may drift as the positions of taps 227 and 233 are adjusted, or when other components are attached to the coil 215.

In other implementations, the voltage $V_2$ from the coil 215 can be applied to the charge terminal $T_1$, and the position of tap 233 can be adjusted such that the phase delay ($\Phi$) of the total effective height ($h_{TE}$) approximately equals the angle ($\Psi$) of the guided surface wave tilt at $R_x$. The position of the coil tap 224 can be adjusted until the operating point is reached, resulting in the ground current through the ammeter 236 substantially reaching a maximum. The resultant fields are substantially mode-matched to a guided surface waveguide mode on the surface of the lossy conducting medium 203, and a guided surface wave is launched along the surface of the lossy conducting medium 203. This can be verified by measuring field strength along a radial extending from the guided surface waveguide probe 200. The system may be further adjusted to improve coupling by iteratively adjusting the position of the tap 227 for the excitation source 212 to be at the 50Ω point on the coil 215 and adjusting the position of tap 224 and/or 233 to maximize the ground current through the ammeter 236.

Referring back to FIG. 12, operation of a guided surface waveguide probe 200 may be controlled to adjust for variations in operational conditions associated with the guided surface waveguide probe 200. For example, a probe control system 230 can be used to control the feed network 209 and/or positioning of the charge terminal $T_1$ and/or compensation terminal $T_2$ to control the operation of the guided surface waveguide probe 200. Operational conditions can include, but are not limited to, variations in the characteristics of the lossy conducting medium 203 (e.g., conductivity σ and relative permittivity $\varepsilon_r$), variations in field strength and/or variations in loading of the guided surface waveguide probe 200. As can be seen from Equations (41)-(44), the index of refraction (n), the complex Brewster angle ($\theta_{i,B}$ and $\psi_{i,B}$), the wave tilt ($|W|e^{j\Psi}$) and the complex effective height ($h_{eff}=h_p e^{j\Phi}$) can be affected by changes in soil conductivity and permittivity resulting from, e.g., weather conditions.

Equipment such as, e.g., conductivity measurement probes, permittivity sensors, ground parameter meters, field meters, current monitors and/or load receivers can be used to monitor for changes in the operational conditions and provide information about current operational conditions to the probe control system 230. The probe control system 230 can then make one or more adjustments to the guided surface waveguide probe 200 to maintain specified operational conditions for the guided surface waveguide probe 200. For instance, as the moisture and temperature vary, the conductivity of the soil will also vary. Conductivity measurement probes and/or permittivity sensors may be located at multiple locations around the guided surface waveguide probe 200. Generally, it would be desirable to monitor the conductivity and/or permittivity at or about the Hankel crossover distance R, for the operational frequency. Conductivity measurement probes and/or permittivity sensors may be located at multiple locations (e.g., in each quadrant) around the guided surface waveguide probe 200.

Figure 16:
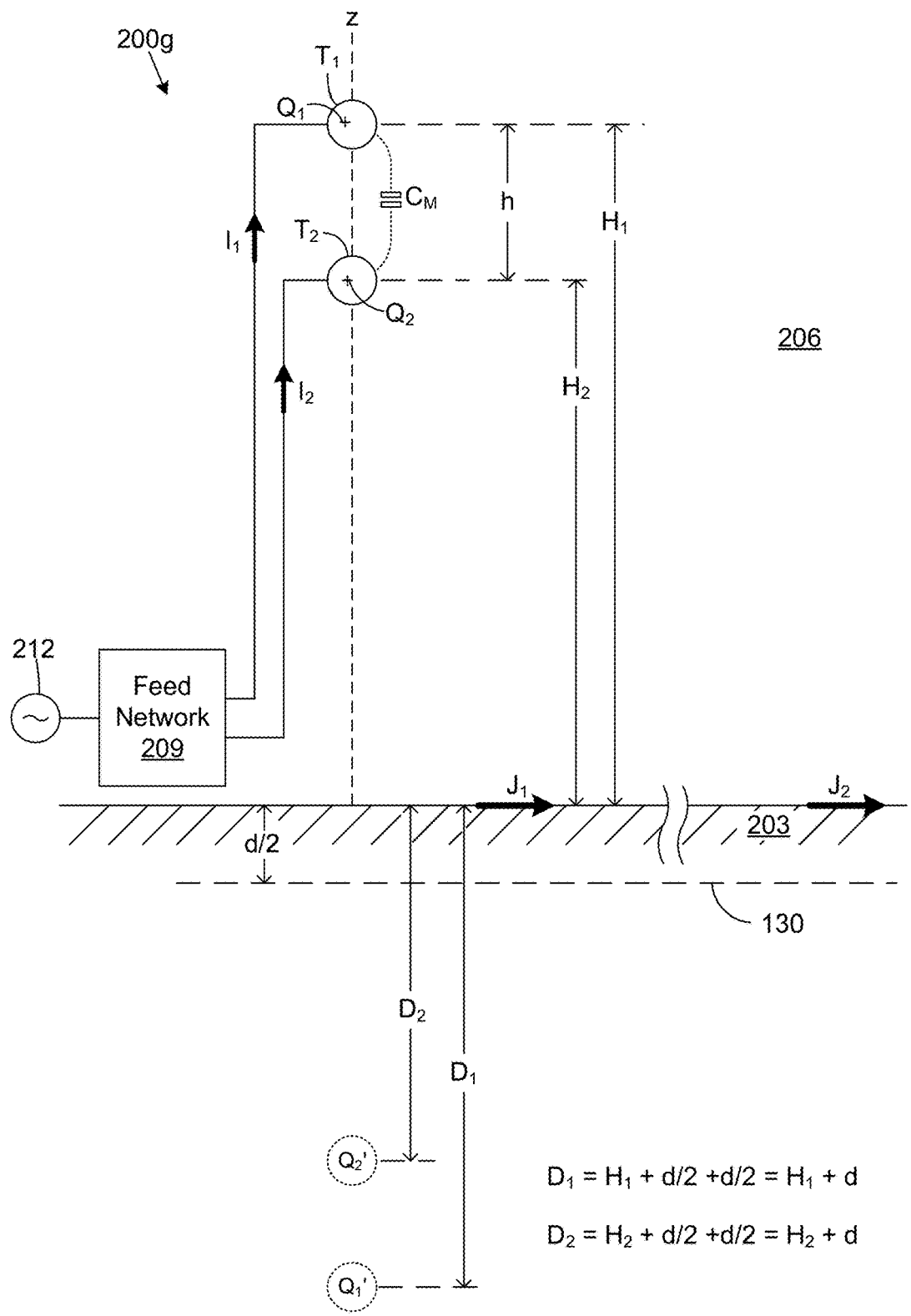
FIG. 16 is a drawing that illustrates an example of a guided surface waveguide probe according to various embodiments of the present disclosure.

With reference then to FIG. 16, shown is an example of a guided surface waveguide probe 200g that includes a charge terminal $T_1$ and a charge terminal $T_2$ that are arranged along a vertical axis z. The guided surface waveguide probe 200g is disposed above a lossy conducting medium 203, which makes up Region 1. In addition, a second medium 206 shares a boundary interface with the lossy conducting medium 203 and makes up Region 2. The charge terminals $T_1$ and $T_2$ are positioned over the lossy conducting medium 203. The charge terminal $T_1$ is positioned at height $H_1$, and the charge terminal $T_2$ is positioned directly below $T_1$ along the vertical axis z at height $H_2$, where $H_2$ is less than $H_1$. The height h of the transmission structure presented by the guided surface waveguide probe 200g is h=$H_1$−$H_2$. The guided surface waveguide probe 200g includes a feed network 209 that couples an excitation source 212 such as an AC source, for example, to the charge terminals $T_1$ and $T_2$.

The charge terminals $T_1$ and/or $T_2$ include a conductive mass that can hold an electrical charge, which may be sized to hold as much charge as practically possible. The charge terminal $T_1$ has a self-capacitance $C_1$, and the charge terminal $T_2$ has a self-capacitance $C_2$, which can be determined using, for example, equation (24). By virtue of the placement of the charge terminal $T_1$ directly above the charge terminal $T_2$, a mutual capacitance $C_M$ is created between the charge terminals $T_1$ and $T_2$. Note that the charge terminals $T_1$ and $T_2$ need not be identical, but each can have a separate size and shape, and can include different conducting materials. Ultimately, the field strength of a guided surface wave launched by a guided surface waveguide probe 200g is directly proportional to the quantity of charge on the terminal $T_1$. The charge $Q_1$ is, in turn, proportional to the self-capacitance $C_1$ associated with the charge terminal $T_1$ since $Q_1=C_1V$, where V is the voltage imposed on the charge terminal $T_1$.

When properly adjusted to operate at a predefined operating frequency, the guided surface waveguide probe 200g generates a guided surface wave along the surface of the lossy conducting medium 203. The excitation source 212 can generate electrical energy at the predefined frequency that is applied to the guided surface waveguide probe 200g to excite the structure. When the electromagnetic fields generated by the guided surface waveguide probe 200g are substantially mode-matched with the lossy conducting medium 203, the electromagnetic fields substantially synthesize a wave front incident at a complex Brewster angle that results in little or no reflection. Thus, the surface waveguide probe 200g does not produce a radiated wave, but launches a guided surface traveling wave along the surface of a lossy conducting medium 203. The energy from the excitation source 212 can be transmitted as Zenneck surface currents to one or more receivers that are located within an effective transmission range of the guided surface waveguide probe 200g.

One can determine asymptotes of the radial Zenneck surface current $J_\rho(\rho)$ on the surface of the lossy conducting medium 203 to be $J_1(\rho)$ close-in and $J_2(\rho)$ far-out, where $$\text{Close-in } (\rho < \lambda/8): J_\rho(\rho) \sim J_1 = \frac{I_1 + I_2}{2\pi\rho} + \frac{E_\rho^{QS}(Q_1) + E_\rho^{QS}(Q_2)}{Z_\rho}, \text{ and} \quad (90)$$

$$\text{Far-out } (\rho \gg \lambda/8): J_\rho(\rho) \sim J_2 = \frac{j\gamma\omega Q_1}{4} \times \sqrt{\frac{2\gamma}{\pi}} \times \frac{e^{-(\alpha+j\beta)\rho}}{\sqrt{\rho}}. \quad (91)$$

where $I_1$ is the conduction current feeding the charge $Q_1$ on the first charge terminal and $I_2$ is the conduction current feeding the charge $Q_2$ on the second charge terminal $T_2$. The charge $Q_1$ on the upper charge terminal $T_1$ is determined by $Q_1=C_1V_1$, where $C_1$ is the isolated capacitance of the charge terminal $T_1$. Note that there is a third component to $J_1$ set forth above given by $(E_\rho^{Q1})/Z_\rho$, which follows from the Leontovich boundary condition and is the radial current contribution in the lossy conducting medium 203 pumped by the quasi-static field of the elevated oscillating charge on the first charge terminal $Q_1$. The quantity $Z_\rho = j\omega\mu_o/\gamma_e$ is the radial impedance of the lossy conducting medium, where $\gamma_e = (j\omega\mu_1\sigma_1 - \omega^2\mu_1\varepsilon_1)^{1/2}$.

The asymptotes representing the radial current close-in and far-out as set forth by equations (90) and (91) are complex quantities. According to various embodiments, a physical surface current $J(\rho)$ is synthesized to match as close as possible the current asymptotes in magnitude and phase. That is to say close-in, $|J(\rho)|$ is to be tangent to $|J_1|$, and far-out $|J(\rho)|$ is to be tangent to $|J_2|$. Also, according to the various embodiments, the phase of $J(\rho)$ should transition from the phase of $J_1$ close-in to the phase of $J_2$ far-out.

In order to match the guided surface wave mode at the site of transmission to launch a guided surface wave, the phase of the surface current $|J_2|$ far-out should differ from the phase of the surface current $|J_1|$ close-in by the propagation phase corresponding to $e^{-j\beta(\rho_2-\rho_1)}$ plus a constant of approximately 45 degrees or 225 degrees. This is because there are two roots for $\sqrt{\gamma}$, one near $\pi/4$ and one near $5\pi/4$. The properly adjusted synthetic radial surface current is $$J_\rho(\rho, \phi, 0) = \frac{I_0\gamma}{4} H_1^{(2)}(-j\gamma\rho). \quad (92)$$

Note that this is consistent with equation (17). By Maxwell's equations, such a $J(\rho)$ surface current automatically creates fields that conform to $$H_\phi = \frac{-\gamma I_o}{4} e^{-u_2 z} H_1^{(2)}(-j\gamma\rho), \quad (93)$$

$$E_\rho = \frac{-\gamma I_o}{4}\left(\frac{u_2}{j\omega\varepsilon_o}\right)e^{-u_2 z} H_1^{(2)}(-j\gamma\rho), \text{ and} \quad (94)$$

$$E_z = \frac{-\gamma I_o}{4}\left(\frac{-\gamma}{\omega\varepsilon_o}\right)e^{-u_2 z} H_0^{(2)}(-j\gamma\rho). \quad (95)$$

Thus, the difference in phase between the surface current $|J_2|$ far-out and the surface current $|J_1|$ close-in for the guided surface wave mode that is to be matched is due to the characteristics of the Hankel functions in equations (93)-(95), which are consistent with equations (1)-(3). It is of significance to recognize that the fields expressed by equations (1)-(6) and (17) and equations (92)-(95) have the nature of a transmission line mode bound to a lossy interface, not radiation fields that are associated with ground-wave propagation.

In order to obtain the appropriate voltage magnitudes and phases for a given design of a guided surface waveguide probe 200g at a given location, an iterative approach may be used. Specifically, analysis may be performed of a given excitation and configuration of a guided surface waveguide probe 200g taking into account the feed currents to the terminals $T_1$ and $T_2$, the charges on the charge terminals $T_1$ and $T_2$, and their images in the lossy conducting medium 203 in order to determine the radial surface current density generated. This process may be performed iteratively until an optimal configuration and excitation for a given guided surface waveguide probe 200g is determined based on desired parameters. To aid in determining whether a given guided surface waveguide probe 200g is operating at an optimal level, a guided field strength curve 103 (FIG. 1) may be generated using equations (1)-(12) based on values for the conductivity of Region 1 ($\sigma_1$) and the permittivity of Region 1 ($\varepsilon_1$) at the location of the guided surface waveguide probe 200g. Such a guided field strength curve 103 can provide a benchmark for operation such that measured field strengths can be compared with the magnitudes indicated by the guided field strength curve 103 to determine if optimal transmission has been achieved.

In order to arrive at an optimized condition, various parameters associated with the guided surface waveguide probe 200g may be adjusted. One parameter that may be varied to adjust the guided surface waveguide probe 200g is the height of one or both of the charge terminals $T_1$ and/or $T_2$ relative to the surface of the lossy conducting medium 203. In addition, the distance or spacing between the charge terminals $T_1$ and $T_2$ may also be adjusted. In doing so, one may minimize or otherwise alter the mutual capacitance $C_M$ or any bound capacitances between the charge terminals $T_1$ and $T_2$ and the lossy conducting medium 203 as can be appreciated. The size of the respective charge terminals $T_1$ and/or $T_2$ can also be adjusted. By changing the size of the charge terminals $T_1$ and/or $T_2$, one will alter the respective self-capacitances $C_1$ and/or $C_2$, and the mutual capacitance $C_M$ as can be appreciated.

Still further, another parameter that can be adjusted is the feed network 209 associated with the guided surface waveguide probe 200g. This may be accomplished by adjusting the size of the inductive and/or capacitive reactances that make up the feed network 209. For example, where such inductive reactances comprise coils, the number of turns on such coils may be adjusted. Ultimately, the adjustments to the feed network 209 can be made to alter the electrical length of the feed network 209, thereby affecting the voltage magnitudes and phases on the charge terminals $T_1$ and $T_2$.

Note that the iterations of transmission performed by making the various adjustments may be implemented by using computer models or by adjusting physical structures as can be appreciated. By making the above adjustments, one can create corresponding "close-in" surface current h and "far-out" surface current $J_2$ that approximate the same currents $J(\rho)$ of the guided surface wave mode specified in Equations (90) and (91) set forth above. In doing so, the resulting electromagnetic fields would be substantially or approximately mode-matched to a guided surface wave mode on the surface of the lossy conducting medium 203.

While not shown in the example of FIG. 16, operation of the guided surface waveguide probe 200g may be controlled to adjust for variations in operational conditions associated with the guided surface waveguide probe 200. For example, a probe control system 230 shown in FIG. 12 can be used to control the feed network 209 and/or positioning and/or size of the charge terminals $T_1$ and/or $T_2$ to control the operation of the guided surface waveguide probe 200g. Operational conditions can include, but are not limited to, variations in the characteristics of the lossy conducting medium 203 (e.g., conductivity $\sigma$ and relative permittivity $\varepsilon_r$), variations in field strength and/or variations in loading of the guided surface waveguide probe 200g.

Figure 17:
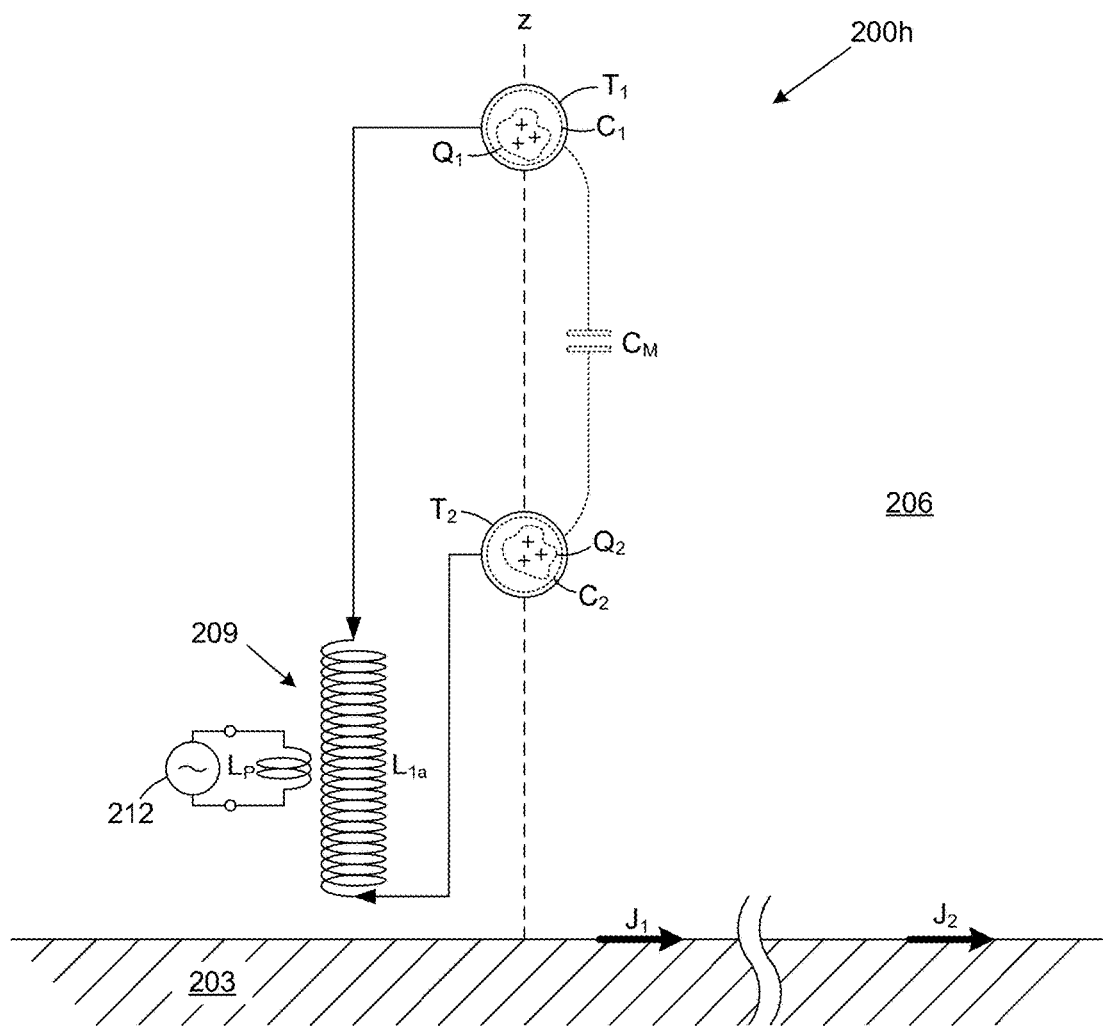
FIG. 17 is a graphical representation of an example of a guided surface waveguide probe of FIG. 16 according to various embodiments of the present disclosure.

Referring now to FIG. 17, shown is an example of the guided surface waveguide probe 200g of FIG. 16, denoted herein as guided surface waveguide probe 200h. The guided surface waveguide probe 200h includes the charge terminals $T_1$ and $T_2$ that are positioned along a vertical axis z that is substantially normal to the plane presented by the lossy conducting medium 203 (e.g., the Earth). The second medium 206 is above the lossy conducting medium 203. The charge terminal $T_1$ has a self-capacitance $C_1$, and the charge terminal $T_2$ has a self-capacitance $C_2$. During operation, charges $Q_1$ and $Q_2$ are imposed on the charge terminals $T_1$ and $T_2$, respectively, depending on the voltages applied to the charge terminals $T_1$ and $T_2$ at any given instant. A mutual capacitance $C_M$ may exist between the charge terminals $T_1$ and $T_2$ depending on the distance therebetween. In addition, bound capacitances may exist between the respective charge terminals $T_1$ and $T_2$ and the lossy conducting medium 203 depending on the heights of the respective charge terminals $T_1$ and $T_2$ with respect to the lossy conducting medium 203.

The guided surface waveguide probe 200h includes a feed network 209 that comprises an inductive impedance comprising a coil $L_{1a}$ having a pair of leads that are coupled to respective ones of the charge terminals $T_1$ and $T_2$. In one embodiment, the coil $L_{1a}$ is specified to have an electrical length that is one-half (½) of the wavelength at the operating frequency of the guided surface waveguide probe 200h.

While the electrical length of the coil $L_{1a}$ is specified as approximately one-half (½) the wavelength at the operating frequency, it is understood that the coil $L_{1a}$ may be specified with an electrical length at other values. According to one embodiment, the fact that the coil $L_{1a}$ has an electrical length of approximately one-half (½) the wavelength at the operating frequency provides for an advantage in that a maximum voltage differential is created on the charge terminals $T_1$ and $T_2$. Nonetheless, the length or diameter of the coil $L_{1a}$ may be increased or decreased when adjusting the guided surface waveguide probe 200h to obtain optimal excitation of a guided surface wave mode. Adjustment of the coil length may be provided by taps located at one or both ends of the coil. In other embodiments, it may be the case that the inductive impedance is specified to have an electrical length that is significantly less than or greater than one-half (½) the wavelength at the operating frequency of the guided surface waveguide probe 200h.

The excitation source 212 can be coupled to the feed network 209 by way of magnetic coupling. Specifically, the excitation source 212 is coupled to a coil $L_P$ that is inductively coupled to the coil $L_{1a}$. This may be done by link coupling, a tapped coil, a variable reactance, or other coupling approach as can be appreciated. To this end, the coil $L_P$ acts as a primary, and the coil $L_{1a}$ acts as a secondary as can be appreciated.

In order to adjust the guided surface waveguide probe 200h for the transmission of a desired guided surface wave, the heights of the respective charge terminals $T_1$ and $T_2$ may be altered with respect to the lossy conducting medium 203 and with respect to each other. Also, the sizes of the charge terminals $T_1$ and $T_2$ may be altered. In addition, the size of the coil $L_{1a}$ may be altered by adding or eliminating turns or by changing some other dimension of the coil $L_{1a}$. The coil $L_{1a}$ can also include one or more taps for adjusting the electrical length as shown in FIG. 17. The position of a tap connected to either charge terminal $T_1$ or $T_2$ can also be adjusted.

Figure 18A:
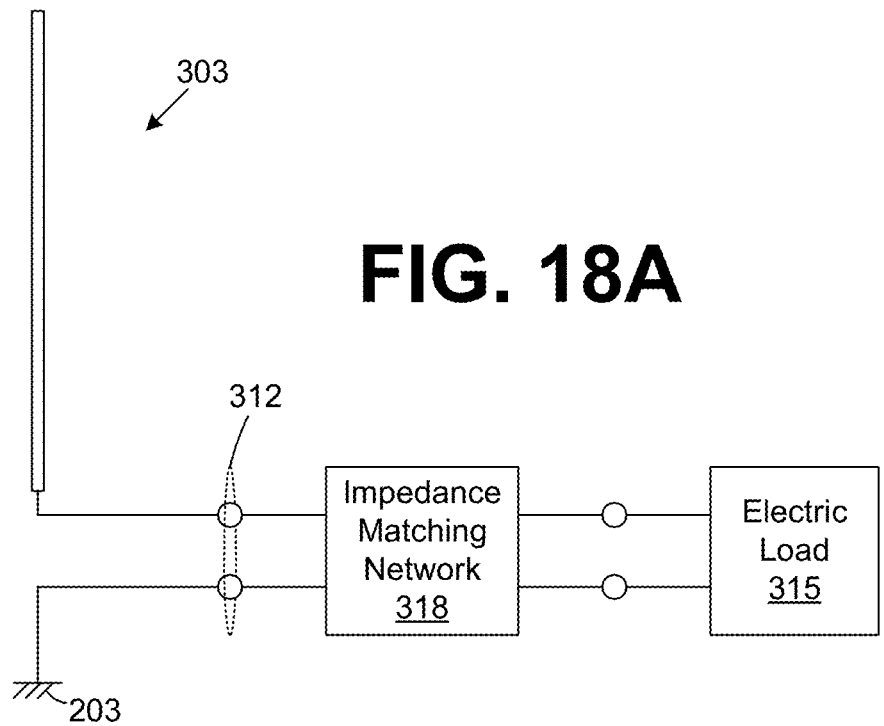
FIGS. 18A through 18C depict examples of receiving structures that can be employed to receive energy transmitted in the form of a guided surface wave launched by a guided surface waveguide probe according to the various embodiments of the present disclosure.
Figure 18B:
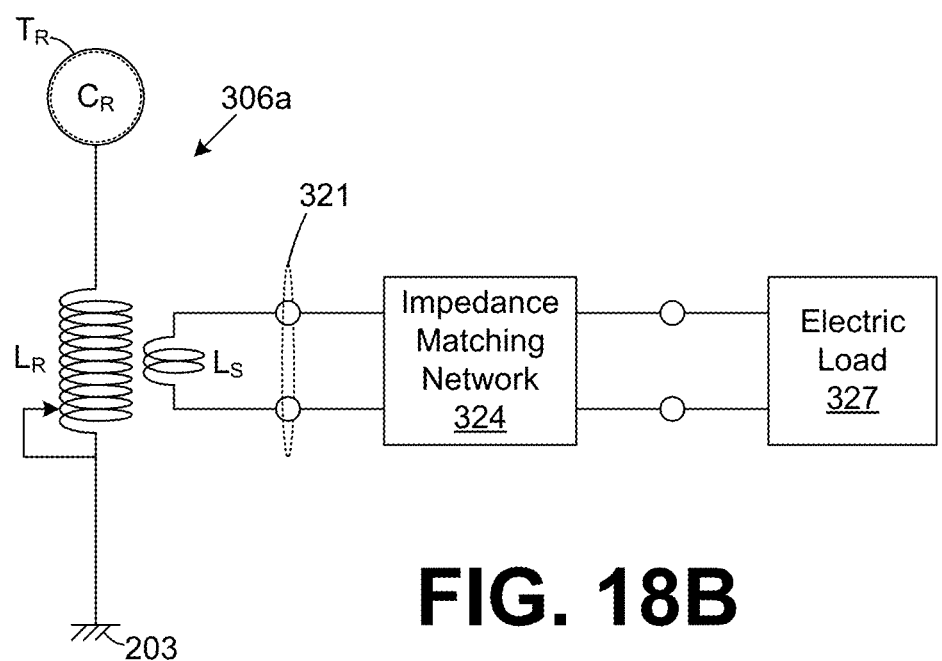
Figure 18C:
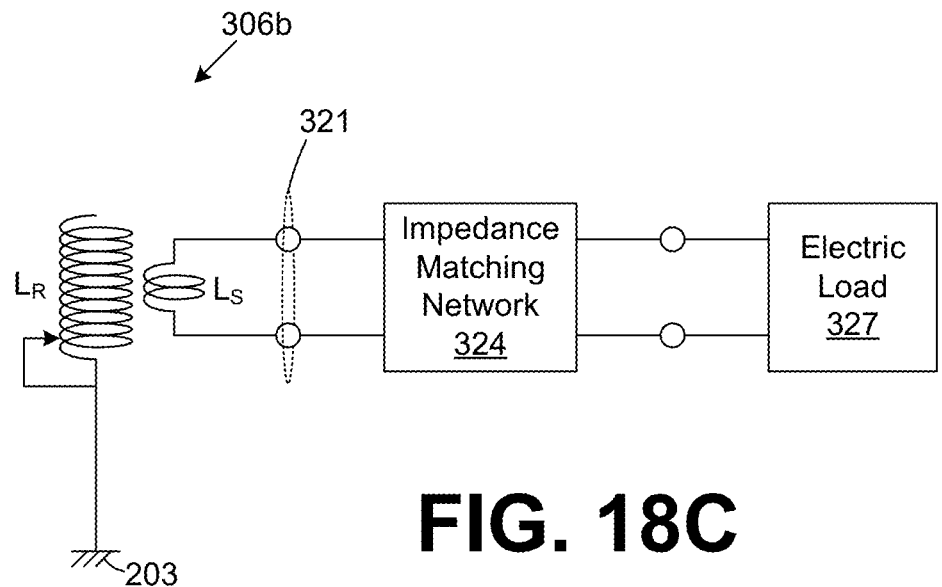
Figure 19:
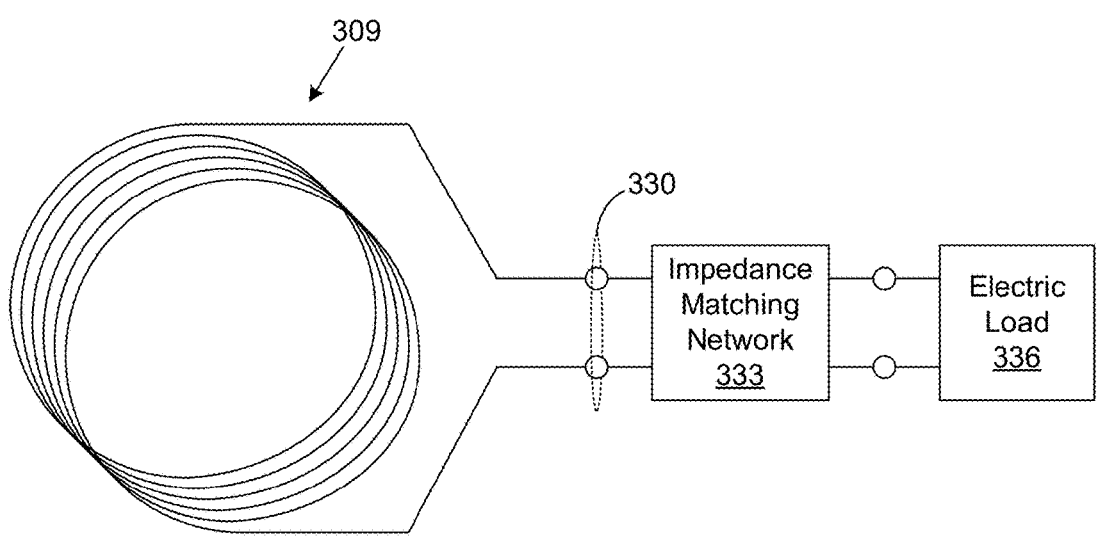
FIG. 19 depicts an example of an additional receiving structure that can be employed to receive energy transmitted in the form of a guided surface wave launched by a guided surface waveguide probe according to the various embodiments of the present disclosure.

Referring next to FIGS. 18A, 18B, 18C and 19, shown are examples of generalized receive circuits for using the surface-guided waves in wireless power delivery systems. FIG. 18A depict a linear probe 303, and FIGS. 18B and 18C depict tuned resonators 306a and 306b, respectively. FIG. 19 is a magnetic coil 309 according to various embodiments of the present disclosure. According to various embodiments, each one of the linear probe 303, the tuned resonators 306a/b, and the magnetic coil 309 may be employed to receive power transmitted in the form of a guided surface wave on the surface of a lossy conducting medium 203 according to various embodiments. As mentioned above, in one embodiment the lossy conducting medium 203 comprises a terrestrial medium (or Earth).

With specific reference to FIG. 18A, the open-circuit terminal voltage at the output terminals 312 of the linear probe 303 depends upon the effective height of the linear probe 303. To this end, the terminal point voltage may be calculated as $$V_T = \int_0^{h_e} E_{inc} \cdot dl, \qquad (96)$$

where $E_{inc}$ is the strength of the incident electric field induced on the linear probe 303 in Volts per meter, dl is an element of integration along the direction of the linear probe 303, and $h_e$ is the effective height of the linear probe 303. An electrical load 315 is coupled to the output terminals 312 through an impedance matching network 318.

When the linear probe 303 is subjected to a guided surface wave as described above, a voltage is developed across the output terminals 312 that may be applied to the electrical load 315 through a conjugate impedance matching network 318 as the case may be. In order to facilitate the flow of power to the electrical load 315, the electrical load 315 should be substantially impedance matched to the linear probe 303 as will be described below.

Referring to FIG. 18B, a ground current excited coil $L_R$ possessing a phase delay equal to the wave tilt of the guided surface wave includes a charge terminal $T_R$ that is elevated (or suspended) above the lossy conducting medium 203. The charge terminal $T_R$ has a self-capacitance $C_R$. In addition, there may also be a bound capacitance (not shown) between the charge terminal $T_R$ and the lossy conducting medium 203 depending on the height of the charge terminal $T_R$ above the lossy conducting medium 203. The bound capacitance should preferably be minimized as much as is practicable, although this may not be entirely necessary in every instance.

The tuned resonator 306a also includes a receiver network comprising a coil $L_R$ having a phase delay $\Phi$. One end of the coil $L_R$ is coupled to the charge terminal $T_R$, and the other end of the coil $L_R$ is coupled to the lossy conducting medium 203. The receiver network can include a vertical supply line conductor that couples the coil $L_R$ to the charge terminal $T_R$. To this end, the coil $L_R$ (which may also be referred to as tuned resonator $L_R$-$C_R$) comprises a series-adjusted resonator as the charge terminal $C_R$ and the coil $L_R$ are situated in series. The phase delay of the coil $L_R$ can be adjusted by changing the size and/or height of the charge terminal $T_R$, and/or adjusting the size of the coil $L_R$ so that the phase delay $\Phi$ of the structure is made substantially equal to the angle of the wave tilt $\Psi$. The phase delay of the vertical supply line can also be adjusted by, e.g., changing length of the conductor.

For example, the reactance presented by the self-capacitance $C_R$ is calculated as $1/j\omega_R$. Note that the total capacitance of the tuned resonator 306a may also include capacitance between the charge terminal $T_R$ and the lossy conducting medium 203, where the total capacitance of the tuned resonator 306a may be calculated from both the self-capacitance $C_R$ and any bound capacitance as can be appreciated. According to one embodiment, the charge terminal $T_R$ may be raised to a height so as to substantially reduce or eliminate any bound capacitance. The existence of a bound capacitance may be determined from capacitance measurements between the charge terminal $T_R$ and the lossy conducting medium 203 as previously discussed.

The inductive reactance presented by a discrete-element coil $L_R$ may be calculated as $j\omega L$, where L is the lumped-element inductance of the coil $L_R$. If the coil $L_R$ is a distributed element, its equivalent terminal-point inductive reactance may be determined by conventional approaches. To tune the tuned resonator 306a, one would make adjustments so that the phase delay is equal to the wave tilt for the purpose of mode-matching to the surface waveguide at the frequency of operation. Under this condition, the receiving structure may be considered to be "mode-matched" with the surface waveguide. A transformer link around the structure and/or an impedance matching network 324 may be inserted between the probe and the electrical load 327 in order to couple power to the load. Inserting the impedance matching network 324 between the probe terminals 321 and the electrical load 327 can effect a conjugate-match condition for maximum power transfer to the electrical load 327.

When placed in the presence of surface currents at the operating frequencies power will be delivered from the surface guided wave to the electrical load 327. To this end, an electrical load 327 may be coupled to the tuned resonator 306a by way of magnetic coupling, capacitive coupling, or conductive (direct tap) coupling. The elements of the coupling network may be lumped components or distributed elements as can be appreciated.

In the embodiment shown in FIG. 18B, magnetic coupling is employed where a coil $L_S$ is positioned as a secondary relative to the coil $L_R$ that acts as a transformer primary. The coil $L_S$ may be link-coupled to the coil $L_R$ by geometrically winding it around the same core structure and adjusting the coupled magnetic flux as can be appreciated. In addition, while the tuned resonator 306a comprises a series-tuned resonator, a parallel-tuned resonator or even a distributed-element resonator of the appropriate phase delay may also be used.

While a receiving structure immersed in an electromagnetic field may couple energy from the field, it can be appreciated that polarization-matched structures work best by maximizing the coupling, and conventional rules for probe-coupling to waveguide modes should be observed. For example, a $TE_{20}$ (transverse electric mode) waveguide probe may be optimal for extracting energy from a conventional waveguide excited in the $TE_{20}$ mode. Similarly, in these cases, a mode-matched and phase-matched receiving structure can be optimized for coupling power from a surface-guided wave. The guided surface wave excited by a guided surface waveguide probe 200 on the surface of the lossy conducting medium 203 can be considered a waveguide mode of an open waveguide. Excluding waveguide losses, the source energy can be completely recovered. Useful receiving structures may be E-field coupled, H-field coupled, or surface-current excited.

The receiving structure can be adjusted to increase or maximize coupling with the guided surface wave based upon the local characteristics of the lossy conducting medium 203 in the vicinity of the receiving structure. To accomplish this, the phase delay (Φ) of the receiving structure can be adjusted to match the angle (Ψ) of the wave tilt of the surface traveling wave at the receiving structure. If configured appropriately, the receiving structure may then be tuned for resonance with respect to the perfectly conducting image ground plane at complex depth z=−d/2.

For example, consider a receiving structure comprising the tuned resonator 306a of FIG. 18B, including a coil $L_R$ and a vertical supply line connected between the coil $L_R$ and a charge terminal $T_R$. With the charge terminal $T_R$ positioned at a defined height above the lossy conducting medium 203, the total phase delay Φ of the coil $L_R$ and vertical supply line can be matched with the angle (Ψ) of the wave tilt at the location of the tuned resonator 306a. From Equation (22), it can be seen that the wave tilt asymptotically passes to $$W = |W|e^{j\Psi} = \frac{E_\rho}{E_z} \xrightarrow[\rho\to\infty]{} \frac{1}{\sqrt{\varepsilon_r - j\frac{\sigma_1}{\omega\varepsilon_o}}} \qquad (97)$$

where $\varepsilon_r$ comprises the relative permittivity and $\sigma_1$ is the conductivity of the lossy conducting medium 203 at the location of the receiving structure, $\varepsilon_0$ is the permittivity of free space, and $\omega=2\pi f$, where f is the frequency of excitation. Thus, the wave tilt angle (Ψ) can be determined from Equation (97).

The total phase delay ($\Phi=\theta_c+\theta_y$) of the tuned resonator 306a includes both the phase delay ($\theta_c$) through the coil $L_R$ and the phase delay of the vertical supply line ($\theta_y$). The spatial phase delay along the conductor length $l_w$ of the vertical supply line can be given by $\theta_y=\beta_w l_w$, where $\beta_w$ is the propagation phase constant for the vertical supply line conductor. The phase delay due to the coil (or helical delay line) is $\theta_c=\beta_p l_c$, with a physical length of $l_c$ and a propagation factor of $$\beta_p = \frac{2\pi}{\lambda_p} = \frac{2\pi}{V_f \lambda_0}, \qquad (98)$$

where $V_f$ is the velocity factor on the structure, $\lambda_0$ is the wavelength at the supplied frequency, and $\lambda_p$ is the propagation wavelength resulting from the velocity factor $V_f$. One or both of the phase delays ($\theta_c+\theta_y$) can be adjusted to match the phase delay (Φ) to the angle (Ψ) of the wave tilt. For example, a tap position may be adjusted on the coil $L_R$ of FIG. 18B to adjust the coil phase delay ($\theta_c$) to match the total phase delay to the wave tilt angle (Φ=Ψ). For example, a portion of the coil can be bypassed by the tap connection as illustrated in FIG. 18B. The vertical supply line conductor can also be connected to the coil $L_R$ via a tap, whose position on the coil may be adjusted to match the total phase delay to the angle of the wave tilt.

Once the phase delay (Φ) of the tuned resonator 306a has been adjusted, the impedance of the charge terminal $T_R$ can then be adjusted to tune to resonance with respect to the perfectly conducting image ground plane at complex depth z=−d/2. This can be accomplished by adjusting the capacitance of the charge terminal $T_1$ without changing the traveling wave phase delays of the coil $L_R$ and vertical supply line. In some embodiments, a lumped element tuning circuit can be included between the lossy conducting medium 203 and the coil $L_R$ to allow for resonant tuning of the tuned resonator 306a with respect to the complex image plane as discussed above with respect to the guided surface waveguide probe 200. The adjustments are similar to those described with respect to FIGS. 9A-9C.

The impedance seen "looking down" into the lossy conducting medium 203 to the complex image plane is given by:

$$Z_{in}=R_{in}+jX_{in}=Z_o \tan h(j\beta_o(d/2)), \qquad (99)$$

where $\beta_o=\sqrt{\omega\mu_o\varepsilon_o}$. For vertically polarized sources over the Earth, the depth of the complex image plane can be given by:

$$d/2 \approx 1/\sqrt{j\omega\mu_1\sigma_1-\omega^2\mu_1\varepsilon_1}, \qquad (100)$$

where $\mu_1$ is the permeability of the lossy conducting medium 203 and $\varepsilon_1=\varepsilon_r\varepsilon_o$.

At the base of the tuned resonator 306a, the impedance seen "looking up" into the receiving structure is $Z_\uparrow=Z_{base}$ as illustrated in FIG. 9A or $Z_\uparrow=Z_{tuning}$ as illustrated in FIG. 9C. With a terminal impedance of:

$$Z_R = \frac{1}{j\omega C_R}, \qquad (101)$$

where $C_R$ is the self-capacitance of the charge terminal $T_R$, the impedance seen "looking up" into the vertical supply line conductor of the tuned resonator 306a is given by:

$$Z_2 = Z_W \frac{Z_R + Z_w \tanh(j\beta_w h_w)}{Z_w + Z_R \tanh(j\beta_w h_w)} = Z_W \frac{Z_R + Z_w \tanh(j\theta_y)}{Z_w + Z_R \tanh(j\theta_y)}, \qquad (102)$$

and the impedance seen "looking up" into the coil $L_R$ of the tuned resonator 306a is given by:

$$Z_{base} = R_{base} + jX_{base} = Z_R \frac{Z_2 + Z_R \tanh(j\beta_p H)}{Z_R + Z_2 \tanh(j\beta_p H)} = Z_c \frac{Z_2 + Z_R \tanh(j\theta_c)}{Z_R + Z_2 \tanh(j\theta_c)}. \qquad (103)$$

By matching the reactive component ($X_{in}$) seen "looking down" into the lossy conducting medium 203 with the reactive component ($X_{base}$) seen "looking up" into the tuned resonator 306a, the coupling into the guided surface waveguide mode may be maximized.

Where a lumped element tank circuit is included at the base of the tuned resonator 306a, the self-resonant frequency of the tank circuit can be tuned to add positive or negative impedance to bring the tuned resonator 306b into standing wave resonance by matching the reactive component ($X_{in}$) seen "looking down" into the lossy conducting medium 203 with the reactive component ($X_{tuning}$) seen "looking up" into the lumped element tank circuit.

Referring next to FIG. 18C, shown is an example of a tuned resonator 306b that does not include a charge terminal $T_R$ at the top of the receiving structure. In this embodiment, the tuned resonator 306b does not include a vertical supply line coupled between the coil $L_R$ and the charge terminal $T_R$. Thus, the total phase delay ($\Phi$) of the tuned resonator 306b includes only the phase delay ($\theta_r$) through the coil $L_R$. As with the tuned resonator 306a of FIG. 18B, the coil phase delay $\theta_c$ can be adjusted to match the angle ($\Psi$) of the wave tilt determined from Equation (97), which results in $\Phi=\Psi$. While power extraction is possible with the receiving structure coupled into the surface waveguide mode, it is difficult to adjust the receiving structure to maximize coupling with the guided surface wave without the variable reactive load provided by the charge terminal $T_R$. Including a lumped element tank circuit at the base of the tuned resonator 306b provides a convenient way to bring the tuned resonator 306b into standing wave resonance with respect to the complex image plane.

Figure 18D:
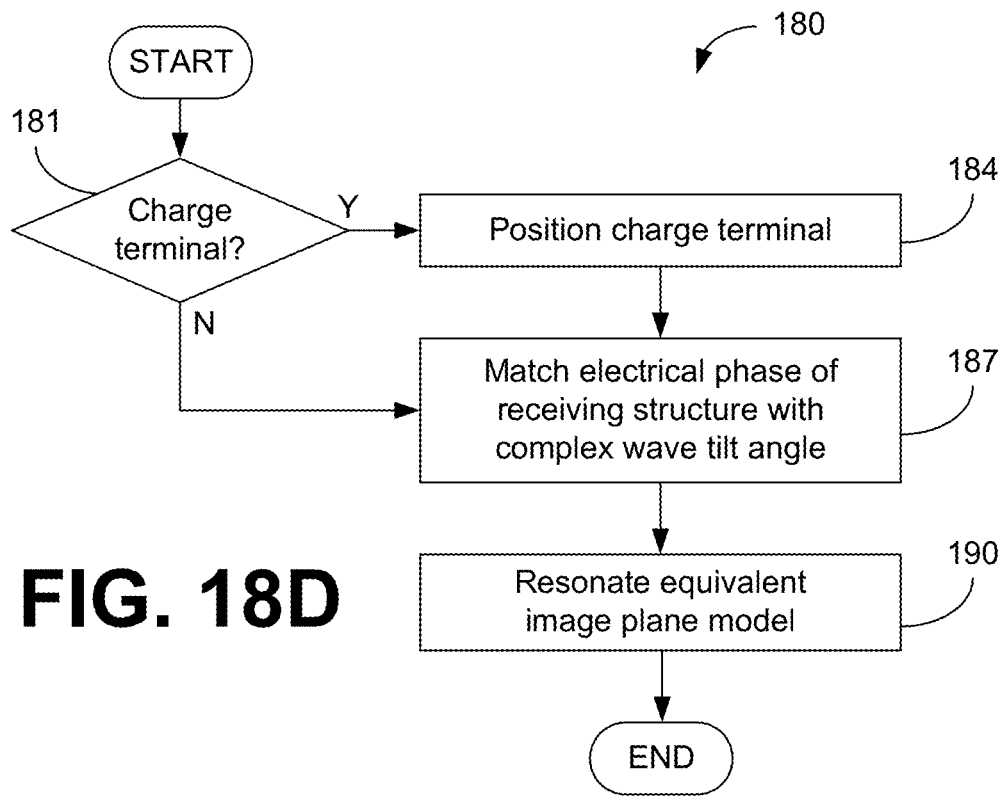
FIG. 18D is a flow chart illustrating an example of adjusting a receiving structure according to various embodiments of the present disclosure.

Referring to FIG. 18D, shown is a flow chart 180 illustrating an example of adjusting a receiving structure to substantially mode-match to a guided surface waveguide mode on the surface of the lossy conducting medium 203. Beginning with 181, if the receiving structure includes a charge terminal $T_R$ (e.g., of the tuned resonator 306a of FIG. 18B), then the charge terminal $T_R$ is positioned at a defined height above a lossy conducting medium 203 at 184. As the surface guided wave has been established by a guided surface waveguide probe 200, the physical height ($h_p$) of the charge terminal $T_R$ may be below that of the effective height. The physical height may be selected to reduce or minimize the bound charge on the charge terminal $T_R$ (e.g., four times the spherical diameter of the charge terminal). If the receiving structure does not include a charge terminal $T_R$ (e.g., of the tuned resonator 306b of FIG. 18C), then the flow proceeds to 187.

At 187, the electrical phase delay $\Phi$ of the receiving structure is matched to the complex wave tilt angle $\Psi$ defined by the local characteristics of the lossy conducting medium 203. The phase delay ($\theta_c$) of the helical coil and/or the phase delay ($\theta_y$) of the vertical supply line can be adjusted to make $\Phi$ equal to the angle ($\Psi$) of the wave tilt (W). The angle ($\Psi$) of the wave tilt can be determined from Equation (86). The electrical phase delay $\Phi$ can then be matched to the angle of the wave tilt. For example, the electrical phase delay $\Phi=\theta_c+\theta_y$ can be adjusted by varying the geometrical parameters of the coil $L_R$ and/or the length (or height) of the vertical supply line conductor.

Next at 190, the resonator impedance can be tuned via the load impedance of the charge terminal $T_R$ and/or the impedance of a lumped element tank circuit to resonate the equivalent image plane model of the tuned resonator 306a. The depth (d/2) of the conducting image ground plane 139 (FIGS. 9A-9C) below the receiving structure can be determined using Equation (100) and the values of the lossy conducting medium 203 (e.g., the Earth) at the receiving structure, which can be locally measured. Using that complex depth, the phase shift ($\theta_d$) between the image ground plane 139 and the physical boundary 136 (FIGS. 9A-9C) of the lossy conducting medium 203 can be determined using $\theta_d=\beta_o d/2$. The impedance ($Z_{in}$) as seen "looking down" into the lossy conducting medium 203 can then be determined using Equation (99). This resonance relationship can be considered to maximize coupling with the guided surface waves.

Based upon the adjusted parameters of the coil $L_R$ and the length of the vertical supply line conductor, the velocity factor, phase delay, and impedance of the coil $L_R$ and vertical supply line can be determined. In addition, the self-capacitance ($C_R$) of the charge terminal $T_R$ can be determined using, e.g., Equation (24). The propagation factor ($\beta_p$) of the coil $L_R$ can be determined using Equation (98), and the propagation phase constant ($\beta_w$) for the vertical supply line can be determined using Equation (49). Using the self-capacitance and the determined values of the coil $L_R$ and vertical supply line, the impedance ($Z_{base}$) of the tuned resonator 306 as seen "looking up" into the coil $L_R$ can be determined using Equations (101), (102), and (103).

The equivalent image plane model of FIGS. 9A-9C also apply to the tuned resonator 306a of FIG. 18B. The tuned resonator 306a can be tuned to resonance with respect to the complex image plane by adjusting the load impedance $Z_R$ of the charge terminal $T_R$ such that the reactance component $X_{base}$ of $Z_{base}$ cancels out the reactance component of $X_{in}$ of $Z_{in}$, or $X_{base}+X_{in}=0$. Where the tuned resonator 306 of FIGS. 18B and 18C includes a lumped element tank circuit, the self-resonant frequency of the parallel circuit can be adjusted such that the reactance component $X_{tuning}$ of $Z_{tuning}$ cancels out the reactance component of $X_{in}$ of $Z_{in}$, or $X_{tuning}+X_{in}=0$. Thus, the impedance at the physical boundary 136 (FIG. 9A) "looking up" into the coil of the tuned resonator 306 is the conjugate of the impedance at the physical boundary 136 "looking down" into the lossy conducting medium 203. The load impedance $Z_R$ can be adjusted by varying the capacitance ($C_R$) of the charge terminal $T_R$ without changing the electrical phase delay $\Phi=\theta_c+\theta_y$ seen by the charge terminal $T_R$. The impedance of the lumped element tank circuit can be adjusted by varying the self-resonant frequency ($f_p$) as described with respect to FIG. 9D. An iterative approach may be taken to tune the resonator impedance for resonance of the equivalent image plane model with respect to the conducting image ground plane 139. In this way, the coupling of the electric field to a guided surface waveguide mode along the surface of the lossy conducting medium 203 (e.g., Earth) can be improved and/or maximized.

Referring to FIG. 19, the magnetic coil 309 comprises a receive circuit that is coupled through an impedance matching network 333 to an electrical load 336. In order to facilitate reception and/or extraction of electrical power from a guided surface wave, the magnetic coil 309 may be positioned so that the magnetic flux of the guided surface wave, $H_\varphi$, passes through the magnetic coil 309, thereby inducing a current in the magnetic coil 309 and producing a terminal point voltage at its output terminals 330. The magnetic flux of the guided surface wave coupled to a single turn coil is expressed by $$\mathcal{F} = \iint_{A_{CS}} \mu_r \mu_o \vec{H} \cdot \hat{n} dA, \tag{104}$$

where $\mathcal{F}$ is the coupled magnetic flux, $\mu_r$ is the effective relative permeability of the core of the magnetic coil 309, $\mu_o$ is the permeability of free space, $\vec{H}$ is the incident magnetic field strength vector, $\hat{n}$ is a unit vector normal to the cross-sectional area of the turns, and $A_{CS}$ is the area enclosed by each loop. For an N-turn magnetic coil 309 oriented for maximum coupling to an incident magnetic field that is uniform over the cross-sectional area of the magnetic coil 309, the open-circuit induced voltage appearing at the output terminals 330 of the magnetic coil 309 is $$V = -N\frac{d\mathcal{F}}{dt} \approx -j\omega\mu_r\mu_0 NH A_{CS}, \tag{105}$$

where the variables are defined above. The magnetic coil 309 may be tuned to the guided surface wave frequency either as a distributed resonator or with an external capacitor across its output terminals 330, as the case may be, and then impedance-matched to an external electrical load 336 through a conjugate impedance matching network 333.

Assuming that the resulting circuit presented by the magnetic coil 309 and the electrical load 336 are properly adjusted and conjugate impedance matched, via impedance matching network 333, then the current induced in the magnetic coil 309 may be employed to optimally power the electrical load 336. The receive circuit presented by the magnetic coil 309 provides an advantage in that it does not have to be physically connected to the ground.

With reference to FIGS. 18A, 18B, 18C and 19, the receive circuits presented by the linear probe 303, the tuned resonator 306, and the magnetic coil 309 each facilitate receiving electrical power transmitted from any one of the embodiments of guided surface waveguide probes 200 described above. To this end, the energy received may be used to supply power to an electrical load 315/327/336 via a conjugate matching network as can be appreciated. This contrasts with the signals that may be received in a receiver that were transmitted in the form of a radiated electromagnetic field. Such signals have very low available power, and receivers of such signals do not load the transmitters.

It is also characteristic of the present guided surface waves generated using the guided surface waveguide probes 200 described above that the receive circuits presented by the linear probe 303, the tuned resonator 306, and the magnetic coil 309 will load the excitation source 212 (e.g., FIGS. 3, 12 and 16) that is applied to the guided surface waveguide probe 200, thereby generating the guided surface wave to which such receive circuits are subjected. This reflects the fact that the guided surface wave generated by a given guided surface waveguide probe 200 described above comprises a transmission line mode. By way of contrast, a power source that drives a radiating antenna that generates a radiated electromagnetic wave is not loaded by the receivers, regardless of the number of receivers employed.

Thus, together one or more guided surface waveguide probes 200 and one or more receive circuits in the form of the linear probe 303, the tuned resonator 306a/b, and/or the magnetic coil 309 can make up a wireless distribution system. Given that the distance of transmission of a guided surface wave using a guided surface waveguide probe 200 as set forth above depends upon the frequency, it is possible that wireless power distribution can be achieved across wide areas and even globally.

The conventional wireless-power transmission/distribution systems extensively investigated today include "energy harvesting" from radiation fields and also sensor coupling to inductive or reactive near-fields. In contrast, the present wireless-power system does not waste power in the form of radiation which, if not intercepted, is lost forever. Nor is the presently disclosed wireless-power system limited to extremely short ranges as with conventional mutual-reactance coupled near-field systems. The wireless-power system disclosed herein probe-couples to the novel surface-guided transmission line mode, which is equivalent to delivering power to a load by a wave-guide or a load directly wired to the distant power generator. Not counting the power required to maintain transmission field strength plus that dissipated in the surface waveguide, which at extremely low frequencies is insignificant relative to the transmission losses in conventional high-tension power lines at 60 Hz, all of the generator power goes only to the desired electrical load. When the electrical load demand is terminated, the source power generation is relatively idle.

Figure 20:
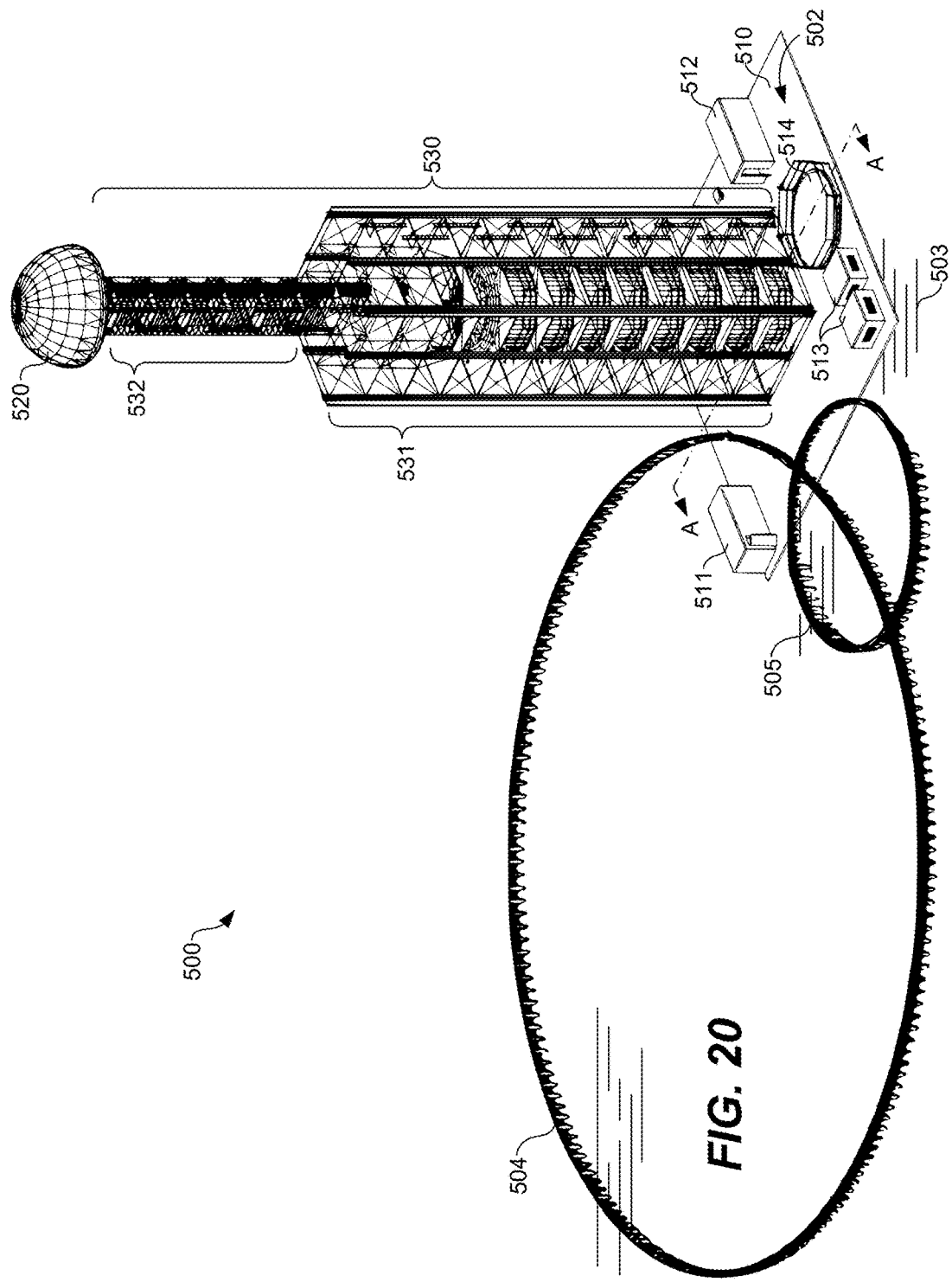
FIG. 20 illustrates an example guided surface waveguide probe according to various embodiments of the present disclosure.

Referring next to FIG. 20, an example of a guided surface waveguide probe 500 is illustrated according to various embodiments of the present disclosure. The guided surface waveguide probe 500 is situated on a probe site. The guided surface waveguide probe 500 is provided as an example of the types of structures that can be used to launch guided surface waves on a lossy conducting media, but is not intended to be limiting or exhaustive as to those structures. Not all the structures that make up the guided surface waveguide probe 500 shown in FIG. 20 are necessary in all cases, and various structures can be omitted. Similarly, the guided surface waveguide probe 500 can include other structures not illustrated in FIG. 20.

Among other parts, components, or structures, the guided surface waveguide probe 500 is constructed with a substructure 502 constructed in a lossy conducting medium 503, such as the Earth. The substructure 502 forms a substructure of the guided surface waveguide probe 500 and may be used to house various equipment as will be described. In one embodiment, the guided surface waveguide probe 500 includes one or more external phasing coils 504 and 505. The external phasing coils 504 and 505 can provide both phase delay and phase shift as described below. In various embodiments, the external phasing coils 504 and 505 may not be used and can be omitted depending on design considerations such as the frequency of operation and other considerations as described above.

The guided surface waveguide probe 500 can be constructed at any suitable geographic location on the Earth. In some cases, a portion of the lossy conducting medium 503 around the guided surface waveguide probe 500 can be conditioned to adjust its permittivity, conductivity, or related characteristics. The external phasing coils 504 and 505 can be constructed at any suitable locations, including around (e.g., encircling) the guided surface waveguide probe 500 as will be further described below.

The substructure 502 includes a covering support slab 510 at a ground surface elevation of the lossy conducting medium 503. To provide entry and exit points to the guided surface waveguide probe 500 for individuals, the substructure 502 includes entryways 511 and 512, leading to staircases, for example, leading down into the substructure 502. The substructure 502 also includes a number of vents 513 to exhaust forced air, for example, from heating, ventilation, and air conditioning (HVAC) systems in the substructure 502 and for potentially other purposes. Also, the vents 513 may be used for air intake as needed. Additionally, the substructure 502 includes an access opening 514 which can be used to lower various types of equipment down into the substructure 502.

The guided surface waveguide probe 500 includes a charge reservoir or terminal 520 ("charge terminal 520") elevated to a height above the lossy conducting medium 503 over the substructure 502. The guided surface waveguide probe 500 also includes a support structure 530. The support structure 530 includes a truss frame 531 and a charge terminal truss extension 532 ("the truss extension 532"). The truss frame 531 is secured to and supported by the covering support slab 510 and substructure elements in the substructure 502 such as pillars and beams as will be described.

Figure 21:
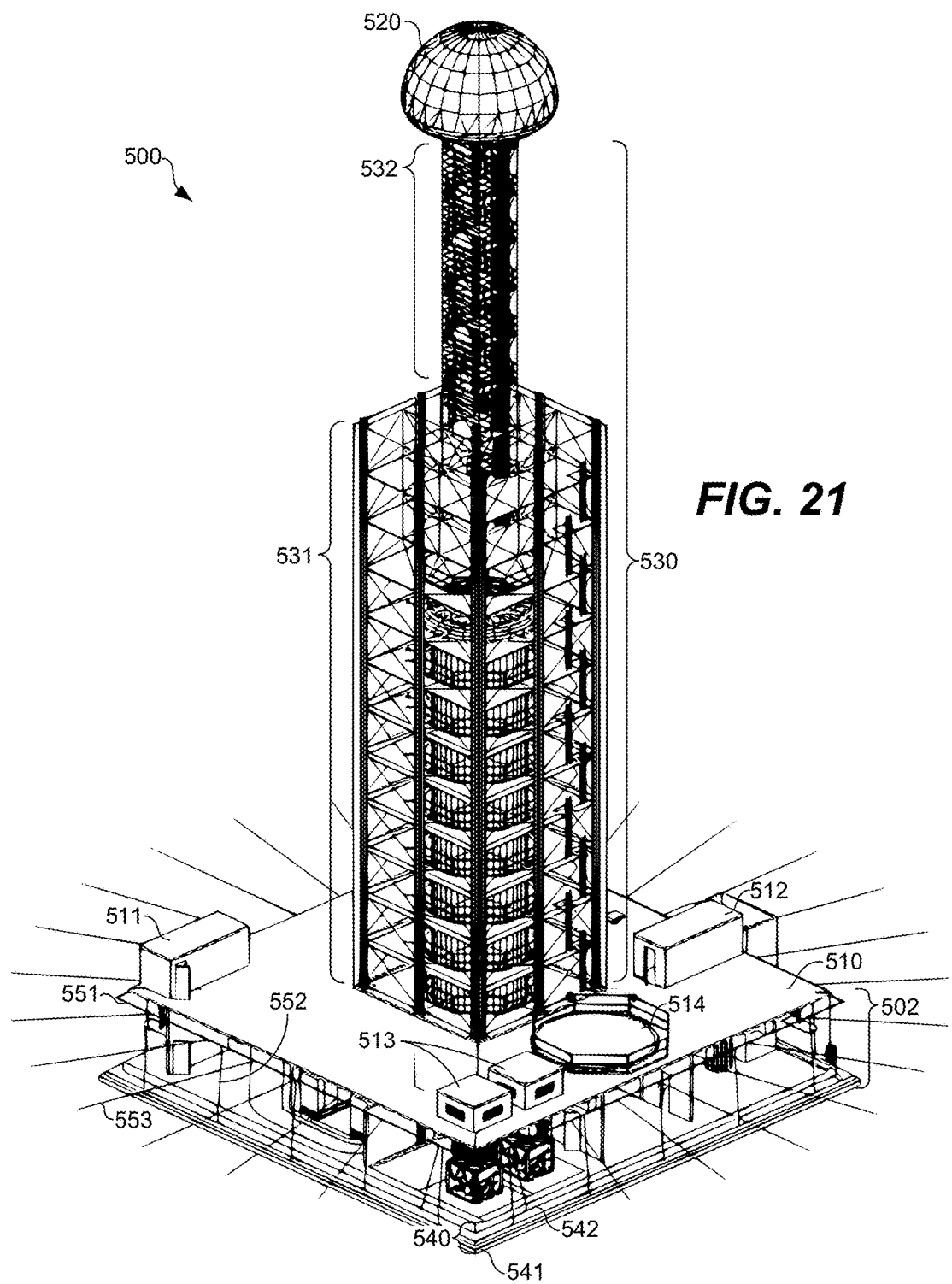
FIG. 21 illustrates the guided surface waveguide probe and substructure of the site shown in FIG. 20 according to various embodiments of the present disclosure.

With reference to FIG. 21, shown is a further view of the guided surface waveguide probe 500 according to various embodiments of the present disclosure. As shown, the substructure 502 is constructed to a large extent within the lossy conducting medium 503. The substructure 502 provides a supporting, foundational substructure for the guided surface waveguide probe 500, similar to the way a basement or cellar provides a below-ground foundation for a building. In one example case, the substructure 502 can be constructed to include one floor or level at a depth of about 18 feet deep from the ground surface of the lossy conducting medium 503. In other embodiments, the substructure 502 can include additional underground floors and be constructed to other depths. Additional aspects of the substructure 502 are described below with reference to FIGS. 30 and 31.

The truss frame 531 includes a number of platforms supported, respectively, at elevated heights above the covering support slab 510. Among other components of the guided surface waveguide probe 500, a number of internal phasing coil sections of the guided surface waveguide probe 500 can be supported at one or more of the platforms as discussed in further detail below. The truss extension 532 is supported at one end by a transitional truss support region of the truss frame 531. The truss extension 532 also supports, at another end, the charge terminal 520 above the lossy conducting medium 503.

To provide an example frame of reference for the size of the guided surface waveguide probe 500, the substructure 502 can be constructed at a size of about 92 feet in width and length, although it can be constructed to any other suitable size. The guided surface waveguide probe 500 can be constructed to a height of over 200 feet in one embodiment. In that case, the charge terminal 520 can be elevated to a height of approximately 190 feet above the lossy conducting medium 503. However, it is understood that the height of the charge terminal 520 depends upon the design considerations described above, where the guided surface waveguide probe 500 is designed to position the charge terminal 520 at a predetermined height depending on various parameters of the lossy conducting medium 503 at the site of transmission and other operating factors. In one example, the base of the truss frame 531 can be constructed as a square with sides about 32 feet in length and width. It is understood that the truss frame 531 can be constructed to other shapes and dimensions. To this end, the guided surface waveguide probe 500 is not limited to any particular size or dimensions and can be constructed to any suitable size among the embodiments based on various factors and design considerations set forth above.

Figure 23:
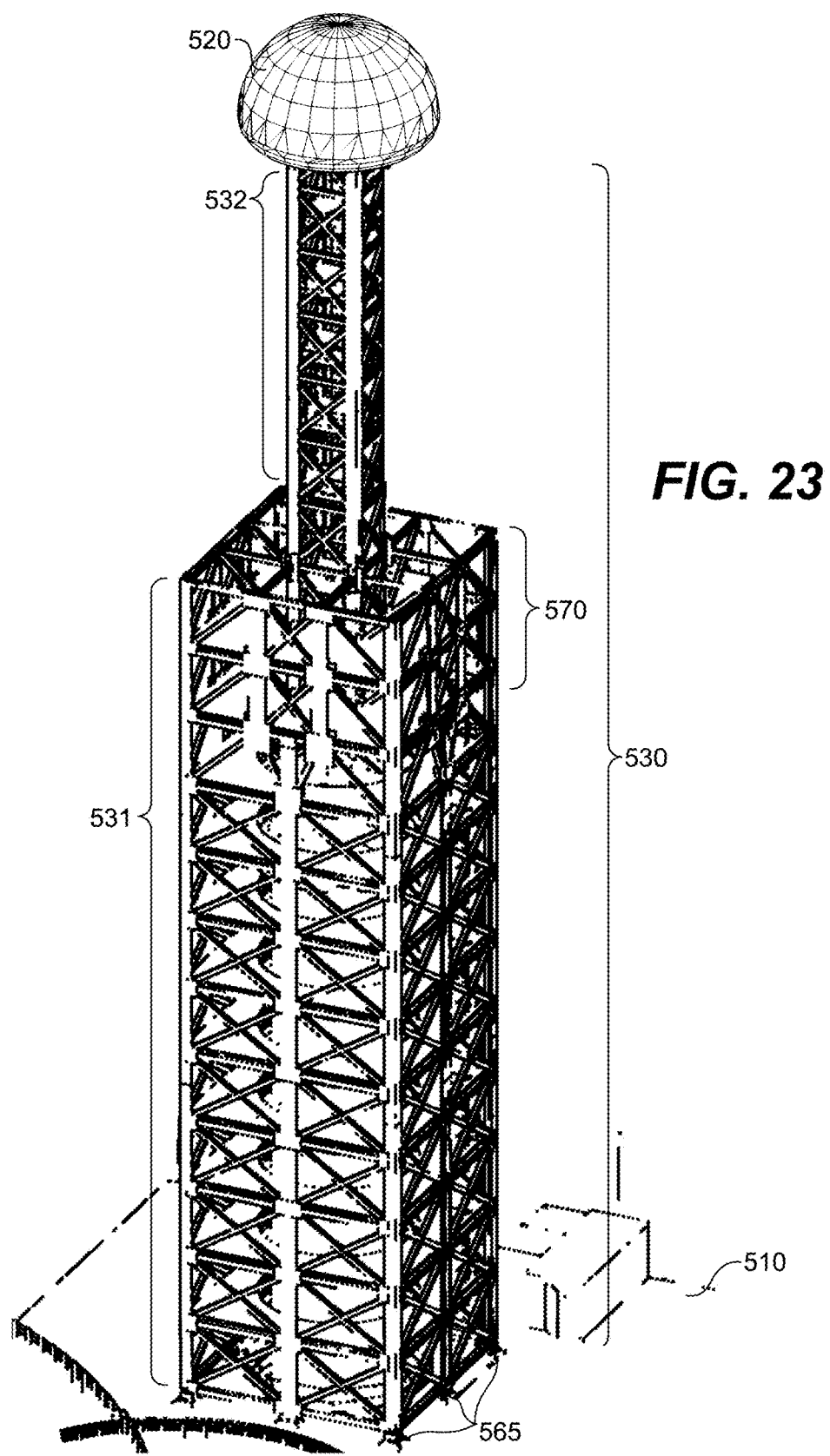
FIGS. 23 and 24 illustrate an example of the support structure of the probe shown in FIG. 20 according to various embodiments of the present disclosure.

For simplicity, the truss frame 531 and the truss extension 532 of the guided surface waveguide probe 500 are drawn representatively in FIG. 20. Particularly, a number of vertical, horizontal, and cross beam support bars of the truss frame 531 and the truss extension 532 are omitted from view in FIG. 20. Additionally, a number of gusset plates of the truss frame 531 and the truss extension 532 are omitted from view. The vertical, horizontal, and cross beam support bars, gusset plates, connecting hardware, and other parts of the guided surface waveguide probe 500 are formed from nonconductive materials so as not to adversely affect the operation of the guided surface waveguide probe 500. The parts of the truss frame 531 and the truss extension 532 of the guided surface waveguide probe 500 are shown in FIG. 23 and described in further detail below.

FIG. 21 illustrates an example of the substructure 502 associated with the guided surface waveguide probe 500 shown in FIG. 20. The lossy conducting medium 503 and sidewalls of the substructure 502 are omitted from view in FIG. 20. As further described below, the substructure 502 includes a number of rooms or areas to store equipment, such as power transformers, variable power and frequency power transmitters, supervisory control and data acquisition (SCADA) systems, human-machine interface systems, electrical systems, power transmission system monitoring and control systems, heating, ventilation, and air conditioning (HVAC) systems, building monitoring and security systems, fire protection systems, water and air cooling systems, and other systems. Examples of the equipment in the substructure 502 is described in further detail below with reference to FIGS. 30 and 31.

Among a number of internal and external walls described below, the substructure 502 includes a foundation base 540 including a seal slab 541 and a base slab 542. The seal slab 541 can be formed from poured concrete. According to one embodiment, the base slab 542 is also formed from poured concrete and is reinforced with fiberglass bars as will be described.

A grounding system, which is described in further detail below with reference to FIGS. 32A and 32B, is formed and sealed in the seal slab 541 of the foundation base 540. The grounding system also includes a grounding grid (not shown) in the seal slab 541, a grounding ring 551, connecting conductors 552, grounding radials 553, and other components not individually referenced in FIG. 21. As described below, each of the grounding radials 553 is electrically connected or coupled at one end to the grounding ring 551. The other end of each of the grounding radials 553 extends out from the grounding ring 551 radially away from the guided surface waveguide probe 500 to a staked location in the lossy conducting medium 503.

In one example case, the grounding radials 553 extend out about 100 feet from the guided surface waveguide probe 500, although other lengths of grounding radials 553 can be used. Further, the grounding radials 553 extend out from the grounding ring 551 at a depth below the ground surface of the lossy conducting medium 503. For example, in one embodiment, the grounding radials 553 extend radially away from the grounding ring 551 and the guided surface waveguide probe 500 at a depth of about 12 to 24 inches below the ground surface of the lossy conducting medium 503, although they can be buried at other depths. The grounding grid (not shown) in the seal slab 541, the grounding ring 551, and the grounding radials 553 provide electrical contact with the lossy conducting medium 503 for the guided surface waveguide probe 500 and various equipment in the substructure 502.

Figure 22:
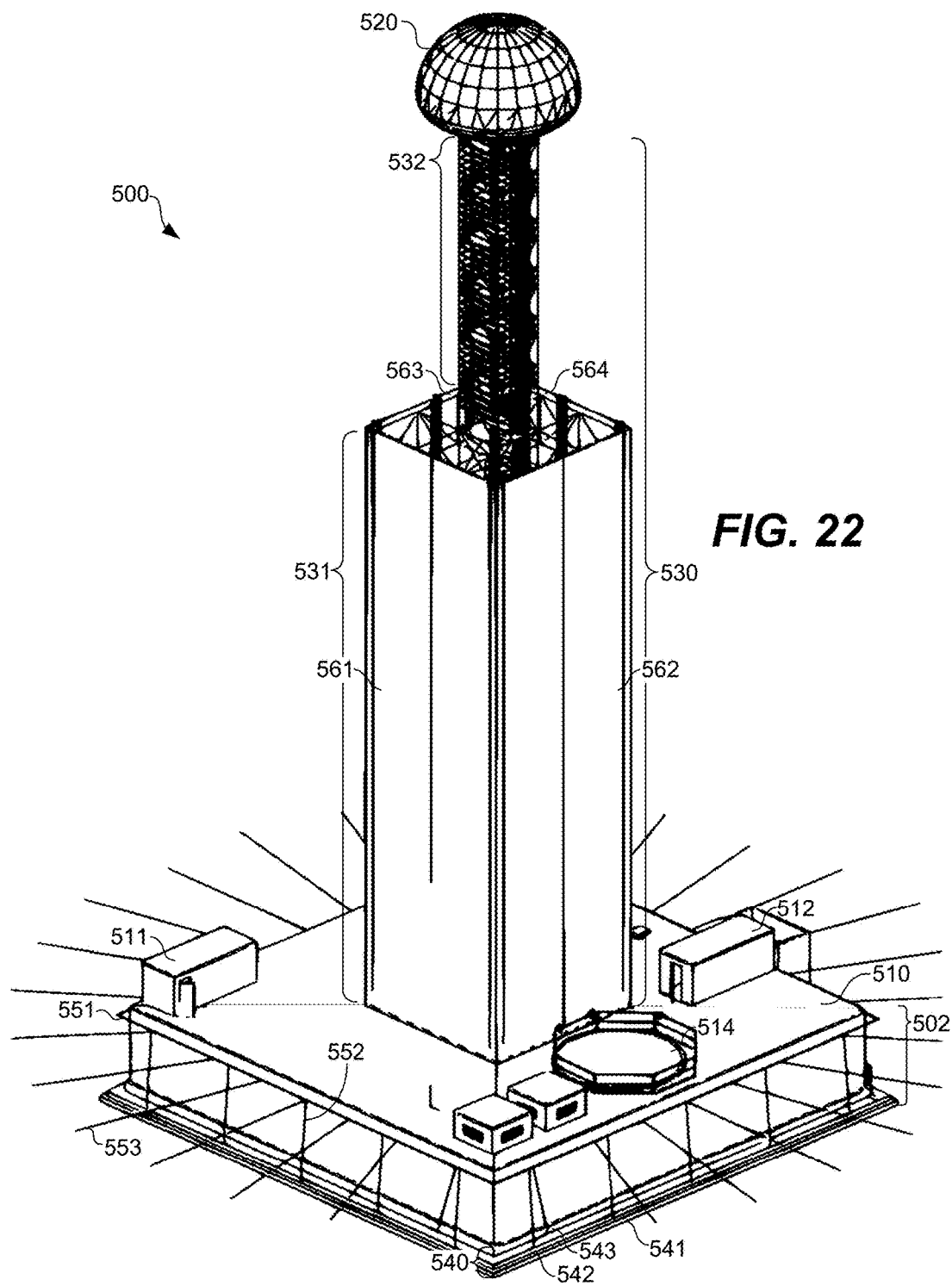
FIG. 22 illustrates the guided surface waveguide probe shown in FIG. 20 with an exterior covering according to various embodiments of the present disclosure.

FIG. 22 illustrates the guided surface waveguide probe 500 shown in FIG. 20 with exterior coverings 561-564 according to various embodiments of the present disclosure. The exterior coverings 561-564, among others, can be installed around one or both of the truss frame 531, as shown in FIG. 22, and the truss extension 532. The exterior coverings 561-564 can be installed to insulate and protect the truss frame 531 and the truss extension 532 from the sun and various meteorological processes and events. The exterior coverings 561-564 can also be installed to facilitate forced-air heating and cooling of the guided surface waveguide probe 500 using HVAC systems, for example, installed in the substructure 502 or other location. Similar to the other parts of the truss frame 531 and the truss extension 532, the exterior coverings 561-564 of the guided surface waveguide probe 500 are formed from non-conductive materials so as not to interfere electrically with the operation of the guided surface waveguide probe 500.

FIG. 23 illustrates an example of the support structure 530 of the guided surface waveguide probe 500. As shown in FIG. 23, the support structure 530 of the guided surface waveguide probe 500 can be formed as a truss, including a number of vertical, horizontal, and cross beam support bar members joined together using gusset plates and fasteners at a number of nodes. Cross beam support bar members, the gusset plates, and the fasteners are all nonconductive having been made from nonconductive materials such as pultruded fiber reinforced polymer (FRP) composite structural products.

External forces on the support structure 530 primarily act at the nodes (e.g., gusset plates, fasteners) of the support structure 530 and result in support bar member forces that are either tensile or compressive that exert sheer forces on the gusset plates and fasteners. The support structure 530 is constructed so as not to exert moment forces on the gusset plates and the fasteners that form the junctions in the support structure 530. This accommodates the fact that the fasteners are constructed from nonconductive materials that might have difficulty withstanding such forces without failure. The support structure 530 is secured to the covering support slab 510 using a number of base brackets 565, which can be formed from metal or other appropriate material. In one embodiment, the base brackets 565 are formed from stainless steel to reduce the possibility that the base brackets 565 would become magnetized.

As shown in FIG. 23, the support structure 530 includes a transitional truss region 570 between the truss frame 531 and the terminal truss extension 532. The transitional truss region 570 includes a number of additional cross beam support bars that extend and are secured between nodes in the truss frame 531 and nodes in the terminal truss extension 532. The additional cross beams in the transitional truss region 570 secure the terminal truss extension 532 to the truss frame 531.

Figure 24:
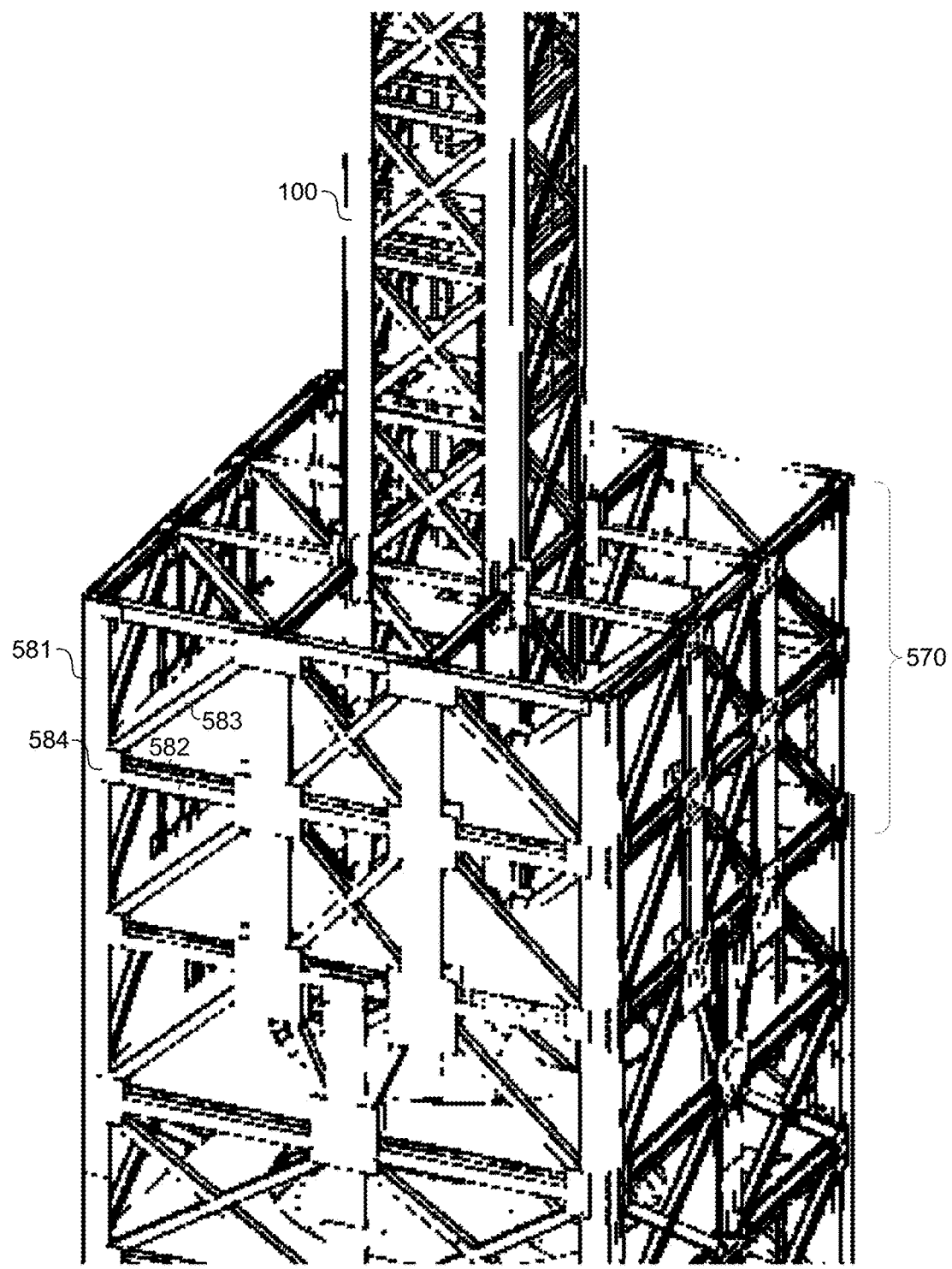

FIG. 24 illustrates a closer view of the transitional truss region 570 of the guided surface waveguide probe 500, in which examples of the vertical support bars 581, the horizontal support bars 582, the cross beam support bars 583 (collectively, "the bars 581-583), and the gusset plates 584 can be more clearly seen. As shown in FIG. 24, the truss frame 531 and the terminal truss extension 532 can be constructed using a number of vertical support bars 581, horizontal support bars 582, cross beam support bars 583, and gusset plates 584 of various shapes and sizes. For example, the bars 581-583 can be formed as L beams, I or H beams, T beams, etc. at various lengths and cross-sectioned sizes. In that context, the bars 581-583 can be designed to translate loads to the gusset plates 584.

The gusset plates 584 can be formed as relatively thick plates of material and are used to connect a number of the bars 581-583 together at various nodes in the support structure 530. Each of the gusset plates 584 can be fastened to a number of the bars 581-583 using nonconductive bolts or other nonconductive fastening means, or a combination of fastening means. As noted above, external forces on the support structure 530 primarily act at the nodes gusset plates 584.

As previously mentioned, the vertical support bars 581, horizontal support bars 582, cross beam support bars 583, gusset plates 584, fasteners, and/or other connecting hardware, and other parts of the truss frame 531 and the truss extension 532 can be formed (entirely or substantially) from non-conductive materials. For example, such support bars 582, cross beam support bars 583, gusset plates 584, fasteners, and other connecting hardware may be constructed of pultruded fiber reinforced polymer (FRP) composite structural products. Alternatively, the same may be made out of wood or resin impregnated wood structural products. In addition, other non-conductive materials may be used.

Figure 25:
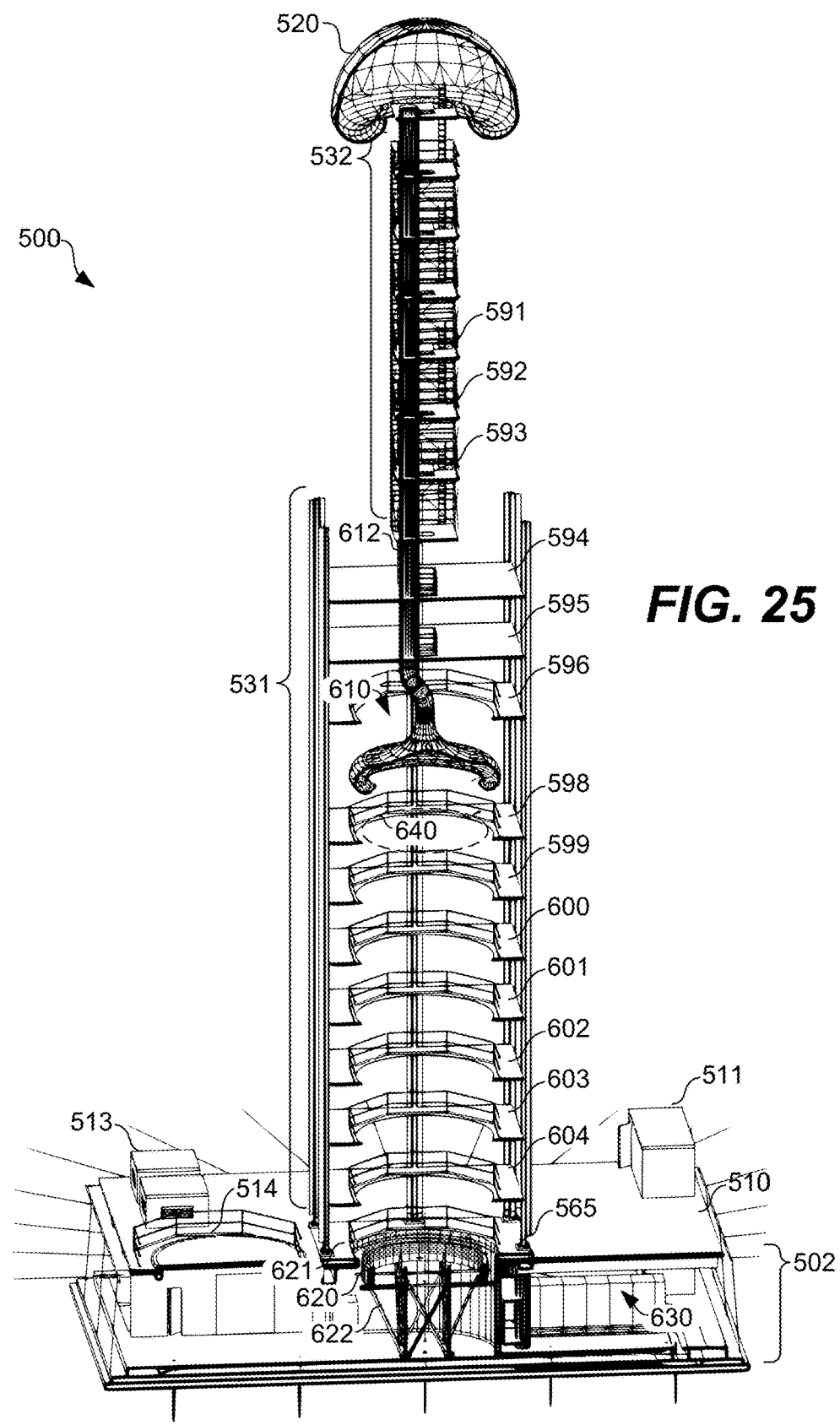
FIG. 25 is the cross-sectional view A-A designated in FIG. 20 according to various embodiments of the present disclosure.

FIG. 25 is the cross-sectional view A-A of the guided surface waveguide probe 500 designated in FIG. 20. In FIG. 25, the bars 581-583 and the gusset plates 584 of the truss frame 531 and the terminal truss extension 532 are omitted from view. Thus, among others, a number of platforms 591-604 of the guided surface waveguide probe 500 are shown. The platform 597 (FIG. 28) is omitted from view in FIG. 25 so as not to obscure other components of the guided surface waveguide probe 500. The platforms 591-593 are supported by the truss extension 532, and platforms 594-604 are supported by the truss frame 531. In various embodiments, individuals can access the platforms 591-604, among others, using ladders, staircases, elevators, etc. between them, as also shown in FIG. 21.

A number of additional components of the guided surface waveguide probe 500 are shown in FIG. 25, including a corona hood 610 and a coil 620 that, in one embodiment, can be used to inductively couple power to other electrical components of the guided surface waveguide probe 500 as will be described. The coil 620 is supported by a coil support stand 622. A power transmitter bank 630 is housed in the substructure 502.

The corona hood 610 comprises an annular canopy that tapers into a tube 612. The tube 612 extends along (and through the platforms 591-596 of) a portion of the truss frame 531 and the truss extension 532 into a bottom opening of the charge terminal 520. The corona hood 610 is positioned within an opening in the platform 597 (FIG. 28), similar to the opening 640 in the platform 598 and the other platforms 599-604. In various embodiments, the corona hood 610 can be formed from one or more conductive materials such as copper, aluminum, or other metal.

In one embodiment, the covering support slab 510 includes a square opening close to its center, and the truss frame 531 is secured to the covering support slab 510 at the base brackets 565 positioned along the periphery of this square opening. Further, a base plate 621 can be secured over the square opening in the covering support slab 510 between the covering support slab 510 and the truss frame 531. As shown, the base plate 621 can include a circular opening in its center. The coil 620 can be supported by the coil support stand 622 below, within, or above the circular opening through the base plate 621. According to one embodiment, the base plate 621 may be constructed of nonconductive materials such as pultruded fiber reinforced polymer (FRP) composite structural material and/or other nonconductive materials according to one embodiment.

In one embodiment, the external phasing coils 504 and 505 (FIG. 20) are positioned such that at least one edge of the external phasing coils 504 and/or 505 is relatively close or adjacent to the square opening in the covering support slab 510 and the truss frame 531. In that configuration, it is possible to minimize the lengths of conductors extending between power sources in the substructure 502 and the external phasing coils 504 and/or 505, and/or between the external phasing coils 504 and/or 505 and other electrical components, such as internal phasing coils in the tower structure of the guided surface waveguide probe 500. In addition, other openings may be created in the covering support slab 510 to accommodate conductors that extend from a power source in the substructure 502 to one or both of the external phasing coils 504 and/or 505. In one embodiment, a distance between an edge of one or both of the external phasing coils 504 and/or 505 and an internal phasing coil positioned in the interior of the tower structure of the guided surface waveguide probe 500 is less than $\frac{1}{8}^{th}$ of the periphery of the respective coils 504 and/or 505.

The coil 620 can be embodied as a length of conductor, such as wire or pipe, for example, wrapped and supported around a coil support structure. The coil support structure may comprise a cylindrical body or other support structure to which the wire or pipe is attached in the form of a coil. In one example case, the coil 620 can be embodied as a number of turns of a conductor wrapped around a support structure such as a cylindrical housing at about 19 feet in diameter, although the coil 620 can be formed to other sizes.

The power transmitter bank 630, which acts as a power source for the guided surface waveguide probe 500, is configured to convert bulk power to a range of output power over a range of sinusoidal output frequencies, such as up to a megawatt of power, for example, over a range of frequencies from about 6 kHz-100 kHz, or other frequencies or frequency ranges. As described in further detail below with reference to FIG. 30, the guided surface waveguide probe 500 can include a number of power transmitter cabinets, controllers, combiners, etc., such as the power transmitter bank 630 and others. The power transmitter bank 630 is not limited to any particular range of output power or output frequencies; however, as the guided surface waveguide probe 500 can be operated at various power levels and frequencies. In one example embodiment, the power transmitter bank 630 comprises various components including amplifier cabinets, control cabinet, and a combiner cabinet. The amplifier cabinets may be, for example, model D120R Amplifiers manufactured by Continental Electronics of Dallas, Tex. Likewise the control cabinet and combiner cabinet are also manufactured by Continental Electronics of Dallas Tex. It is understood, however, that power transmitter equipment manufactured by others may be used. In addition, it is understood that types of power sources other than power transmitter equipment may be used including, for example, generators or other sources.

Depending upon the operating configuration of the guided surface waveguide probe 500, the output of the power transmitter bank 630 (and other power transmitter banks) can be electrically coupled to the coil 620. In turn, power can be inductively coupled from the power transmitter bank 630 to other electrical components of the guided surface waveguide probe 500 using the coil 620. For example, power can be inductively coupled from the coil 620 to the internal phasing coils 651 shown in FIG. 26. Alternatively, one or more other coils positioned relative (or adjacent) to the external phasing coils 504 and/or 505 can be used to inductively couple power from the power transmitter bank 630 to one or both of the external phasing coils 504 and/or 505. For example, such coils can be wrapped around (and supported by) the same support structure around which the external phasing coils 504 or 505 are supported. In one embodiment, such coils might be placed on the ground adjacent to or below one or both of the external phasing coils 504 and/or 505.

Generally, depending upon the operating frequency of the guided surface waveguide probe 500 (e.g., 400 Hz, 8 kHz, or 20 kHz operation), the output of the power transmitter bank 630 can be electrically coupled to one or more coils similar to the coil 620 for inductive coupling to one or more internal or external phasing coils of the guided surface waveguide probe 500 as described herein. Additionally or alternatively, the output of the power transmitter bank 630 can be electrically coupled to one or more coils similar to the coil 620 for inductive coupling to one or more tank (inductive) coils of the guided surface waveguide probe 500 as described herein.

Figure 26:
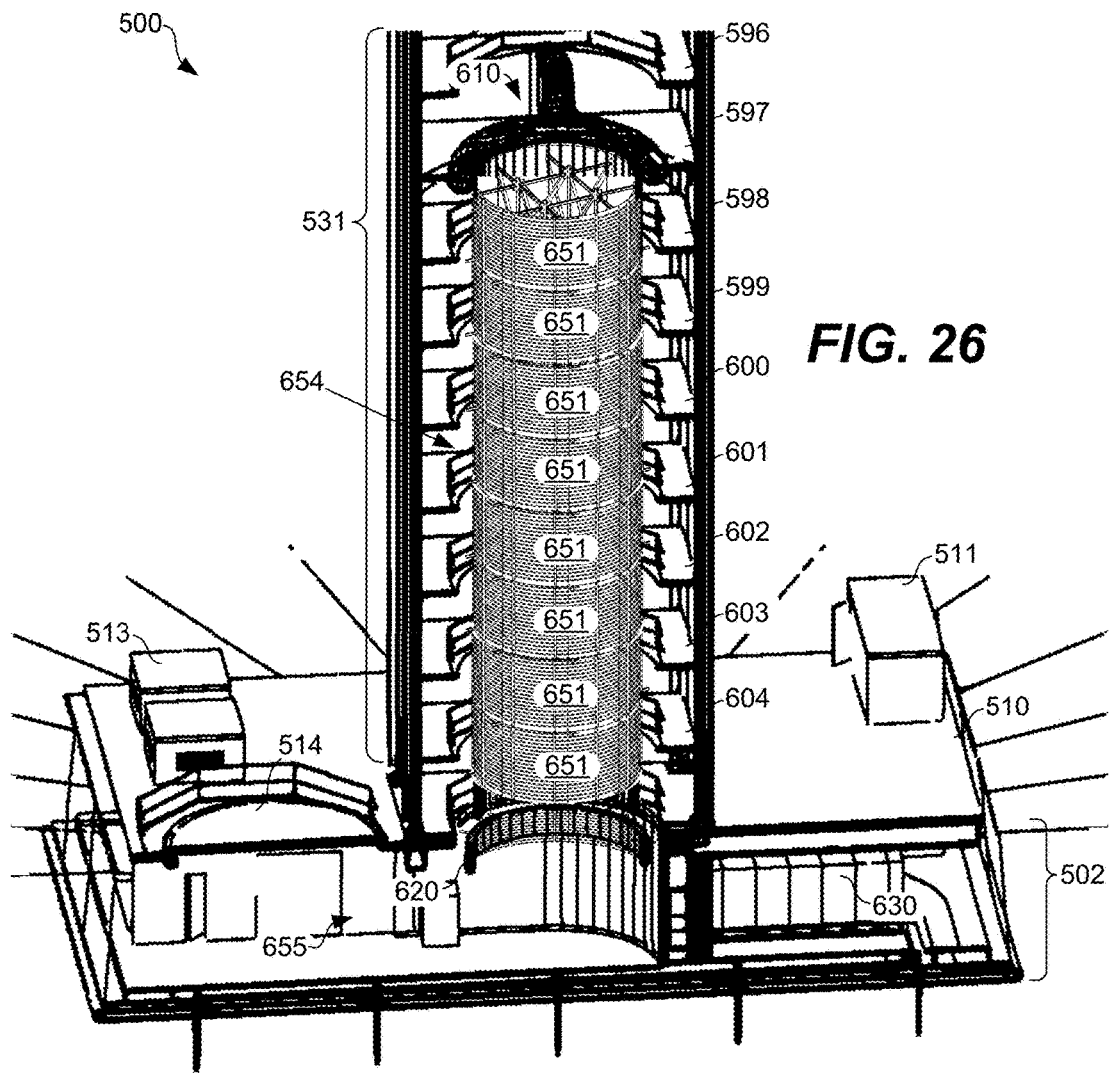
FIG. 26 is the cross-sectional view A-A designated in FIG. 20 and illustrates a number of sections of a coil of the probe according to various embodiments of the present disclosure.

FIG. 26 is the cross-sectional view A-A designated in FIG. 20 and illustrates a number of internal phasing coils 651 of the guided surface waveguide probe 500 according to various embodiments of the present disclosure. The internal phasing coils 651 are termed "internal" given that they are supported within the truss frame 531, although similar coils can be positioned outside of the truss frame 531. Similarly, the external phasing coils 504 and 505 are termed "external" given that they are placed outside of the truss frame 531.

It should be noted that the internal phasing coils 651 shown in FIG. 26 are analogous to the phasing coil 215 shown in FIGS. 7A and 7B. The internal phasing coils 651 are also analogous to the phasing coil 215a shown in FIG. 7C. Additionally, the external phasing coils 504 and 505 are analogous to the phasing coil 215b shown in FIG. 7C. Further, the guided surface waveguide probe 500 can include a tank circuit as described below with reference to FIGS. 33A and 33B below, and the components in that tank circuit are analogous to the components of the tank circuit 260 shown in FIGS. 7B and 7C.

In one embodiment, the internal phasing coils 651 are positioned adjacent to each other to create one large single internal phasing coil 654. To this end, the internal phasing coils 651 may be positioned such that any discontinuity in the turn by turn spacing of the internal phasing coils 651 at the junction between two respective internal phasing coils 651 is minimized or eliminated, assuming that the turn by turn spacing of each of the internal phasing coils 651 is the same. In other embodiments, the turn by turn spacing of the internal phasing coils 651 may differ from one internal phasing coil 651 to the next. In one embodiment, the internal phasing coils 651 may be in one or more groups, where each group has a given turn by turn spacing. Alternatively, in another embodiment, each internal phasing coil 651 may have a turn by turn spacing that is unique with respect to all others depending on the ultimate design of the guided surface waveguide probe 500. In addition, the diameters of respective ones of the internal phasing coils 651 may vary as well.

Each of the internal phasing coils 651 can be embodied as a length of conductor, such as wire or pipe, for example, wrapped and supported around a support structure. In one embodiment, the support structure may comprise a cylindrical housing or some other structural arrangement. As one example, the internal phasing coils 651 can be about 19 feet in diameter, although other sizes can be used depending on design parameters.

The internal phasing coils 651 can be supported at one or more of the platforms 598-604 and/or the covering support slab 510. The guided surface waveguide probe 500 is not limited to the use of any particular number of the internal phasing coils 651 or, for that matter, any particular number of turns of conductors in the internal phasing coils 651. Instead, based on the design of the guided surface waveguide probe 500, which can vary based on various operating and design factors, any suitable number of internal phasing coils 651 can be used, where the turn by turn spacing and diameter of such internal phasing coils 651 can vary as described above.

To configure the guided surface waveguide probe 500 for use, the internal phasing coils 651 can be individually lowered through the access opening 514 in the covering support slab 510, lowered into the passageway 655, and moved through the passageway 655 to a position below the truss frame 531. From below the truss frame 531, the internal phasing coils 651 can be raised up into position within the openings in the platforms 598-604 and supported at one or more of the platforms 598-604. In one embodiment, each of the internal phasing coils 651 may be hung from the structural members of a respective platform 598-

604. Alternatively, each of the internal phasing coils 651 may rest on structural members associated with a respective platform 598-604.

To raise one of the internal phasing coils 651, it can be secured to a winch line and lifted using a winch. The winch can be positioned in the truss frame 531, the truss extension 532, and/or the charge terminal 520. An example winch is shown and described below with reference to FIG. 29A. In the event that a winch is positioned in the truss frame 531 or the truss extension 532, it may be attached in a temporary manner so that the winch may be removed when necessary. In this manner, such a winch would be removably attached to the truss frame 531 or the truss extension 532 given that such a winch would be made of conductive materials that are likely to interfere with the operation of the guided surface waveguide probe 500.

In one embodiment, a conductor that extends from the bottom end of the bottom most internal phasing coil 651 is coupled to the grounding grid described below with reference to FIGS. 32A and 32B. Alternatively, the conductor that extends from the bottom end of the bottom most internal phasing coil 651 can be coupled to an external phasing coil, such as one of the external phasing coils 504 and/or 505. Intermediate ones of the internal phasing coils 651 are electrically coupled to adjacent ones of the internal phasing coils 651. A conductor that extends from the top end of the top most internal phasing coil 651 that is part of the single internal phasing coil 654 is electrically coupled to the corona hood 610 and/or the charge terminal 520. If coupled to the corona hood 610, the top most internal phasing coil 651 is coupled to the corona hood 610 at a point that is recessed up into the underside of the corona hood 610 to avoid the creation of corona as will be described.

When power is provided from the power transmitter bank 630 to the coil 620 at a certain voltage and sinusoidal frequency, electrical energy is transferred from the coil 620 to the internal phasing coils 651 by magnetic induction. To this end, the coil 620 acts as a type of primary coil for inductive power transfer and the single internal phasing coil 654 acts as a type of secondary coil. To the extent that the internal phasing coils 651 together are considered a single internal phasing coil 654, then the single internal phasing coil 654 acts as the secondary. To facilitate magnetic induction between them, the coil 620 can be positioned and supported by the coil support stand 622 (FIG. 25) or another suitable structure below, within, or above the circular opening through the base plate 621. Further, in various cases, the coil 620 can be positioned below, within, wholly overlapping outside, or partially overlapping outside one of the internal phasing coils 651. If the coil 620 is outside of the internal phasing coils 651, then the coil 620 may wholly or partially overlap a respective one of the internal phasing coils 651. According to one embodiment, the coil 620 is positioned below, within, or outside a bottom most one of the internal phasing coils 651 to facilitate a maximum charge on the charge terminal 520 as described above.

Figure 27:
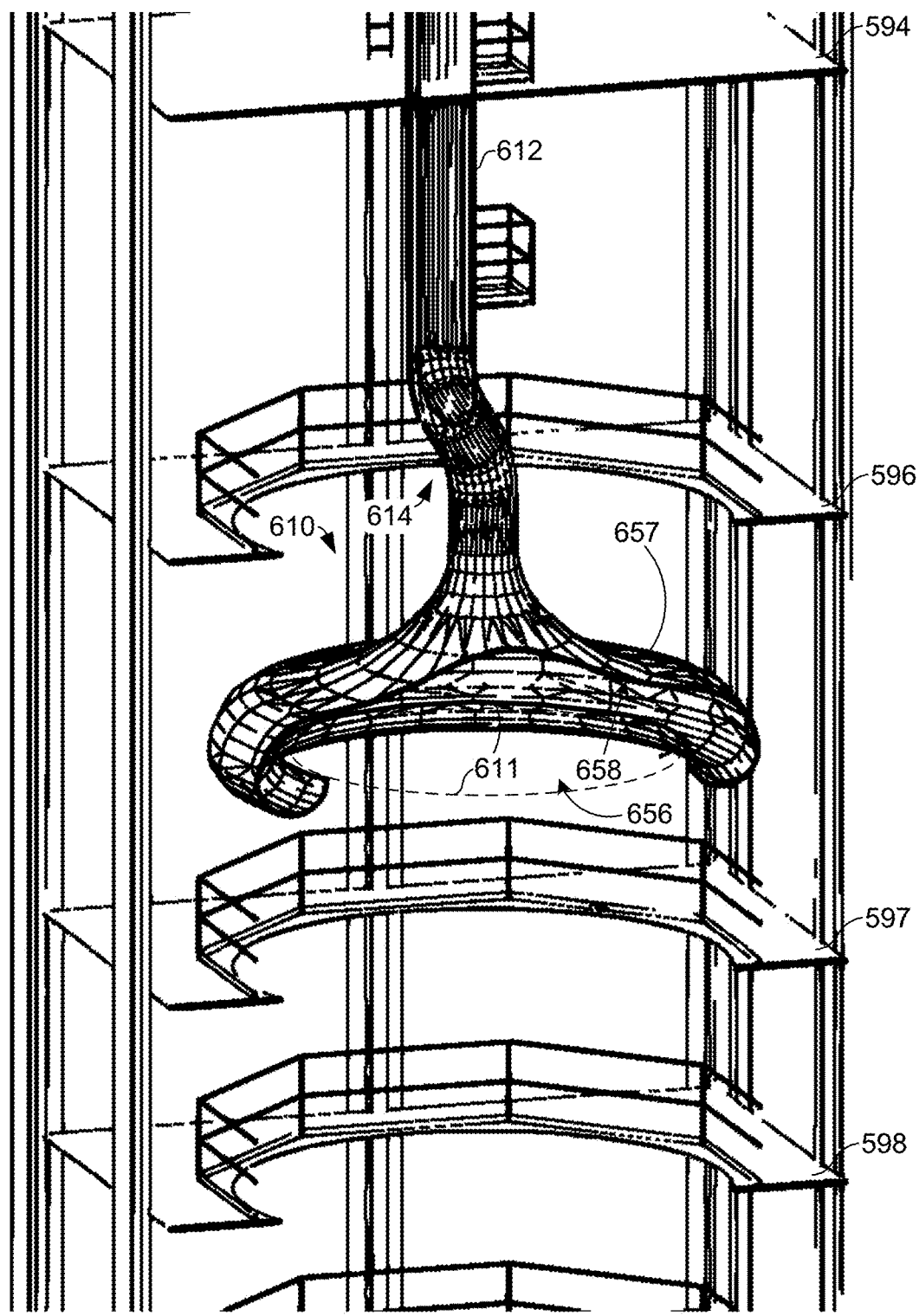
FIG. 27 is an enlarged portion of the cross-sectional view A-A designated in FIG. 20 according to various embodiments of the present disclosure.

To more clearly illustrate the corona hood 610, FIG. 27 is an enlarged portion of the cross-sectional view A-A designated in FIG. 20. The shape and size of the corona hood 610 is provided as an example in FIG. 27, as other shapes and sizes are within the scope of the embodiments. As described in further detail below with reference to FIG. 27, the corona hood 610 can be positioned above and to cover at least a portion of the top most internal phasing coil 651 (FIG. 26) in the guided surface waveguide probe 500. One could also say that the corona hood 610 is positioned above and covers at least an end or top winding of the single internal phasing coil 654 (FIG. 26). Depending upon the number and position of internal phasing coils 651 installed in the guided surface waveguide probe 500, the position of the corona hood 610 may be adjusted. Generally, the corona hood 610 can be positioned and secured at any of the platforms 594-604 of the truss frame 531. However, the position of the corona hood 610 generally needs to be at a sufficient height so as not to create an unacceptable amount of bound capacitance in accordance with the discussion above. If necessary, sections of the tube 612 can be installed (or removed) to adjust the position of the corona hood 610 to one of the platforms 594-604.

The corona hood 610 is designed to minimize or reduce atmospheric discharge around the conductors of the end windings of the top-most internal phasing coil 651. To this end, atmospheric discharge may occur as Trichel pulses, corona, and/or a Townsend discharge. The Townsend discharge may also be called avalanche discharge. All of these different types of atmospheric discharges represent wasted energy in that electrical energy flows into the atmosphere around the electrical component causing the discharge to no effect. As the voltage on a conductor is continually raised from low voltage potential to high voltage potential, atmospheric discharge may manifest itself first as Trichel pulses, then as corona, and finally as a Townsend discharge. Corona discharge in particular essentially occurs when current flows from a conductor node at high potential, into a neutral fluid such as air, ionizing the fluid and creating a region of plasma. Corona discharge and Townsend discharges often form at sharp corners, points, and edges of metal surfaces. Thus, to reduce the formation of atmospheric discharges from the corona hood 610, the corona hood 610 is designed to be relatively free from sharp corners, points, edges, etc.

To this end, the corona hood 610 terminates along an edge 611 that curves around in a smooth arc and ultimately is pointed toward the underside of the corona hood 610. The corona hood 610 is an inverted bowl-like structure having a recessed interior that forms a hollow 656 in the underside of the corona hood 610. An outer surface 657 of the bowl-like structure curves around in the smooth arc mentioned above such that the edge of the bowl-like structure is pointed toward the recessed interior surface 658 of the hollow 656.

During operation of the guided surface waveguide probe 500, the charge density on the outer surface 657 of the corona hood 610 is relatively high as compared to the charge density on the recessed interior surface 658 of the corona hood 610. As a consequence, the electric field experienced within the hollow 656 bounded by the recessed interior surface 658 of the corona hood 610 will be relatively small as compared to the electric field experienced near the outer surface 657 of the corona hood 610. According to the various embodiments, the end most windings of the top-most internal phasing coil 651 are recessed into the hollow 656 bounded by the recessed interior surface 658 of the corona hood 610. Given that the electric fields in the hollow 656 are relatively low, atmospheric discharge is prevented or at least minimized from conductors recessed into the hollow 656. Specifically, in this arrangement, atmospheric discharge is prevented or minimized from the end most windings of the top-most internal phasing coil 651 that are recessed into the hollow 656. Also, atmospheric discharge is prevented from forming or minimized from the lead that extends from the end most winding of the top-most internal phasing coil 651 to an attachment point on the recessed interior surface 658 of the corona hood 610. Thus, by positioning the corona hood 610 such that the top winding(s) of the highest most internal phasing coil 651 is recessed into the hollow 656 having lower electric fields, atmospheric discharge is prevented from forming or is minimized around the top winding and the lead extending from the top winding which experience the highest electrical potential of the entire system.

The corona hood 610 terminates by tapering into a tube 612 that extends from the corona hood 610 to the charge terminal 520. The tube 612 acts as a conductor between the corona hood 610 and the charge terminal 520 and includes one or more bends or turns 614 from the corona hood 610 to the charge terminal 520. In the case of the guided surface waveguide probe 500, the turn 614 is relied upon to shift the tube 612 to an off-center position within the platforms 591-593, among others, in the truss extension 532. In that way, space can be reserved on the platforms 591-593 for individuals to stand and service the guided surface waveguide probe 500. The tube 612 may include a pivot junction above the turn 614 that would allow the tube 612 to be swung out of position over the corona hood 610 to leave an open hole in the tube 612 or the tapered portion of the corona hood 610 just above the corona hood 610. This is done to allow a cable to pass through the center of the corona hood 610 to facilitate lifting coil sections into place as described herein. Alternatively, a portion of the tube 612 may be removable at the first bend of the turn 614 to allow a cable to pass through the center of the corona hood 619.

Given that the corona hood 610 and the tube 612 are formed from a conductive material, the highest-installed internal coil 651 can be electrically coupled to the corona hood 610 by connecting the top most winding to the corona hood 610 at a point on the recessed interior surface 658 of the corona hood 610 to prevent atmospheric discharge from occurring around the connection point as well as the lead extending from the top most winding to the connection point on the recessed interior surface 658 of the corona hood 610. Alternatively, if such atmospheric discharge is not prevented entirely, then it is at least minimized in order to minimize unwanted losses. In that case, the conductor can be electrically coupled to the recessed interior surface 658 of the corona hood 610 at a point where the corona hood 610 tapers into the tube 612, for example, or at any other suitable location.

FIG. 28 is a cross-sectional view of the charge terminal 520 of the guided surface waveguide probe 500 shown in FIG. 20. The charge terminal 520 is positioned at the top of the guided surface waveguide probe 500 above the truss extension 532. Individuals can access the interior space within the charge terminal 520 using ladders 660 and 661, among others, to reach the top platform 670 of the truss extension 532. The top platform 670 includes an opening 671 through which a winch line can pass. As described in further detail below with reference to FIGS. 29A and 29B, a winch can be used to raise one or more of the internal phasing coils 651 into place, so that they can be secured at one or more of the platforms 598-604 (FIG. 25).

The charge terminal 520 can be formed from any suitable conductive metal or metals, or other conductive materials, to serve as a charge reservoir for the guided surface waveguide probe 500. As shown, the charge terminal 520 includes a hollow hemisphere portion 680 at the top that transitions into a hollow toroid portion 681 at the bottom. The hollow toroid portion 681 turns to the inside of the charge terminal 520 and ends at an annular ring lip 682.

For an electrical connection to the internal phasing coils 651, the tube 612 can extend further up toward the top of the charge terminal 520. As shown in the inset in FIG. 28, one or more coupling conductors 690, formed from a conductive material, can extend radially away from the top of the tube 612. The coupling conductors 690 can be mechanically and electrically coupled to any point on the inner surface of the charge terminal 520. For example, the coupling conductors 690 can be electrically and mechanically connected to points around the annular ring lip 682. Alternatively, the coupling conductors 690 can be mechanically and electrically coupled to points on the inside surface of the hollow toroid portion 681 or the hollow hemisphere portion 680. The charge terminal 520 is generally attached to and supported by the truss extension 532 as described below with reference to FIGS. 29A and 29B.

Figure 29A:
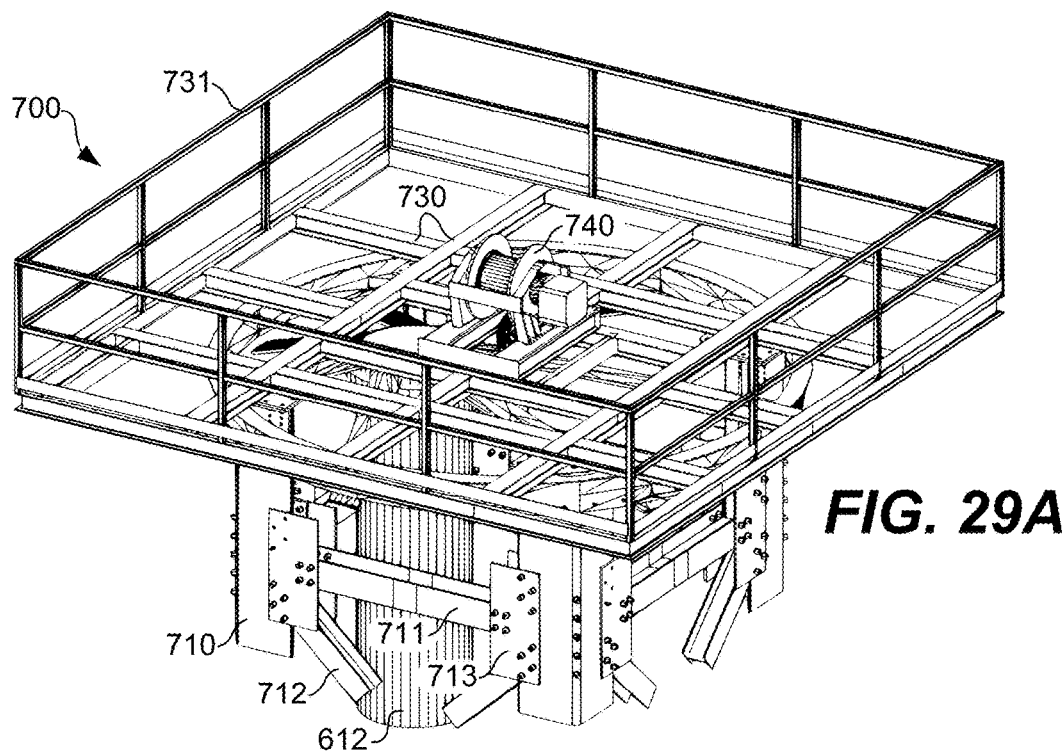
FIGS. 29A and 29B illustrate top and bottom perspective views of a top support platform of the probe shown in FIG. 20 according to various embodiments of the present disclosure.
Figure 29B:
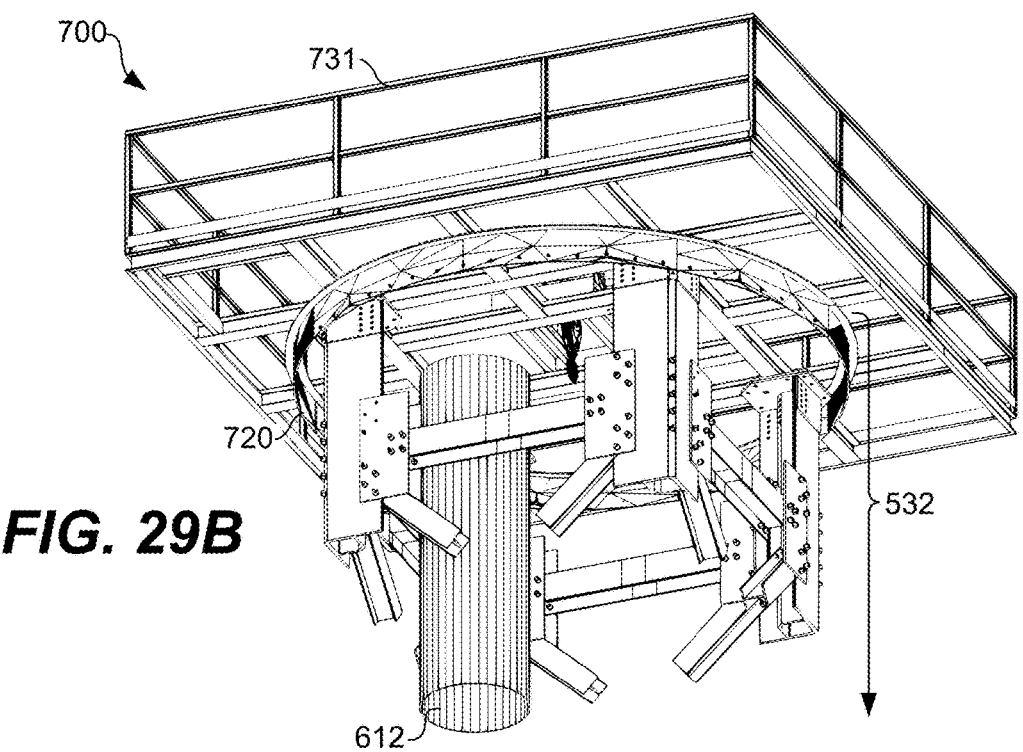

FIGS. 29A and 29B illustrate top and bottom perspective views, respectively, of a top support platform 700 of the guided surface waveguide probe 500 shown in FIG. 20 according to various embodiments of the present disclosure. In the example of the guided surface waveguide probe 500 described and illustrated herein, the charge terminal 520 shown in FIG. 28 can surround the top support platform 700.

The top support platform 700 is supported at the top of the truss extension 532 of the guided surface waveguide probe 500. Similar to the bars 581-583 referenced in FIG. 24, the truss extension 532 includes a number of vertical support bars 710, horizontal support bars 711, and cross beam support bars 712. The truss extension 532 also includes a number of gusset plates 713 to secure the vertical support bars 710, horizontal support bars 711, and cross beam support bars 712 together.

Secured at the top of the truss extension 532, the top support platform 700 includes a mounting ring 720 as shown in FIG. 29B. In one embodiment, the annular ring lip 682 of the charge terminal 520 can be secured to the mounting ring 720 using bolts or other suitable hardware. In that way, the charge terminal 520 can be mounted to the top support platform 700, which is secured to the truss extension 532.

The top support platform 700 includes an arrangement of platform joists 730 and a railing 731. The top platform 670 (FIG. 28) can be seated upon and secured to the platform joists 730. The top support platform 700 also includes a winch 740. The winch 740 can be used to install, reconfigure, and maintain various components of the guided surface waveguide probe 500. For example, a winch line of the winch 740 can be routed through the top support platform 700, through the opening 671 (FIG. 28) in the top platform 670, and down into the truss extension 532 and the truss frame 531. The winch line can be lowered down toward and into the passageway 655 (FIG. 26) in the substructure 502 (FIG. 26). From there, the winch line can be secured to one of the internal phasing coils 651 (FIG. 27), and the internal phasing coil 651 can be lifted up into the truss frame 531 and secured. Given that the winch 740 is located inside the charge terminal 520, the winch 740 is located in the region of uniform electric potential and is safe from discharge, eddy currents, or interference. In order to power the winch 740, an electrical cord may be brought up to the winch 740 from a power source such as utility power when the guided surface waveguide probe 500 is not operational. During operation, however, such an electrical cord would be removed.

The components of the top support platform 700, including the vertical support bars 710, horizontal support bars 711, cross beam support bars 712, gusset plates 713, platform joists 730, railing 731, etc. may be formed (entirely or substantially) from non-conductive materials. Alternatively, the same may be formed from conductive materials since they are located in a region of uniform electrical potential. In any event, such components may be constructed from lightweight materials such as aluminum or titanium so as to reduce the physical load on the entire structure of the guided surface waveguide probe 500.

Figure 30:
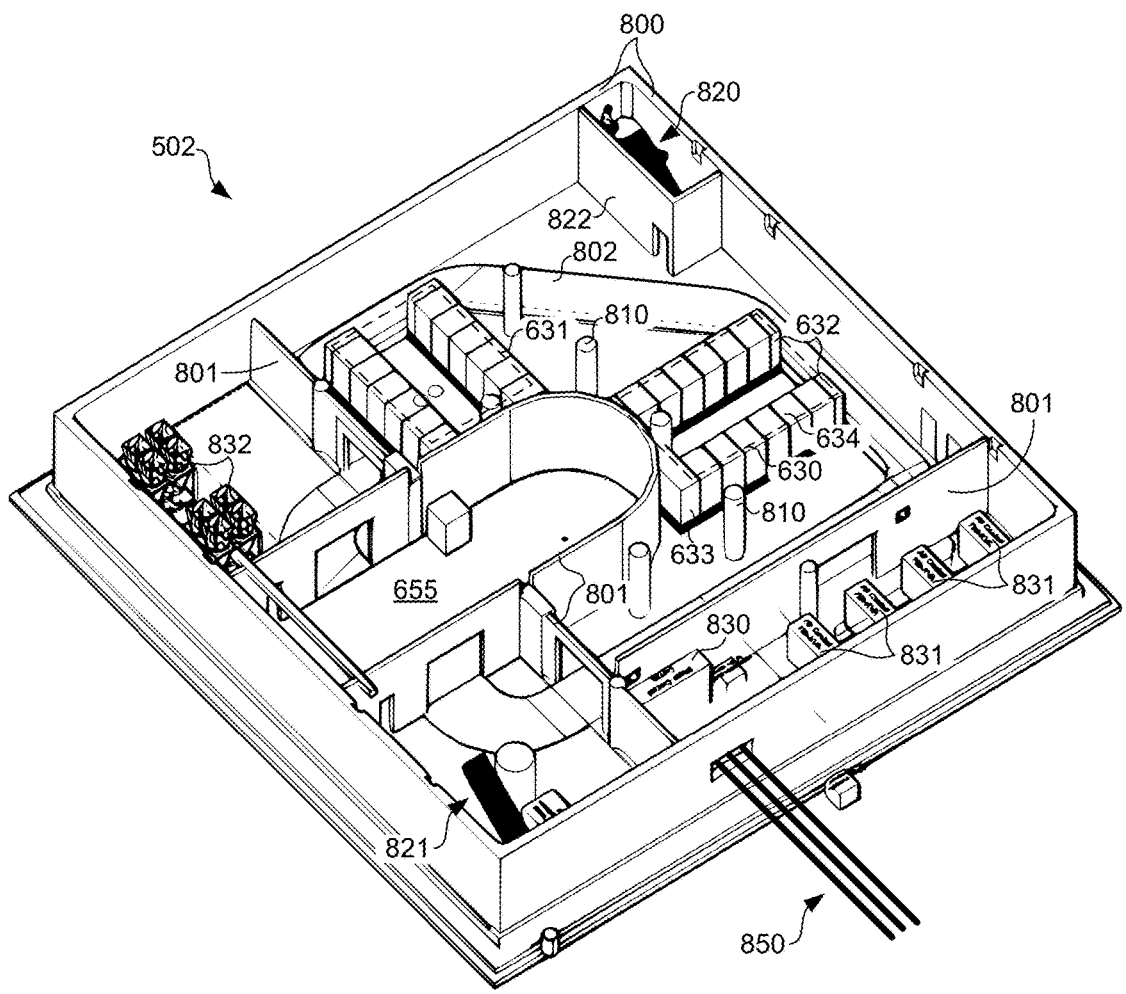
FIGS. 30 and 31 illustrate various components inside the substructure of the probe shown in FIG. 20 according to various embodiments of the present disclosure.
Figure 31:
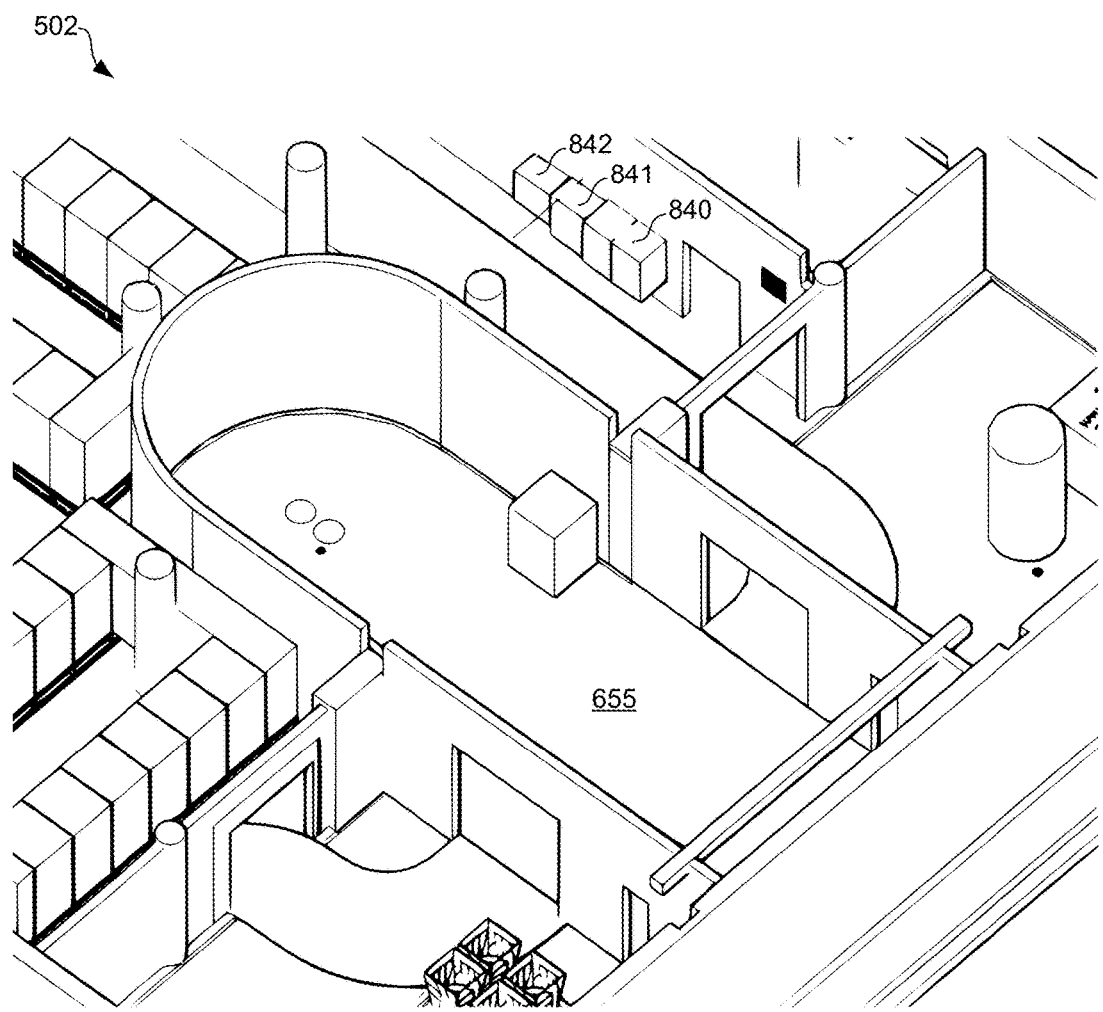

FIGS. 30 and 31 illustrate various components inside the substructure 502 of the guided surface waveguide probe 500 shown in FIG. 20 according to various embodiments of the present disclosure. The arrangement of the rooms, compartments, sections, stairwells, etc., in the substructure 502 is provided as a representative example in FIGS. 30 and 31. In other embodiments, the space within the substructure 502 can be configured for use in any suitable way, and the equipment described below can be installed in various locations.

The substructure 502 includes external walls 800 and internal walls 801. According to one embodiment, the external walls 800 and internal walls 801 are formed from poured concrete and, in some cases, reinforced with fiberglass rebar as will be described. For safety, the internal walls 801 can be designed at a suitable thickness and/or structural integrity to withstand or retard the spread of fire, coronal discharge, etc. Various entryways and passages through the internal walls 801 permit individuals and equipment to move throughout the substructure 502. The entryways and passages can be sealed using any suitable types of doors, including standard doors, sliding doors, overhead doors, etc. As also shown, a pathway 802 is reserved through various areas in the substructure 502 for individuals to walk around and install, service, and move the equipment in the substructure 502, as necessary.

A number of the pillars 810, not all of which are individually referenced in FIG. 30, support the covering support slab 510 (FIG. 20) of the guided surface waveguide probe 500. The pillars 810 can be formed from reinforced concrete or other suitable materials as will be described. A central group of the pillars 810 are positioned under each of the base brackets 565 to support the truss frame 531 and the rest of the structure.

Stairwells 820 and 821 are provided at opposite corners of the substructure 502. The stairwells 820 and 821 lead up to the entryways 511 and 512 (FIG. 20). The stairwell 820 is surrounded by a stairwell enclosure 822, but stairwell enclosures are not necessary in every case. For example, the stairwell 821 is not shown as being enclosed in FIG. 30. The enclosure around each stairwell 820 and 821 provides for safety in case of fire or other calamity. Also, the stairwell enclosure 822 prevents or retards the entry of water into the substructure 502.

The substructure 502 includes a number of different rooms, compartments, or sections separated by the internal walls 801. Various types of equipment are installed in the rooms or compartments of the substructure 502. Among other types of equipment and systems, a power transmitter banks 630 and 631, a motor controller 830, a number of transformers 831, and an HVAC system 832 can be installed in the substructure 502 as shown in FIG. 30. Further, as shown in FIG. 31, a supervisory control and data acquisition (SCADA) system 840, an arc flash detection system 841, and a fire protection system 842 can be installed in the substructure 502. Additionally, although not referenced in FIGS. 30 and 31, an electrical switching gear can be installed in the substructure 502 to receive power over one or more power transmission cables 850 and connect the power to the transformers 831 and, in turn, other equipment in the substructure 502.

In one embodiment, the power transmitter bank 630 can be embodied as a number of variable power, variable frequency, power transmitters capable of outputting power over a range of sinusoidal output frequencies, such as up to a megawatt of power, for example, over a range of frequencies from about 6 kHz-100 kHz. However, the power transmitter bank 630 can provide output power at lower and higher wattages and at lower and higher frequencies in various embodiments. The power transmitter banks 630 and 631 are examples of various power sources that may be used such as, for example, generators and other power sources. The power transmitter bank 630 includes a control cabinet 632, a combiner 633, and a number of power transmitters 634. Each of the power transmitters 634 can include a number of power amplifier boards, and the outputs of the power transmitters 634 can be tied or combined together in the combiner 633 before being fed to the coil 620 (FIG. 25) of the guided surface waveguide probe 500, for example. The second power transmitter bank 631 is similar in form and function as the power transmitter bank 630.

Depending upon the operating configuration of the guided surface waveguide probe 500, the output of the power transmitter banks 630 and 631 can be electrically coupled to the coil 620 within the substructure 502, where the coil 620 acts as a primary coil to inductively couple electrical energy into the internal phasing coils 651. Alternatively, the output of the power transmitter banks 630 and 631 may be coupled to coils acting as primaries that are positioned around the external phasing coils 504 and 505, or the inductive coil 263/942 (FIG. 7C/FIGS. 33A and B) as described herein. Thus, electrical energy may be applied to the guided surface waveguide probe 500 by way of inductive coupling from a coil acting as a primary to any one of the internal phasing coils 651, the external phasing coils 504/505, or inductive coils 263/942.

In one embodiment, power can be fed from the power transmission cables 850 at a voltage level for power transmission at 138 kV (or higher), at the voltage level for sub-transmission at 26 kV or 69 kV, at the voltage level for primary customers at 13 kV or 4 kV, at the voltage level for internal customers at 120V, 240V, or 480V, or at another suitable voltage level.

The power can be fed through electrical switch gear and to the transformers 831. The electrical switch gear can include a number of relays, breakers, switchgears, etc., to control (e.g., connect and disconnect) the connection of power from the cables 850 to the equipment inside the substructure 502. The power can be fed from the transformers 831, at a stepped-up or stepped-down voltage, to the power transmitter banks 630 and 631. Alternatively, the power transmitter banks 630 and 631 can be supplied directly with power at a suitable voltage, such as 480V or 4160V, for example, from the cables 850.

The motor controller 830 can control a number of forced air and water heating and/or cooling subsystems in the substructure 502, among other subsystems. To this end, various ducts and piping are employed to route cooling air and water to various locations and components of the guided surface waveguide probe 500 to prevent damage to the system and structure due to heat. The SCADA system 840 can be relied upon to monitor and control equipment in the guided surface waveguide probe 500, such as the power transmitter banks 630 and 631, motor controller 830, transformers 831, HVAC system 832, arc flash detection system 841, and fire protection system 842, among others.

In one embodiment, the entire substructure 502 including the foundation base 540, seal slab 541, external walls 800, internal walls 801, pillars 810, and the covering support slab 510 (FIG. 20) is formed using poured concrete reinforced with Glass Fiber Reinforced Polymer (GFRP) rebar. The concrete used may include an additive that reduces the amount of moisture in the cement to reduce the conductivity of the cement to prevent eddy currents and the like in the cement itself. In one embodiment, such an additive may comprise XYPEX™ manufactured by Xypex Chemical Corporation of Richmond, British Columbia, Canada, or other appropriate additive. The GFRP rebar ensures that there are no conductive pathways in the cement upon which eddy currents might be produced.

FIGS. 32A and 32B illustrate the grounding system 900 of the guided surface waveguide probe 500 shown in FIG. 20. The grounding system 900 includes a grounding grid 910, the grounding ring 551, connecting conductors 552, a number of grounding radials 553, and a number of ground stakes 920. The grounding system 900 is shown as a representative example in FIGS. 32A and 32B and can differ in size, shape, and configuration in other embodiments. The grounding system 900 can be formed from conductive materials and provides an electrical connection to the lossy conducting medium 503 (e.g., the Earth) for the guided surface waveguide probe 500 and the equipment in the substructure 502.

In one embodiment, the grounding grid 910 is surrounded in the seal slab 541 of the foundation base 540 (FIG. 21). The grounding system 900 also includes a number of grounding stakes 920 driven into the lossy conducting medium 503 below the grounding grid 910 and electrically coupled to the grounding grid 910.

The connecting conductors 552 extend from the grounding grid 910 to the grounding ring 551. The grounding radials 553 are electrically coupled at one end to the grounding ring 551 and extend out from the grounding ring 551 radially away from the guided surface waveguide probe 500 to a number of grounding stakes 920 driven into the lossy conducting medium 503. The grounding ring 551 includes an opening or break 930 to prevent circulating current in the grounding ring 551 itself. Together all of the grounding components of the grounding system 900 provide a pathway for current generated by the guided surface waveguide probe 500 to the lossy conducting medium 503 around the guided surface waveguide probe 500.

Figure 33A:
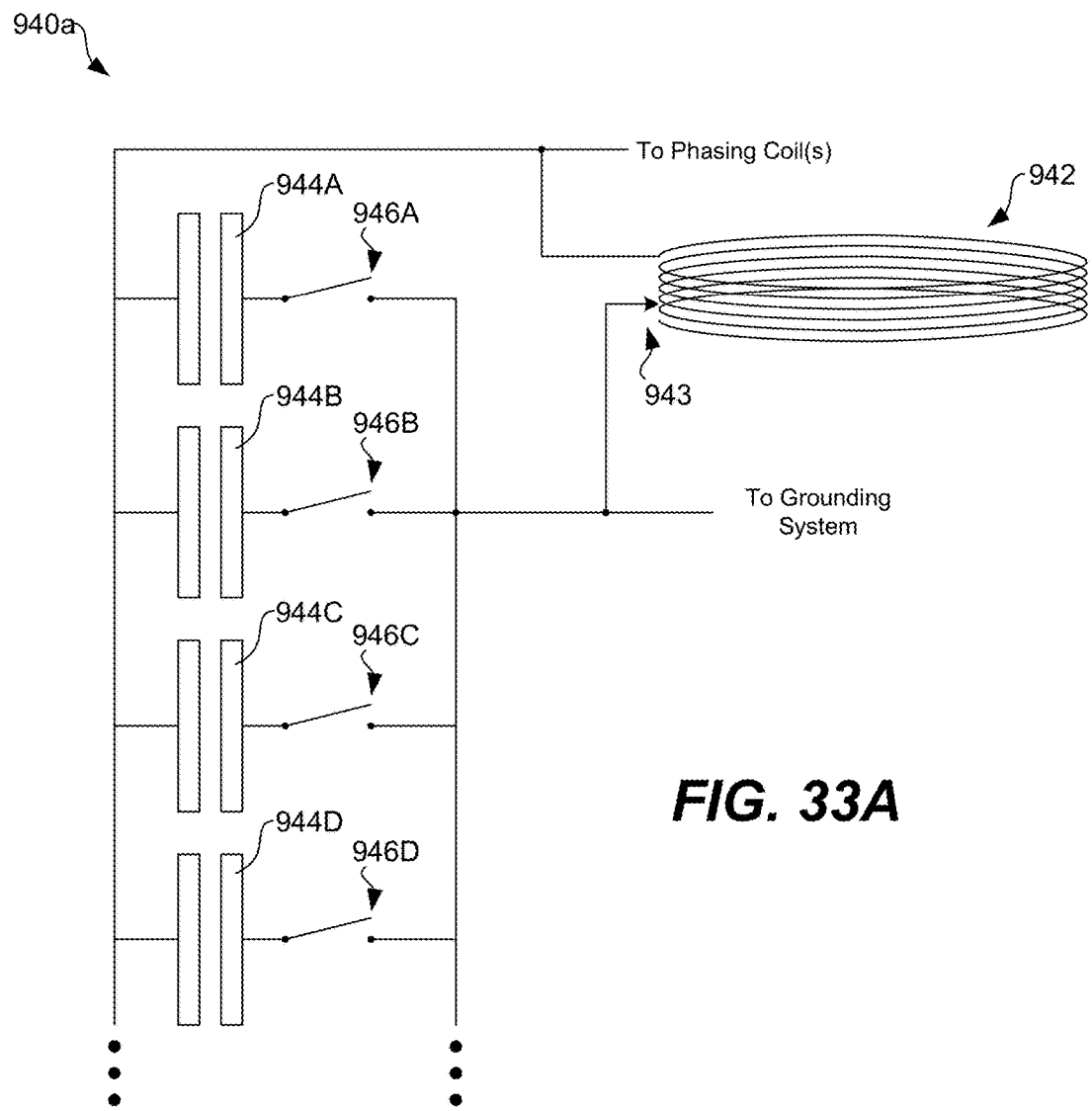
FIGS. 33A and 33B illustrate examples of tank circuits of the probe according to various embodiments of the present disclosure.

FIG. 33A illustrates an example tank circuit 940a of the guided surface waveguide probe 500 according to various embodiments of the present disclosure. The tank circuit 940a includes an inductive coil 942, a number of parallel capacitors 944A-944D, and a number of switches 946A-946D corresponding to the parallel capacitors 944A-944D. With reference to the tank circuit 260 shown in FIGS. 7B and 7C, the inductive coil 942 is analogous to the inductive coil 263 and the parallel capacitors 944A-944D are analogous to the capacitor 266. Note that although only a limited number of capacitors are shown, it is understood that any number of capacitors may be employed and switched into the tank circuit 940a as conditions demand.

The tank circuit 940a can be electrically coupled at one end as shown in FIG. 33A to one or more phasing coils, such as the single internal phasing coil 654, the external phasing coils 504 and/or 505, and/or other phasing coils. The tank circuit 940a can be electrically coupled at another end as shown in FIG. 33A to a grounding system, such as the grounding system 900 shown in FIGS. 32A and 32B.

The capacitors 944A-944D can be embodied as any suitable type of capacitor and each can store the same or different amounts of charge in various embodiments, for flexibility. Any of the capacitors 944A-944D can be electrically coupled into the tank circuit 940a by closing corresponding ones of the switches 946A-946D. Similarly, any of the capacitors 944A-944D can be electrically isolated from the tank circuit 940a by opening corresponding ones of the switches 946A-946D. Thus, the capacitors 944A-944D and the switches 946A-946D can be considered a type of variable capacitor with a variable capacitance depending upon which of the switches 946A-946D are open (and closed). Thus, the equivalent parallel capacitance of the parallel capacitors 944A-944D will depend upon the state of the switches 946A-946D, thereby effectively forming a variable capacitor.

The inductive coil 942 can be embodied as a length of conductor, such as wire or pipe, for example, wrapped and supported around a coil support structure. The coil support structure may comprise a cylindrical body or other support structure to which the wire or pipe is attached in the form of a coil. In some cases, the connection from the inductive coil 942 to the grounding system 900 can be adjusted using one or more taps 943 of the inductive coil 942 as shown in FIG. 7A. Such a tap 943 may comprise, for example, a roller or other structure to facilitate easy adjustment. Alternatively, multiple taps 943 may be employed to vary the size of the inductive coil 942, where one of the taps 943 is connected to the capacitors 944.

As described herein, a phasing coil such as the single internal phasing coil 654 and the external phasing coils 504 and 505 can provide both phase delay and phase shift. Further, the tank circuit 940a that includes the inductive coil 942 can provide a phase shift without a phase delay. In this sense, the inductive coil 942 comprises a lumped element assumed to have a uniformly distributed current throughout. In this respect, the inductive coil 942 is electrically small enough relative to the wavelength of transmission of the guided surface waveguide probe 500 such that any delay it introduces is relatively negligible. That is to say, the inductive coil 942 acts as a lumped element as part of the tank circuit 940a that provides an appreciable phase shift, without a phase delay.

Figure 33B:
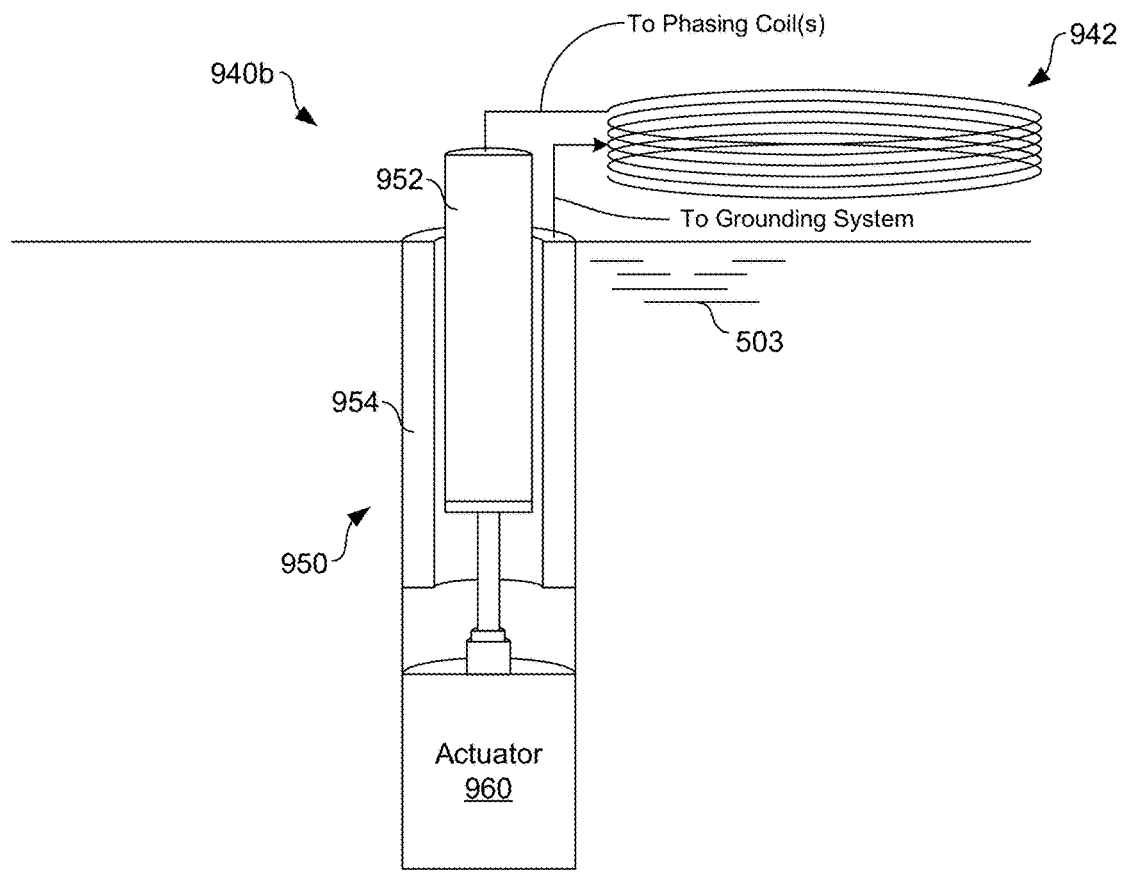

FIG. 33B illustrates another example tank circuit 940b of the guided surface waveguide probe 500 according to various embodiments of the present disclosure. As compared to the tank circuit 940a shown in FIG. 33A, the tank circuit 940b includes a variable capacitor 950 in place of the capacitors 944A-944D and switches 946A-946D. With reference to the tank circuit 260 shown in FIGS. 7B and 7C, the inductive coil 942 is analogous to the inductive coil 263 and the variable capacitor 950 is analogous to the capacitor 266.

As shown, the variable capacitor 950 can be buried or embedded into the lossy conducting medium 503, such as the Earth. The variable capacitor 950 includes a pair of cylindrical, parallel charge conductors 952, 954 and an actuator 960. The actuator 960, which can be embodied as a hydraulic actuator that actuates a hydraulic piston. Alternatively, the actuator 960 may be embodied as an electric actuator that employs a motor or other electrical component that drives a screw shaft or other mechanical lifting structure. Further, the actuator 960 may be embodied as a pneumatic actuator that is employed to raise or lower a pneumatic cylinder. Still other types of actuators may be employed to move the inner charge conductor 952 relative to the outer charge conductor 954, or vice versa, or both. Also, some other type of actuator may be employed beyond those described herein.

The actuator 960 is configured to raise and lower the inner charge conductor 952 within, or relative to, the outer charge conductor 954. By raising and lowering the inner charge plate 952 with respect to the outer charge plate 954, the capacitance of the variable capacitor 950 can be modified and, thus, the electrical characteristics of the tank circuit 940b adjusted.

While the variable capacitor 950 is shown as being buried in the lossy conducting medium 503, it is understood that the variable capacitor 950 may also reside in a building or a substructure such as the substructure 502. Also, while the variable capacitor 950 is depicted as being cylindrical in shape, it is possible to use any shape such as rectangular, polygonal, or other shape.

Figure 34:
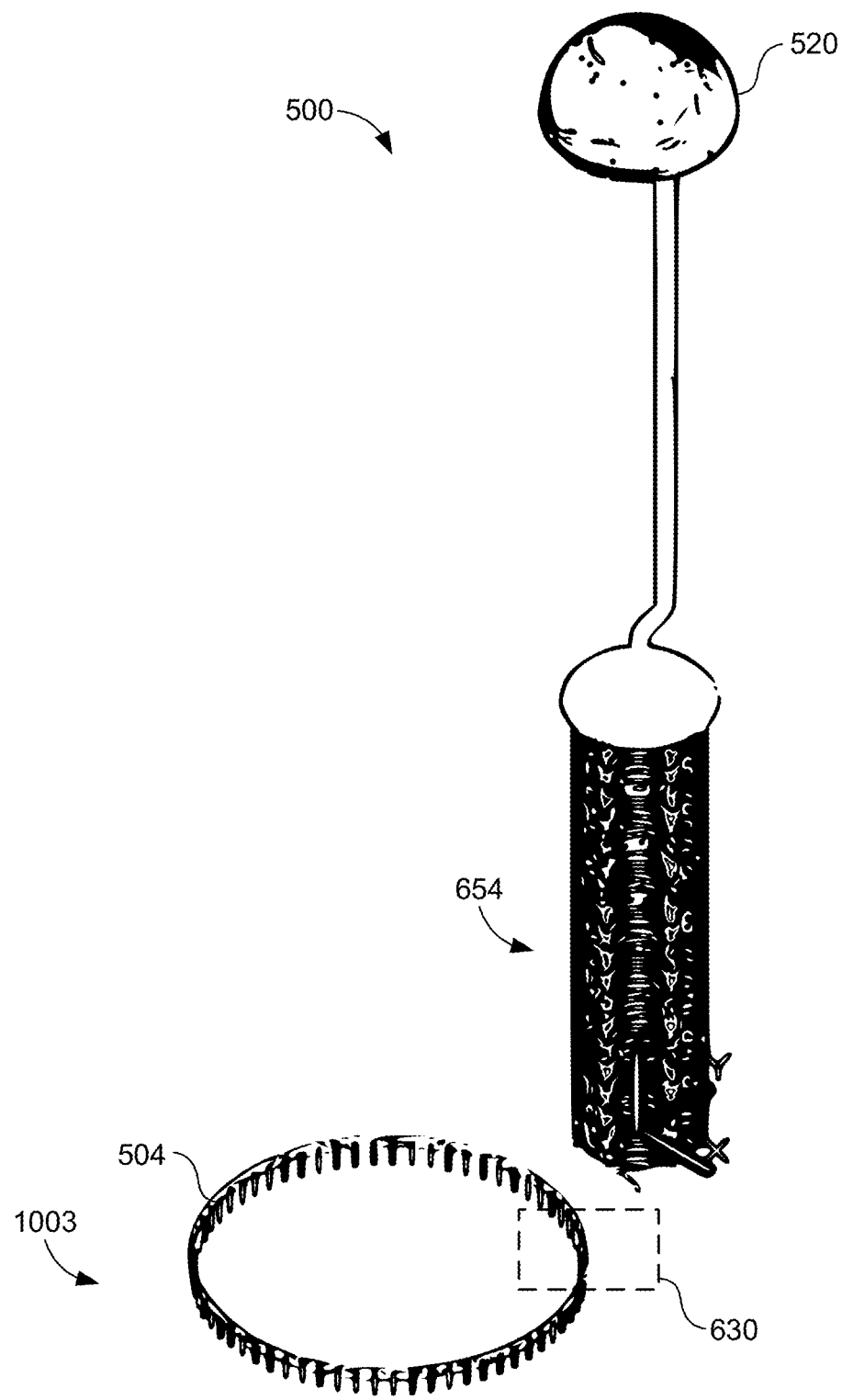
FIGS. 34-38 illustrate examples of external phasing coil arrangements in relation to the probe according to various embodiments of the present disclosure.

Referring next to FIG. 34, shown is an example of a guided surface waveguide probe 500 according to various embodiments of the present disclosure. The guided surface waveguide probe 500 includes an internal phasing coil 654, a coil support structure 1003, and a power transmission bank 630. The coil support structure 1003 can include a primary coil and a secondary coil. The charge terminal 520 can be positioned outside of a circumference of the coil support structure 1003. As shown in the example of FIG. 34, the secondary coil is an external phasing coil 504. The power transmission bank 630 operates as an excitation source and can be located within a substructure under a concrete slab 510 as illustrated in FIGS. 25 and 26.

According to one embodiment, the power transmission bank 630 is located beneath a circumference of the coil support structure 1003. The power transmission bank 630 can be positioned relative to a primary coil on the coil support structure 1003 to minimize a distance of a lead line from the power transmission bank 630 to the primary coil. The power transmission bank 630 provides a high current signal to the primary coil on the coil support structure 1003.

The primary coil can be coupled to the power transmission bank 630 to receive a high current signal from the power transmission bank 630. The external phasing coil 504 can be inductively coupled to the primary coil such that electrical energy can be supplied to the external phasing coil 504 based on a magnetic field created when a current signal passes through the primary coil. The external phasing coil 504 can provide the electrical energy to the charge terminal 520 of the guided surface waveguide probe 500 through the internal phasing coil 654. The internal phasing coil 654 and external phasing coil 504 can be configured to provide a voltage to a charge terminal 520 of the guided surface waveguide probe 500 with a phase delay)) that matches a wave tilt angle (W) associated with a complex Brewster angle of incidence ($\theta_{i,B}$) associated with the lossy conducting medium 503 (FIG. 20).

Figure 37:
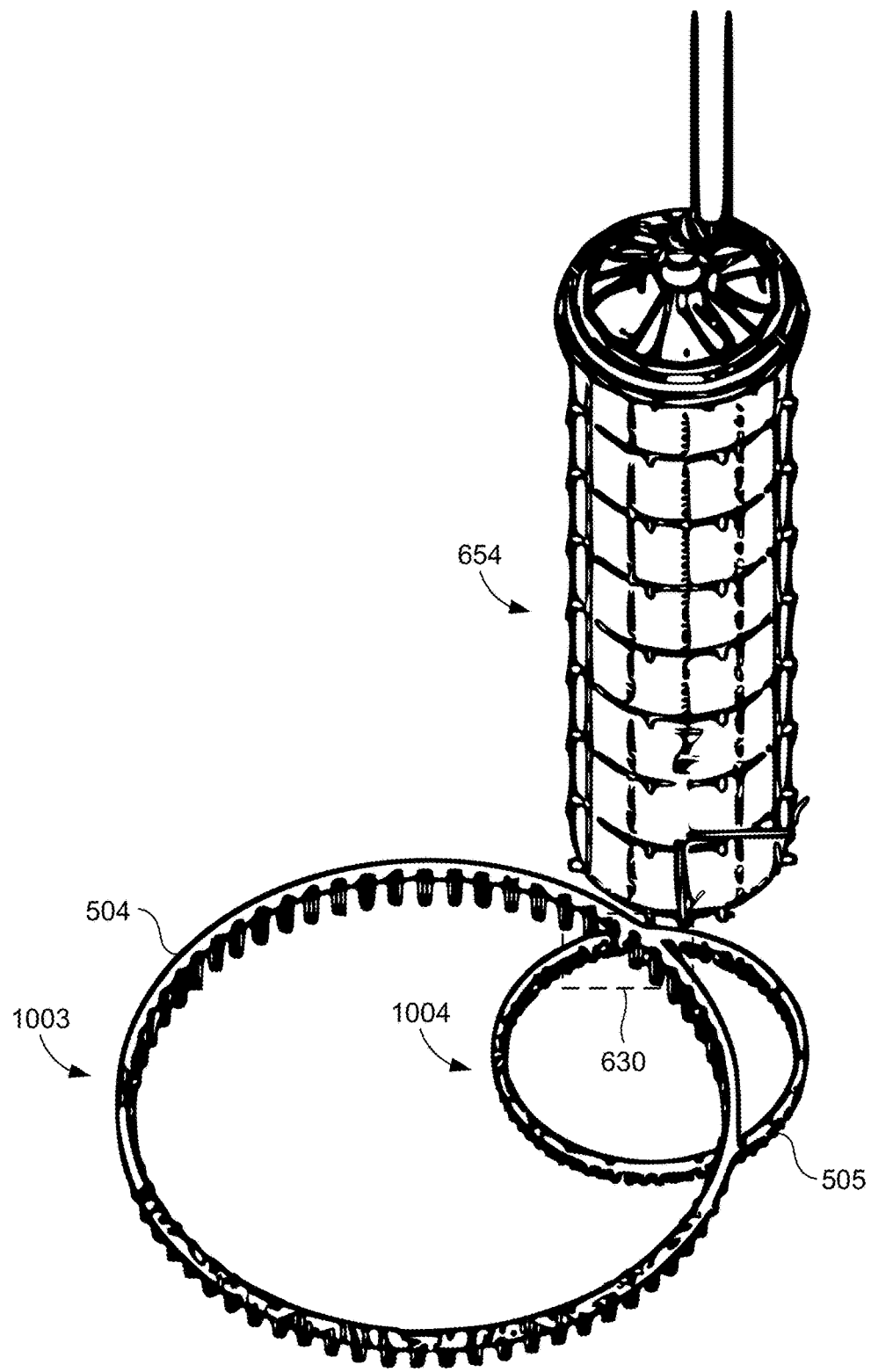
Figure 38:
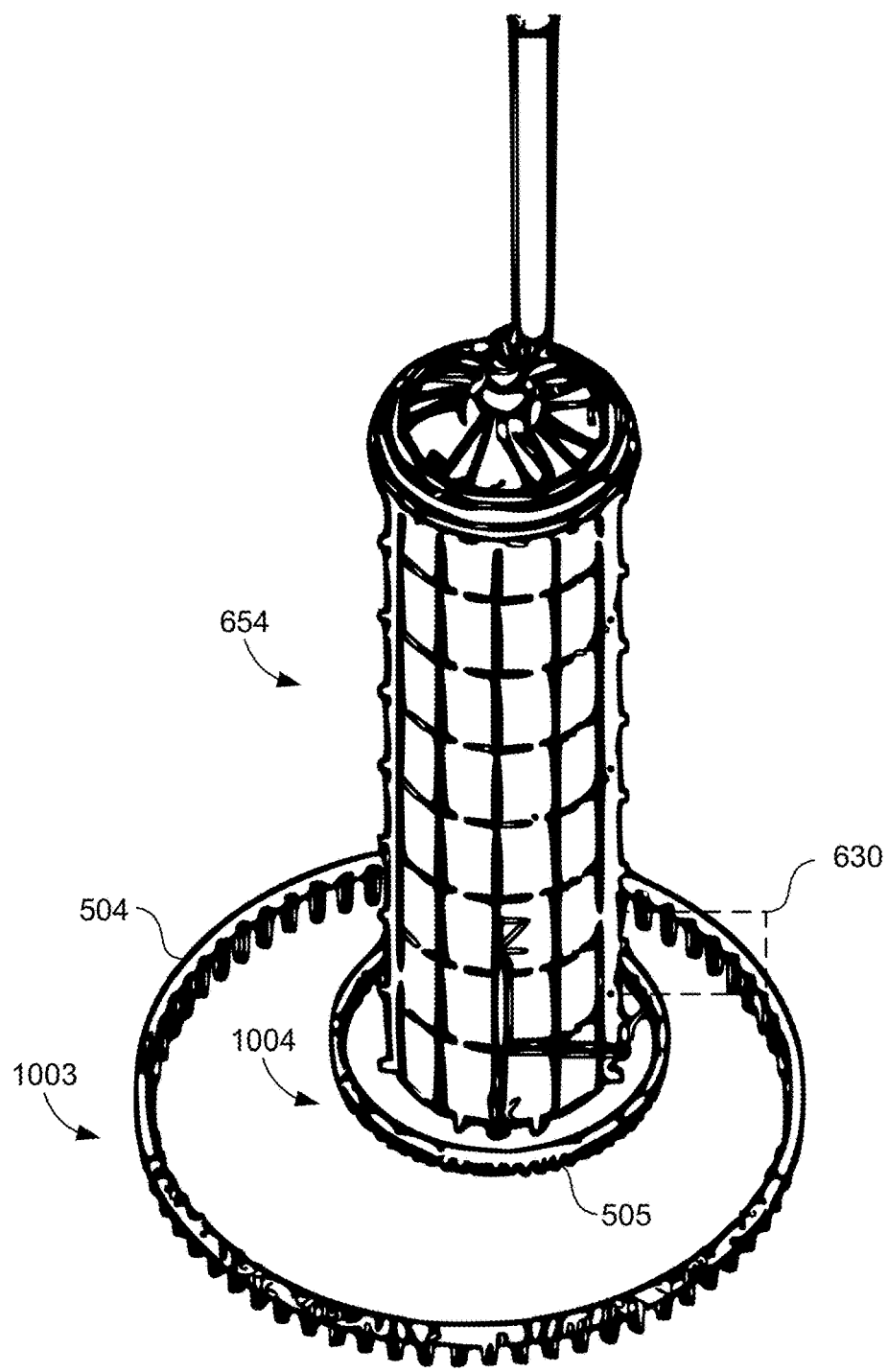

In some implementations, the secondary coil can be one of a plurality of external phasing coils such as, e.g., coils 504 and 505 as shown in FIGS. 37 and 38. The phasing coils can be connected in series with the internal phasing coil 654 to excite the charge terminal 520 with the appropriate phase delay. The internal phasing coil 654 and the external phasing coil 504 can have different circumferences. In some embodiments, the external phasing coil 504 has a greater circumference than the internal phasing coil 654 resulting in difference phase delays for each coil. Similarly, the external phasing coils 504 and 505 can have different circumferences. Each of the coils can create a phase delay in the signal traveling through the coils. A phase delay resulting from the external phasing coil(s) 504 (505) can be greater than a phase delay resulting from the internal phasing coil 654.

According to some embodiments, the secondary coil can be part of a lumped element tank circuit 260 as shown in 7C. For example, the secondary coil can be the inductive coil 263, or inductive coil 942 as shown in the examples of FIGS. 33A and 33B. In some embodiments, the primary coil and the inductive coil 263 or 942 can be supported on a support structure 1003. The inductive coil 263 or 942 can be coupled to an external phasing coil 504 or directly to an internal phasing coil 654. As such, the power transmission bank 630 can be positioned proximate to the inductive coil 263 or 942 to minimize a distance of a lead line from the power transmission bank 630. Electrical energy can be supplied to the charge terminal 520 through the inductive coil 263 or 942, via the external phasing coil 504 and/or the internal phasing coil 654.

The example of FIG. 34 shows the coil support structure 1003 located to one side of the charged terminal 520 of the guided surface waveguide probe 500. The power transmitter bank 630 is located on the same side as the charged terminal 520 and proximate to the circumference of the coil support structure 1003. The power transmitter bank 630 is shown with a dotted line to illustrate that the power transmitter bank can be located at an elevation that is below the coil support structure 1003. In some embodiments, the power transmitter bank 630 is located within a substructure below a surface level elevation. As such, the power transmitter bank 630 can be at an elevation lower than the concrete slab 510 and directly below at least a portion of the concrete slab 510.

Figure 35:
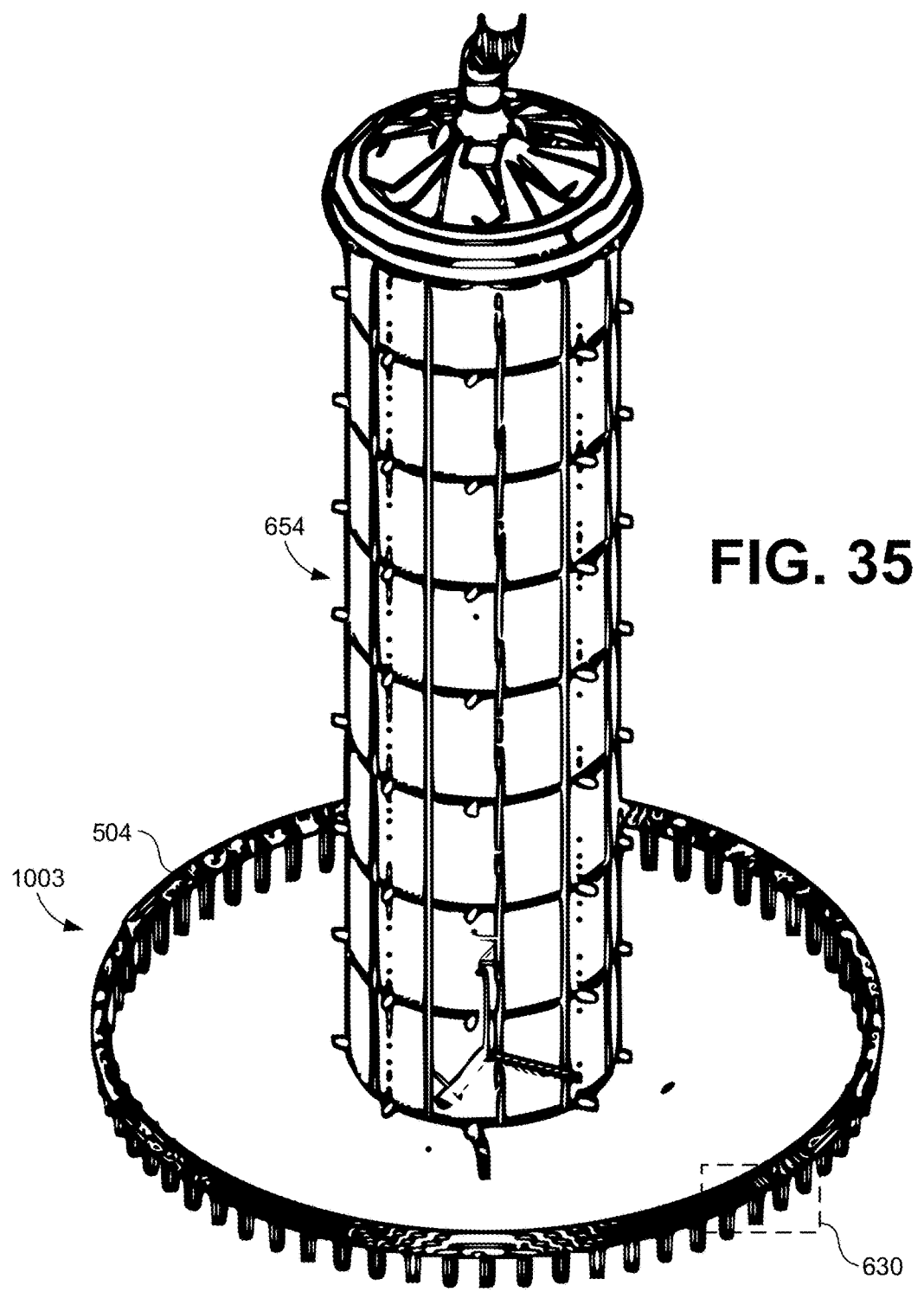

With reference to FIG. 35, shown is an example of a guided surface waveguide probe 500 according to various embodiments of the present disclosure. A charge terminal 520 (not shown) of the guided surface waveguide probe 500 can be positioned over the internal phase coil 654, and within a circumference of the coil support structure 1003. The coil support structure 1003 can be positioned to surround the support structure of the guided surface waveguide probe 500. In some embodiments, the coil support structure 1003 can be positioned such that a center of the external phasing coil 504 corresponds to a center of the charged terminal 520. The power transmitter bank 630 can be positioned beneath a circumference of the coil support structure 1003.

Figure 36:
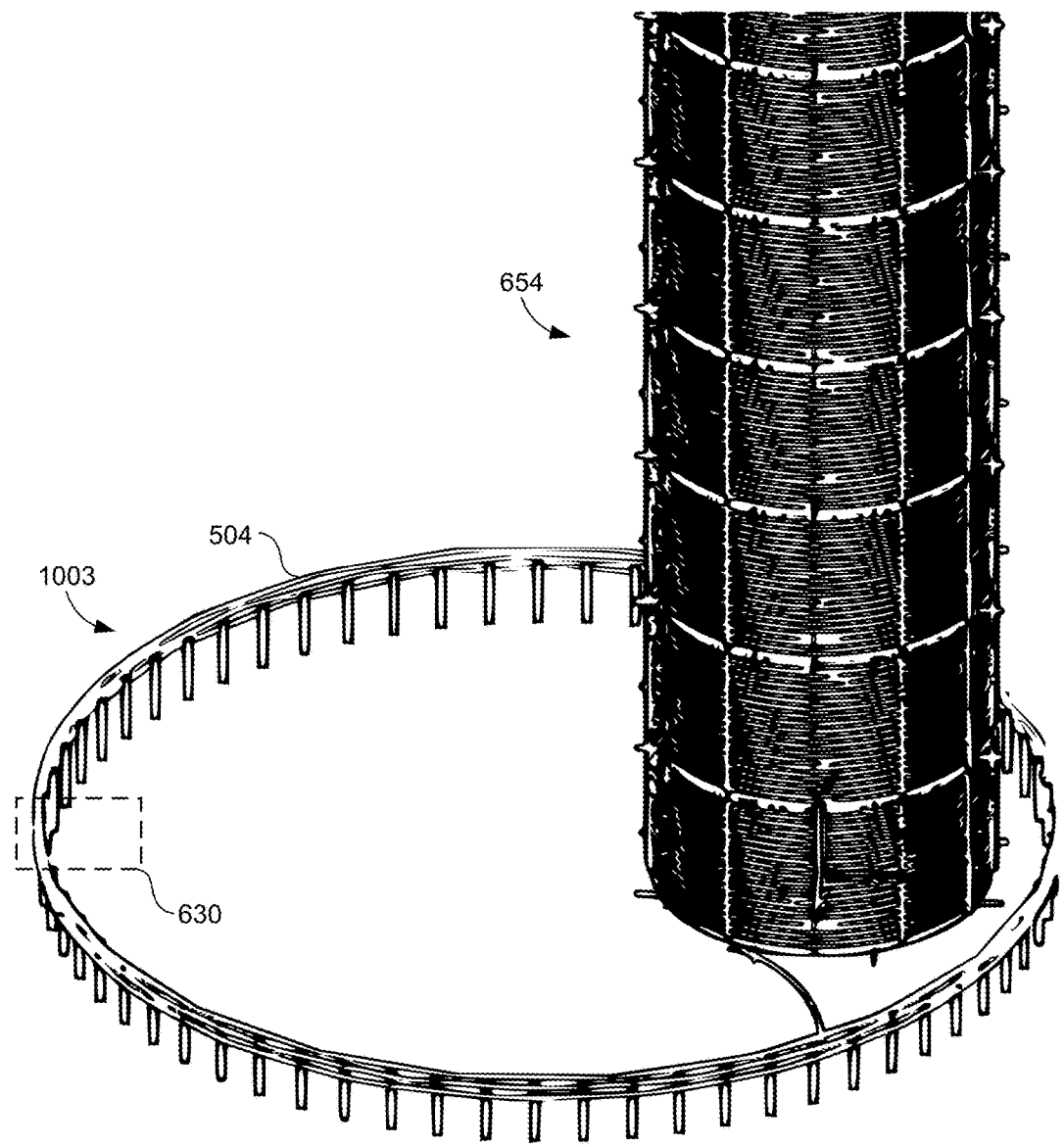

With reference to FIG. 36, shown is an example of a guided surface waveguide probe 500 according to various embodiments of the present disclosure. A charge terminal 520 (not shown) of the guided surface waveguide probe 500 can be positioned over the internal phasing coil 654 and within a circumference of the coil support structure 1003. The coil support structure 1003 can be positioned to surround a structure of the guided surface waveguide probe 500 with one side of the coil support structure 1003 being closer to the support structure of the guided surface waveguide probe 500 than an opposite second side. As shown, the power transmitter bank 630 can be positioned beneath the circumference of the coil support structure 1003 at a position furthest from the structure of the guided surface waveguide probe 500.

With reference to FIG. 37, shown is an example of a guided surface waveguide probe 500 according to various embodiments of the present disclosure. The guided surface waveguide probe 500 can include one or more external phasing coils 504 and 505. A first coil support structure 1003 and a second coil support structure 1004 are shown located to one side of the charged terminal 520 (not shown) elevated over the internal phasing coil 654. The coil support structures 1003/1004 have an intersection proximate to a support structure of the guided surface waveguide probe 500. A first angle with respect to the center of the guided surface waveguide probe 500 to a center of the first coil support structure 1003 can differ from a second angle with respect to the center of the guided surface waveguide probe 500 to a center of the second coil support structure 1004.

In some embodiments, the first angle and the second angle are offset from one another to facilitate the intersection of the structure of the circumferences of the coil support structures 1003/1004. As an example, as shown the first angle and the second angle differ by approximately 20 degree, which, based on the radiuses of the two coil support structures 1003/1004, results in an angle of intersection of the two circumferences being greater than 30 degrees. A delta of the first and second angle can be selected based on providing a non-parallel intersection of the circumferences.

The charge terminal 520 can be positioned outside of a circumference of the coil support structure(s) 1003 (1004). As an example, a position of a vertical axis corresponding to the charge terminal 520 that is normal to a horizontal plane defined by the coil support structures 1003/1004 (or a coil wrapped on the coil support structures) can be outside of a circumference of one or more of the coil support structures 1003/1004. It is understood that additional external phasing coils and additional coil support structures could also be used either alone or in combination with external phasing coils 504 and 505 on coil support structures 1003 and 1004.

The power transmission bank 630 can be located below a circumference of one or more of the coil support structures 1003/1004. As an example, the power transmission bank 630 can be positioned below an intersection of the circumferences of two or more coil support structure 1003/1004. The power transmission bank 630 can be configured to supply energy to primary coils located on either of the coil support structures 1003/1004. By locating the power transmission bank 630 adjacent to the intersection of the coil support structures 1003/1004, the lead length can be minimized or reduced.

As previously discussed, the external phasing coil 504 can have a different circumference than the internal phasing coil 654. The circumference for each external phasing coil 504 can be based on a frequency of a guided surface wave for which the external phasing coil 504 is used. Similarly, in some embodiments, the internal phasing coil 654 includes a coil designed for a specific frequency. In these embodiments, when the specific frequency is used from the internal phasing coil 654, the external phasing coils 504/505 can be omitted or not used because the coil (see coil 620 in FIG. 25).

In some embodiments, the guided surface waveguide probe 500 is configured to operate at one of several predefined frequencies. The guided surface waveguide probe 500 can be adjusted to operate at a different one of the predefined frequencies. Each of the predefined frequencies can correspond to a different coil having a different circumference or a combination of coils. As an example, the inner phasing coil 654 can be used to operate at a first frequency, the external phasing coil 504 can be used with the internal phasing coil 654 to operate at a second frequency, and the external phasing coil 505 can be used with the internal phasing coil 654 to operate at a third frequency. In these embodiments, a phase delay can be created by the phasing coils with a first component corresponding to a phase delay of the external phasing coil 504 or 505 and a second component corresponding to a phase delay of the internal phasing coil 654. The first component can be a greater phase delay in contrast to second component. In some embodiments, another frequency can be achieved by using both of the external phasing coils 504 and 505 and the inner phasing coil 654.

With reference to FIG. 38, shown is an example of a guided surface waveguide probe 500 according to various embodiments of the present disclosure. A charge terminal 520 (not shown) elevated over the internal phasing coil 654 of the guided surface waveguide probe 500 can be positioned within a circumference of the coil support structures 1003/1004. Similar to FIG. 36, both a first coil support structure 1003 and a second coil support structure 1004 are moved to surround a support structure of the guided surface waveguide probe 500 with a first side of the coil support structures 1003/1004 being closer to the structure of the guided surface waveguide probe 500 than an opposite second side. As shown, the power transmitter bank 630 can be positioned beneath the circumference of the coil support structures 1003/1004. As an example, a position of a vertical axis corresponding to the charge terminal 520 normal to a horizontal plane can be within a circumference of one or more of the coil support structures 1003/1004. The charge terminal can be positioned along the vertical axis that is normal to the horizontal plane defined by the coil support structures 1003/1004 (or a coil wrapped on the coil support structures).

Figure 39:
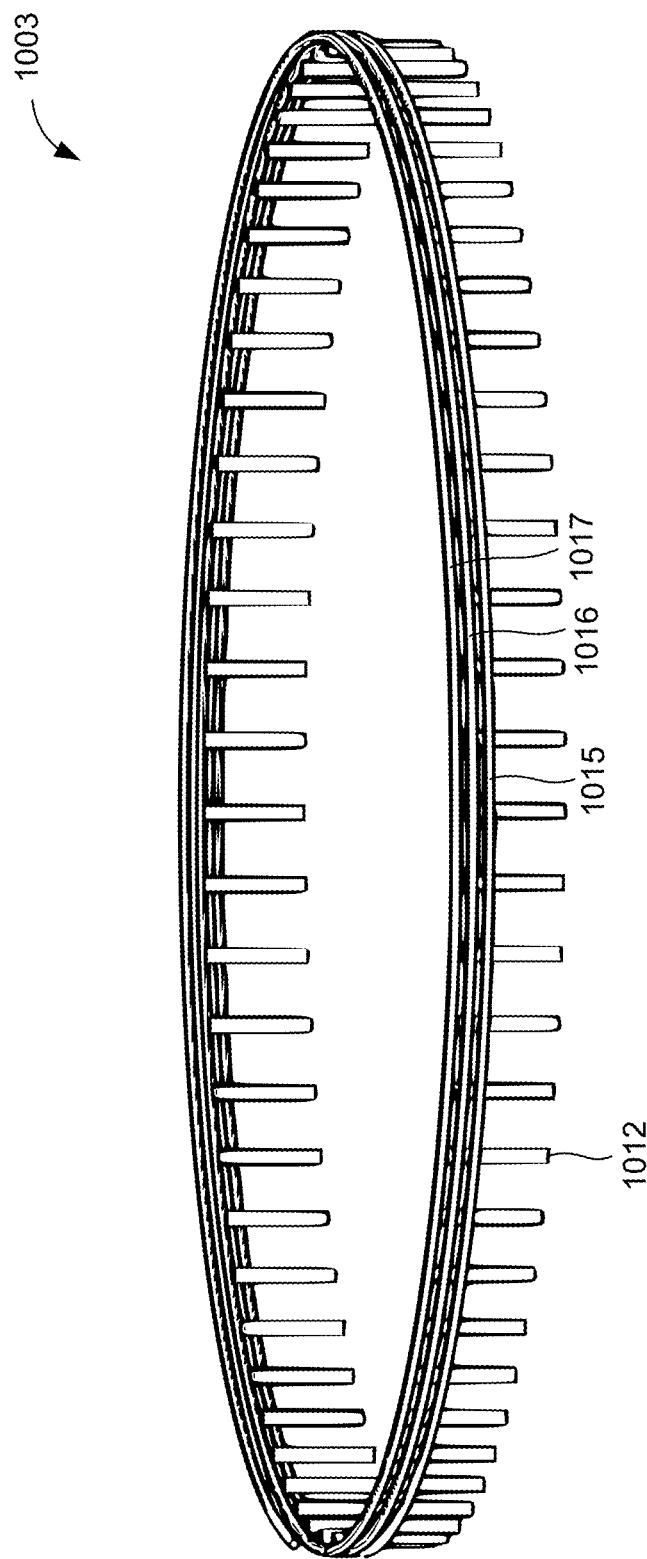
FIG. 39 illustrates an external phasing coil according to various embodiments of the present disclosure.

With reference to FIG. 39, shown is an example of a coil support structure 1003 according to various embodiments of the present disclosure. The coil support structure 1003 can include a fence (or an array of supports) 1012 and wire wrapped around the fence. The fence 1012 can be in the shape of a circle with a corresponding circumference. Each wrap of the wire around the fence 1012 can be referred to as a turn or wrapping 1015, 1016, and 1017. Two different wires can be wrapped around the fence 1012 to create a two different coils (e.g., primary and secondary), each of the coils can include multiple turns (or partial turns), such as wrappings 1015-1017. One of the coils can be coupled to the power transmitter bank 630 on both ends, and wrapped around the fence 1012 in the middle to form a primary coil. The first one of the coils can be referred to as the primary coil, and the second one of the coils can be referred to as the secondary coil. For example, the secondary coil can be an external phasing coil 504 or 505, or can be an inductive coil 260 or 942 of a lumped element tank circuit. By being wrapped around the same fence 1012, the secondary coil can be inductively coupled to the primary coil by the magnetic field generated by current passing through the primary coil.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims. In addition, all optional and preferred features and modifications of the described embodiments and dependent claims are usable in all aspects of the disclosure taught herein. Furthermore, the individual features of the dependent claims, as well as all optional and preferred features and modifications of the described embodiments are combinable and interchangeable with one another.

Therefore, the following is claimed:

1. An arrangement comprising:
 a guided surface waveguide probe comprising a charge terminal elevated over a lossy conducting medium;
 a feed network configured to provide a voltage to the charge terminal with a phase delay ($\Phi$) that matches a wave tilt angle ($\Psi$) associated with a complex Brewster angle of incidence ($\theta_{i,B}$) associated with the lossy conducting medium;
 an excitation source located within a substructure; and
 a primary coil coupled to the excitation source, the primary coil configured to inductively couple with a secondary coil in the feed network.

2. The arrangement of claim 1, wherein the secondary coil is a phasing coil of the feed network.

3. The arrangement of claim 2, wherein the phasing coil is an external phasing coil.

4. The arrangement of claim 3, wherein the feed network comprises an internal phasing coil coupled to the external phasing coil.

5. The arrangement of claim 4, wherein a first phase delay associated with the external phasing coil exceeds a second phase delay associated with the internal phasing coil.

6. The arrangement of claim 1, wherein the substructure is located directly beneath a portion of a perimeter of the primary coil.

7. The arrangement of claim 1, wherein the substructure is covered by a concrete slab.

8. The arrangement of claim 1, wherein the secondary coil and the primary coil are wrapped around a circular coil support structure.

9. The arrangement of claim 1, wherein the charge terminal is positioned along a vertical axis normal to a horizontal plane defined by the secondary coil of the feed network, where the vertical axis is inside of a perimeter of the secondary coil.

10. The arrangement of claim 1, wherein a position of the charge terminal over a horizontal plane defined by the secondary coil is outside of a perimeter of the secondary coil.

11. The arrangement of claim 1, wherein the secondary coil is an inductive coil of a tank circuit of the feed network, the tank circuit comprising the inductive coil in parallel with a capacitor.

12. A system comprising:
a charge terminal elevated over a lossy conducting medium by a support structure;
a substructure comprising an excitation source;
a feed network comprising at least one phasing coil configured to provide a voltage to the charge terminal with a phase delay ($\Phi$) that matches a wave tilt angle ($\Psi$) associated with a complex Brewster angle of incidence ($\theta_{i,B}$) associated with the lossy conducting medium; and
a primary coil coupled to the excitation source and configured to inductively couple with a coil of the feed network to excite the charge terminal.

13. The system of claim 12, wherein the substructure is located directly beneath a portion of a perimeter of the at least one phasing coil.

14. The system of claim 12, wherein the at least one phasing coil comprises an external phasing coil having first circumference and an internal phasing coil having a second circumference.

15. The system of claim 14, wherein the coil is the external phasing coil, with the primary coil and the external phasing coil wrapped around a coil support structure.

16. The system of claim 12, wherein the charge terminal is positioned along a vertical axis located within a perimeter of the primary coil and normal to a horizontal plane defined by the primary coil.

17. The system of claim 12, wherein the charge terminal is positioned along a vertical axis located outside of a perimeter of the primary coil on a horizontal plane and normal to the horizontal plane defined by the primary coil.

18. The system of claim 12, wherein the coil is an inductive coil of a lumped element tank circuit of the feed network, the lumped element tank circuit comprising the inductive coil in parallel with a capacitor.

19. An arrangement comprising:
a charge terminal elevated by a support structure over a lossy conducting medium;
an excitation source located within a substructure below the support structure;
a primary coil coupled to the excitation source; and
a feed network configured to provide a voltage to the charge terminal with a phase delay ($\Phi$) that matches a wave tilt angle ($\Psi$) associated with a complex Brewster angle of incidence ($\theta_{i,B}$) associated with the lossy conducting medium, the feed network comprising an external phasing coil and an internal phasing coil, the external phasing coil being inductively coupled to the primary coil.

20. The arrangement of claim 19, wherein a first phase delay associated with the external phasing coil exceeds a second phase delay associated with the internal phasing coil.

* * * * *